United States Patent
Parham et al.

(10) Patent No.: US 12,108,665 B2
(45) Date of Patent: Oct. 1, 2024

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Philipp Stoessel, Frankfurt am Main (DE); Christian Ehrenreich, Darmstadt (DE)

(73) Assignee: Merck KGaA, Darmstadt (DE)

( * ) Notice: Subject to any disclaimer, the term of this patent is extended or adjusted under 35 U.S.C. 154(b) by 206 days.

(21) Appl. No.: 17/639,348

(22) PCT Filed: Aug. 31, 2020

(86) PCT No.: PCT/EP2020/074184
§ 371 (c)(1),
(2) Date: Mar. 1, 2022

(87) PCT Pub. No.: WO2021/043703
PCT Pub. Date: Mar. 11, 2021

(65) Prior Publication Data
US 2022/0310932 A1    Sep. 29, 2022

(30) Foreign Application Priority Data
Sep. 2, 2019 (EP) .................................. 19194922

(51) Int. Cl.
| | | |
|---|---|---|
| *H10K 85/60* | (2023.01) | |
| *C07D 251/20* | (2006.01) | |
| *C07D 251/22* | (2006.01) | |
| *C07D 403/10* | (2006.01) | |
| *C07D 403/14* | (2006.01) | |
| *C07D 405/04* | (2006.01) | |
| *C07D 405/14* | (2006.01) | |
| *C07D 471/04* | (2006.01) | |
| *C07D 471/14* | (2006.01) | |
| *C07D 487/04* | (2006.01) | |
| *C07D 498/04* | (2006.01) | |
| *C07D 513/04* | (2006.01) | |
| *C07D 519/00* | (2006.01) | |
| *C09K 11/06* | (2006.01) | |
| *H10K 50/11* | (2023.01) | |
| *H10K 101/10* | (2023.01) | |

(52) U.S. Cl.
CPC ......... *H10K 85/654* (2023.02); *C07D 251/20* (2013.01); *C07D 251/22* (2013.01); *C07D 403/10* (2013.01); *C07D 403/14* (2013.01); *C07D 405/04* (2013.01); *C07D 405/14* (2013.01); *C07D 471/04* (2013.01); *C07D 471/14* (2013.01); *C07D 487/04* (2013.01); *C07D 498/04* (2013.01); *C07D 513/04* (2013.01); *C07D 519/00* (2013.01); *C09K 11/06* (2013.01); *H10K 85/615* (2023.02); *H10K 85/622* (2023.02); *H10K 85/624* (2023.02); *H10K 85/626* (2023.02); *H10K 85/657* (2023.02); *H10K 85/6572* (2023.02); *H10K 85/6574* (2023.02); *H10K 85/6576* (2023.02); *C09K 2211/1018* (2013.01); *H10K 50/11* (2023.02); *H10K 2101/10* (2023.02)

(58) Field of Classification Search
CPC .. H10K 85/615; H10K 85/626; H10K 85/654; H10K 85/6572; C09K 11/06
See application file for complete search history.

(56) References Cited

U.S. PATENT DOCUMENTS

| | | | |
|---|---|---|---|
| 3,984,549 A | 10/1976 | Bochis | |
| 2011/0121236 A1 | 5/2011 | Akino | |
| 2015/0333280 A1 | 11/2015 | Stoessel et al. | |
| 2015/0349277 A1 | 12/2015 | Stoessel et al. | |
| 2016/0308149 A1* | 10/2016 | Stoessel | C09K 11/06 |

FOREIGN PATENT DOCUMENTS

| | | |
|---|---|---|
| AU | 9024301 A | 4/2002 |
| CN | 104870458 A | 8/2015 |
| CN | 104870459 A | 8/2015 |
| KR | 10-2012-0001163 A | 1/2012 |
| WO | 2002/024711 A1 | 3/2002 |
| WO | 2011/116865 A1 | 9/2011 |
| WO | 2011/137951 A1 | 11/2011 |
| WO | 2013/064206 A1 | 5/2013 |
| WO | 2013/082275 A1 | 6/2013 |
| WO | 2013/089212 A1 | 6/2013 |
| WO | 2014/094960 A1 | 6/2014 |
| WO | 2014/094961 A1 | 6/2014 |
| WO | 2014/166577 A1 | 10/2014 |
| WO | 2016/045765 A1 | 3/2016 |
| WO | 2016/079709 A1 | 5/2016 |

(Continued)

OTHER PUBLICATIONS

Cao et al., "Oxidant-Mediated Nitrogenation and Recyclization of Imidazo [1,2-a]pyridines with Sodium Azide: Synthesis of 4H-Pyrido[1,2-a] [1,3,5]triazin-4-ones" Advanced Synthesis & Catalysis, 2018, 360, pp. 881-886.
International Search Report and Written Opinion received for PCT Patent Application No. PCT/EP2020/074184, mailed on Feb. 2, 2021, 29 pages (13 pages of English Translation and 16 pages of Original Document).
Xia et al., "The dearomative annulation between N-2-pyridylamidine and CO2 toward pyrido[1,2-a]-1,3,5-triazin-4-ones", Organic & Biomolecular Chemistry , vol. 15, No. 19, 2017, pp. 4064-4067.

(Continued)

Primary Examiner — Khanh T Nguyen
(74) Attorney, Agent, or Firm — David K. Benson

(57) ABSTRACT

The invention relates to compounds which are suitable for use in electronic devices, and to electronic devices, in particular organic electroluminescent devices, containing said compounds.

14 Claims, No Drawings

(56) References Cited

FOREIGN PATENT DOCUMENTS

| WO | 2016/128103 A1 | 8/2016 |
|---|---|---|
| WO | 2017/046133 A1 | 3/2017 |

OTHER PUBLICATIONS

Zhang et al., "A One-Pot Approach to Pyridyl Isothiocyanates from Amines", Molecules, vol. 19. No. 9, 2014, pp. 13631-13642.

Basawaraj et al., "Synthesis and biological activities of some thiazolotriazines and thiazolothiazolidinones containing 5-chloro-3-methylbenzofuran-2-yl moiety," Indian Journal of Heterocyclic Chemistry, vol. 18, No. 2, Dec. 2008, pp. 173-176.

Chambers et al., "2- and 4-isocyanatopyridines : Transient intermediates," Tetrahedron Letters, vol. 16, Issue 22, Jun. 26, 1975, pp. 2783-2786.

Count et al., "An Improved Synthesis of Pyridyl Isothiocyanates and Thioureas," Synthesis, vol. 8, Aug. 1977, pp. 582-583.

Gizycki et al., "Anellated 1,3,5-triazine-2,4-diones as dimers of heterocyclic isocyanates," Angewandte Chemie, International Edition vol. 7, No. 5, May 1968, pp. 381-382.

Gizycki, U. V. "Pyridine, pyrimidine, and pyrazine derivatives with an isocyanato substituent vicinal to nitrogen," Angewandte Chemie, Internation Edition, vol. 10, No. 6, Jun. 1971, pp. 402-403.

Holt et al., "Nitropyridyl Isocyanates," Journal of Heterocyclic Chemistry, vol. 42, 2005, 259-264.

International Preliminary Report on Patentability received for PCT Patent Application No. PCT/EP2020/074184, mailed on Mar. 8, 2022, 19 pages (9 pages of English Translation and 10 pages of Original Document).

Mahmoud A., A. R., "Addition Reaction of Phenyl Isocyanate and Phenyl Isothiocyanate to Partially Cyclic 1,3-Diaza-1,3-butadienes. Synthesis of Annulated 1,3,5-Triazine-2,4(1H,3H)-diones and -2,4(1H,3H)-dithiones." Bulletin of the Chemical Society of Japan, vol. 66, No. 2, 1993, pp. 510-512.

Marchalin et al., "Thiazolo[3,2-a]-1,3,5-triazines. Preparation of 4-substituted 2-thiazolyl isothiocyanates and their reactions with isocyanates, aldimines and carbodiimides," Collection of Czechoslovak Chemical Communications, vol. 47, No. 4, 1982, pp. 1229-1234.

Saeed et al., "2-Substituted 4H-[1,3]thiazolo[3,2-a][1,3,5]triazine-4-thiones: Synthesis, Crystal Structure, and Antifungal Activity," Journal of Heterocyclic Chemistry, vol. 47, No. 4, pp. 908-912.

Tanaka et al., "Pyrolysis of Benzyl 2-Oxazolecarbamates and Benzyl 4-Alkylallophanates," Chemical and Pharmaceutical Bulletin, vol. 30, No. 11, 1982, pp. 4195-4198.

Troschuetz et al., "Synthesis of 10-(N'-methylpiperazino)-5H-pyrido[2,3-c]-2-benzazepine ("Azaperlapine")," Arc der Pharmazie (Weinheim, Germany), vol. 326, No. 11, 1993, pp. 913-916.

* cited by examiner

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2020/074184, filed Aug. 31, 2020, which claims benefit of European Application No. 19194922.1, filed Sep. 2, 2019, both of which are incorporated herein by reference in their entirety.

The present invention relates to electronic devices, especially organic electroluminescent devices, comprising triazinone derivatives.

Emitting materials used in organic electroluminescent devices (OLEDs) are frequently phosphorescent organometallic complexes. In general terms, there is still a need for improvement in OLEDs, especially also in OLEDs which exhibit triplet emission (phosphorescence), for example with regard to efficiency, operating voltage and lifetime. The properties of phosphorescent OLEDs are not just determined by the triplet emitters used. More particularly, the other materials used, such as matrix materials or charge transport materials, are also of particular significance here. Improvements to these materials can thus also lead to improvements in the OLED properties. Suitable matrix materials for OLEDs are, for example, aromatic lactams as disclosed, for example, in WO 2011/116865, WO 2011/137951 or WO 2013/064206.

The problem addressed by the present invention is that of providing compounds which are suitable for use in an OLED, especially as matrix material for phosphorescent emitters or as electron transport material, and which lead to improved properties therein. It is a further object of the present invention to provide further organic semiconductors for organic electroluminescent devices, in order thus to enable the person skilled in the art to have a greater possible choice of materials for the production of OLEDs.

It has been found that, surprisingly, this object is achieved by particular compounds described in detail hereinafter that are of good suitability for use in OLEDs. These OLEDs especially have a long lifetime, high efficiency and low operating voltage. The present invention therefore provides these compounds and electronic devices, especially organic electroluminescent devices, comprising these compounds.

The present invention provides an electronic device comprising at least one compound of formula (1)

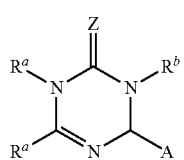

Formula (1)

where the symbols used are as follows:
Z is the same or different at each instance and is O or S;
A is R or Z;
$R^b$ is Ar or a free electron pair;
where, when A=Z, the oxygen or sulfur atom represented by Z is bonded to the carbon atom via a double bond, and $R^b$ is Ar;

in addition, $R^b$ is a free electron pair when A=R, and there is a double bond between the carbon atom to which A is bonded and the nitrogen atom to which $R^b$ is bonded;
$R^a$ is the same or different and is R, or the two $R^a$ groups together with the nitrogen atom and the carbon atom to which they bind form a group of one of the following formulae (2), (3) and (4):

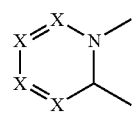

Formula (2)

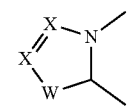

Formula (3)

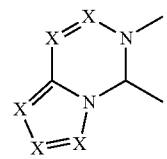

Formula (4)

where the dotted bond in each case indicates the linkage within formula (1);
X is the same or different at each instance and is CR or N; or two adjacent X groups are a group of the following formula (5) or (6):

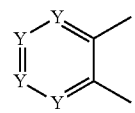

Formula (5)

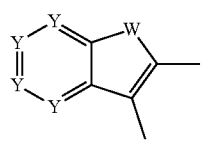

Formula (6)

where the dotted bonds indicate the linkage of this group in the formula (2), formula (3) or formula (4);
Y is the same or different at each instance and is CR or N;
W is the same or different at each instance and is NAr, O, S or $C(R)_2$;
Ar is the same or different at each instance and is an aromatic or heteroaromatic ring system which has 5 to 40 aromatic ring atoms and may be substituted by one or more R radicals;
R is the same or different at each instance and is H, D, F, Cl, Br, I, $N(Ar')_2$, $N(R^1)_2$, $OAr'$, $SAr$, $CN$, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals, where one or more nonadjacent $CH_2$ groups may be replaced by $Si(R^1)_2$, C=O, $NR^1$, O, S or $CONR^1$, or an aromatic or heteroaromatic ring system which has 5 to 60 aromatic ring atoms, preferably 5 to 40 aromatic ring atoms, and may be substituted in each case by one or more $R^1$ radicals; at the same time, two R radicals together may also form an aliphatic, heteroaliphatic, aromatic or heteroaromatic ring system;

Ar' is the same or different at each instance and is an aromatic or heteroaromatic ring system which has 5 to 40 aromatic ring atoms and may be substituted by one or more $R^1$ radicals;

$R^1$ is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may each be substituted by one or more $R^2$ radicals, where one or more nonadjacent $CH_2$ groups may be replaced by $Si(R^2)_2$, C=O, $NR^2$, O, S or $CONR^2$ and where one or more hydrogen atoms in the alkyl, alkenyl or alkynyl group may be replaced by D, F, Cl, Br, I or CN, or an aromatic or heteroaromatic ring system which has 5 to 40 aromatic ring atoms and may be substituted in each case by one or more $R^2$ radicals; at the same time, two or more $R^1$ radicals together may form an aliphatic ring system;

$R^2$ is the same or different at each instance and is H, D, F, CN or an aliphatic, aromatic or heteroaromatic organic radical, especially a hydrocarbyl radical, having 1 to 20 carbon atoms, in which one or more hydrogen atoms may also be replaced by F.

If two adjacent X groups are one of the formulae (5) and (6), the remaining X groups in formulae (2) and (4) are the same or different and are CR or N. In addition, it is also possible in formula (2) or (4) that each of two adjacent pairs X are groups of the formula (5) or (6), such that the group of the formula (2) or (4) may also in each case contain two groups of the formula (5) or (6).

In a preferred embodiment of the invention, the compound of the formula (1) contains at least one substituent Ar, or it contains at least one substituent R which is an aromatic or heteroaromatic ring system.

An aryl group in the context of this invention contains 6 to 40 carbon atoms, a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 60 carbon atoms, preferably 6 to 40 carbon atoms, in the ring system. A heteroaromatic ring system in the context of this invention contains 2 to 60 carbon atoms, preferably 2 to 40 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a non-aromatic unit, for example a carbon, nitrogen or oxygen atom. These shall likewise be understood to mean systems in which two or more aryl or heteroaryl groups are joined directly to one another, for example biphenyl, terphenyl, bipyridine or phenylpyridine. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. Preferred aromatic or heteroaromatic ring systems are simple aryl or heteroaryl groups and groups in which two or more aryl or heteroaryl groups are joined directly to one another, for example biphenyl or bipyridine, and also fluorene or spirobifluorene.

In the context of the present invention, the term "alkyl group" is used as an umbrella term both for linear and branched alkyl groups and for cyclic alkyl groups. Analogously, the terms "alkenyl group" and "alkynyl group" are used as umbrella terms both for linear or branched alkenyl or alkynyl groups and for cyclic alkenyl or alkynyl groups.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group $OR^1$ having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group $SR^1$ having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups, in addition, it is also possible for one or more hydrogen atoms to be replaced by D, F, Cl, Br, I, CN or $NO_2$, preferably F, C or CN, more preferably F or CN.

An aromatic or heteroaromatic ring system which has 5-60 aromatic ring atoms and may also be substituted in each case by the abovementioned R² radicals or a hydrocarbyl radical and which may be joined to the aromatic or heteroaromatic system via any desired positions is understood to mean especially groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from a combination of these systems.

The wording that two or more radicals together may form an aliphatic ring, in the context of the present description, shall be understood to mean, inter alia, that the two radicals are joined to one another by a chemical bond with formal elimination of two hydrogen atoms. This is illustrated by the following scheme:

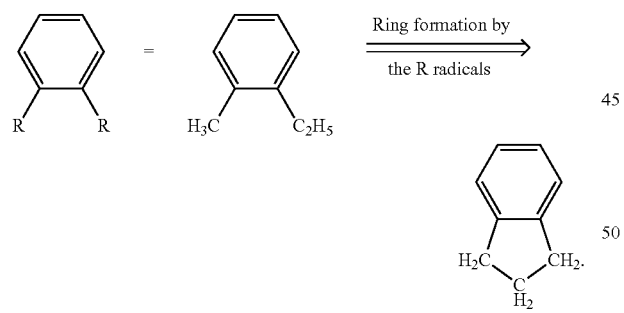

In addition, however, the abovementioned wording shall also be understood to mean that, if one of the two radicals is hydrogen, the second radical binds to the position to which the hydrogen atom was bonded, forming a ring. This shall be illustrated by the following scheme:

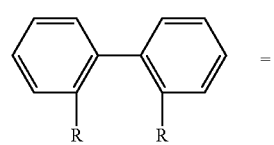

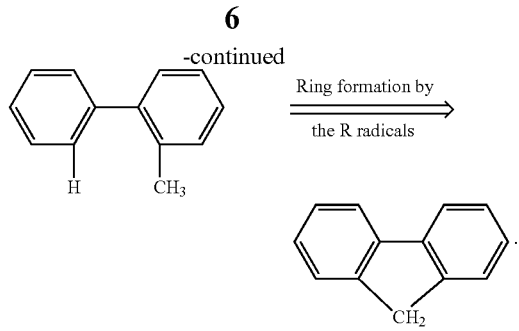

The choice of A and $R^b$ groups gives rise to the compounds of the following formulae (7) and (8):

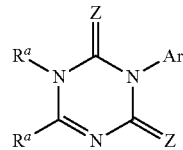

Formula (7)

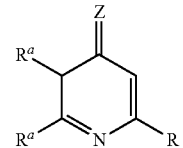

Formula (8)

where the symbols used have the definitions given above.

In a preferred embodiment of the compounds detailed above and hereinafter, Z is O, and so preferred compounds of the formula (7) are the compounds of the following formula (7a) and preferred compounds of the formula (8) are the compounds of the following formula (8a):

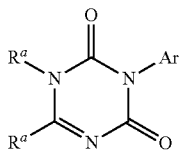

Formula (7a)

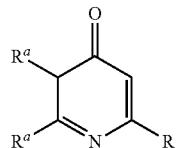

Formula (8a)

where the symbols used have the definitions given above.

In one embodiment, the two $R^a$ groups together with the nitrogen atom and the carbon atom to which they bind form a group of formula (2), (3) or (4). It is preferable here for formula (2) that not more than one X group is N. More preferably, all X are the same or different and are CR, or two adjacent X are a group of the formula (5) or (6) and the remaining X are the same or different at each instance and are CR. It is additionally preferable for formula (3) that the two X are the same or different and are CR, or that the two X together are a group of the formula (5). It is additionally preferable for formula (4) that not more than one X group is N and the remaining X are the same or different and are CR or a group of the formula (5) or (6). When, in formula (4), an X group is N, this is preferably an X group in the five-membered ring. It is additionally preferable when, in formula (4), the two X groups in the six-membered ring together are a group of the formula (5) or (6).

In this case, in the formulae (5) and (6), preferably not more than one Y group is N. More preferably, all Y groups are the same or different at each instance and are CR.

Preferred embodiments of the formula (2) are the groups of the following formulae (2a) to (2m):

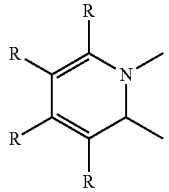
Formula (2a)

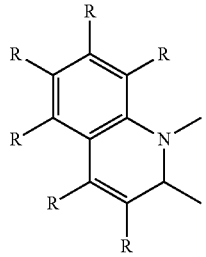
Formula (2b)

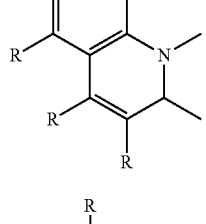
Formula (2c)

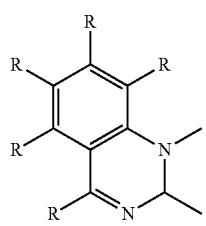
Formula (2d)

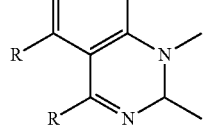

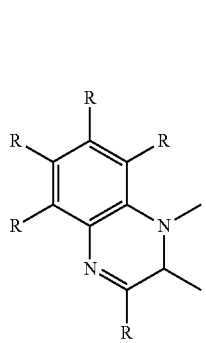
Formula (2e)

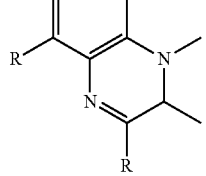

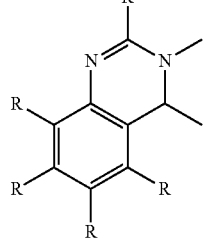
Formula (2f)

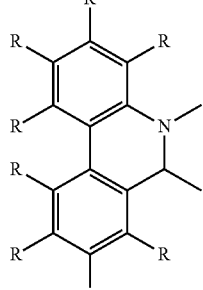
Formula (2g)

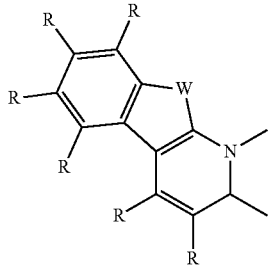
Formula (2h)

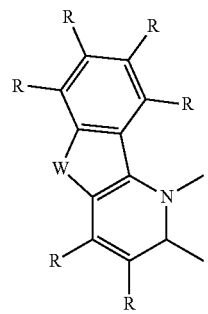
Formula (2i)

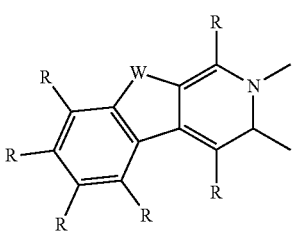
Formula (2j)

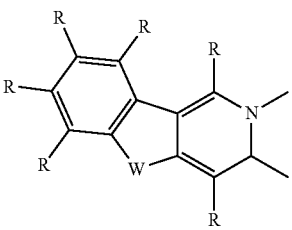
Formula (2k)

-continued

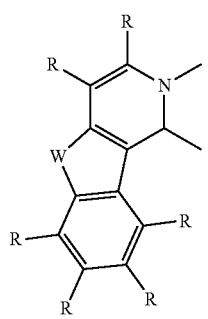
Formula (2l)

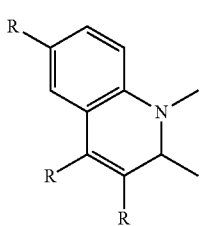
Formula (2m)

where the symbols used have the definitions given above and the dotted bond in each case indicates the linkage within formula (1).

Preferred embodiments of the formulae (2a), (2b) and (2g) are the structures of the following formulae (2a-1), (2b-1) and (2g-1):

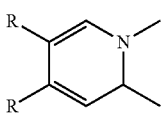
Formula (2a-1)

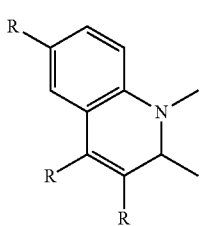
Formula (2b-1)

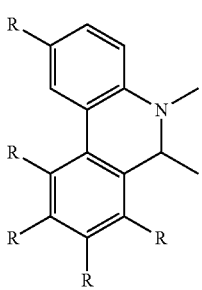
Formula (2g-1)

where the symbols used have the definitions given above.

Preferred embodiments of the formula (3) are the groups of the following formulae (3a) and (3b):

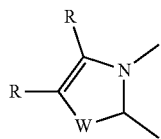
Formula (3a)

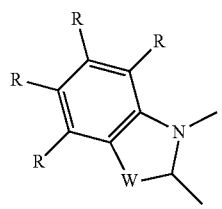
Formula (3b)

where the symbols used have the definitions given above and the dotted bond in each case indicates the linkage within formula (1).

Preferred embodiments of the formula (3b) are the structures of the following formula (3b-1):

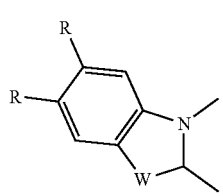
Formula (3b-1)

where the symbols used have the definitions given above.

Preferred embodiments of the formula (4) are the structures of the following formulae (4a) to (4k):

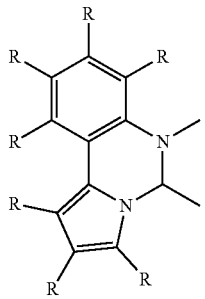
Formula (4a)

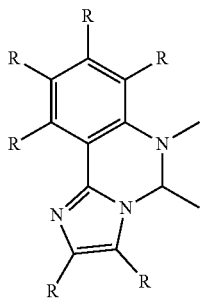
Formula (4b)

-continued
Formula (4c)
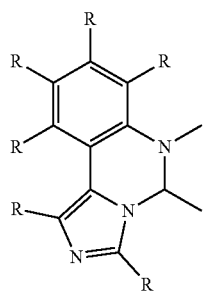
Formula (4d)
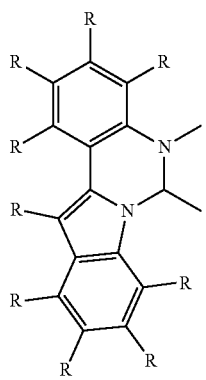
Formula (4e)
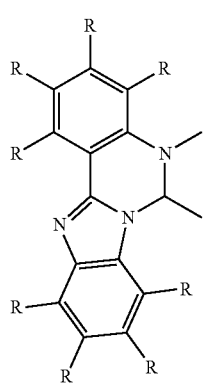
Formula (4f)
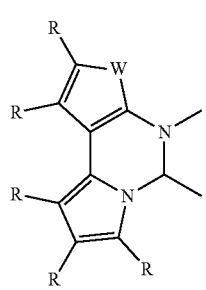
Formula (4g)
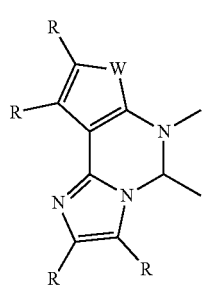
-continued
Formula (4h)
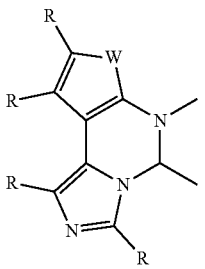
Formula (4i)
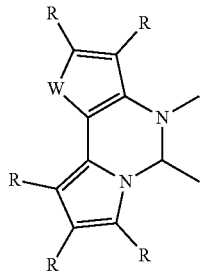
Formula (4j)
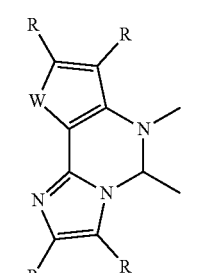
Formula (4k)
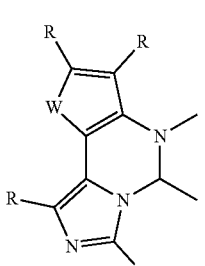
where the symbols used have the definitions given above and the dotted bond in each case indicates the linkage within formula (1).
Preferred embodiments of the formulae (4a), (4b), (4c), (4d) and (4e) are the structures of the following formulae (4a-1), (4b-1), (4c-1), (4d-1) and (4e-1):
Formula (4a-1)
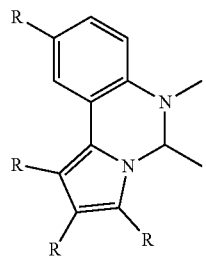

-continued

Formula (4b-1)
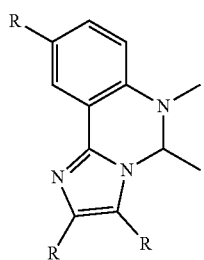

Formula (4c-1)
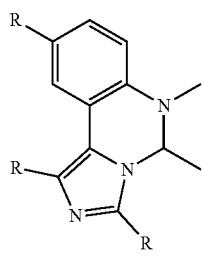

Formula (4d-1)
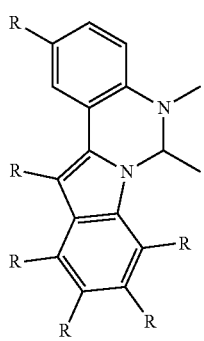

Formula (4e-1)
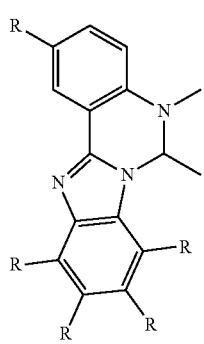

where the symbols used have the definitions given above.

In a further preferred embodiment of the invention, W is the same or different at each instance and is NAr, O or S.

It is possible here for the structures of the formulae (7) and (8) to be combined as desired with the structures of the formulae (2a) to (2m), (3a), (3b) and (4a) to (4k).

In one embodiment of the invention, the two $R^a$ groups are the same or different at each instance and are R, such that the compounds are those of the following formulae (7-1) and (8-1):

Formula (7-1)
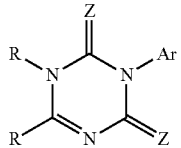

Formula (8-1)
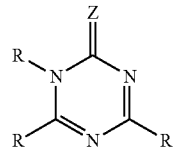

where the symbols used have the definitions given above, where Z is preferably O.

In a further embodiment of the invention, the $R^a$ radicals are a group of the formula (2), (3) or (4), and the compounds of the formula (7) are compounds of the following formulae (7-2) to (7-9):

Formula (7-2)
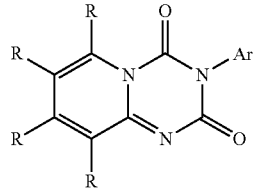

Formula (7-3)
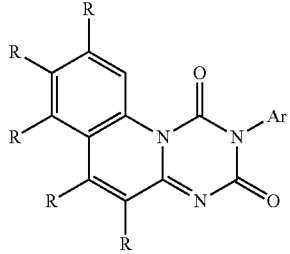

Formula (7-4)
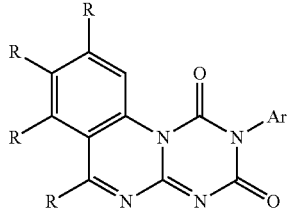

Formula (7-5)
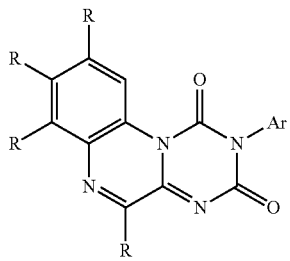

Formula (7-6)
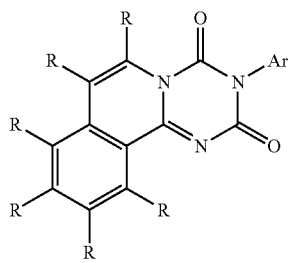

Formula (7-7)
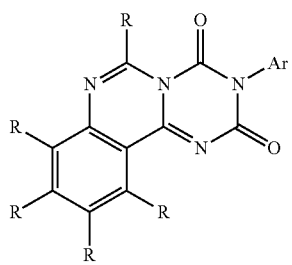

Formula (7-8)
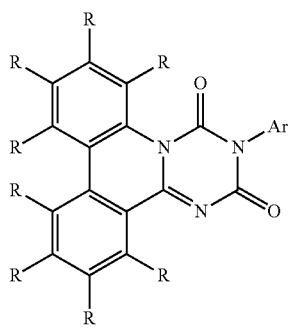

Formula (7-9)
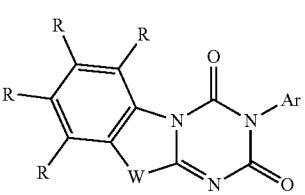

where the symbols have the definitions given above.

Preferred embodiments of the structures of the formulae (7-1) to (7-9) are the structures of the following formulae (7-1a) to (7-9a):

Formula (7-1a)
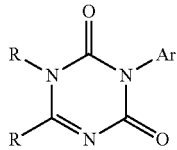

Formula (7-2a)
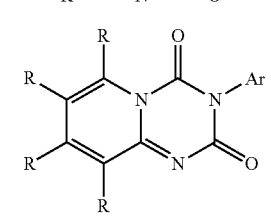

Formula (7-3a)
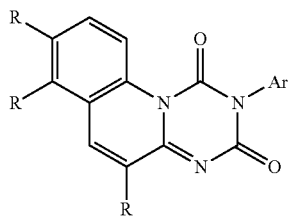

Formula (7-4a)
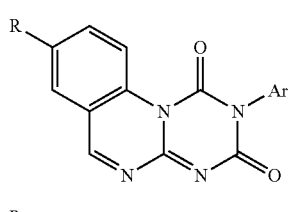

Formula (7-5a)
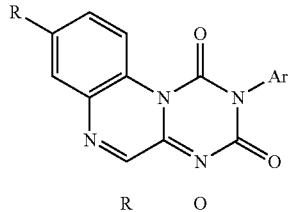

Formula (7-6a)
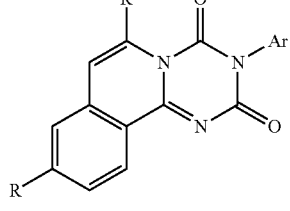

Formula (7-7a)
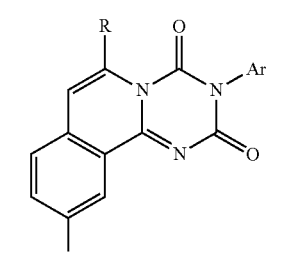

Formula (7-8a)
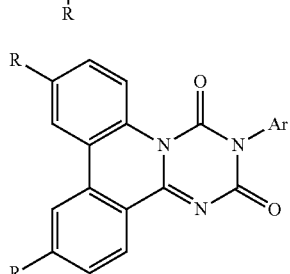

Formula (7-9a)
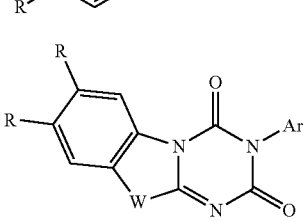

where the symbols have the definitions given above.

If the $R^a$ radicals are a group of the formula (2), (3) or (4), preferred embodiments of the formula (8) are the compounds of the following formulae (8-2) to (8-11):

Formula (8-2)
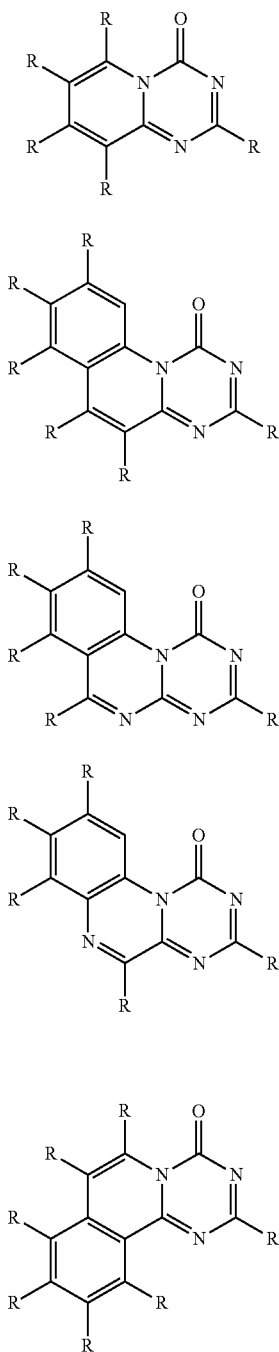
Formula (8-3)
Formula (8-4)
Formula (8-5)
Formula (8-6)
Formula (8-7)
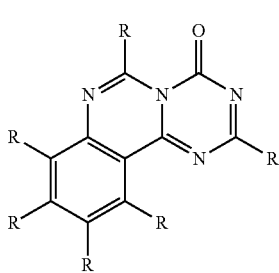
Formula (8-8)
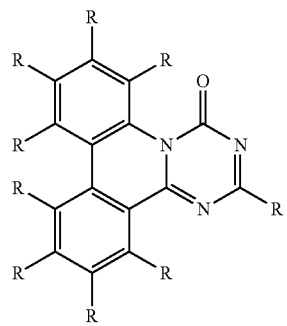
Formula (8-9)
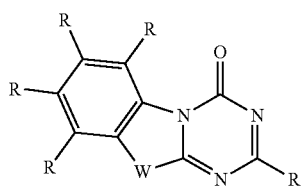
Formula (8-10)
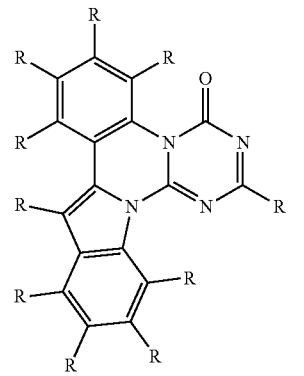
Formula (8-11)
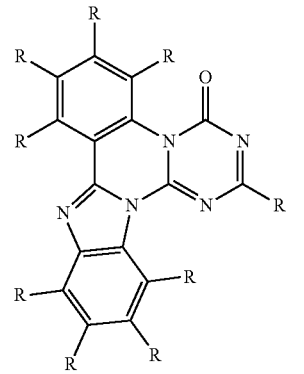
where the symbols have the definitions given above.
Preferred embodiments of the structures of the formulae (8-1) to (8-11) are the structures of the following formulae (8-1a) to (8-11a):
Formula (8-1a)

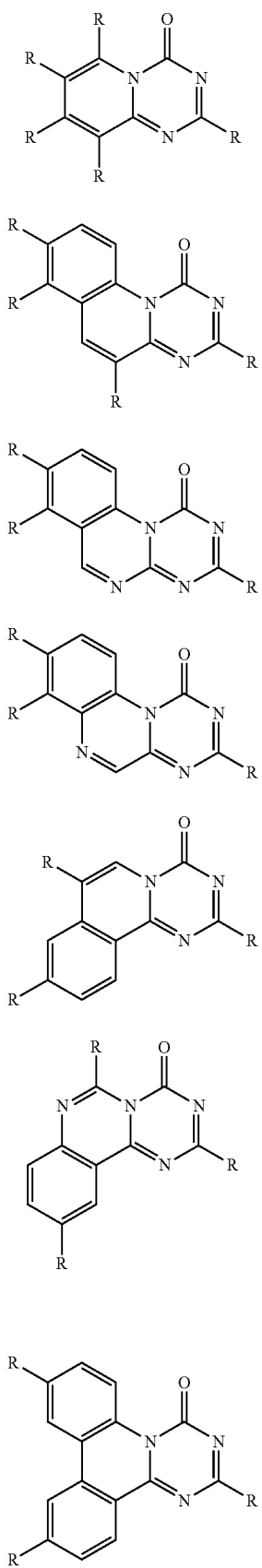

Formula (8-2a)
Formula (8-3a)
Formula (8-4a)
Formula (8-5a)
Formula (8-6a)
Formula (8-7a)
Formula (8-8a)

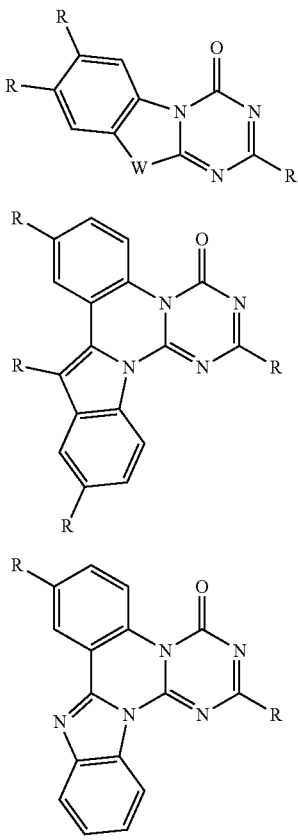

Formula (8-9a)
Formula (8-10a)
Formula (8-11a)

where the symbols have the definitions given above.

Particular preference is given here to the structures of the formulae (7-1a), (7-2a), (7-4a), (7-5a), (7-7a), (7-9a), (8-1a), (8-2a), (8-7a), (8-8a) and (8-9a).

There follows a description of preferred substituents Ar, R, Ar', $R^1$ and $R^2$ in the compounds of the invention. In a particularly preferred embodiment of the invention, the preferences specified hereinafter for Ar, R, Ar', $R^1$ and $R^2$ occur simultaneously and are applicable to the structures of the formula (1) and to all preferred embodiments detailed above.

In a preferred embodiment of the invention, in formula (1), when A=R, this R radical is an aromatic or heteroaromatic ring system which has 5 to 40 aromatic ring atoms and which may be substituted by one or more $R^1$ radicals. Correspondingly, it is preferable that the R radical explicitly shown in formulae (8) and (8-1) to (8-11) which is bonded to the triazinone is an aromatic or heteroaromatic ring system which has 5 to 40 aromatic ring atoms and may be substituted by one or more $R^1$ radicals.

In a preferred embodiment of the invention, Ar is the same or different at each instance and is an aromatic or heteroaromatic ring system which has 6 to 30 aromatic ring atoms and may be substituted by one or more R radicals. More preferably, Ar is the same or different at each instance and is an aromatic or heteroaromatic ring system which has 6 to 24 aromatic ring atoms, especially 6 to 13 aromatic ring atoms, and may be substituted by one or more, preferably nonaromatic, R radicals. When Ar is a heteroaryl group, especially triazine, pyrimidine, quinazoline or carbazole, preference may also be given to aromatic or heteroaromatic substituents R on this heteroaryl group. It may further be preferable when Ar is substituted by an N(Ar')₂ group, such that the Ar substituent constitutes a triarylamine or triheteroarylamine group overall.

Suitable aromatic or heteroaromatic ring systems Ar are the same or different at each instance and are selected from the group consisting of phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more R radicals, preferably nonaromatic R radicals. When Ar is a heteroaryl group, especially triazine, pyrimidine, quinazoline or carbazole, preference may also be given to aromatic or heteroaromatic R radicals on this heteroaryl group.

Ar here is preferably the same or different at each instance and is selected from the groups of the following formulae Ar-1 to Ar-83:

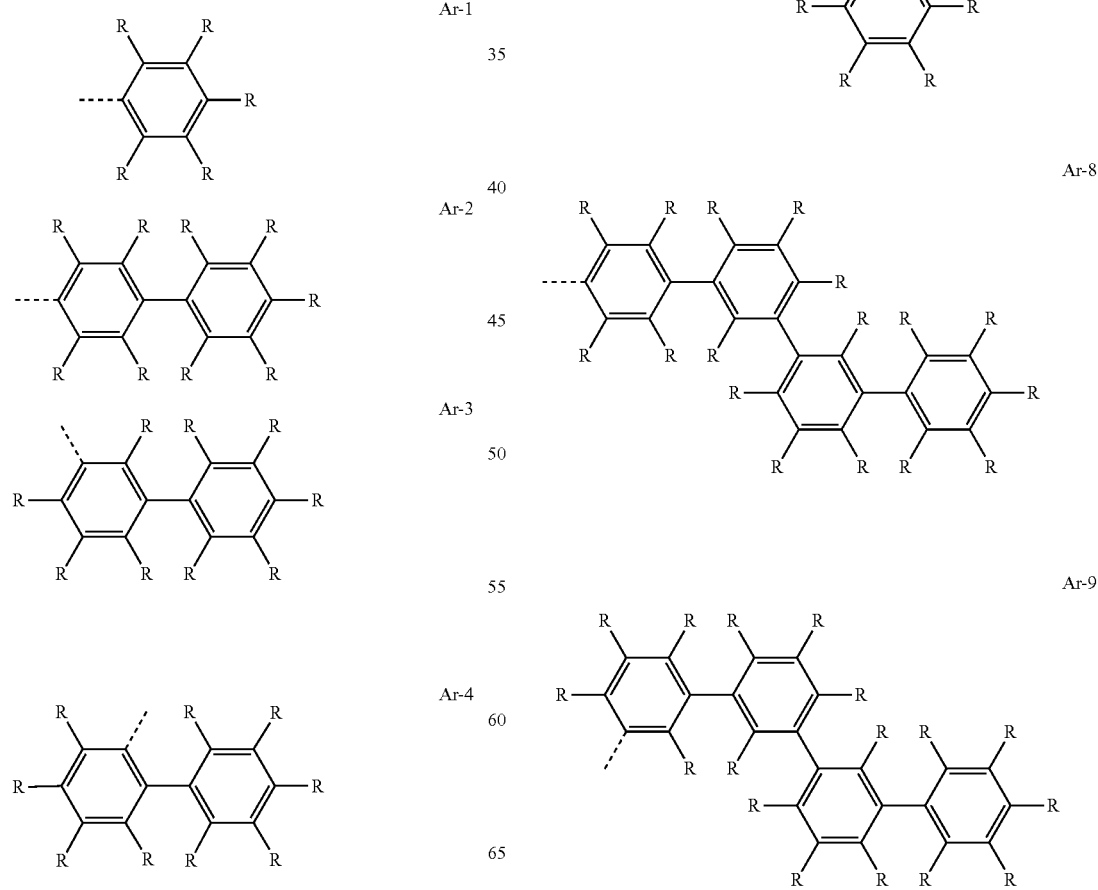

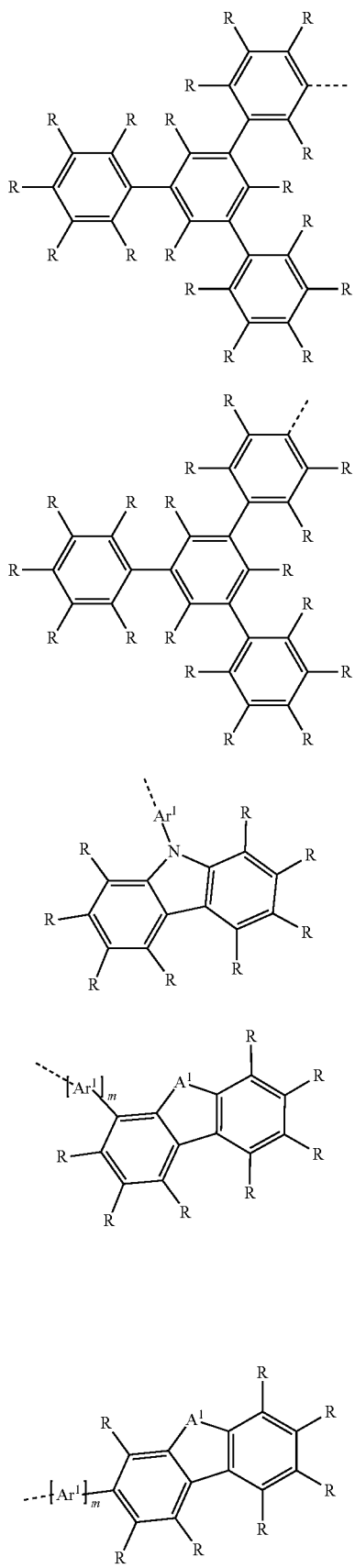

Ar-21
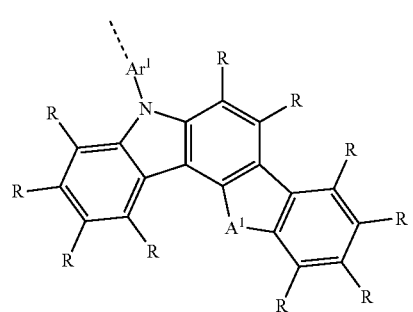
Ar-22
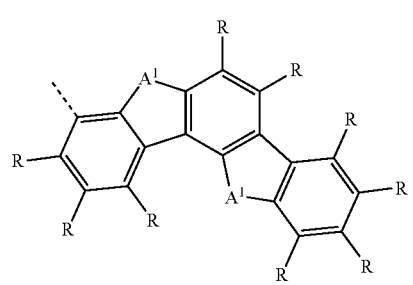
Ar-23
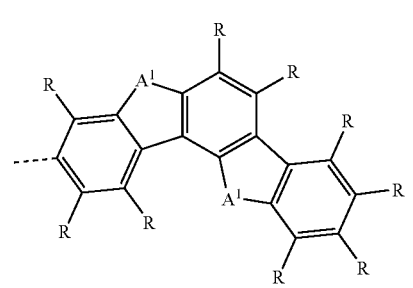
Ar-24
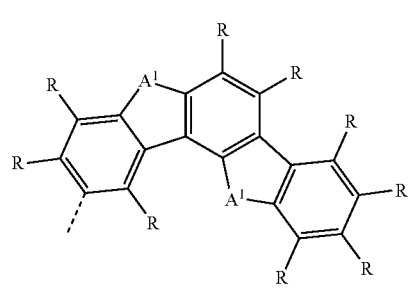
Ar-25
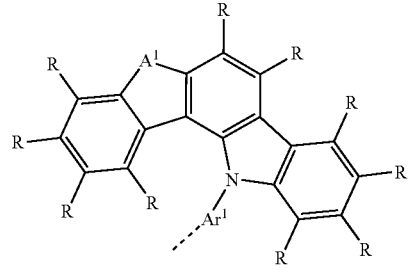
Ar-26
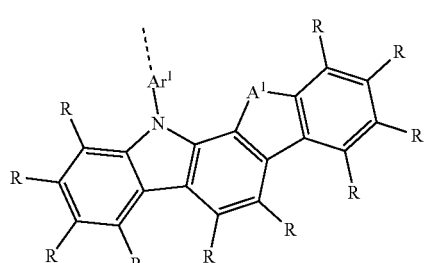
Ar-27
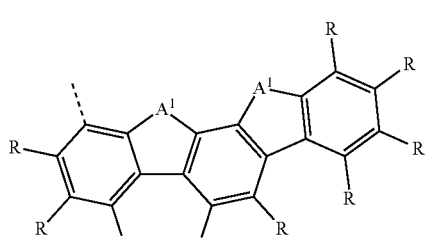
Ar-28
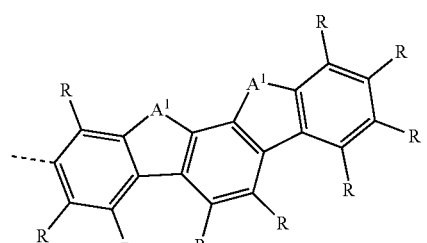
Ar-29
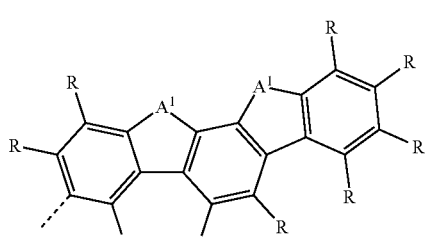
Ar-30
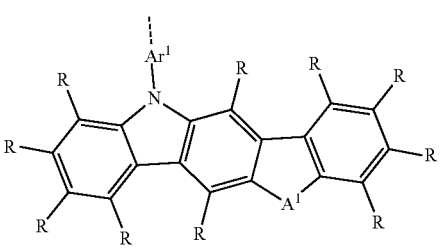
Ar-31
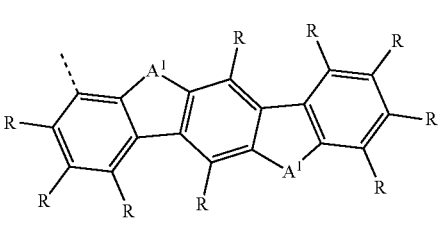

Ar-32
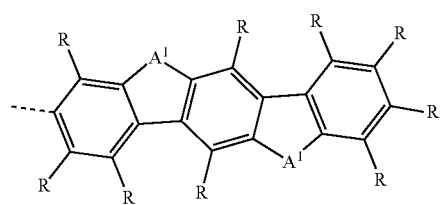
Ar-33
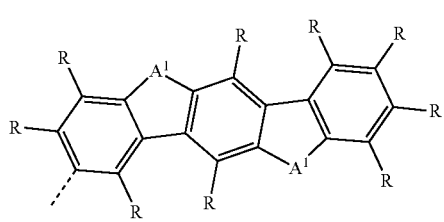
Ar-34
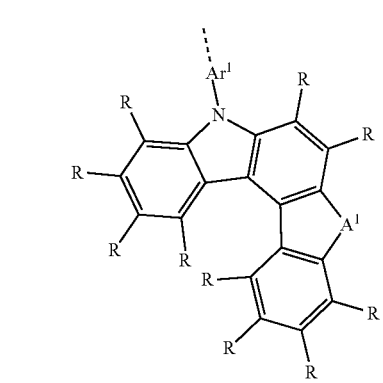
Ar-35
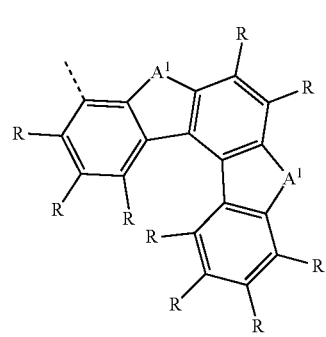
Ar-36
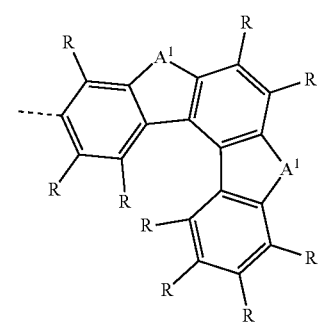
Ar-37
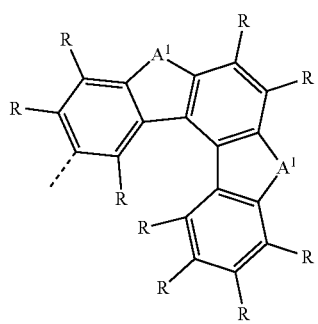
Ar-38
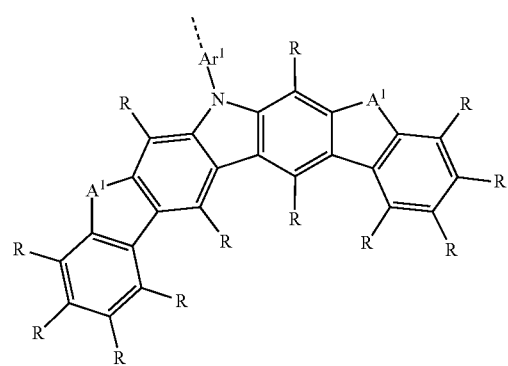
Ar-39
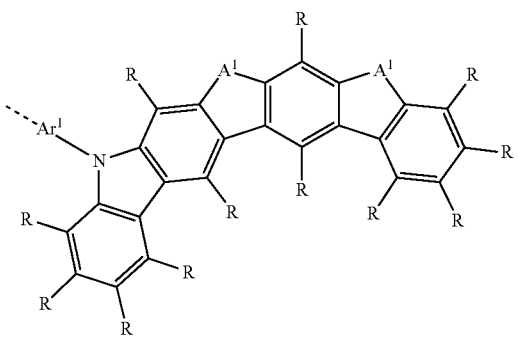
Ar-40
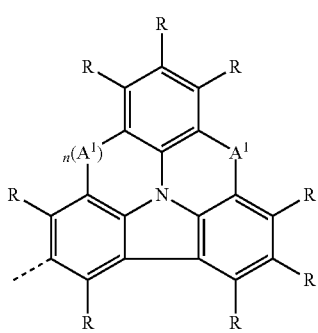

Ar-41
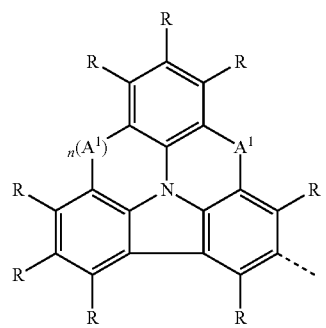
Ar-42
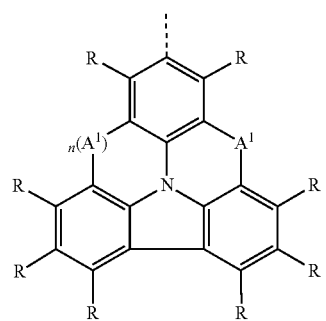
Ar-43
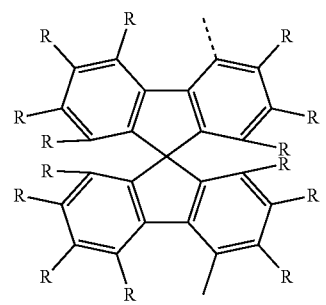
Ar-44
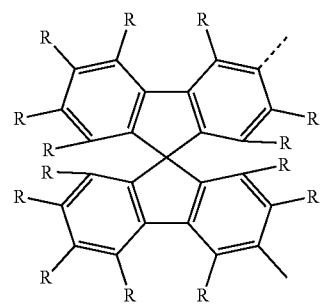
Ar-45
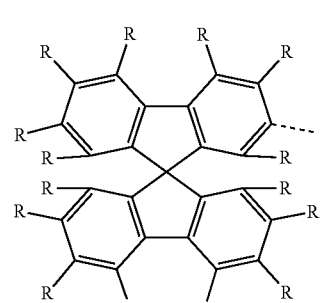
Ar-46
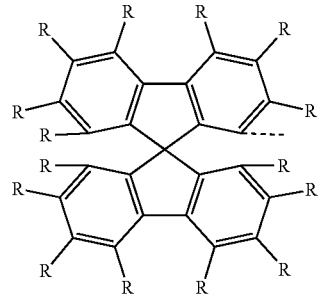
Ar-47
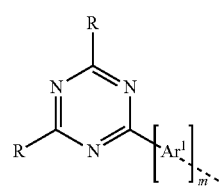
Ar-48
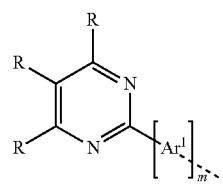
Ar-49
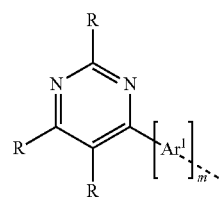
Ar-50
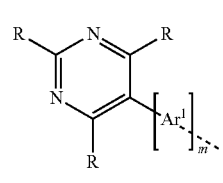
Ar-51
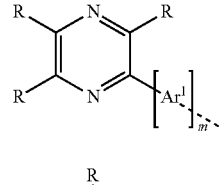
Ar-52
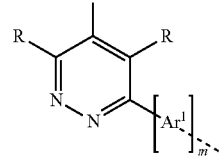
Ar-53
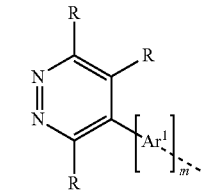

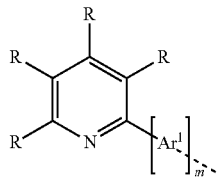
Ar-54
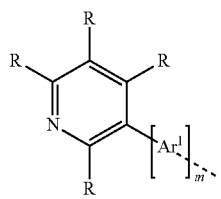
Ar-55
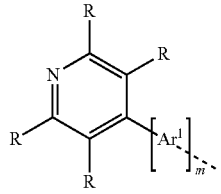
Ar-56
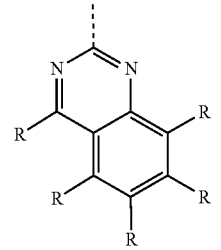
Ar-57
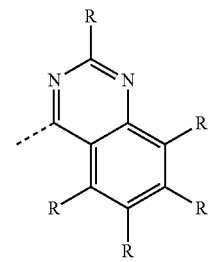
Ar-58
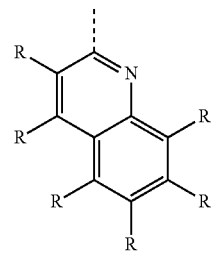
Ar-59
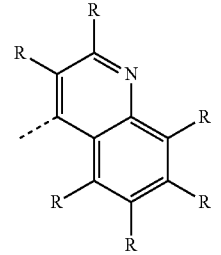
Ar-60
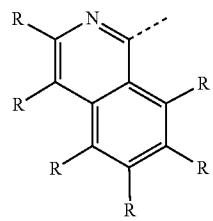
Ar-61
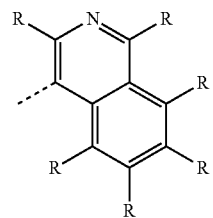
Ar-62
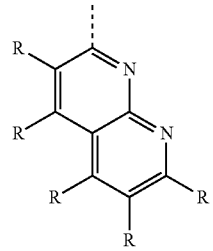
Ar-63
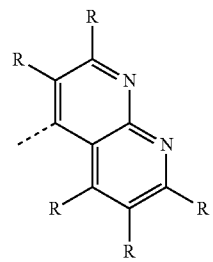
Ar-64
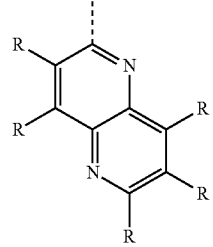
Ar-65
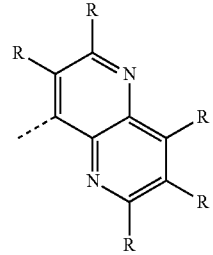
Ar-66

Ar-67
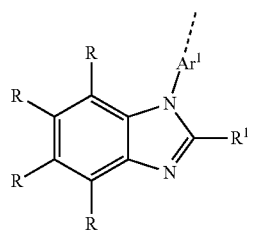
Ar-68
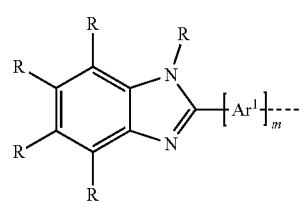
Ar-69
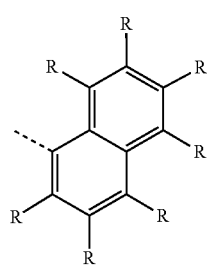
Ar-70
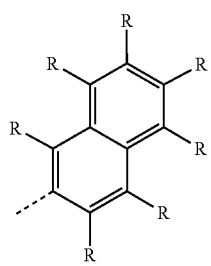
Ar-71
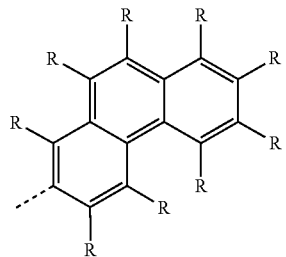
Ar-72
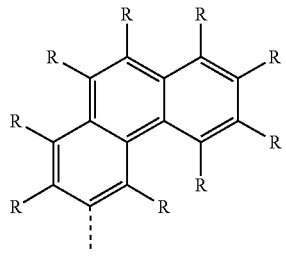
Ar-73
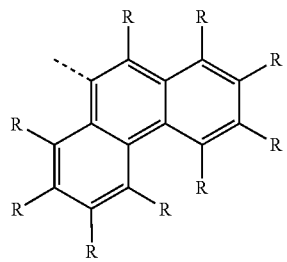
Ar-74
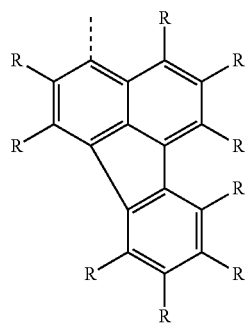
Ar-75
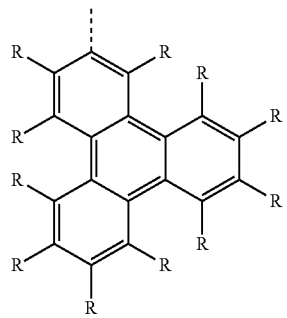
Ar-76
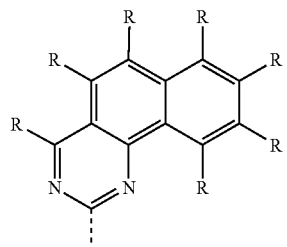
Ar-77
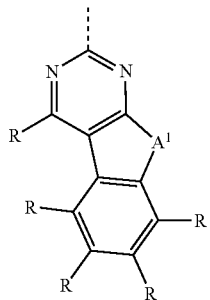

Ar-78 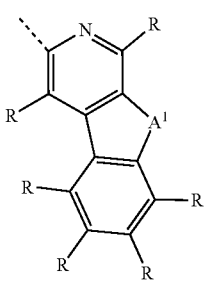

Ar-79 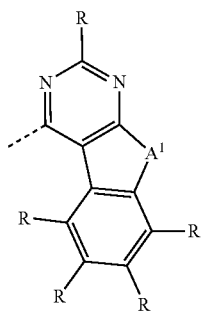

Ar-80 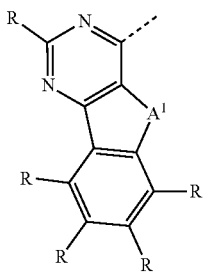

Ar-81 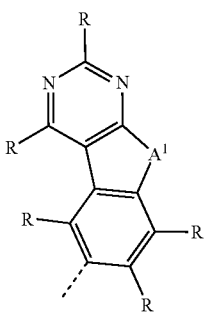

Ar-82 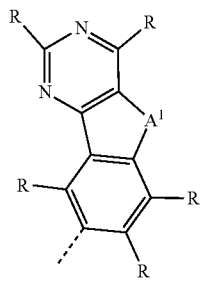

Ar-83 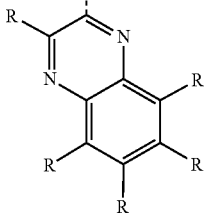

where R has the definitions given above, the dotted bond represents the bond to the nitrogen atom and, in addition:

Ar¹ is the same or different at each instance and is a bivalent aromatic or heteroaromatic ring system which has 6 to 18 aromatic ring atoms and may be substituted in each case by one or more R radicals;

A¹ is the same or different at each instance and is NR, O, S or C(R)₂;

n is 0 or 1, where n=0 means that no A¹ group is bonded at this position and R radicals are bonded to the corresponding carbon atoms instead;

m is 0 or 1, where m=0 means that the Ar⁴ group is absent and that the corresponding aromatic or heteroaromatic group is bonded directly to the nitrogen atom.

In a preferred embodiment of the invention, R is the same or different at each instance and is selected from the group consisting of H, D, F, N(Ar')₂, CN, OR¹, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more R¹ radicals, but is preferably unsubstituted, and where one or more nonadjacent CH₂ groups may be replaced by O, or an aromatic or heteroaromatic ring system which has 6 to 30 aromatic ring atoms and may be substituted in each case by one or more R¹ radicals; at the same time, two R radicals together may also form an aliphatic, aromatic or heteroaromatic ring system. More preferably, R is the same or different at each instance and is selected from the group consisting of H, N(Ar')₂, a straight-chain alkyl group having 1 to 6 carbon atoms, especially having 1, 2, 3 or 4 carbon atoms, or a branched or cyclic alkyl group having 3 to 6 carbon atoms, where the alkyl group in each case may be substituted by one or more R¹ radicals, but is preferably unsubstituted, or an aromatic or heteroaromatic ring system which has 6 to 24 aromatic ring atoms and may be substituted in each case by one or more R¹ radicals, preferably nonaromatic R¹ radicals. Most preferably, R is the same or different at each instance and is selected from the group consisting of H or an aromatic or heteroaromatic ring system which has 6 to 24 aromatic ring atoms and may be substituted in each case by one or more R¹ radicals, preferably nonaromatic R¹ radicals. It may additionally be preferable when R is a triaryl-or-heteroarylamine group which may be substituted by one or more R¹ radicals. This group is one embodiment of an aromatic or heteroaromatic ring system, in which case two or more aryl or heteroaryl groups are joined to one another by a nitrogen atom. When R is a triaryl-or-heteroarylamine group, this group preferably has 18 to 30 aromatic ring atoms and may be substituted by one or more R¹ radicals, preferably nonaromatic R¹ radicals.

In a further preferred embodiment of the invention, Ar' is an aromatic or heteroaromatic ring system which has 6 to 30 aromatic ring atoms and may be substituted by one or more $R^1$ radicals. In a particularly preferred embodiment of the invention, Ar' is an aromatic or heteroaromatic ring system which has 6 to 24 aromatic ring atoms, especially 6 to 13 aromatic ring atoms, and may be substituted by one or more, preferably nonaromatic, $R^1$ radicals.

Suitable aromatic or heteroaromatic ring systems R or Ar' are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more $R^1$ radicals. When R or Ar' is a heteroaryl group, especially triazine, pyrimidine, quinazoline or carbazole, preference may also be given to aromatic or heteroaromatic $R^1$ radicals on this heteroaryl group.

The R groups here, when they are an aromatic or heteroaromatic ring system, or Ar' are preferably selected from the groups of the following formulae R-1 to R-83:

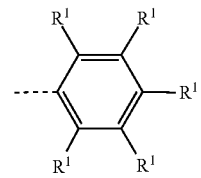
R-1

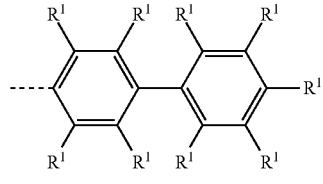
R-2

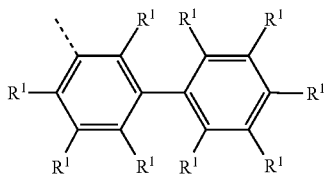
R-3

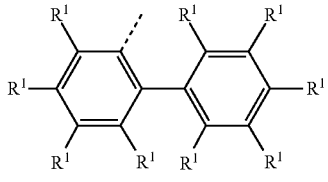
R-4

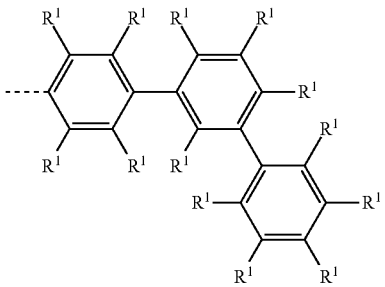
R-5

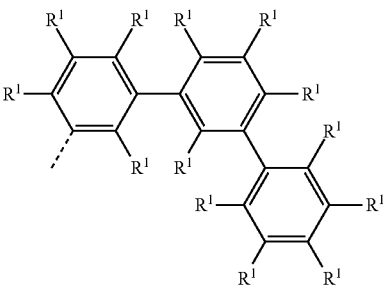
R-6

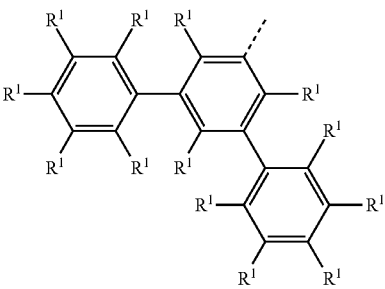
R-7

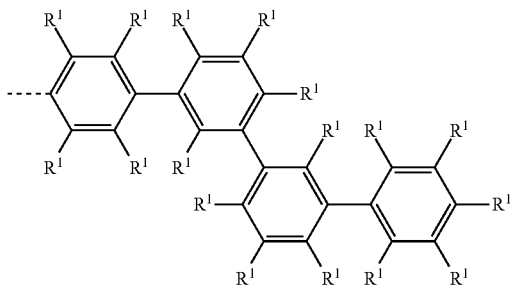
R-8

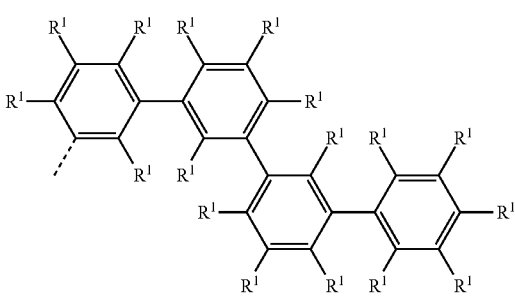
R-9

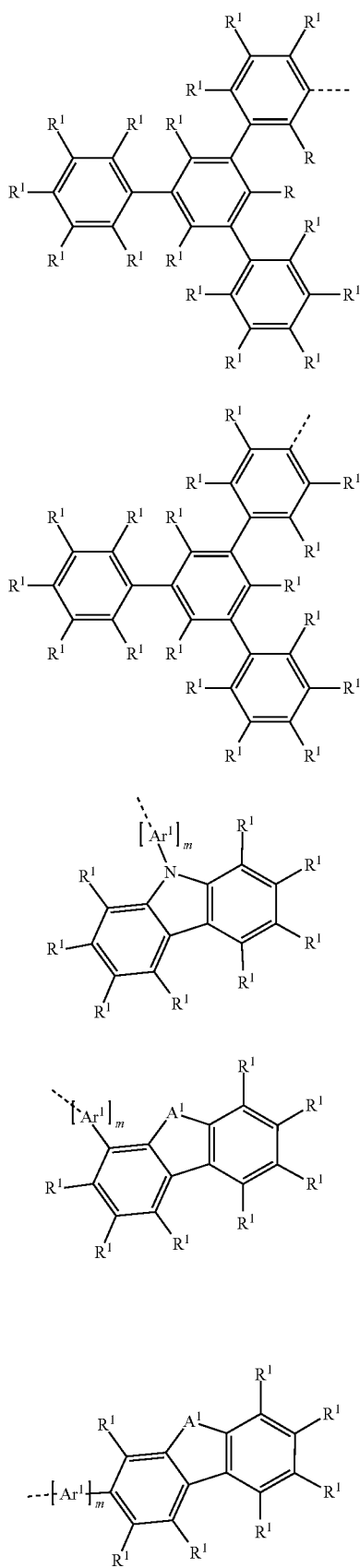
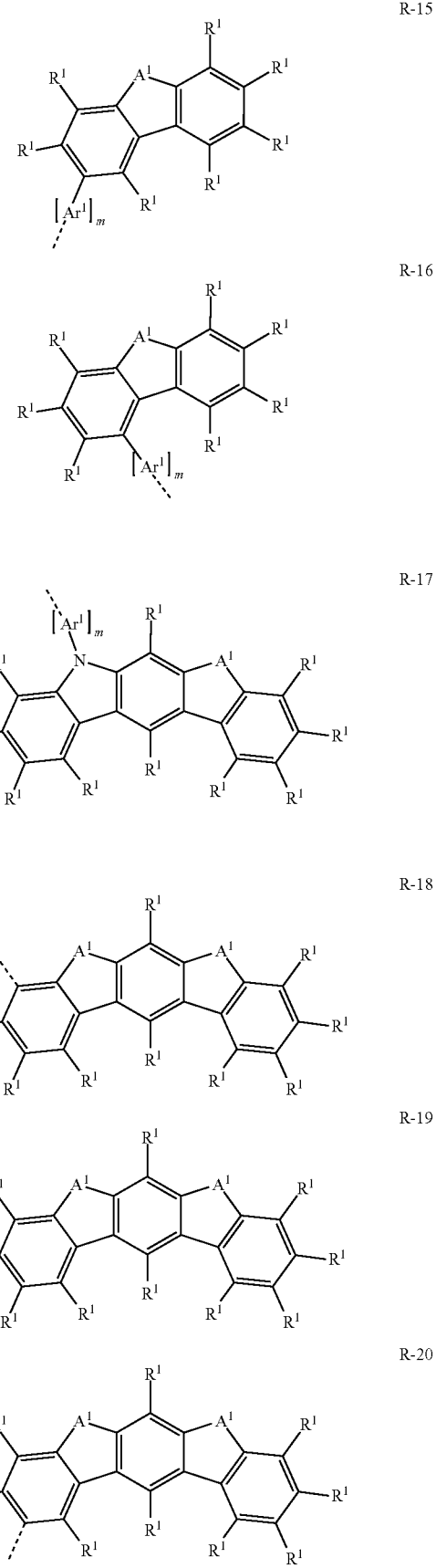

-continued
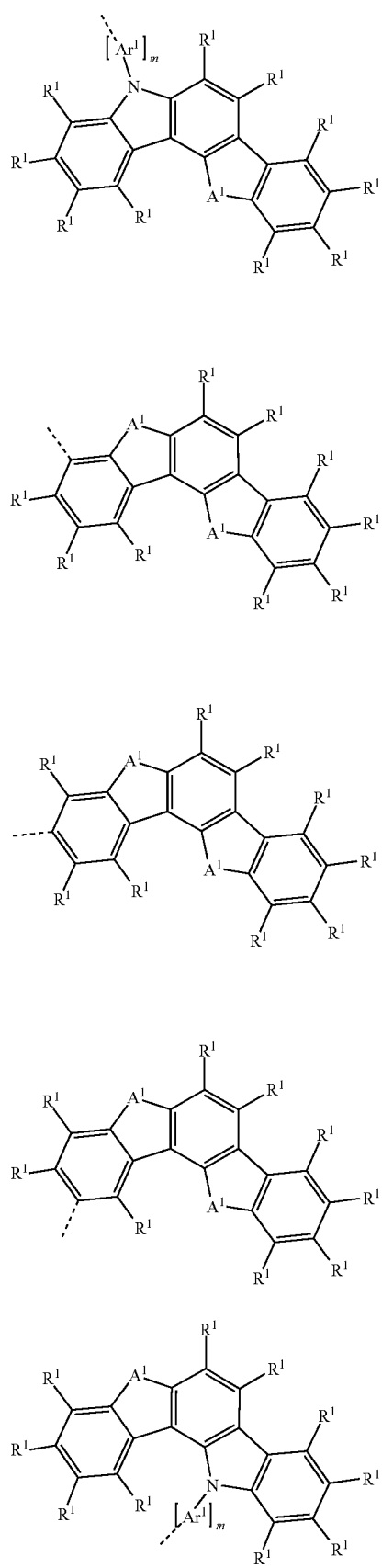
R-21
R-22
R-23
R-24
R-25
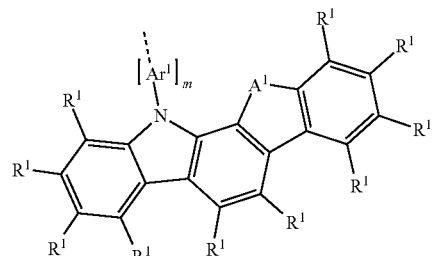
R-26
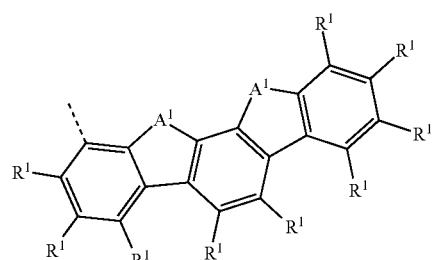
R-27
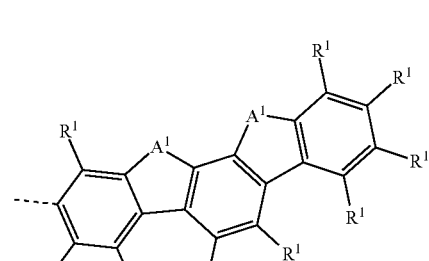
R-28
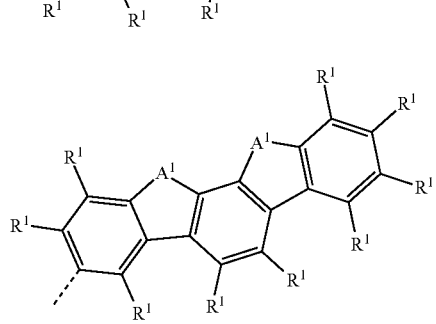
R-29
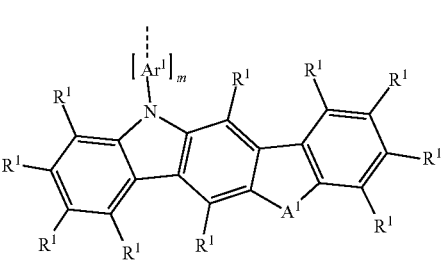
R-30
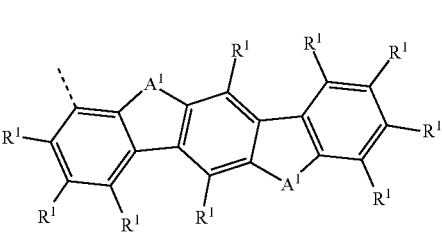
R-31

R-32 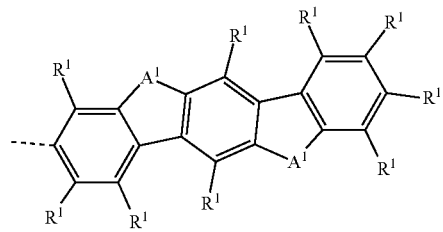
R-33 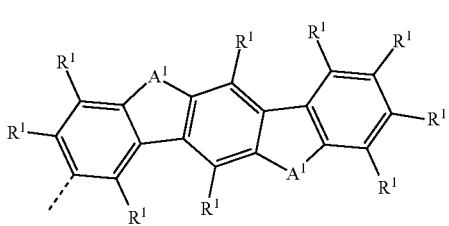
R-34 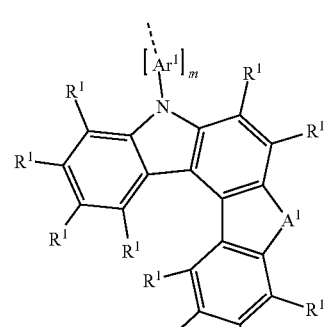
R-35 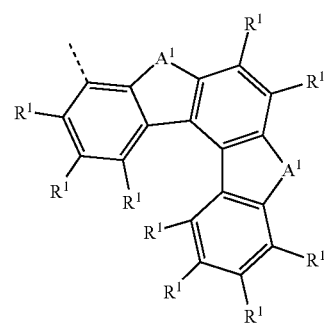
R-36 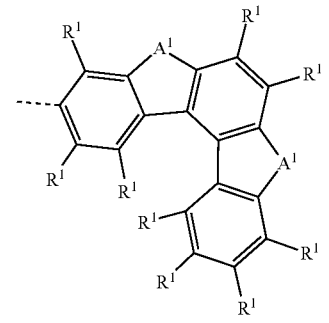
R-37 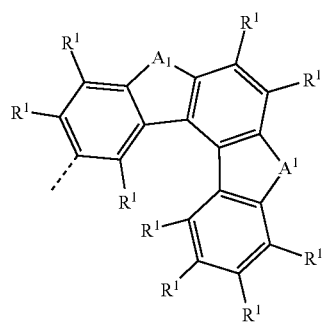
R-38 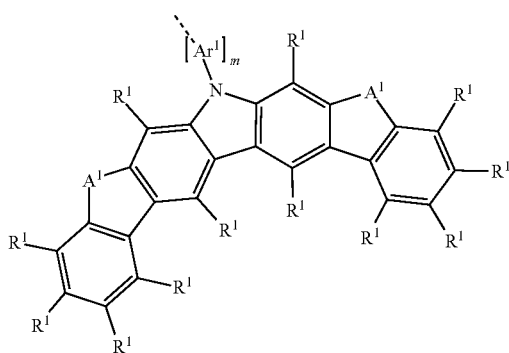
R-39 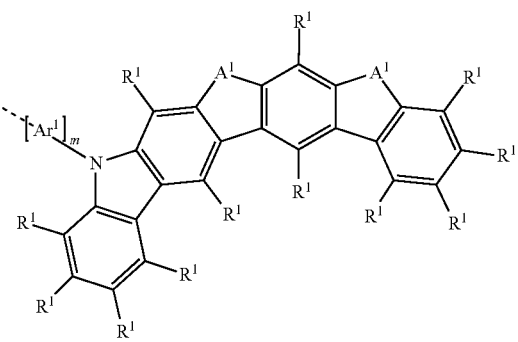
R-40 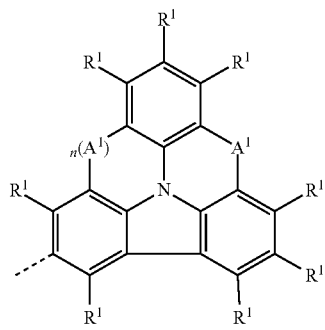

R-41
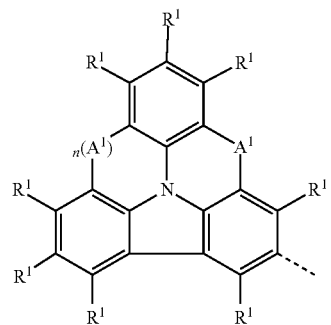
R-42
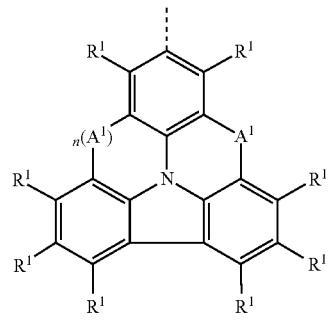
R-43
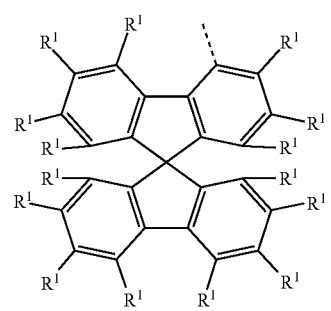
R-44
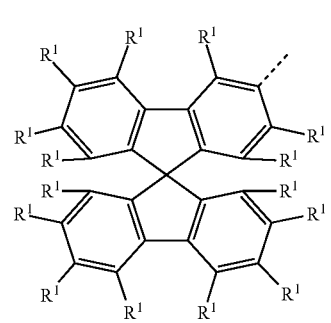
R-45
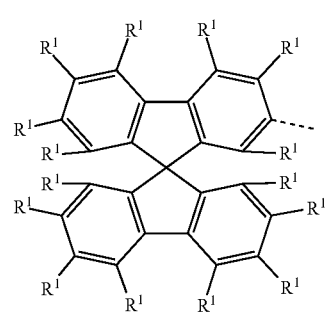
R-46
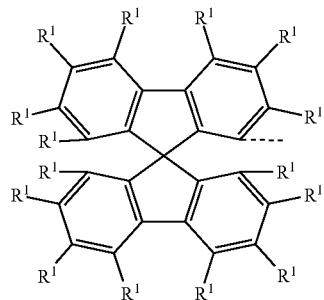
R-47
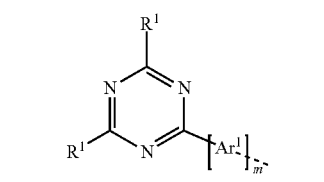
R-48
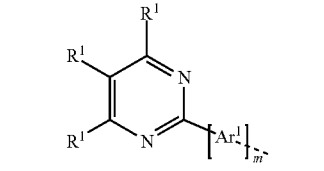
R-49
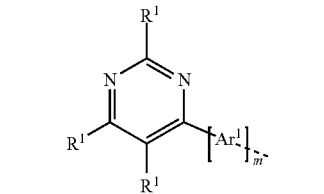
R-50
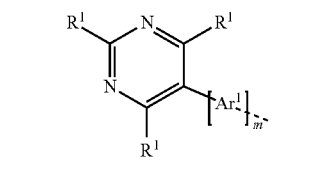
R-51
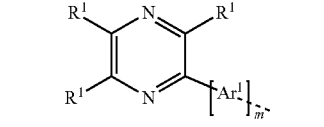
R-52
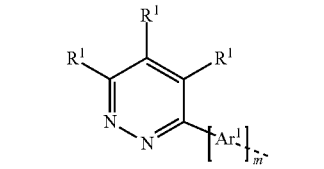
R-53
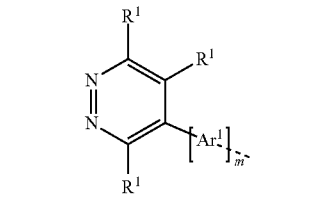

-continued
R-54
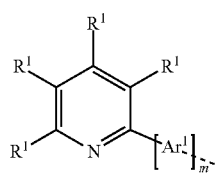
R-55
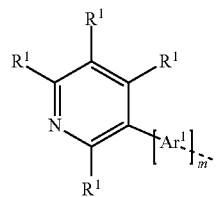
R-56
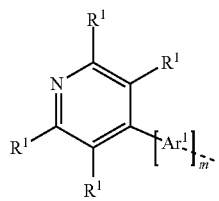
R-57
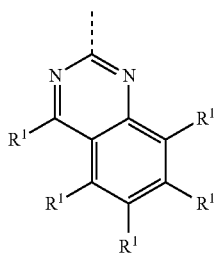
R-58
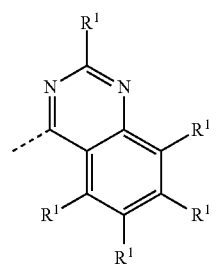
R-59
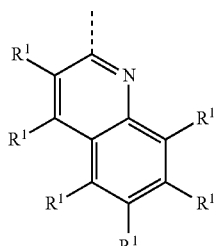
R-60
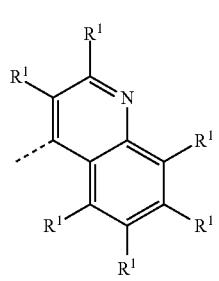
-continued
R-61
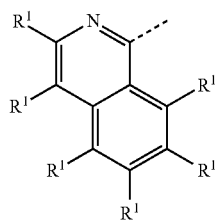
R-62
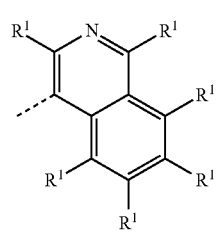
R-63
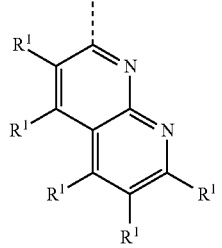
R-64
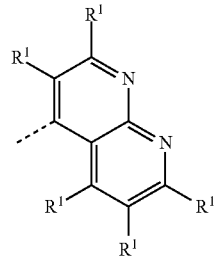
R-65
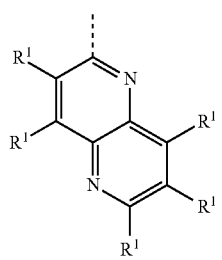
R-66
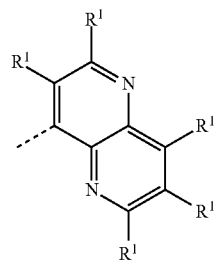

-continued
R-67
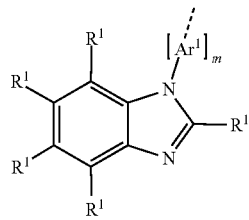
R-68
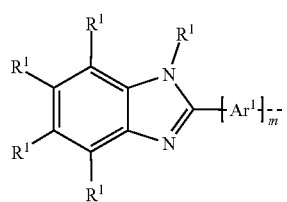
R-69
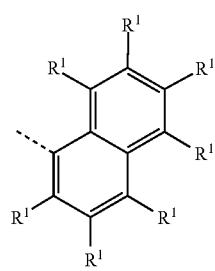
R-70
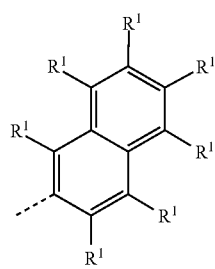
R-71
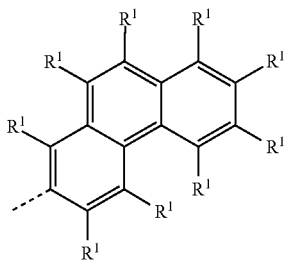
R-72
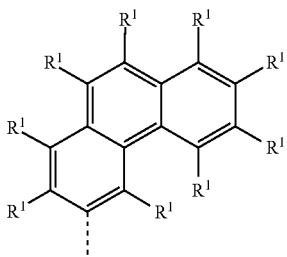
-continued
R-73
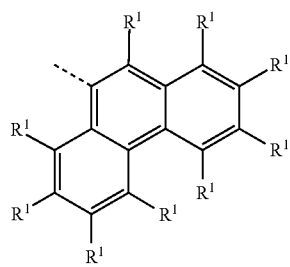
R-74
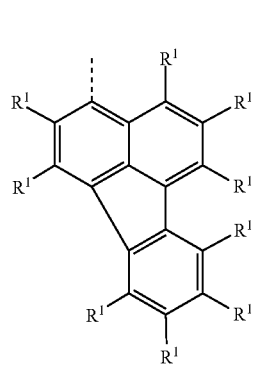
R-75
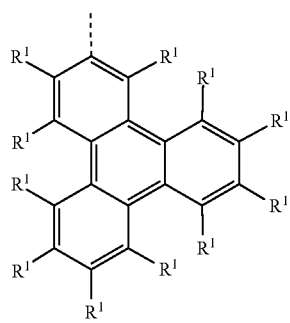
R-76
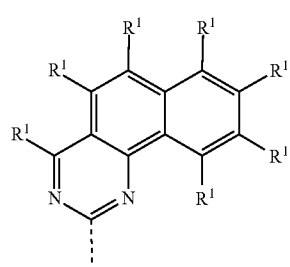
R-77
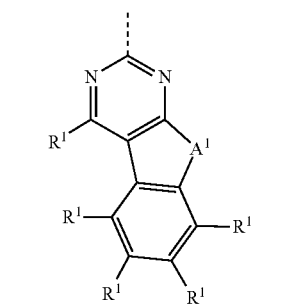

R-78
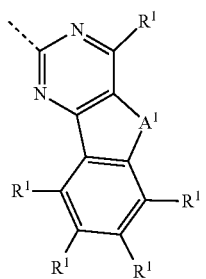

R-79
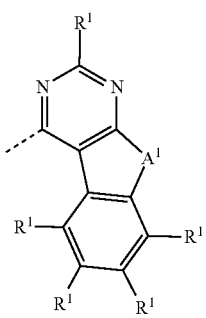

R-80
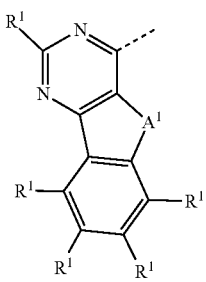

R-81
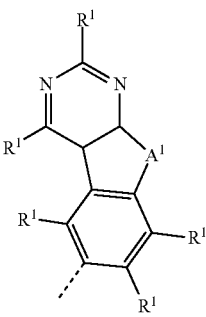

R-82
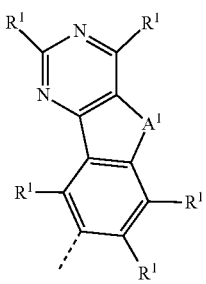

R-83
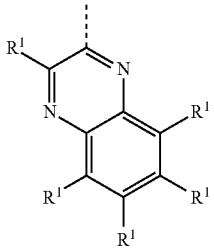

where $R^1$ has the definitions given above, the dotted bond represents the bond to a carbon atom of the base skeleton in formulae (1), (2) and (3) or in the preferred embodiments, or to the nitrogen atom in the $N(Ar')_2$ group and, in addition:

$Ar^1$ is the same or different at each instance and is a bivalent aromatic or heteroaromatic ring system which has 6 to 18 aromatic ring atoms and may be substituted in each case by one or more $R^1$ radicals;

$A^1$ is the same or different at each instance and is $C(R^1)_2$, $NR^1$, O or S;

n is 0 or 1, where n=0 means that no $A^1$ group is bonded at this position and $R^1$ radicals are bonded to the corresponding carbon atoms instead;

m is 0 or 1, where m=0 means that the $Ar^4$ group is absent and that the corresponding aromatic or heteroaromatic group is bonded directly to a carbon atom of the base skeleton in formula (1) or in the preferred embodiments, or to the nitrogen atom in the $N(Ar')_2$ group; with the proviso that m=1 for the structures (R-12), (R-17), (R-21), (R-25), (R-26), (R-30), (R-34), (R-38) and (R-39) when these groups are embodiments of Ar'.

When the abovementioned Ar-1 to Ar-83 groups for Ar and R-1 to R-83 groups for R or Ar' have two or more $A^1$ groups, possible options for these include all combinations from the definition of $A^1$. Preferred embodiments in that case are those in which one $A^1$ group is NR or $NR^1$ and the other $A^1$ group is $C(R)_2$ or $C(R^1)_2$ or in which both $A^1$ groups are NR or $NR^1$ or in which both $A^1$ groups are O. In a particularly preferred embodiment of the invention, in Ar, R or Ar' groups having two or more $A^1$ groups, at least one $A^1$ group is $C(R)_2$ or $C(R^1)_2$ or is NR or $NR^1$.

When $A^1$ is NR or $NR^1$, the substituent R or $R^1$ bonded to the nitrogen atom is preferably an aromatic or heteroaromatic ring system which has 5 to 24 aromatic ring atoms and may also be substituted by one or more $R^1$ or $R^2$ radicals. In a particularly preferred embodiment, this R or $R^1$ substituent is the same or different at each instance and is an aromatic or heteroaromatic ring system which has 6 to 24 aromatic ring atoms, preferably 6 to 12 aromatic ring atoms, and which does not have any fused aryl groups or heteroaryl groups in which two or more aromatic or heteroaromatic 6-membered ring groups are fused directly to one another, and which may also be substituted in each case by one or more $R^1$ or $R^2$ radicals. Particular preference is given to phenyl, biphenyl, terphenyl and quaterphenyl having bonding patterns as listed above for Ar-1 to Ar-11 or R-1 to R-11, where these structures may be substituted by one or more $R^1$ or $R^2$ radicals, but are preferably unsubstituted.

When $A^1$ is $C(R)_2$ or $C(R^1)_2$, the substituents R or $R^1$ bonded to this carbon atom are preferably the same or different at each instance and are a linear alkyl group having 1 to 10 carbon atoms or a branched or cyclic alkyl group having 3 to 10 carbon atoms or an aromatic or heteroaromatic ring system which has 5 to 24 aromatic ring atoms and may also be substituted by one or more $R^1$ or $R^2$ radicals. Most preferably, R or $R^1$ is a methyl group or a phenyl group. In this case, the R or $R^1$ radicals together may also form a ring system, which leads to a spiro system.

In one embodiment of the invention, at least one R radical is an electron-rich heteroaromatic ring system. This electron-rich heteroaromatic ring system is preferably selected from the above-depicted R-13 to R-42 groups, where, in the R-13 to R-16, R-18 to R-20, R-22 to R-24, R-27 to R-29, R-31 to R-33 and R-35 to R-37 groups, at least one $A^1$ group is $NR^1$ where $R^1$ is preferably an aromatic or heteroaromatic ring system, especially an aromatic ring system. Particular preference is given to the R-15 group with m=0 and $A^1=NR^1$.

In a further embodiment of the invention, at least one R radical is an electron-deficient heteroaromatic ring system. This electron-deficient heteroaromatic ring system is preferably selected from the above-depicted R-47 to R-50, R-57, R-58 and R-76 to R-83 groups.

In a further embodiment of the invention, Ar is an electron-deficient heteroaromatic ring system. This electron-deficient heteroaromatic ring system is preferably selected from the above-depicted Ar-47 to Ar-50, Ar-57, Ar-58 and Ar-76 to Ar-83 groups.

In a further preferred embodiment of the invention, $R^1$ is the same or different at each instance and is selected from the group consisting of H, D, F, CN, $OR^2$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may in each case be substituted by one or more $R^2$ radicals, and where one or more nonadjacent $CH_2$ groups may be replaced by O, or an aromatic or heteroaromatic ring system which has 6 to 30 aromatic ring atoms and may be substituted in each case by one or more $R^2$ radicals; at the same time, two or more $R^1$ radicals together may form an aliphatic ring system. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^2$ radicals, but is preferably unsubstituted, or an aromatic or heteroaromatic ring system which has 6 to 24 aromatic ring atoms and may be substituted in each case by one or more $R^2$ radicals, but is preferably unsubstituted.

In a further preferred embodiment of the invention, $R^2$ is the same or different at each instance and is H, F, an alkyl group having 1 to 4 carbon atoms or an aryl group having 6 to 10 carbon atoms, which may be substituted by an alkyl group having 1 to 4 carbon atoms, but is preferably unsubstituted.

Further suitable Ar, R or Ar' groups are groups of the formula $-Ar^4-N(Ar^2)(Ar^3)$ where $Ar^2$, $Ar^3$ and $Ar^4$ are the same or different at each instance and are an aromatic or heteroaromatic ring system which has 5 to 24 aromatic ring atoms and may be substituted in each case by one or more R or $R^1$ radicals. Ar results in such a group when the Ar group is substituted by an $N(Ar')_2$ group. The total number of aromatic ring atoms in $Ar^2$, $Ar^3$ and $Ar^4$ here is not more than 60 and preferably not more than 40.

In this case, $Ar^4$ and $Ar^2$ may also be bonded to one another and/or $Ar^2$ and $Ar^3$ to one another via a group selected from $C(R^1)_2$, $NR^1$, O or S. Preferably, $Ar^4$ and $Ar^2$ are joined to one another and $Ar^2$ and $Ar^3$ to one another in the respective ortho position to the bond to the nitrogen atom. In a further embodiment of the invention, none of the $Ar^2$, $Ar^3$ and $Ar^4$ groups are bonded to one another.

Preferably, $Ar^4$ is an aromatic or heteroaromatic ring system which has 6 to 24 aromatic ring atoms, especially 6 to 12 aromatic ring atoms, and may be substituted in each case by one or more $R^1$ radicals. More preferably, $Ar^4$ is selected from the group consisting of ortho-, meta- or para-phenylene or ortho-, meta- or para-biphenyl, each of which may be substituted by one or more $R^1$ radicals, but are preferably unsubstituted. Most preferably, $Ar^4$ is an unsubstituted phenylene group. This is especially true when $Ar^4$ is bonded to $Ar^2$ via a single bond.

Preferably, $Ar^2$ and $Ar^3$ are the same or different at each instance and are an aromatic or heteroaromatic ring system which has 6 to 24 aromatic ring atoms and may be substituted in each case by one or more $R^1$ radicals. Particularly preferred $Ar^2$ and $Ar^3$ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene, triphenylene or combinations of two, three or four of these groups, each of which may be substituted by one or more $R^1$ radicals. More preferably, $Ar^2$ and $Ar^3$ are the same or different at each instance and are an aromatic ring system which has 6 to 24 aromatic ring atoms and may be substituted by one or more $R^1$ radicals, especially selected from the groups consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene.

At the same time, the alkyl groups in compounds of the invention which are processed by vacuum evaporation preferably have not more than five carbon atoms, more preferably not more than 4 carbon atoms, most preferably not more than 1 carbon atom. For compounds that are processed from solution, suitable compounds are also those substituted by alkyl groups, especially branched alkyl groups, having up to 10 carbon atoms or those substituted by oligoarylene groups, for example ortho-, meta- or para-terphenyl or branched terphenyl or quaterphenyl groups.

When the compounds of the formula (1) or the preferred embodiments are used as matrix material for a phosphorescent emitter or in a layer directly adjoining a phosphorescent layer, it is further preferable when the compound does not contain any fused aryl or heteroaryl groups in which more than two six-membered rings are fused directly to one another. It is especially preferable that the Ar, R, Ar', $R^1$ and $R^2$ radicals do not contain any fused aryl or heteroaryl groups in which two or more six-membered rings are fused directly to one another. An exception to this is formed by phenanthrene, triphenylene and quinazoline, which, because of their high triplet energy, may be preferable in spite of the presence of fused aromatic six-membered rings.

The abovementioned preferred embodiments may be combined with one another as desired within the restrictions defined in claim 1. In a particularly preferred embodiment of the invention, the abovementioned preferences occur simultaneously.
Examples of suitable compounds according to the above-detailed embodiments are the compounds detailed in the following table:
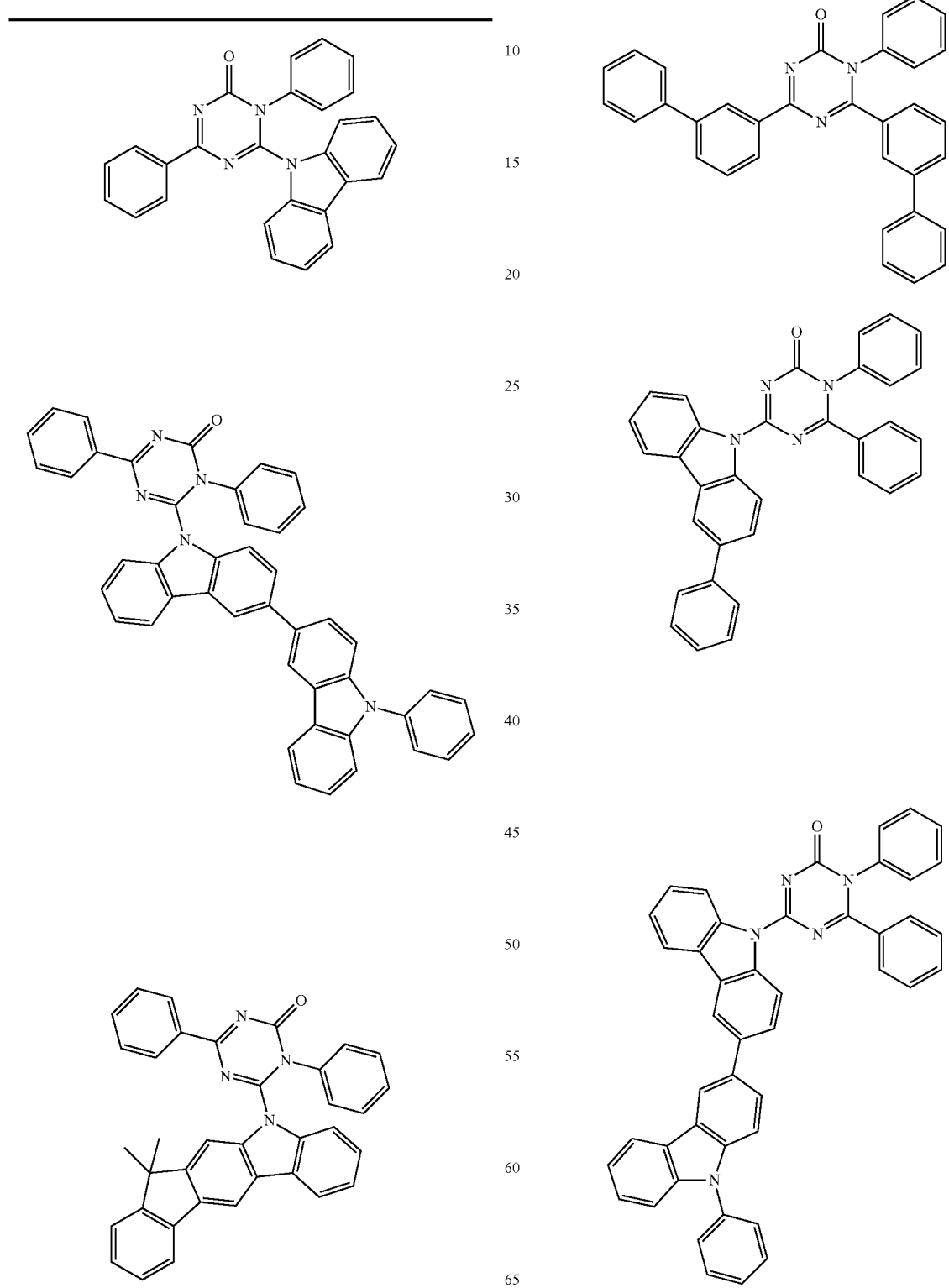

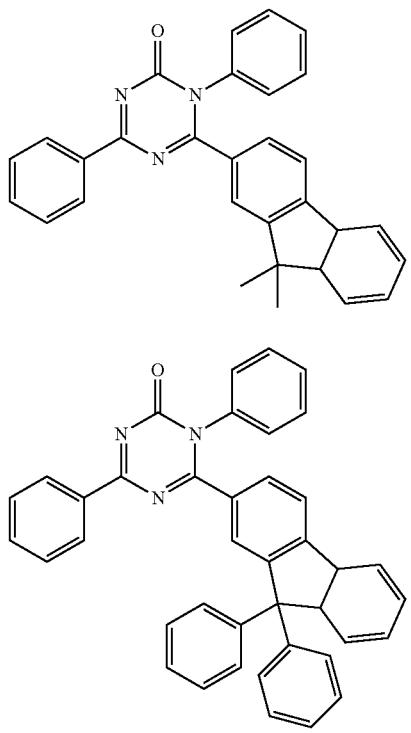
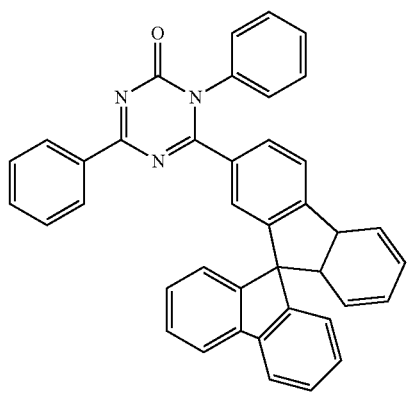 [SMILES: O=c1nc(-c2ccccc2)nc(-c2ccc3c(c2)C2(c4ccccc4-c4ccccc42)C2C=CC=CC32)n1-c1ccccc1]
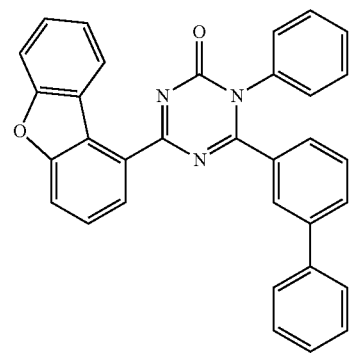 [SMILES: O=c1nc(-c2cccc3oc4ccccc4c23)nc(-c2cccc(-c3ccccc3)c2)n1-c1ccccc1]
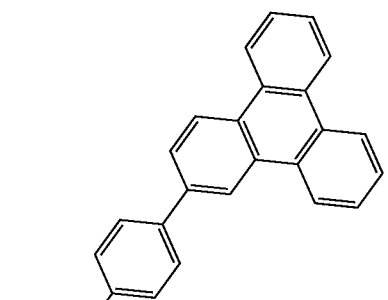
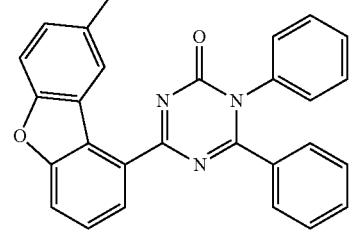
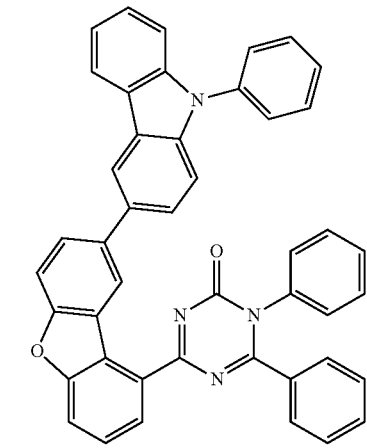 [SMILES: O=c1nc(-c2cccc3oc4ccc(-c5ccc6c(c5)c5ccccc5n6-c5ccccc5)cc4c23)nc(-c2ccccc2)n1-c1ccccc1]
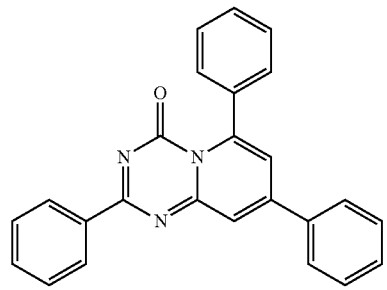 [SMILES: O=c1nc(-c2ccccc2)nc2cc(-c3ccccc3)cc(-c3ccccc3)n12]

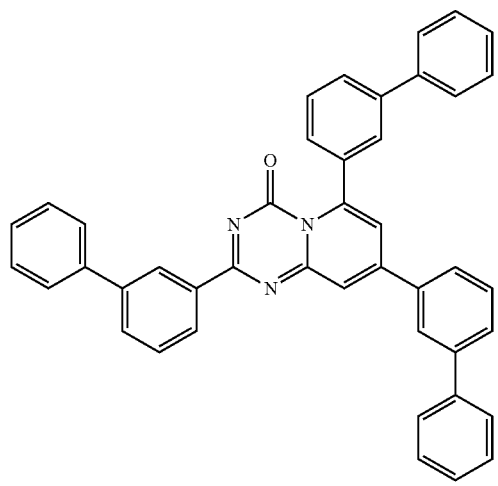 [SMILES: O=c1nc(-c2cccc(-c3ccccc3)c2)nc2cc(-c3cccc(-c4ccccc4)c3)cc(-c3cccc(-c4ccccc4)c3)n12]
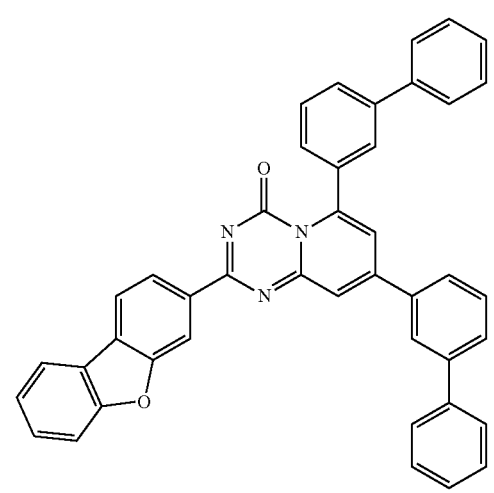 [SMILES: O=c1nc(-c2ccc3c(c2)oc2ccccc23)nc2cc(-c3cccc(-c4ccccc4)c3)cc(-c3cccc(-c4ccccc4)c3)n12]
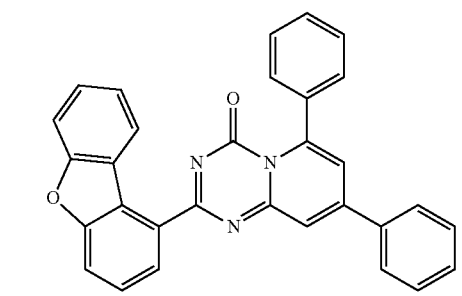 [SMILES: O=c1nc(-c2cccc3oc4ccccc4c23)nc2cc(-c3ccccc3)cc(-c3ccccc3)n12]
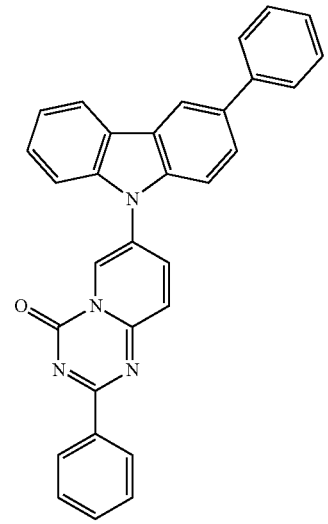 [SMILES: O=c1nc(-c2ccccc2)nc2ccc(-n3c4ccccc4c4cc(-c5ccccc5)ccc43)cn12]
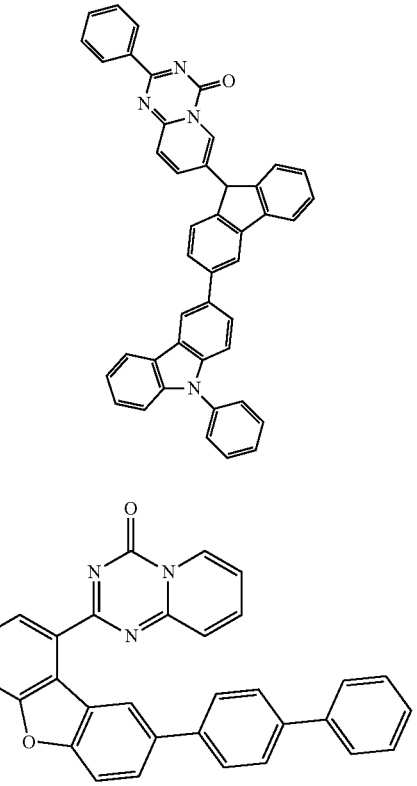
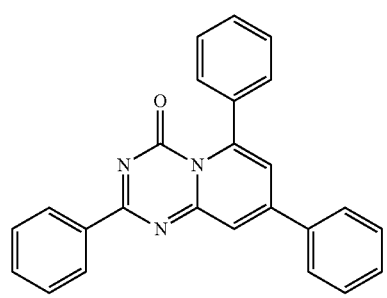 [SMILES: O=c1nc(-c2ccccc2)nc2cc(-c3ccccc3)cc(-c3ccccc3)n12]

| 61 -continued | 62 -continued |
|---|---|
| 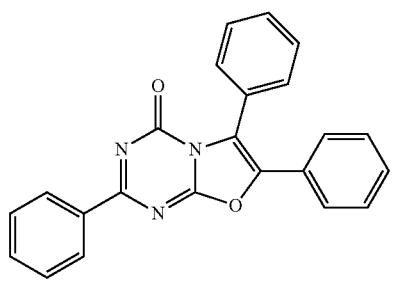 [SMILES: O=c1nc(-c2ccccc2)nc2oc(-c3ccccc3)c(-c3ccccc3)n12] | 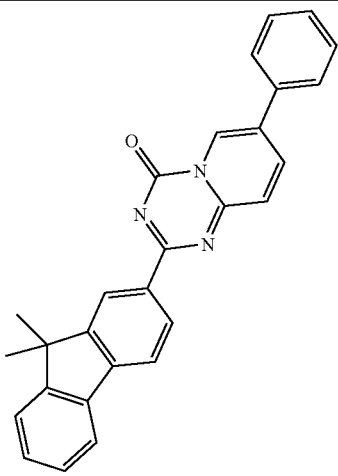 |
| 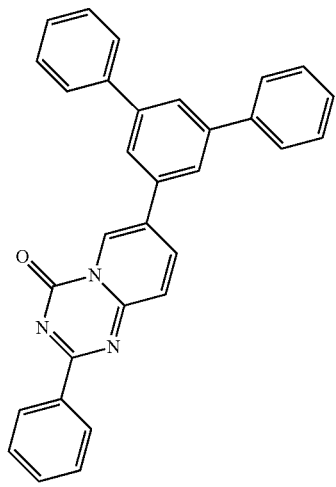 [SMILES: O=c1nc(-c2ccccc2)nc2ccc(-c3cc(-c4ccccc4)cc(-c4ccccc4)c3)cn12] | 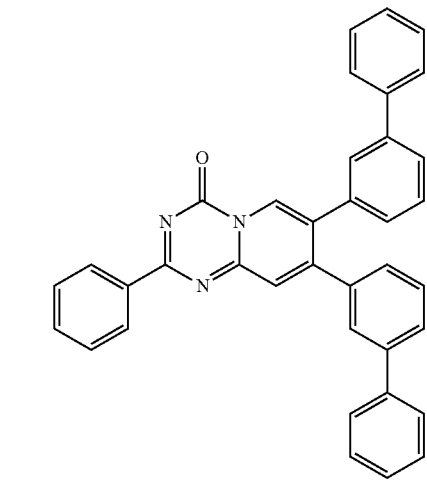 |
| 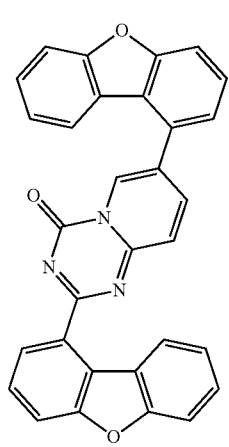 [SMILES: O=c1nc(-c2cccc3oc4ccccc4c23)nc2ccc(-c3cccc4oc5ccccc5c34)cn12] | 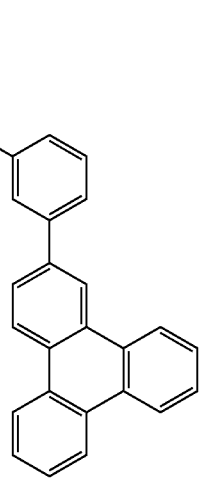 |

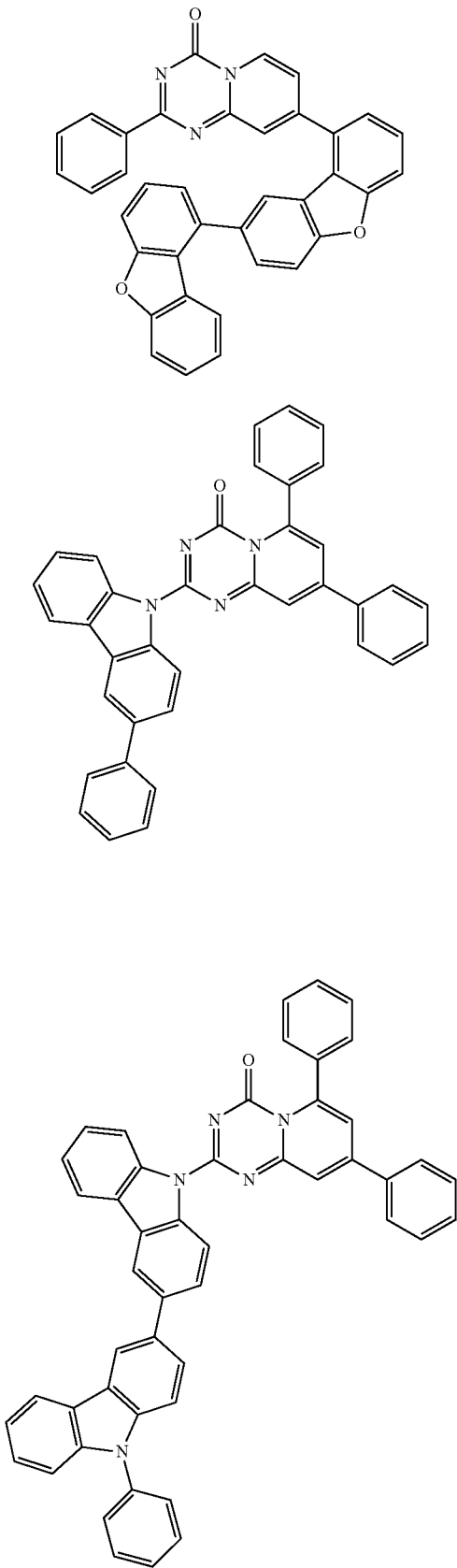
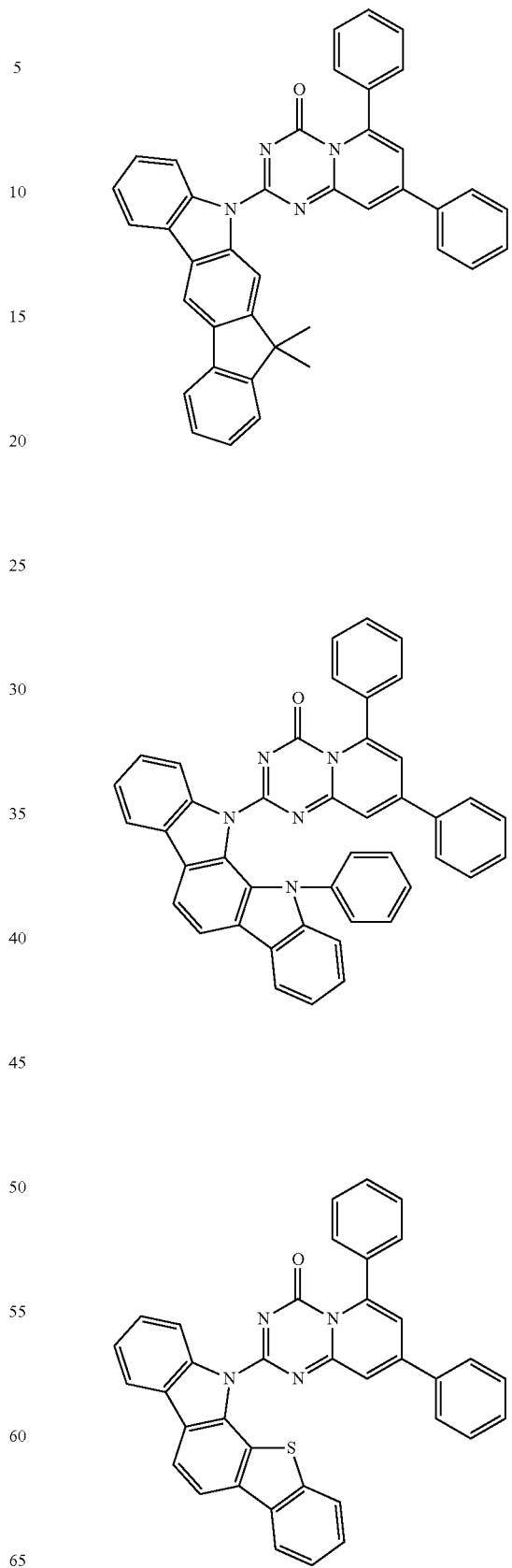

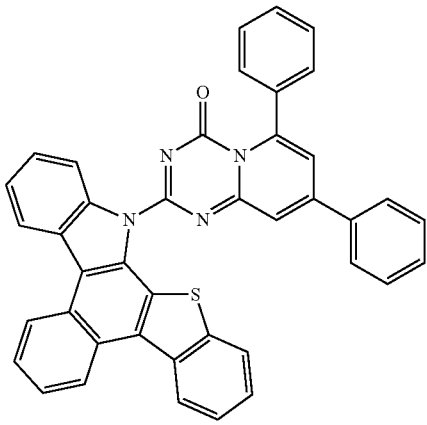 [SMILES: O=c1nc(-n2c3ccccc3c3c4ccccc4c4c5ccccc5sc4c32)nc2cc(-c3ccccc3)cc(-c3ccccc3)n12]
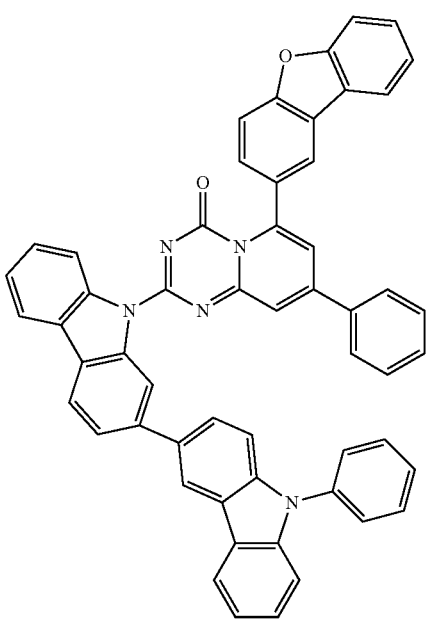 [SMILES: O=c1nc(-n2c3ccccc3c3ccc(-c4ccc5c(c4)c4ccccc4n5-c4ccccc4)cc32)nc2cc(-c3ccccc3)cc(-c3ccc4oc5ccccc5c4c3)n12]
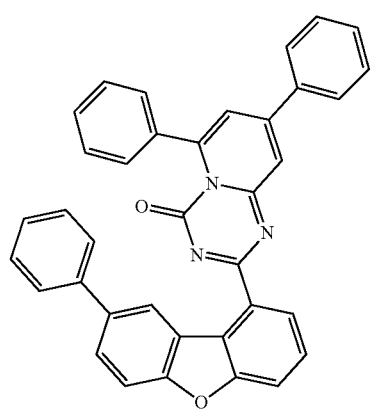 [SMILES: O=c1nc(-c2cccc3oc4ccc(-c5ccccc5)cc4c23)nc2cc(-c3ccccc3)cc(-c3ccccc3)n12]
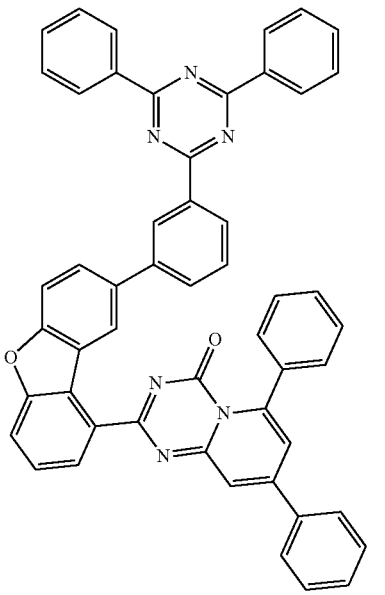 [SMILES: O=c1nc(-c2cccc3oc4ccc(-c5cccc(-c6nc(-c7ccccc7)nc(-c7ccccc7)n6)c5)cc4c23)nc2cc(-c3ccccc3)cc(-c3ccccc3)n12]
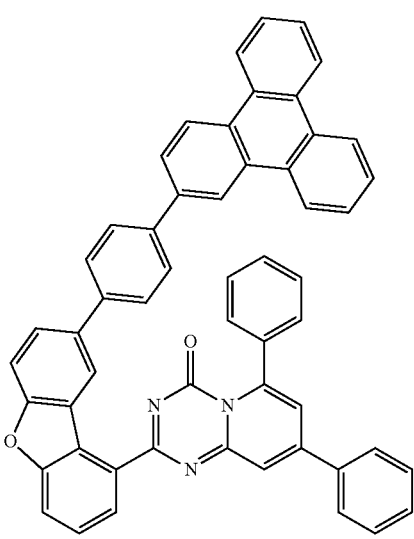 [SMILES: O=c1nc(-c2cccc3oc4ccc(-c5ccc(-c6ccc7c8ccccc8c8ccccc8c7c6)cc5)cc4c23)nc2cc(-c3ccccc3)cc(-c3ccccc3)n12]
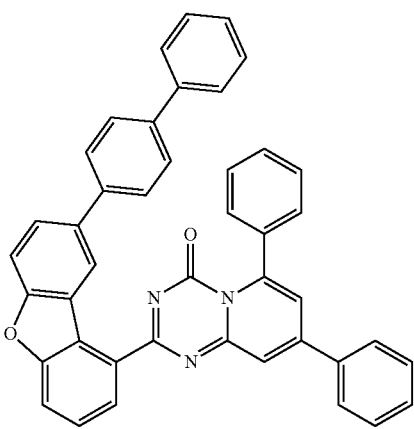 [SMILES: O=c1nc(-c2cccc3oc4ccc(-c5ccc(-c6ccccc6)cc5)cc4c23)nc2cc(-c3ccccc3)cc(-c3ccccc3)n12]

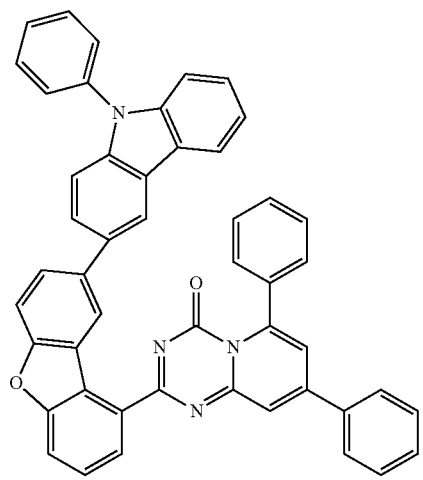 [SMILES: O=c1nc(-c2cccc3oc4ccc(-c5ccc6c(c5)c5ccccc5n6-c5ccccc5)cc4c23)nc2cc(-c3ccccc3)cc(-c3ccccc3)n12]
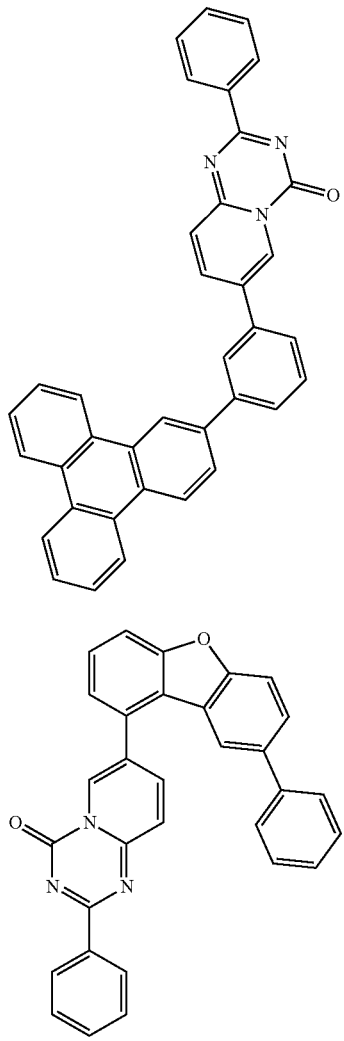
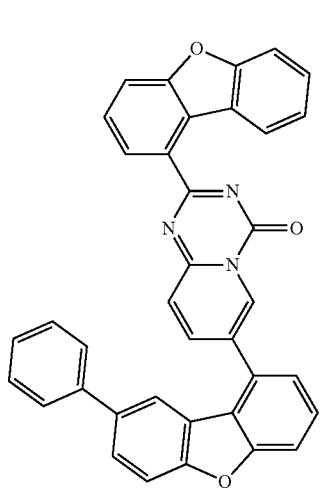 [SMILES: O=c1nc(-c2cccc3oc4ccccc4c23)nc2ccc(-c3cccc4oc5ccc(-c6ccccc6)cc5c34)cn12]

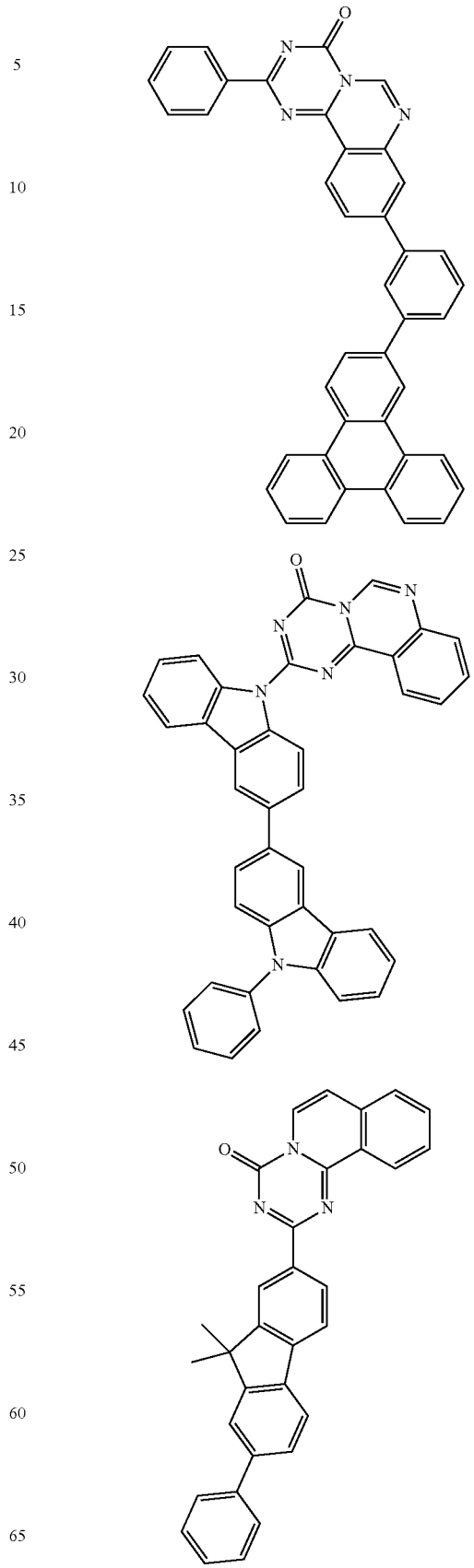

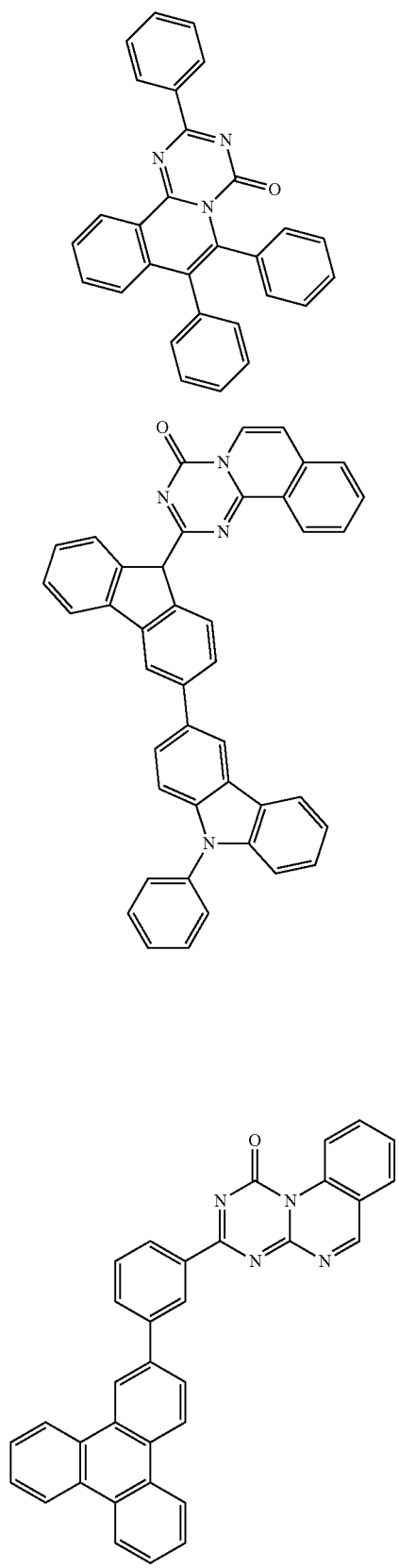
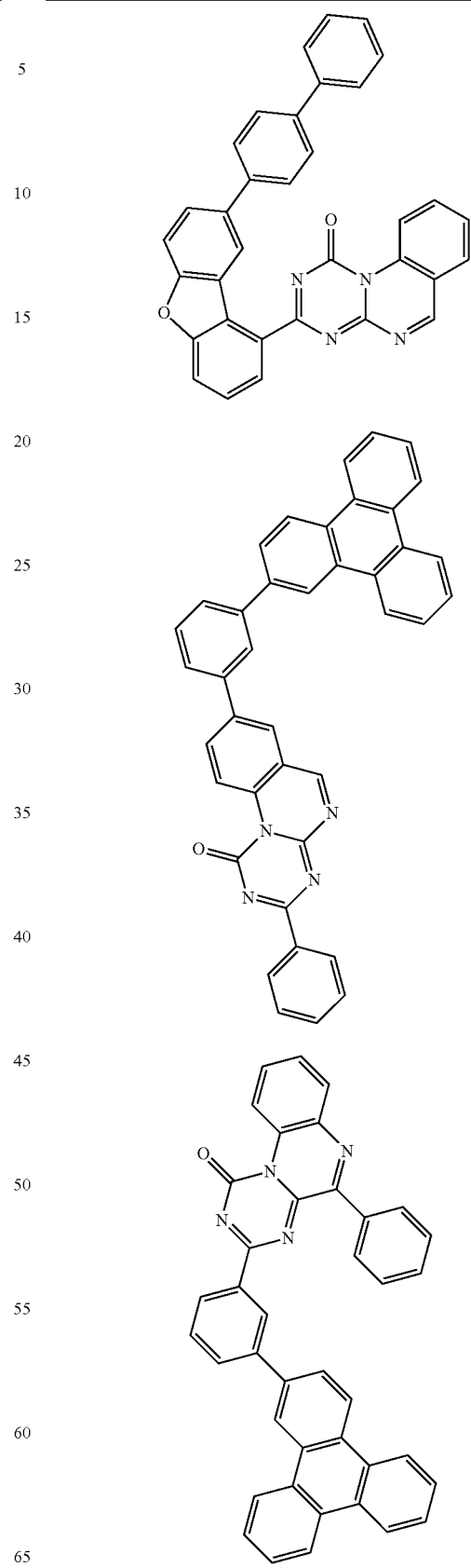

-continued
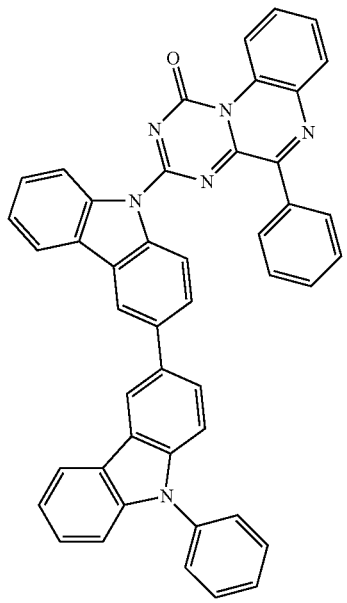 [SMILES: O=c1nc(-n2c3ccccc3c3cc(-c4ccc5c(c4)c4ccccc4n5-c4ccccc4)ccc32)nc2c(-c3ccccc3)nc3ccccc3n12]
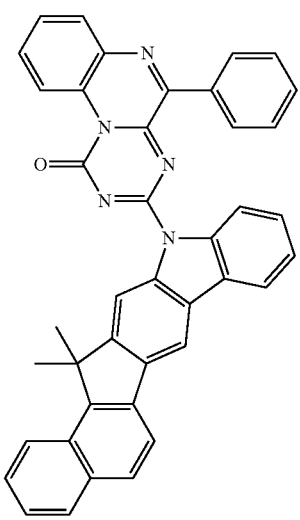 [SMILES: CC1(C)c2cc3c(cc2-c2ccc4ccccc4c21)c1ccccc1n3-c1nc(=O)n2c(n1)c(-c1ccccc1)nc1ccccc12]
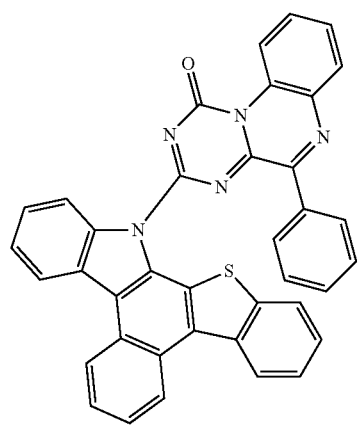 [SMILES: O=c1nc(-n2c3ccccc3c3c4ccccc4c4c5ccccc5sc4c32)nc2c(-c3ccccc3)nc3ccccc3n12]
-continued
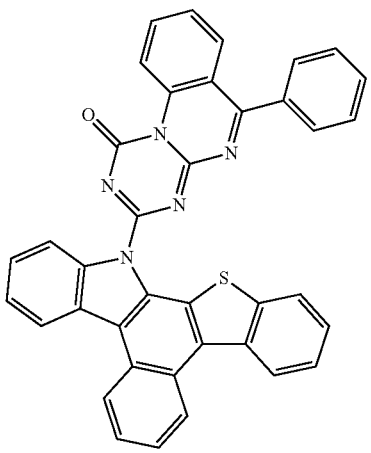 [SMILES: O=c1nc(-n2c3ccccc3c3c4ccccc4c4c5ccccc5sc4c32)nc2nc(-c3ccccc3)c3ccccc3n12]
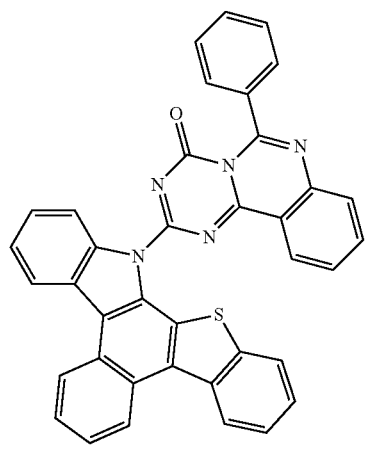 [SMILES: O=c1nc(-n2c3ccccc3c3c4ccccc4c4c5ccccc5sc4c32)nc2c3ccccc3nc(-c3ccccc3)n12]
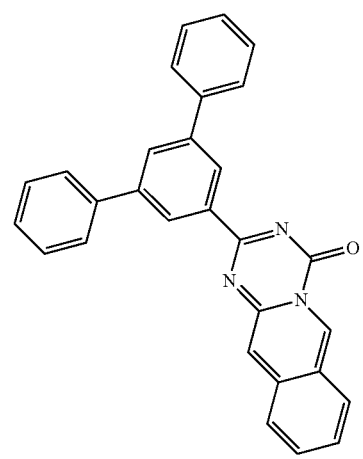 [SMILES: O=c1nc(-c2cc(-c3ccccc3)cc(-c3ccccc3)c2)nc2cc3ccccc3cn12]

-continued
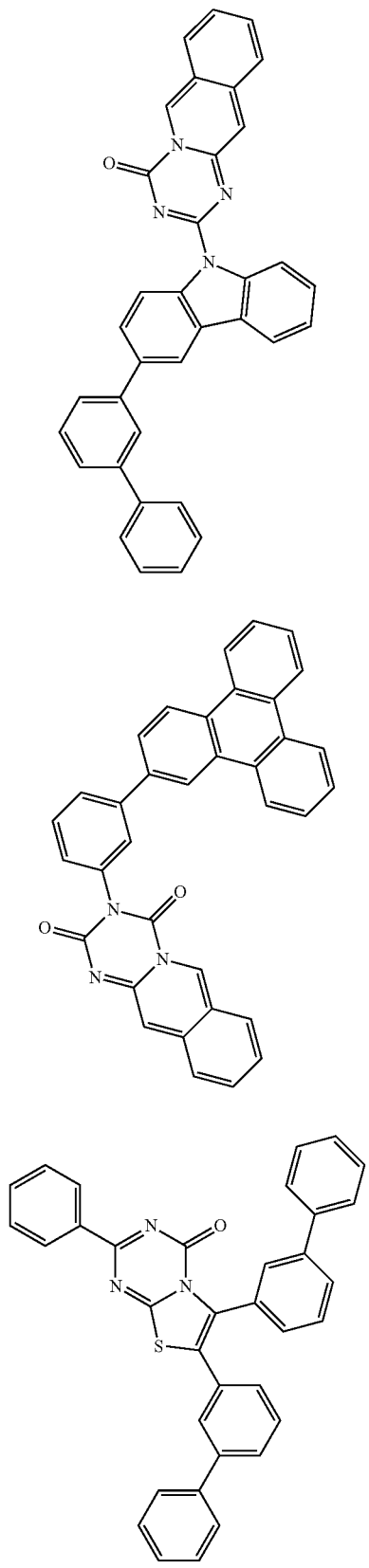
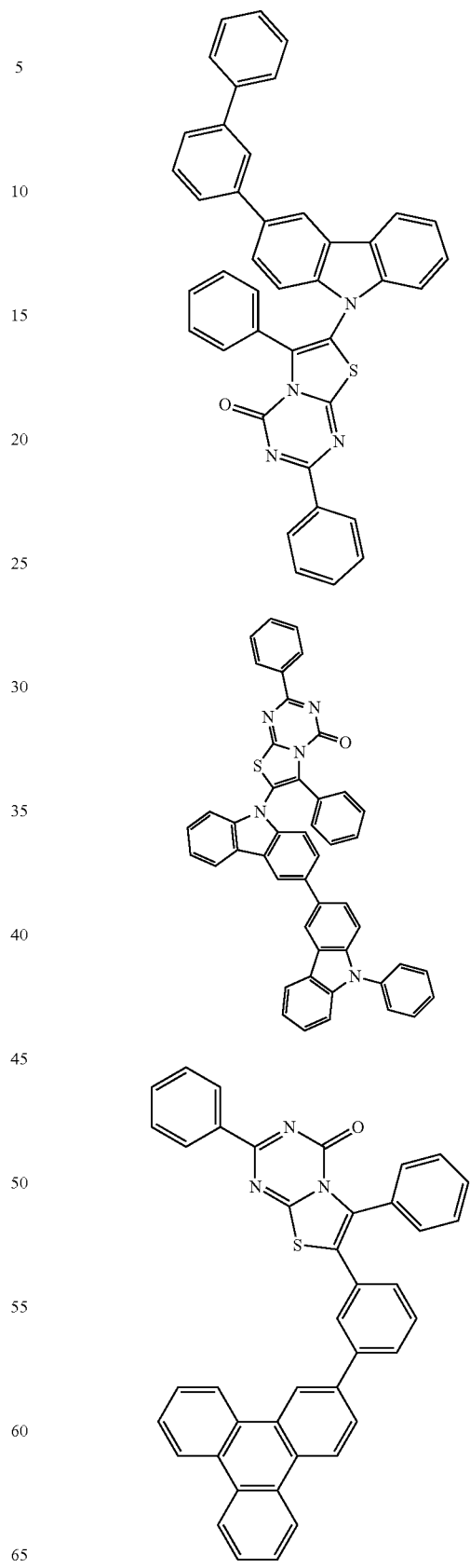

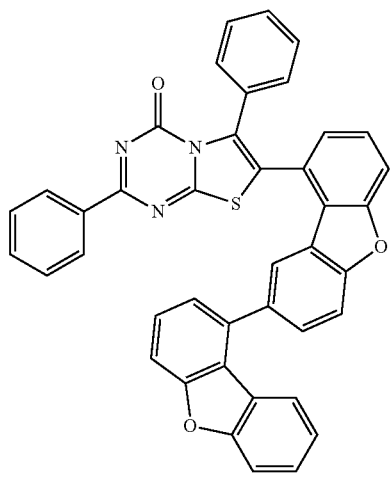 [SMILES: O=c1nc(-c2ccccc2)nc2sc(-c3cccc4oc5ccc(-c6cccc7oc8ccccc8c67)cc5c34)c(-c3ccccc3)n12]
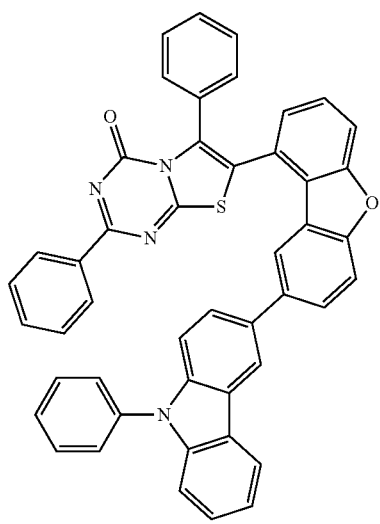 [SMILES: O=c1nc(-c2ccccc2)nc2sc(-c3cccc4oc5ccc(-c6ccc7c(c6)c6ccccc6n7-c6ccccc6)cc5c34)c(-c3ccccc3)n12]
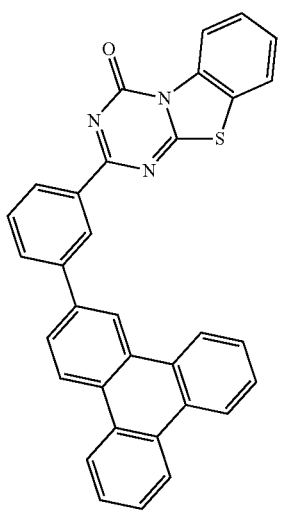 [SMILES: O=c1nc(-c2cccc(-c3ccc4c5ccccc5c5ccccc5c4c3)c2)nc2sc3ccccc3n12]
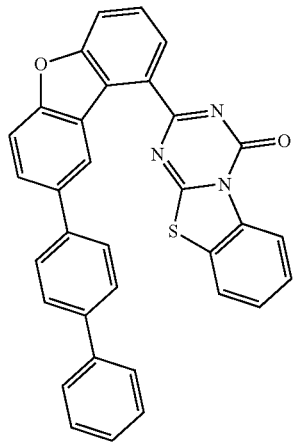 [SMILES: O=c1nc(-c2cccc3oc4ccc(-c5ccc(-c6ccccc6)cc5)cc4c23)nc2sc3ccccc3n12]
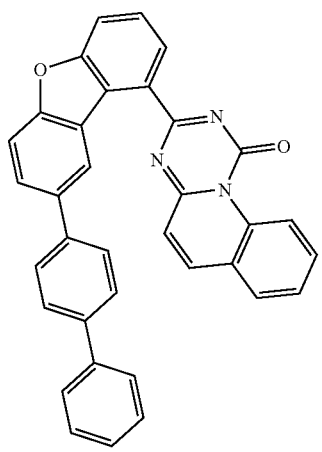 [SMILES: O=c1nc(-c2cccc3oc4ccc(-c5ccc(-c6ccccc6)cc5)cc4c23)nc2ccc3ccccc3n12]
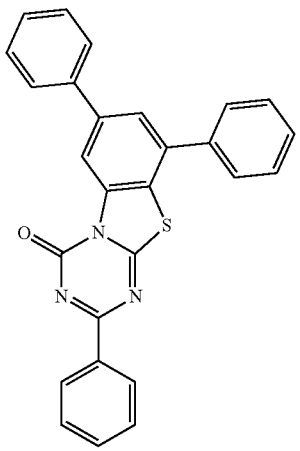 [SMILES: O=c1nc(-c2ccccc2)nc2sc3c(-c4ccccc4)cc(-c4ccccc4)cc3n12]

-continued
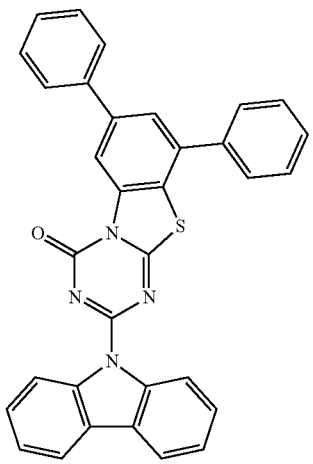 [SMILES: O=c1nc(-n2c3ccccc3c3ccccc32)nc2sc3c(-c4ccccc4)cc(-c4ccccc4)cc3n12]
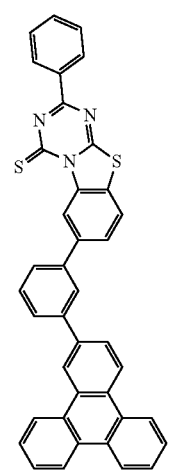 [SMILES: S=c1nc(-c2ccccc2)nc2sc3ccc(-c4cccc(-c5ccc6c7ccccc7c7ccccc7c6c5)c4)cc3n12]
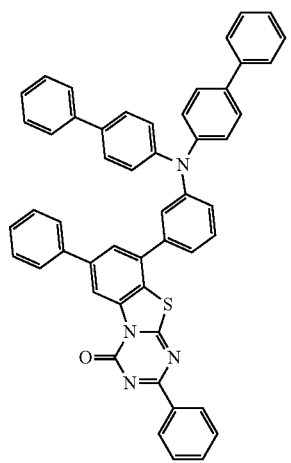 [SMILES: O=c1nc(-c2ccccc2)nc2sc3c(-c4cccc(N(c5ccc(-c6ccccc6)cc5)c5ccc(-c6ccccc6)cc5)c4)cc(-c4ccccc4)cc3n12]
-continued
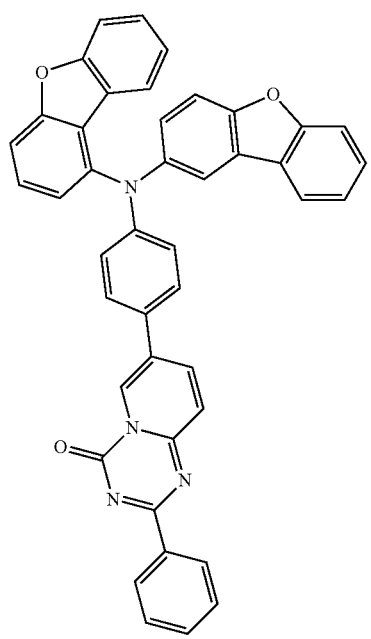 [SMILES: O=c1nc(-c2ccccc2)nc2ccc(-c3ccc(N(c4ccc5oc6ccccc6c5c4)c4cccc5oc6ccccc6c45)cc3)cn12]
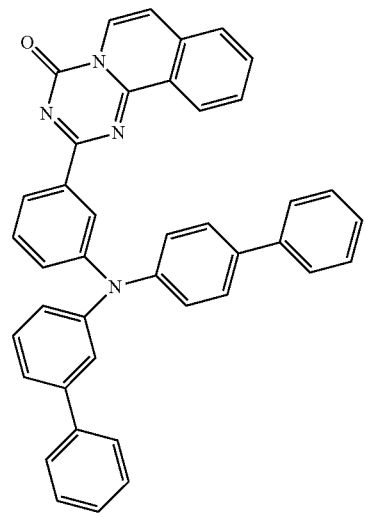 [SMILES: O=c1nc(-c2cccc(N(c3ccc(-c4ccccc4)cc3)c3cccc(-c4ccccc4)c3)c2)nc2c3ccccc3ccn12]
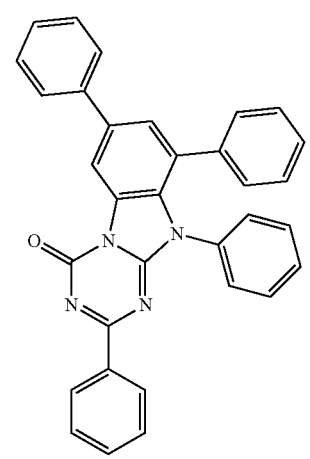 [SMILES: O=c1nc(-c2ccccc2)nc2n(-c3ccccc3)c3c(-c4ccccc4)cc(-c4ccccc4)cc3n12]

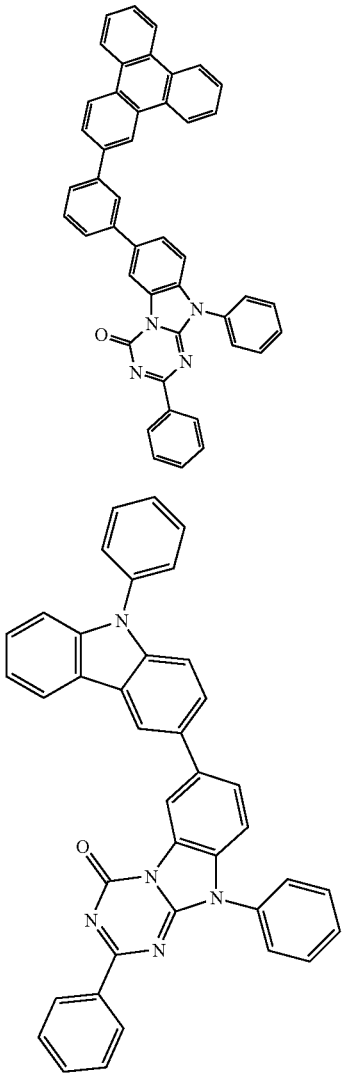
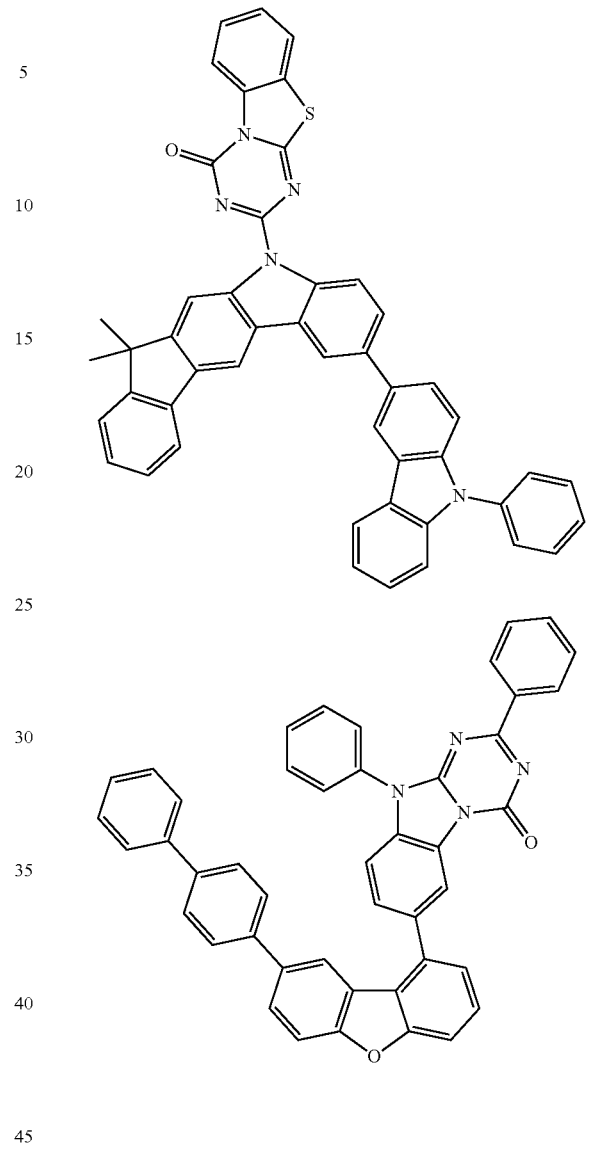
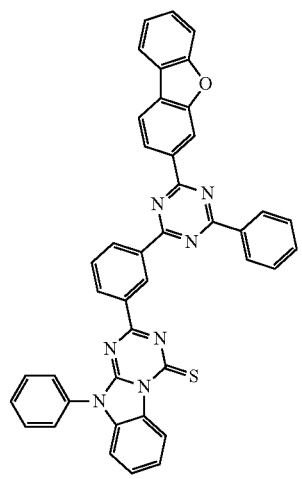 [SMILES: S=c1nc(-c2cccc(-c3nc(-c4ccccc4)nc(-c4ccc5c(c4)oc4ccccc45)n3)c2)nc2n(-c3ccccc3)c3ccccc3n12]
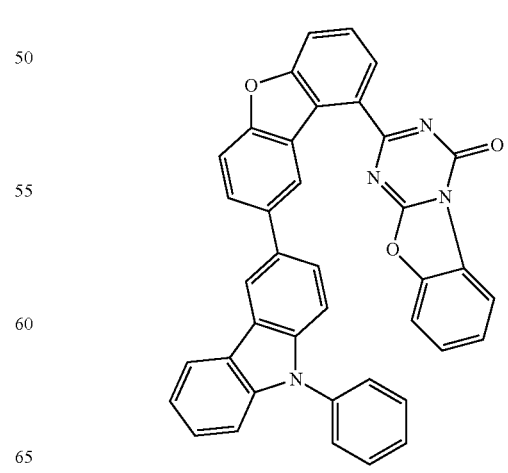

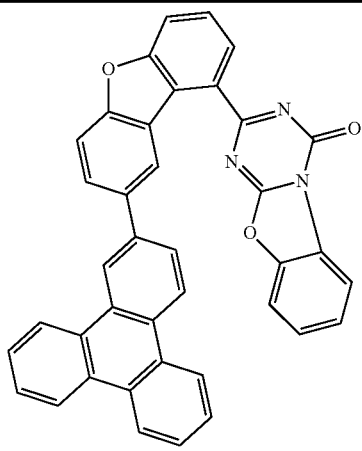
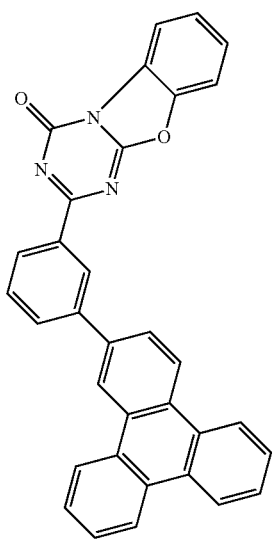 [SMILES: O=c1nc(-c2cccc(-c3ccc4c5ccccc5c5ccccc5c4c3)c2)nc2oc3ccccc3n12]
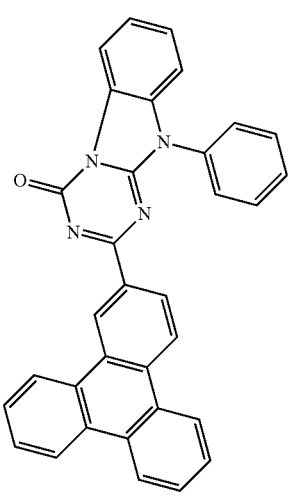 [SMILES: O=c1nc(-c2ccc3c4ccccc4c4ccccc4c3c2)nc2n(-c3ccccc3)c3ccccc3n12]
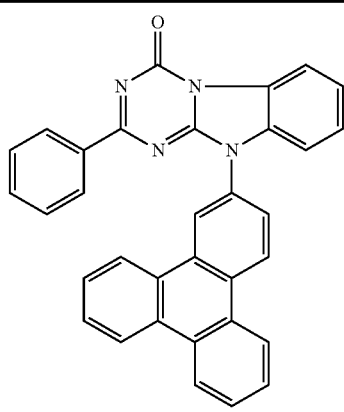
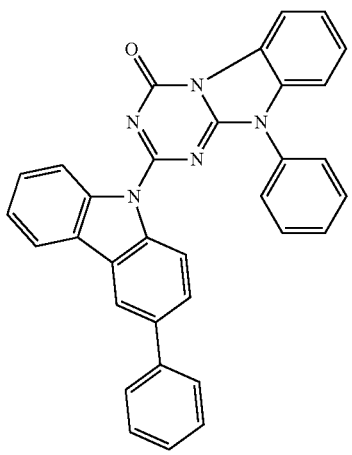 [SMILES: O=c1nc(-n2c3ccccc3c3cc(-c4ccccc4)ccc32)nc2n(-c3ccccc3)c3ccccc3n12]
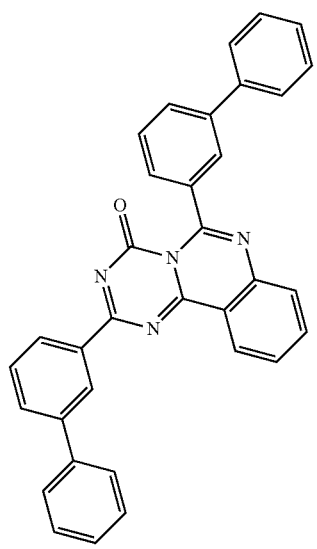 [SMILES: O=c1nc(-c2cccc(-c3ccccc3)c2)nc2c3ccccc3nc(-c3cccc(-c4ccccc4)c3)n12]

-continued
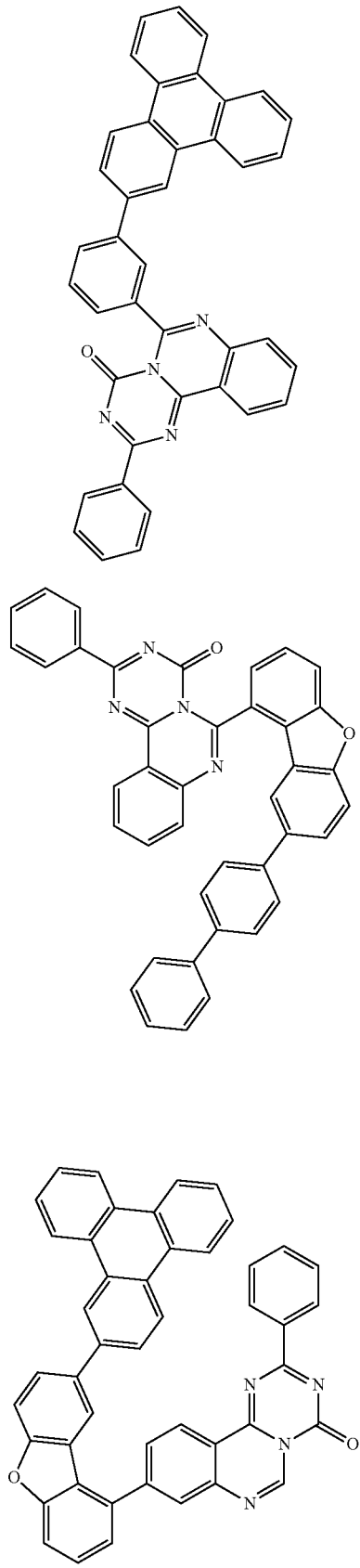
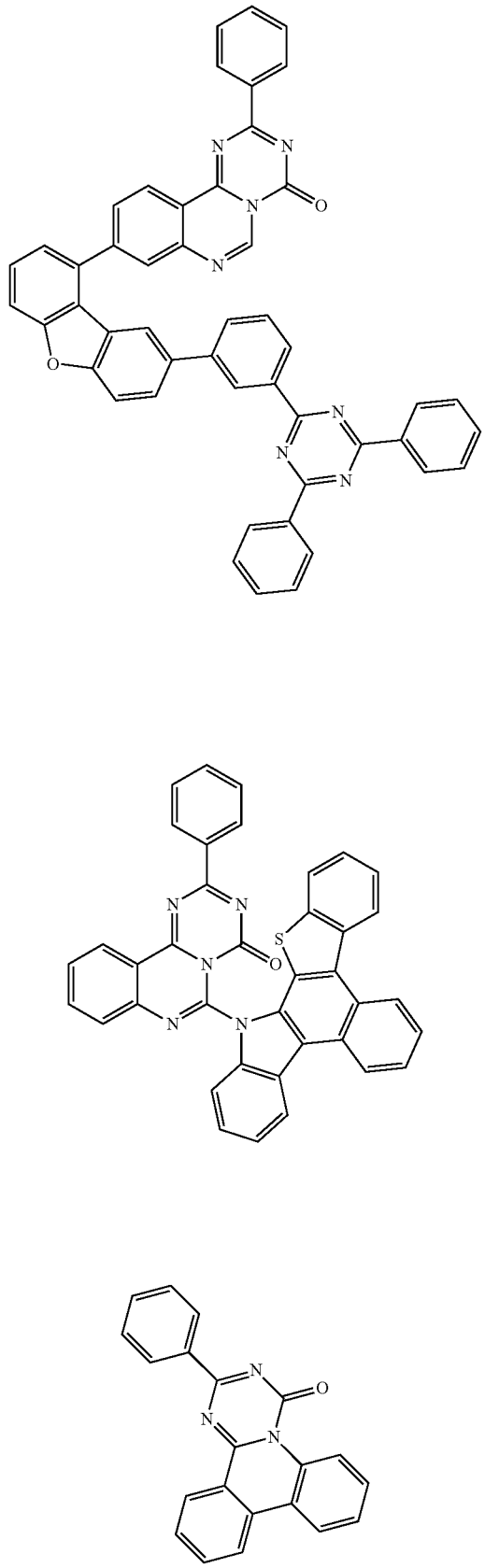

87
-continued
88
-continued
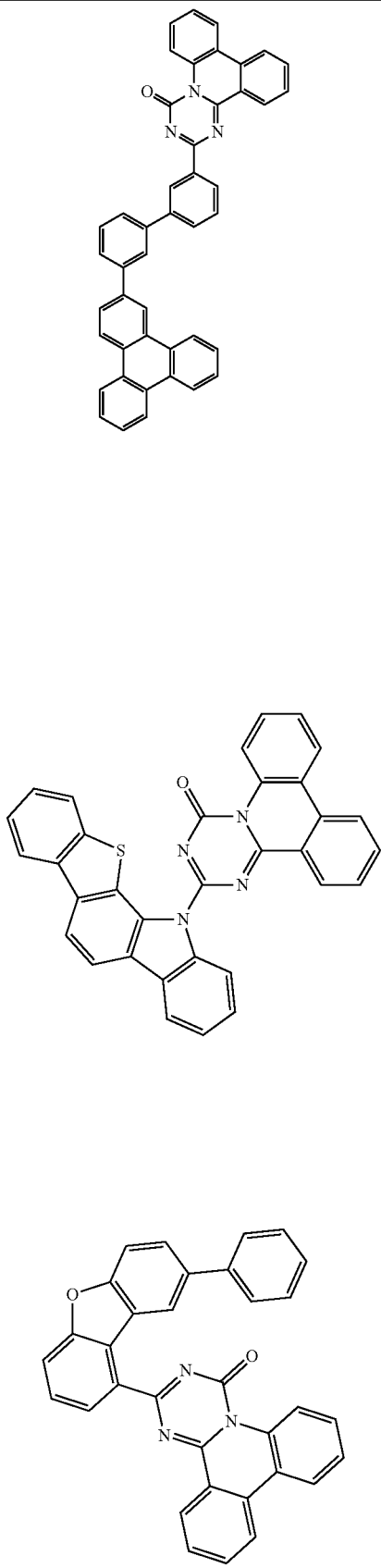
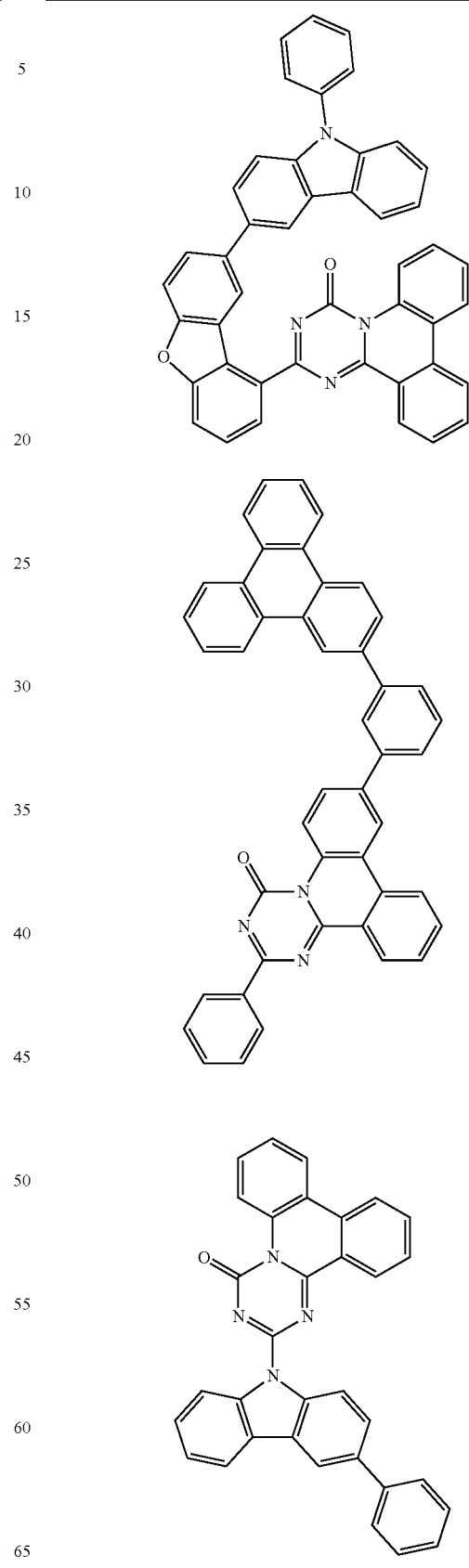

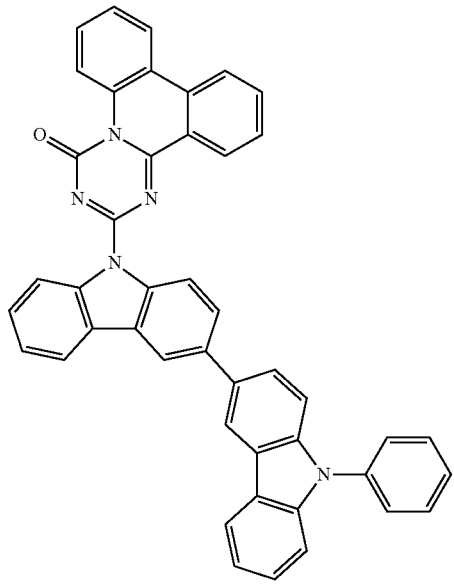 [SMILES: O=c1nc(-n2c3ccccc3c3cc(-c4ccc5c(c4)c4ccccc4n5-c4ccccc4)ccc32)nc2c3ccccc3c3ccccc3n12]
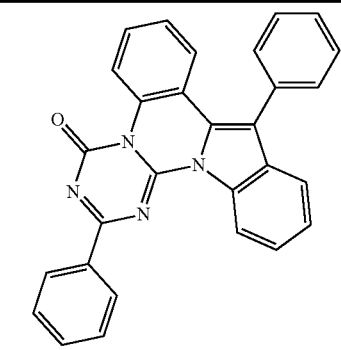

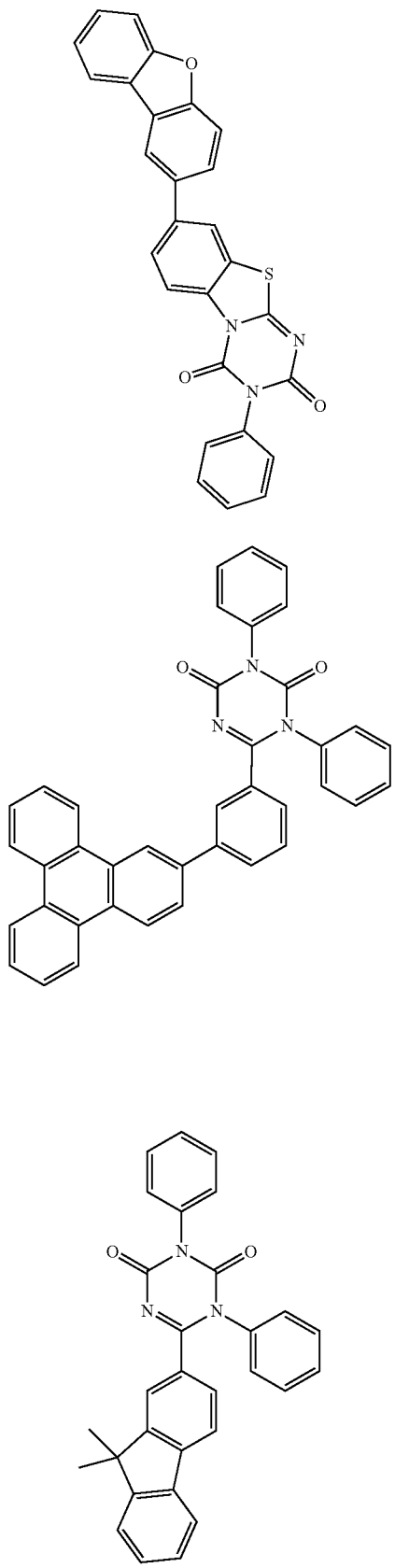
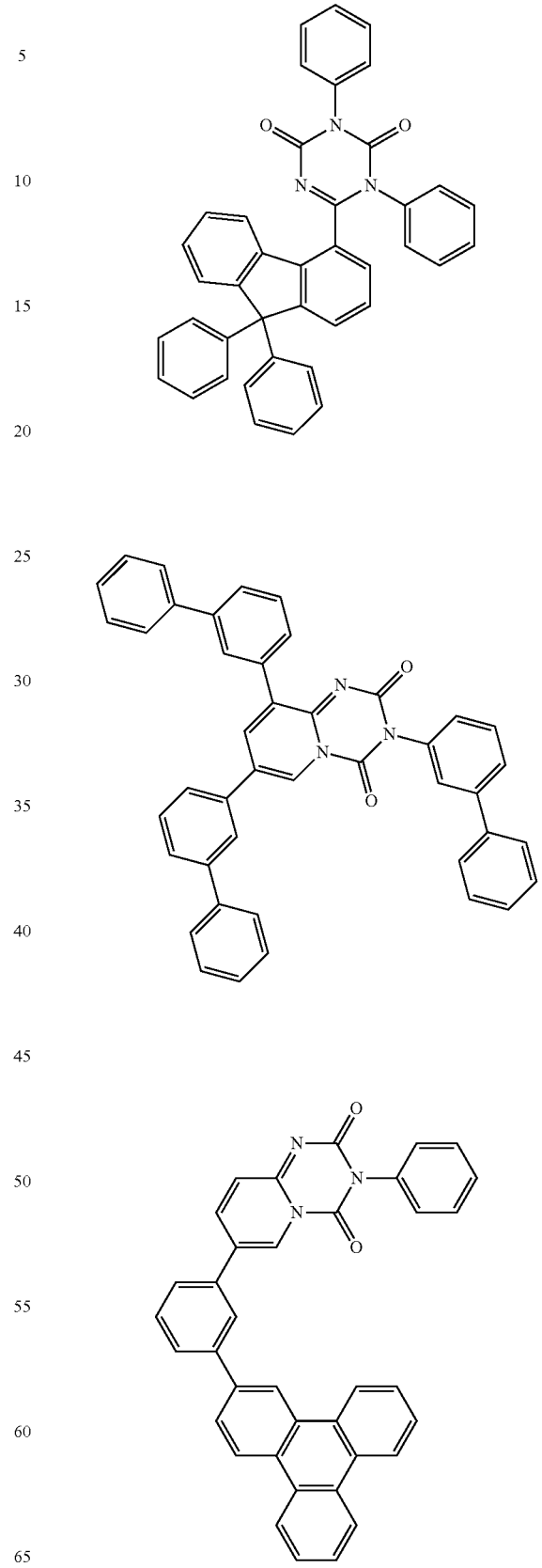

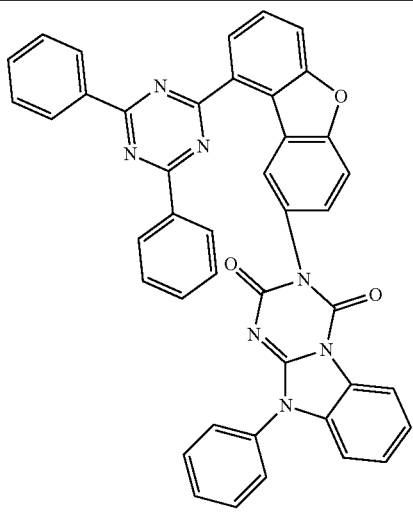
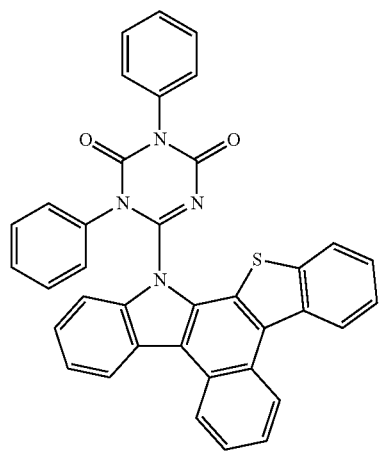 [SMILES: O=c1nc(-n2c3ccccc3c3c4ccccc4c4c5ccccc5sc4c32)n(-c2ccccc2)c(=O)n1-c1ccccc1]
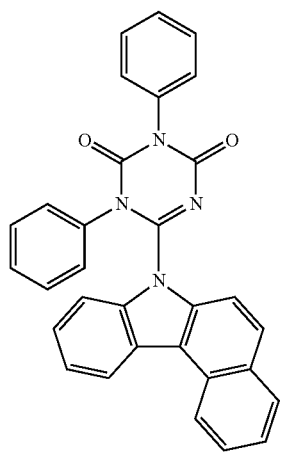 [SMILES: O=c1nc(-n2c3ccccc3c3c4ccccc4ccc32)n(-c2ccccc2)c(=O)n1-c1ccccc1]
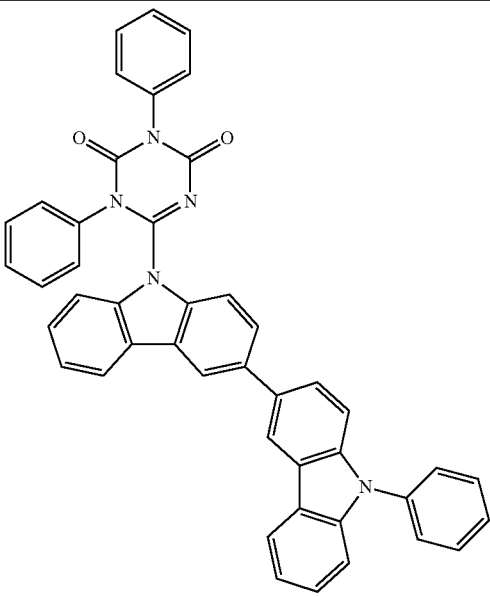
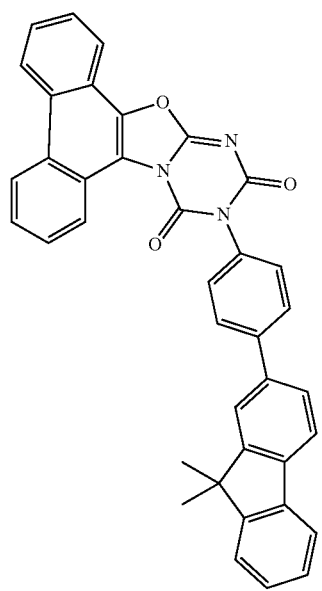 [SMILES: CC1(C)c2ccccc2-c2ccc(-c3ccc(-n4c(=O)nc5oc6c7ccccc7c7ccccc7c6n5c4=O)cc3)cc21]

-continued
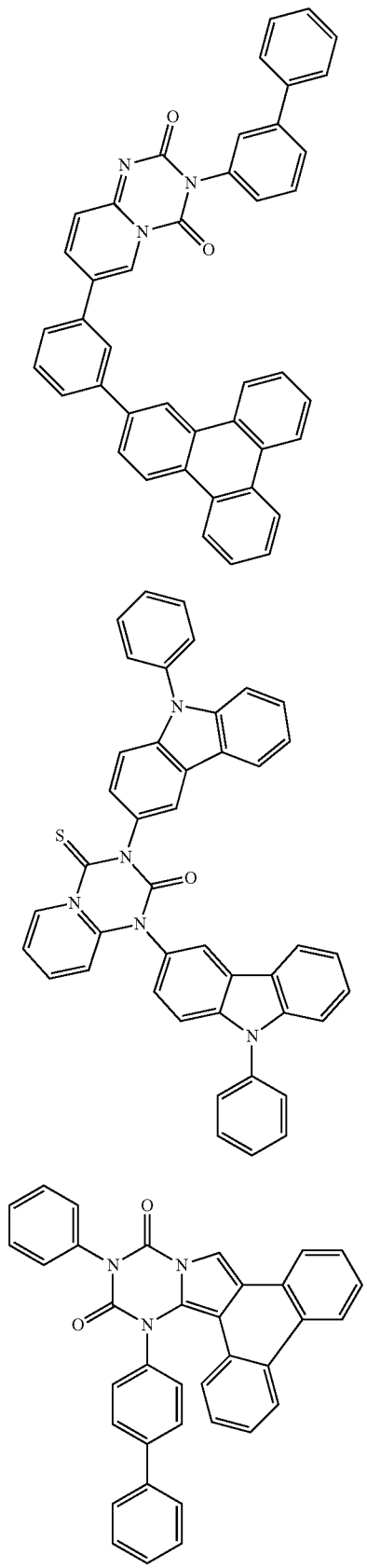
-continued
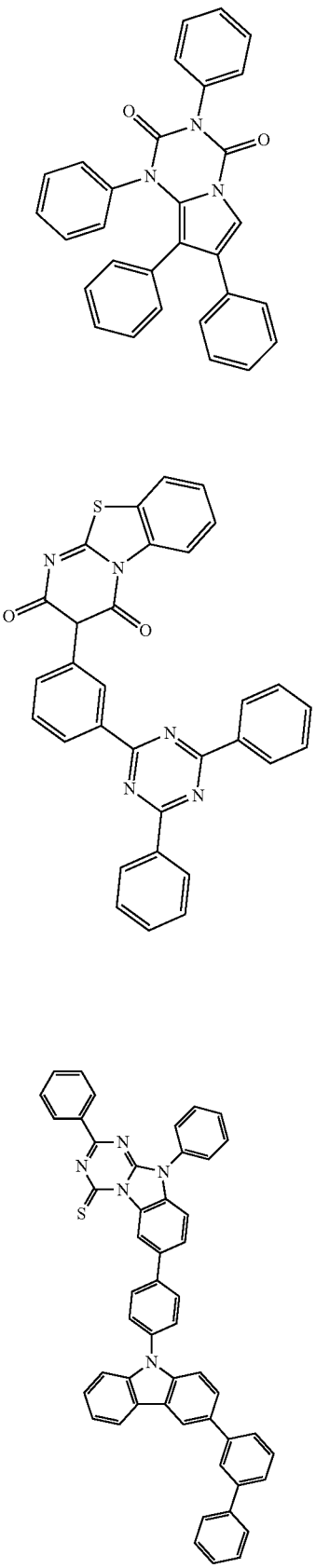

97
-continued
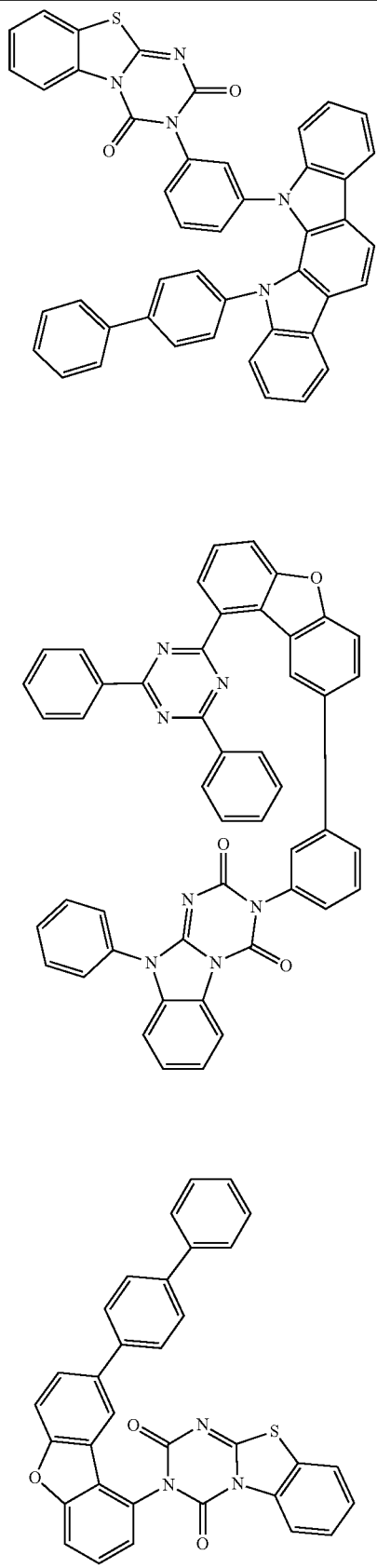
98
-continued
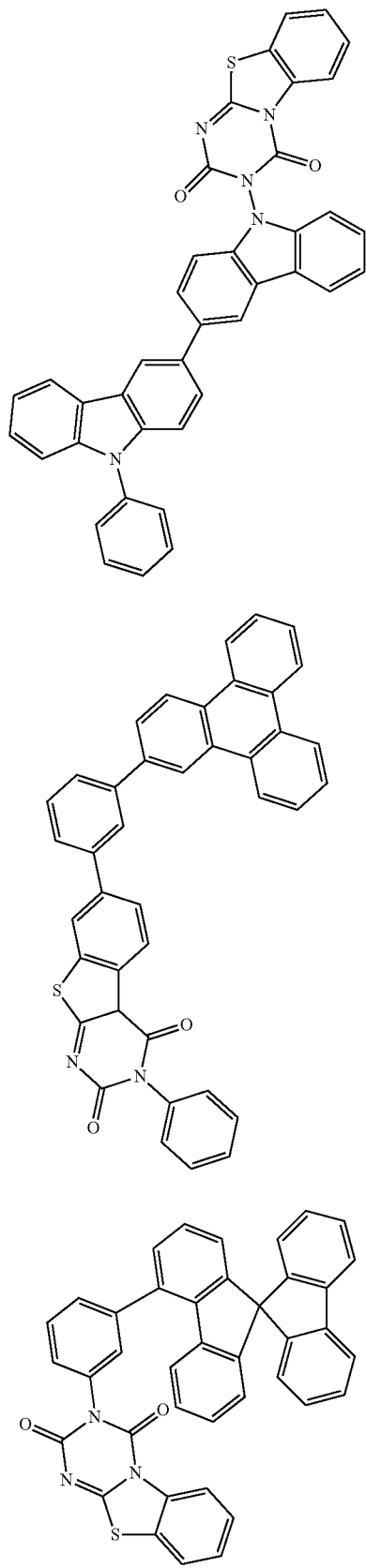

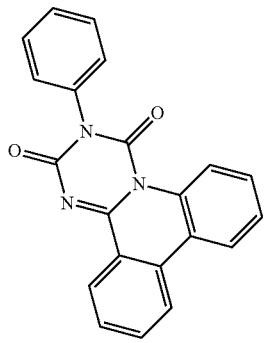 [SMILES: O=c1nc2c3ccccc3c3ccccc3n2c(=O)n1-c1ccccc1]
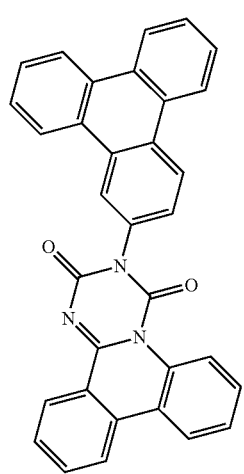 [SMILES: O=c1nc2c3ccccc3c3ccccc3n2c(=O)n1-c1ccc2c3ccccc3c3ccccc3c2c1]
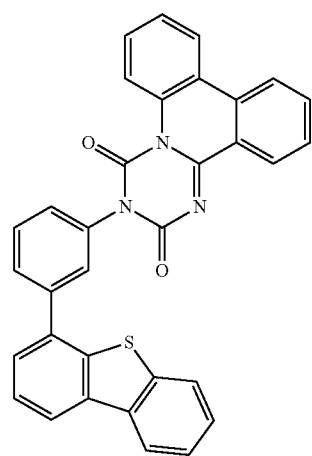 [SMILES: O=c1nc2c3ccccc3c3ccccc3n2c(=O)n1-c1cccc(-c2cccc3c2sc2ccccc23)c1]
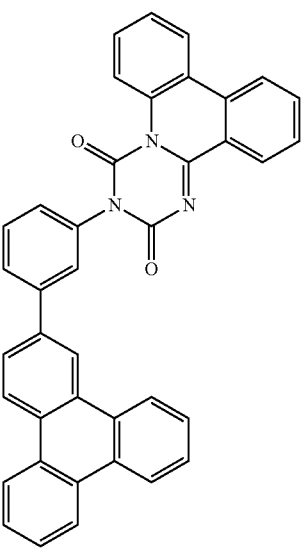 [SMILES: O=c1nc2c3ccccc3c3ccccc3n2c(=O)n1-c1cccc(-c2ccc3c4ccccc4c4ccccc4c3c2)c1]
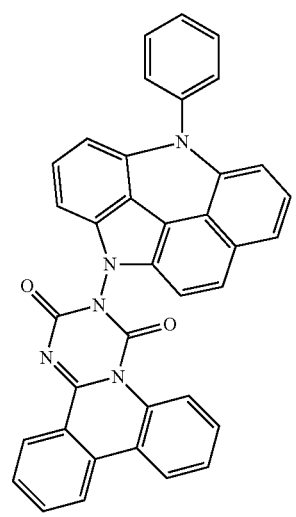 [SMILES: O=c1nc2c3ccccc3c3ccccc3n2c(=O)n1-n1c2cccc3c2c2c4c(cccc4ccc21)N3c1ccccc1]
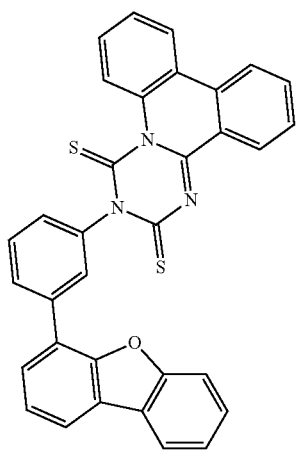 [SMILES: S=c1nc2c3ccccc3c3ccccc3n2c(=S)n1-c1cccc(-c2cccc3c2oc2ccccc23)c1]

| 101 -continued | 102 -continued |
|---|---|
| 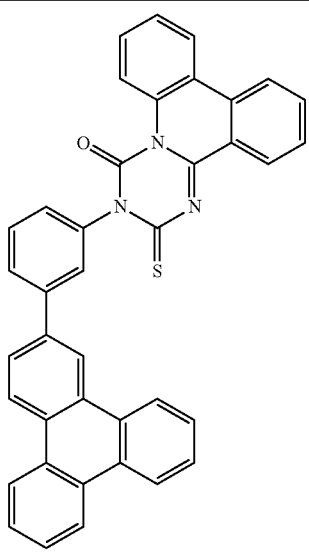 | 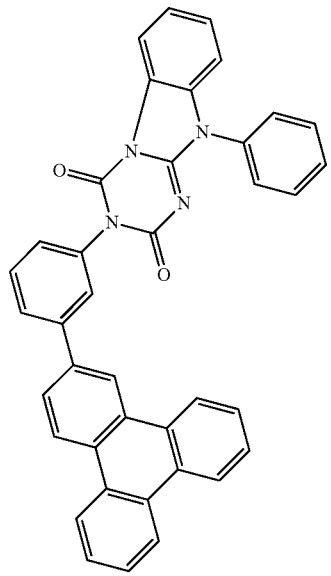 |
| 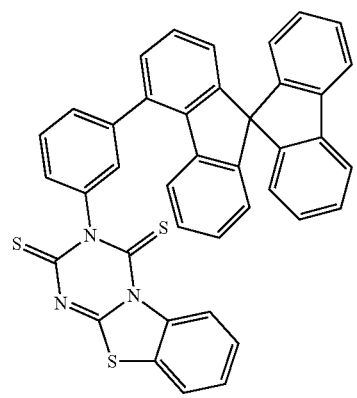 [SMILES: S=c1nc2sc3ccccc3n2c(=S)n1-c1cccc(-c2cccc3c2-c2ccccc2C32c3ccccc3-c3ccccc32)c1] | 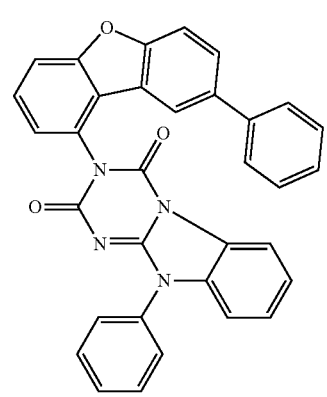 |
| 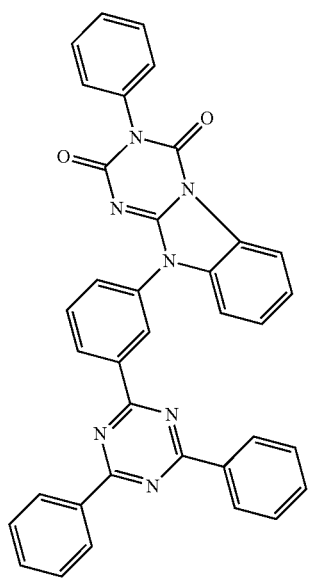 [SMILES: O=c1nc2n(-c3cccc(-c4nc(-c5ccccc5)nc(-c5ccccc5)n4)c3)c3ccccc3n2c(=O)n1-c1ccccc1] | 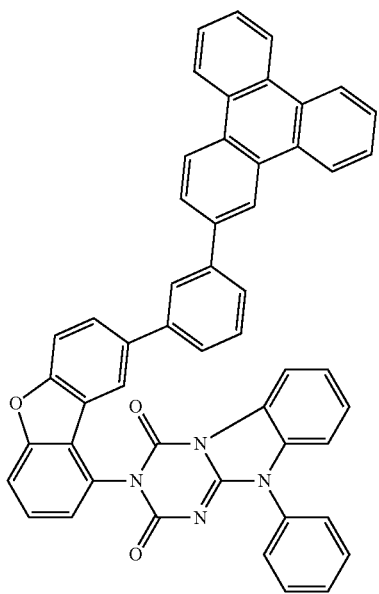 [SMILES: O=c1nc2n(-c3ccccc3)c3ccccc3n2c(=O)n1-c1cccc2oc3ccc(-c4cccc(-c5ccc6c7ccccc7c7ccccc7c6c5)c4)cc3c12] |

103
-continued
104
-continued
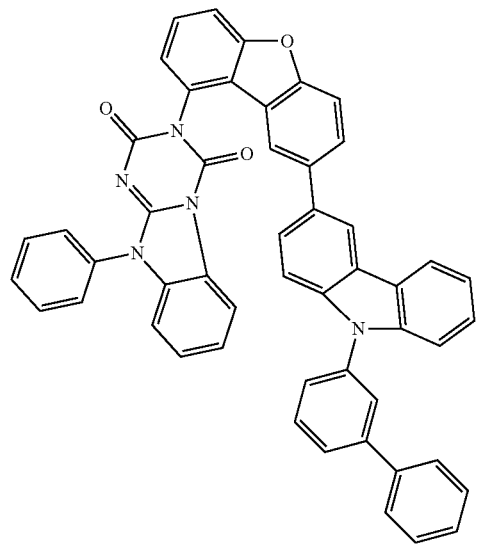 [SMILES: O=c1nc2n(-c3ccccc3)c3ccccc3n2c(=O)n1-c1cccc2oc3ccc(-c4ccc5c(c4)c4ccccc4n5-c4cccc(-c5ccccc5)c4)cc3c12]
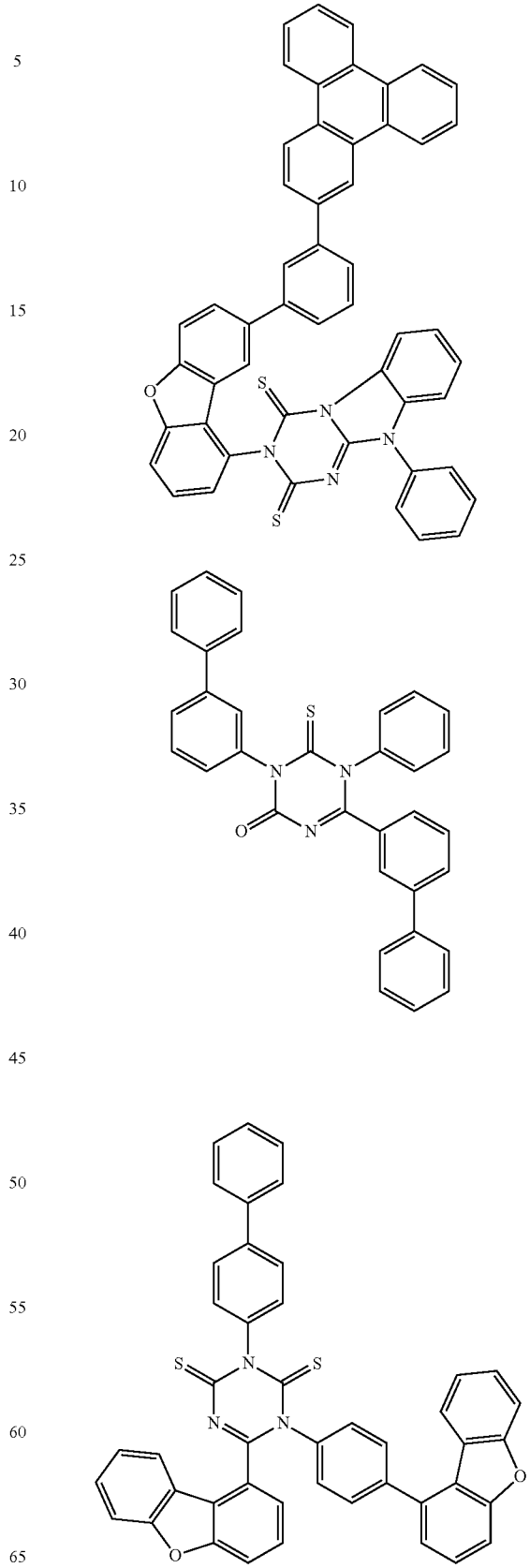

105
-continued
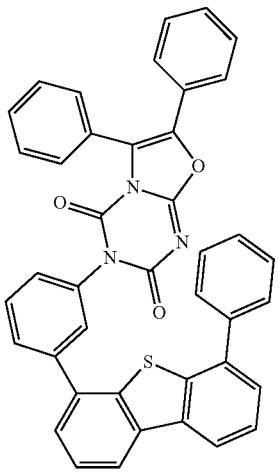 [SMILES: O=c1nc2oc(-c3ccccc3)c(-c3ccccc3)n2c(=O)n1-c1cccc(-c2cccc3c2sc2c(-c4ccccc4)cccc23)c1]
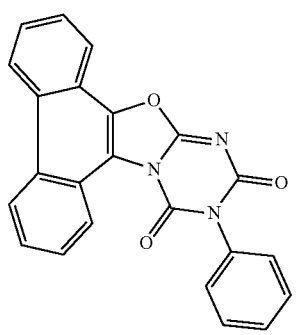 [SMILES: O=c1nc2oc3c4ccccc4c4ccccc4c3n2c(=O)n1-c1ccccc1]
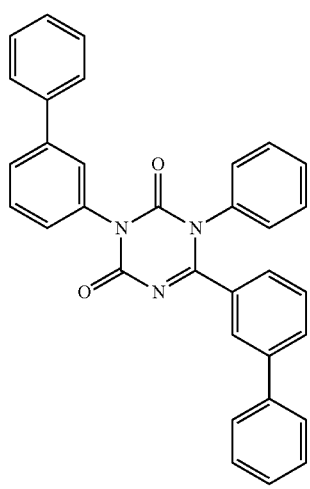 [SMILES: O=c1nc(-c2cccc(-c3ccccc3)c2)n(-c2ccccc2)c(=O)n1-c1cccc(-c2ccccc2)c1]
106
-continued
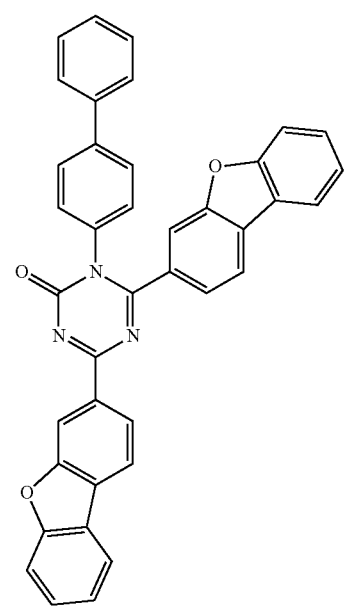 [SMILES: O=c1nc(-c2ccc3c(c2)oc2ccccc23)nc(-c2ccc3c(c2)oc2ccccc23)n1-c1ccc(-c2ccccc2)cc1]
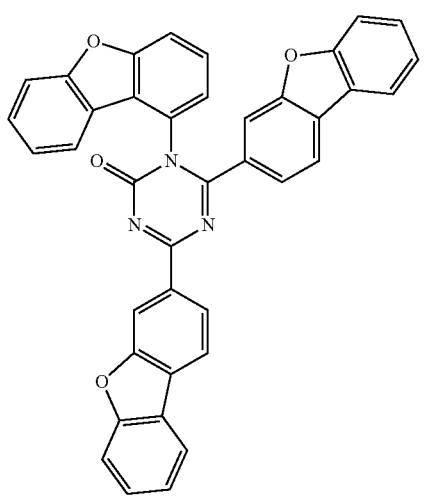 [SMILES: O=c1nc(-c2ccc3c(c2)oc2ccccc23)nc(-c2ccc3c(c2)oc2ccccc23)n1-c1cccc2oc3ccccc3c12]
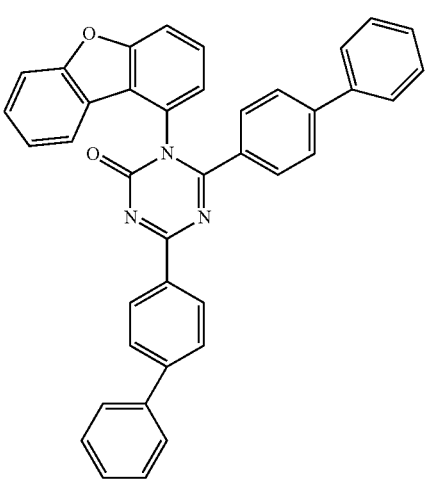 [SMILES: O=c1nc(-c2ccc(-c3ccccc3)cc2)nc(-c2ccc(-c3ccccc3)cc2)n1-c1cccc2oc3ccccc3c12]

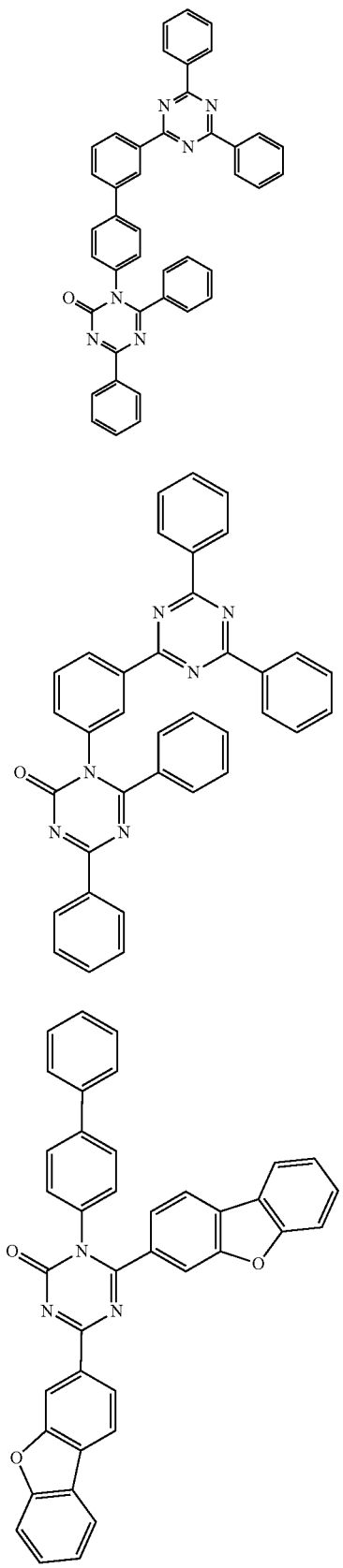
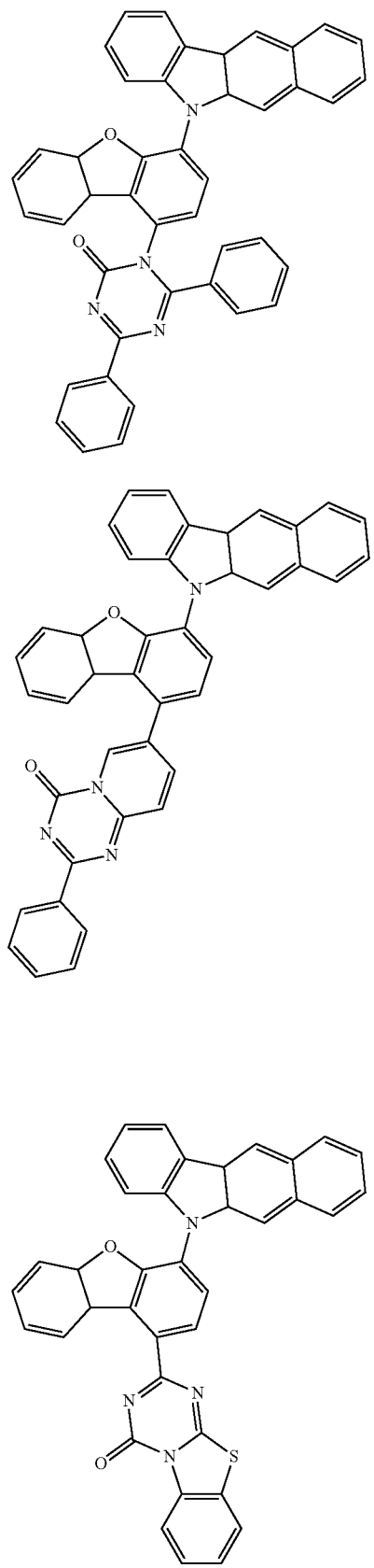

109
-continued
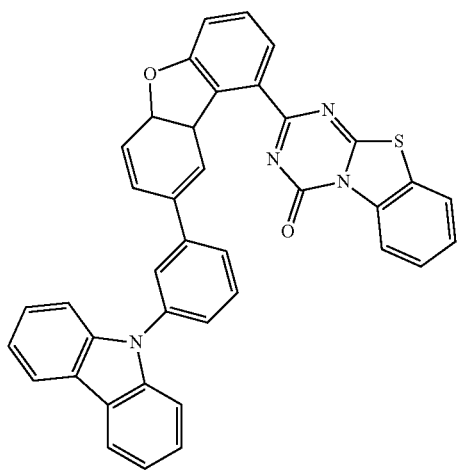 [SMILES: O=c1nc(-c2cccc3c2C2C=C(c4cccc(-n5c6ccccc6c6ccccc65)c4)C=CC2O3)nc2sc3ccccc3n12]
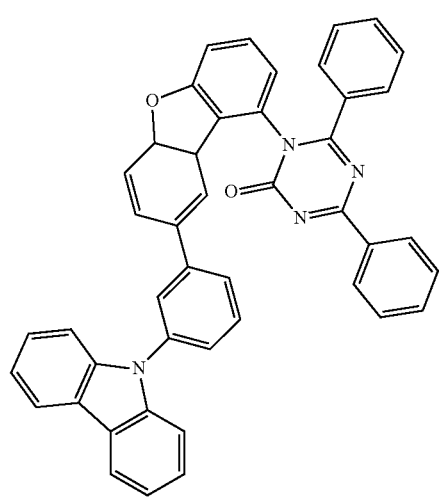 [SMILES: O=c1nc(-c2ccccc2)nc(-c2ccccc2)n1-c1cccc2c1C1C=C(c3cccc(-n4c5ccccc5c5ccccc54)c3)C=CC1O2]
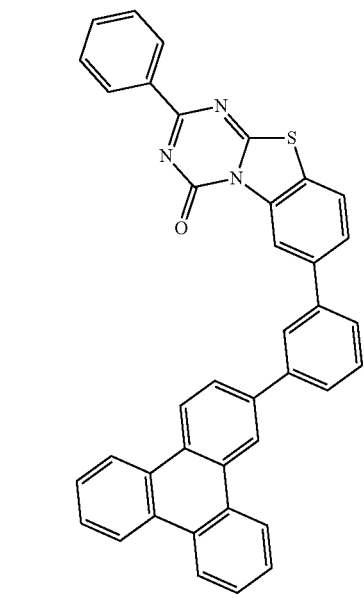 [SMILES: O=c1nc(-c2ccccc2)nc2sc3ccc(-c4cccc(-c5ccc6c7ccccc7c7ccccc7c6c5)c4)cc3n12]
110
-continued
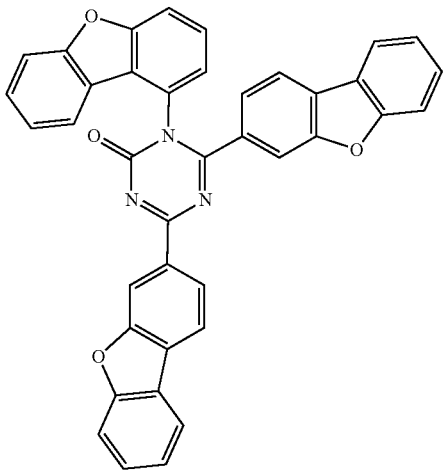 [SMILES: O=c1nc(-c2ccc3c(c2)oc2ccccc23)nc(-c2ccc3c(c2)oc2ccccc23)n1-c1cccc2oc3ccccc3c12]
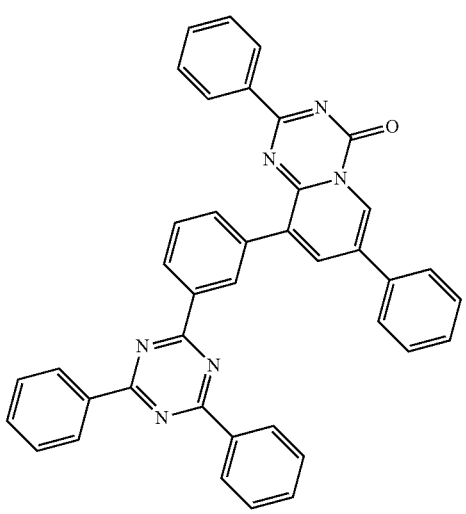 [SMILES: O=c1nc(-c2ccccc2)nc2c(-c3cccc(-c4nc(-c5ccccc5)nc(-c5ccccc5)n4)c3)cc(-c3ccccc3)cn12]
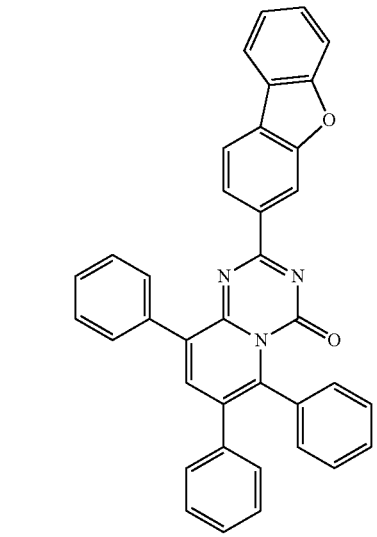 [SMILES: O=c1nc(-c2ccc3c(c2)oc2ccccc23)nc2c(-c3ccccc3)cc(-c3ccccc3)c(-c3ccccc3)n12]

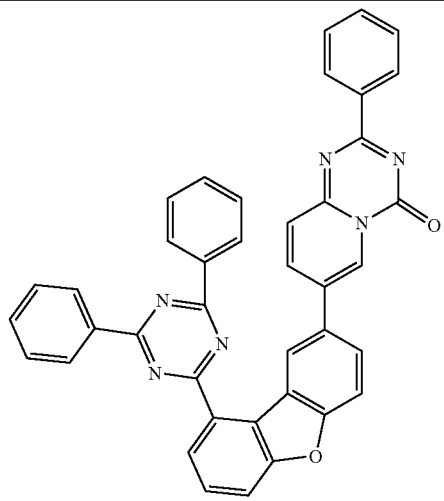
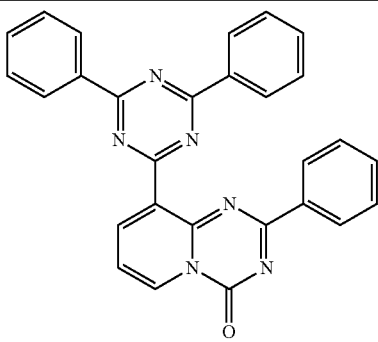
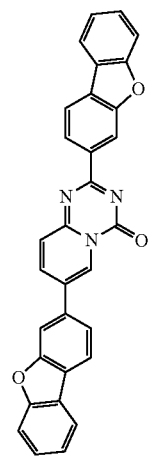 [SMILES: O=c1nc(-c2ccc3c(c2)oc2ccccc23)nc2ccc(-c3ccc4c(c3)oc3ccccc34)cn12]
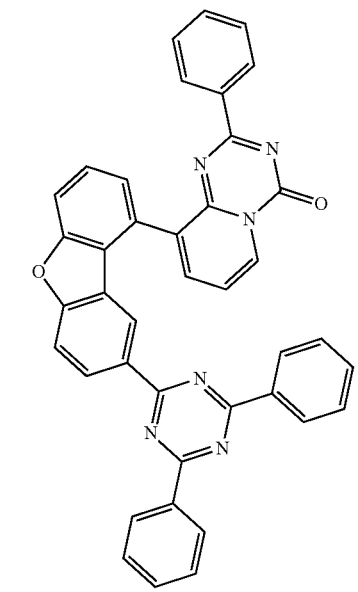
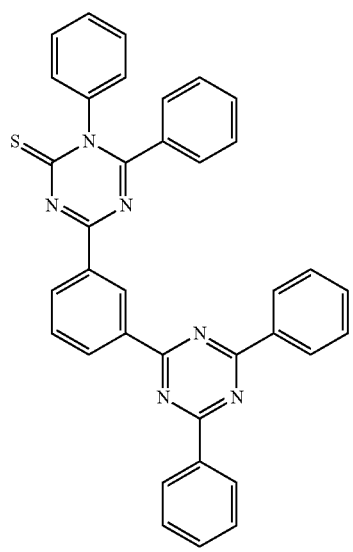 [SMILES: S=c1nc(-c2cccc(-c3nc(-c4ccccc4)nc(-c4ccccc4)n3)c2)nc(-c2ccccc2)n1-c1ccccc1]
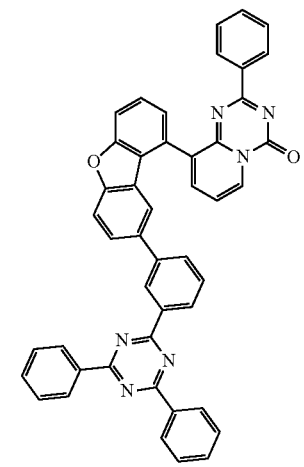 [SMILES: O=c1nc(-c2ccccc2)nc2c(-c3cccc4oc5ccc(-c6cccc(-c7nc(-c8ccccc8)nc(-c8ccccc8)n7)c6)cc5c34)cccn12]

113
-continued
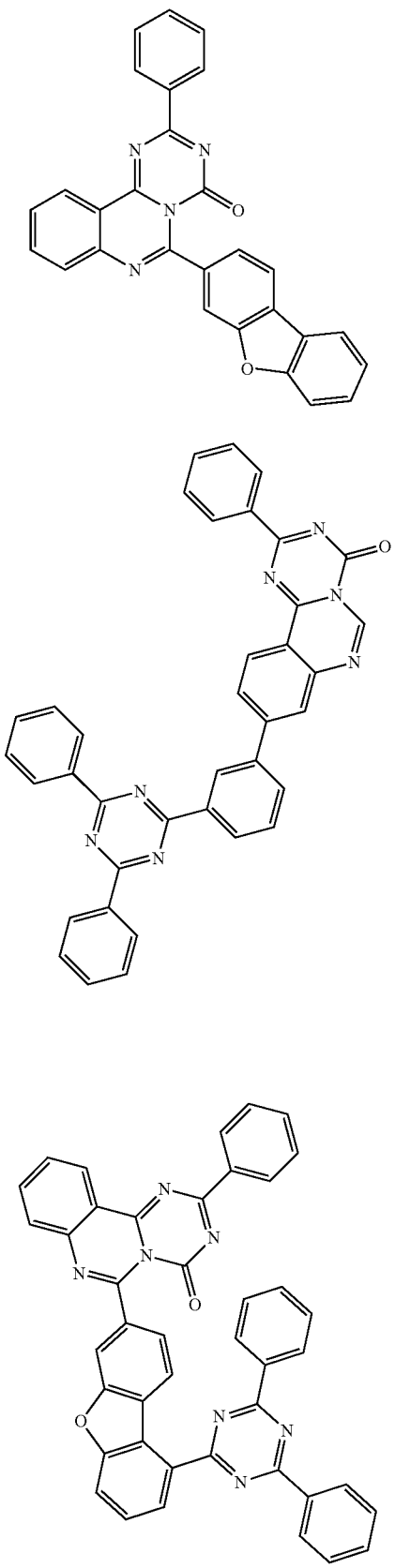
114
-continued
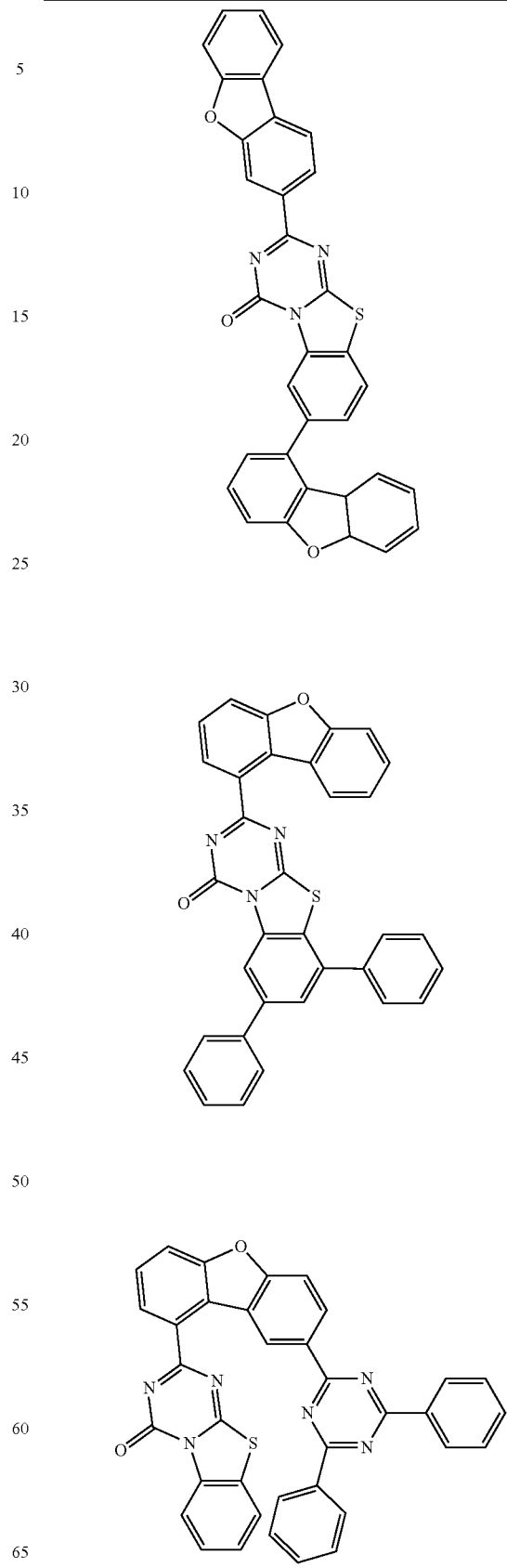

115
-continued
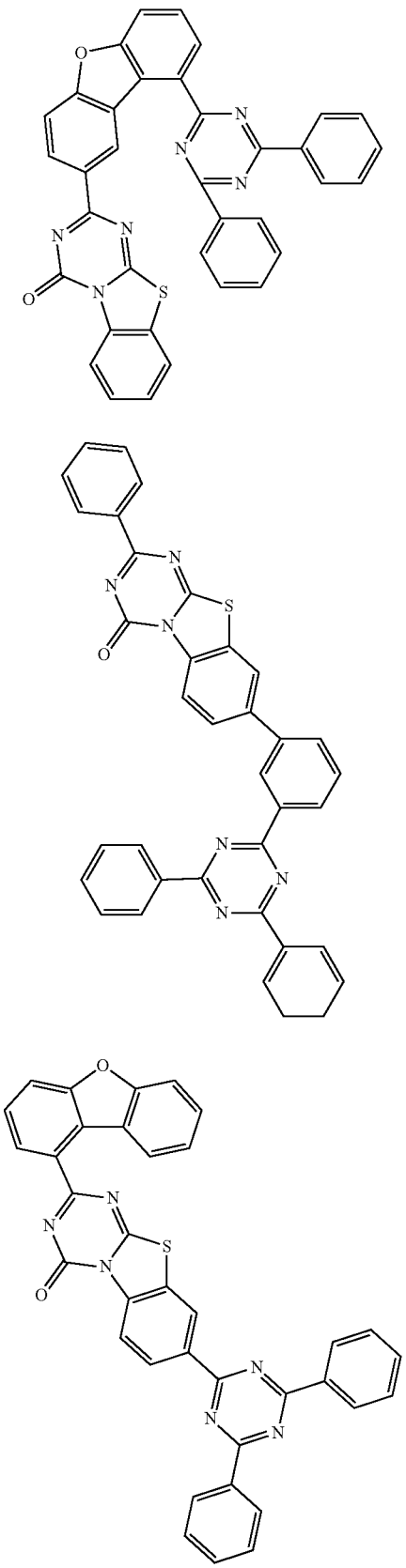
116
-continued
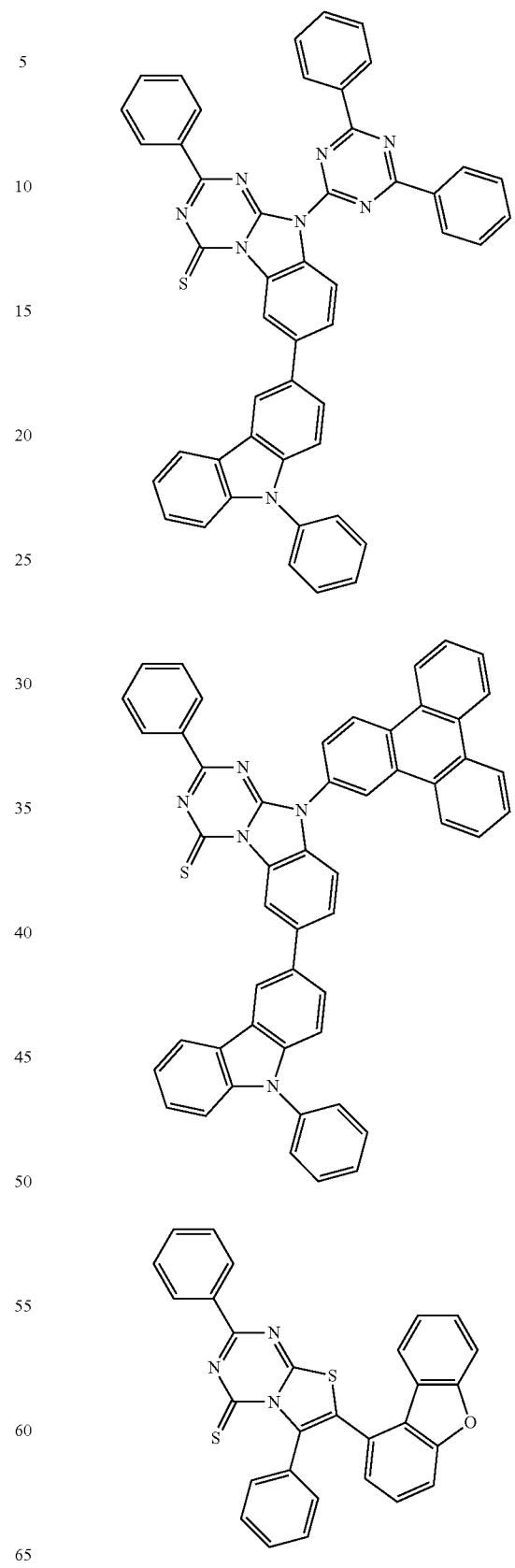

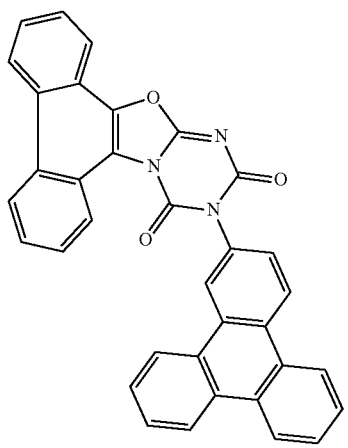 [SMILES: O=c1nc2oc3c4ccccc4c4ccccc4c3n2c(=O)n1-c1ccc2c3ccccc3c3ccccc3c2c1]
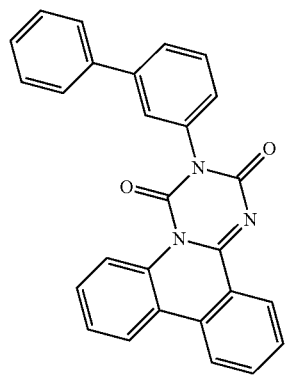
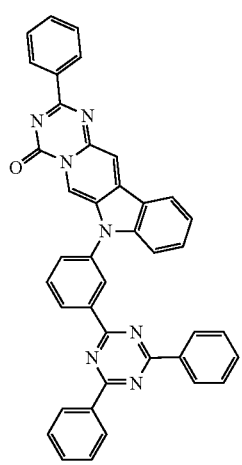 [SMILES: O=c1nc(-c2ccccc2)nc2cc3c4ccccc4n(-c4cccc(-c5nc(-c6ccccc6)nc(-c6ccccc6)n5)c4)c3cn12]
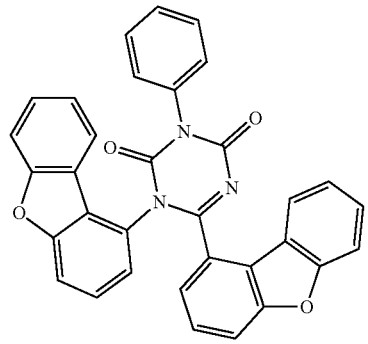
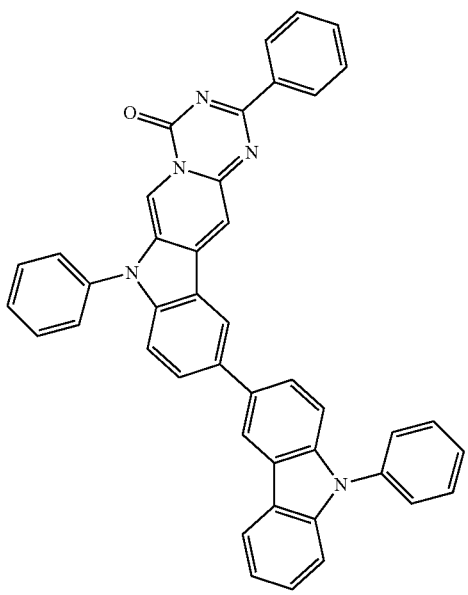 [SMILES: O=c1nc(-c2ccccc2)nc2cc3c4cc(-c5ccc6c(c5)c5ccccc5n6-c5ccccc5)ccc4n(-c4ccccc4)c3cn12]
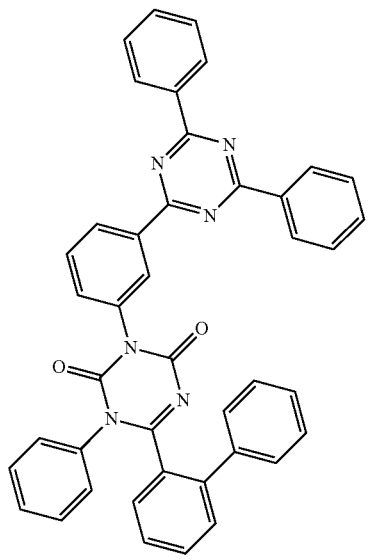 [SMILES: O=c1nc(-c2ccccc2-c2ccccc2)n(-c2ccccc2)c(=O)n1-c1cccc(-c2nc(-c3ccccc3)nc(-c3ccccc3)n2)c1]

119
-continued
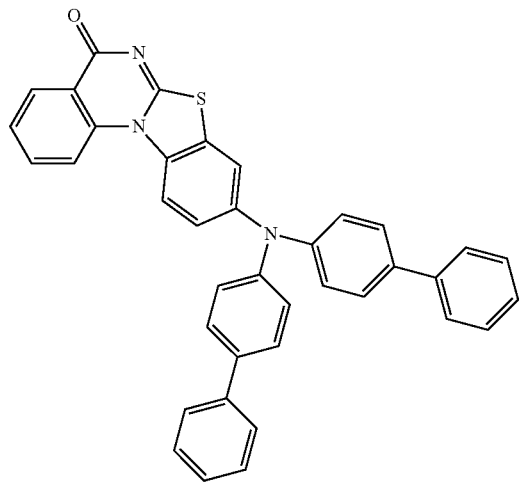 [SMILES: O=c1nc2sc3cc(N(c4ccc(-c5ccccc5)cc4)c4ccc(-c5ccccc5)cc4)ccc3n2c2ccccc12]
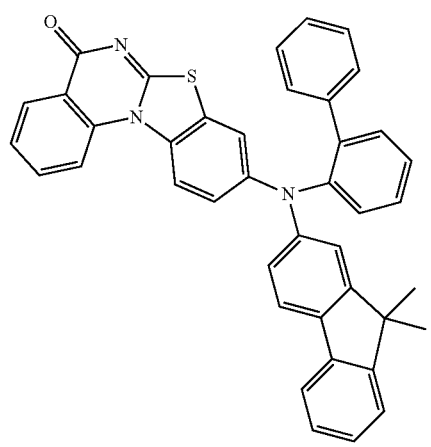 [SMILES: CC1(C)c2ccccc2-c2ccc(N(c3ccc4c(c3)sc3nc(=O)c5ccccc5n34)c3ccccc3-c3ccccc3)cc21]
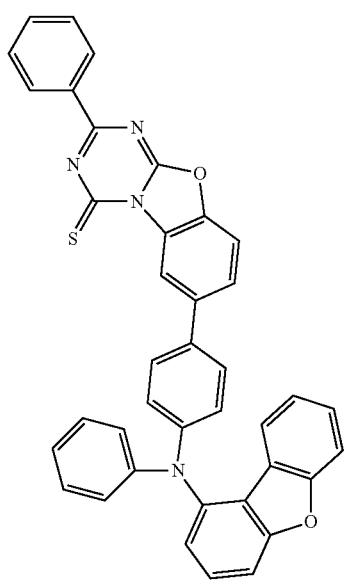
120
-continued
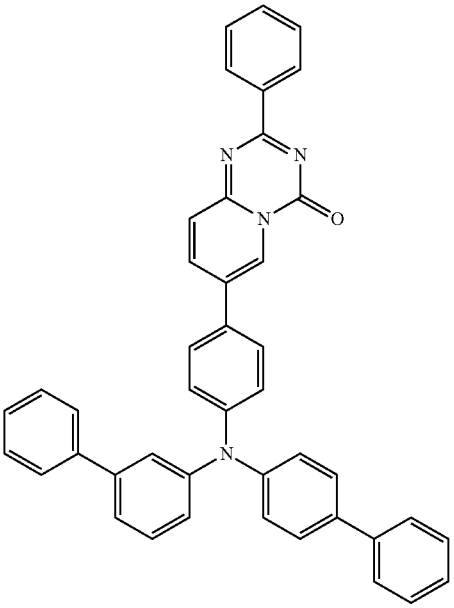 [SMILES: O=c1nc(-c2ccccc2)nc2ccc(-c3ccc(N(c4ccc(-c5ccccc5)cc4)c4cccc(-c5ccccc5)c4)cc3)cn12]
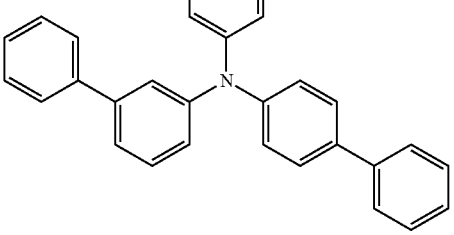
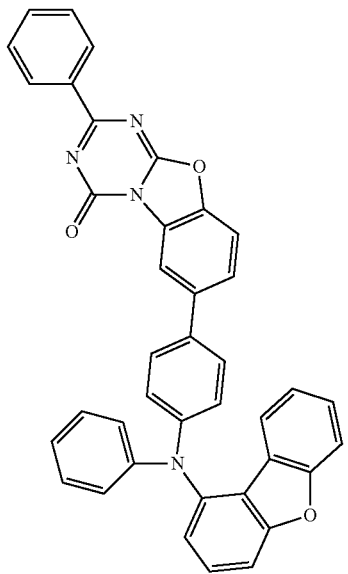 [SMILES: O=c1nc(-c2ccccc2)nc2oc3ccc(-c4ccc(N(c5ccccc5)c5cccc6oc7ccccc7c56)cc4)cc3n12]

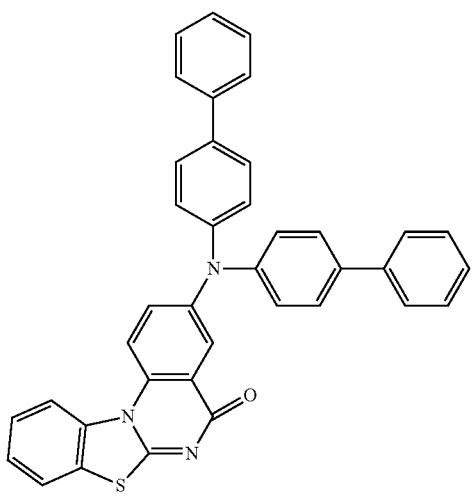 [SMILES: O=c1nc2sc3ccccc3n2c2ccc(N(c3ccc(-c4ccccc4)cc3)c3ccc(-c4ccccc4)cc3)cc12]
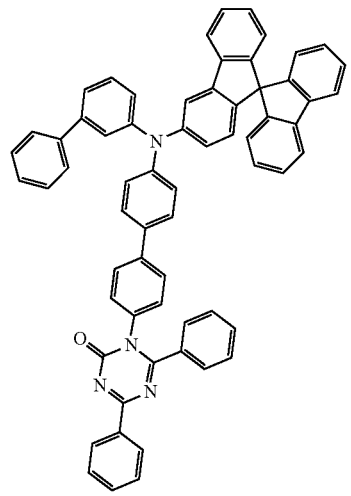
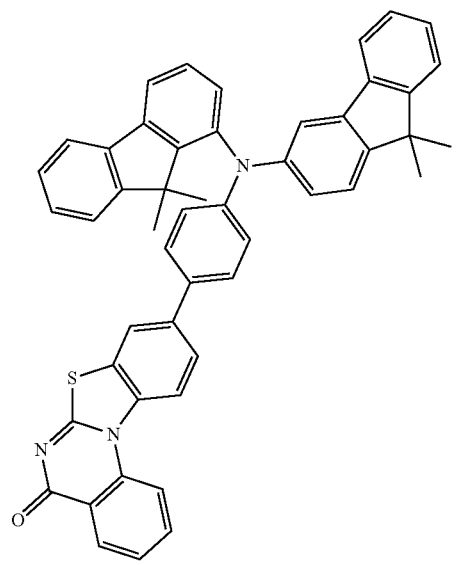 [SMILES: CC1(C)c2ccccc2-c2cc(N(c3ccc(-c4ccc5c(c4)sc4nc(=O)c6ccccc6n45)cc3)c3cccc4c3C(C)(C)c3ccccc3-4)ccc21]
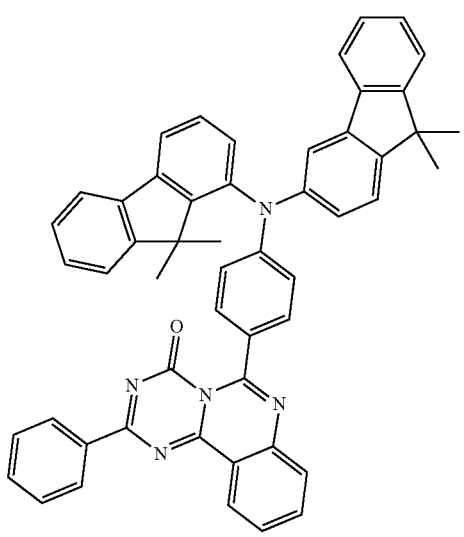 [SMILES: CC1(C)c2ccccc2-c2cc(N(c3ccc(-c4nc5ccccc5c5nc(-c6ccccc6)nc(=O)n45)cc3)c3cccc4c3C(C)(C)c3ccccc3-4)ccc21]
The base structure of the compounds of the invention is known in the literature. These can be prepared and functionalized by the routes outlined in the schemes that follow.
Scheme 1
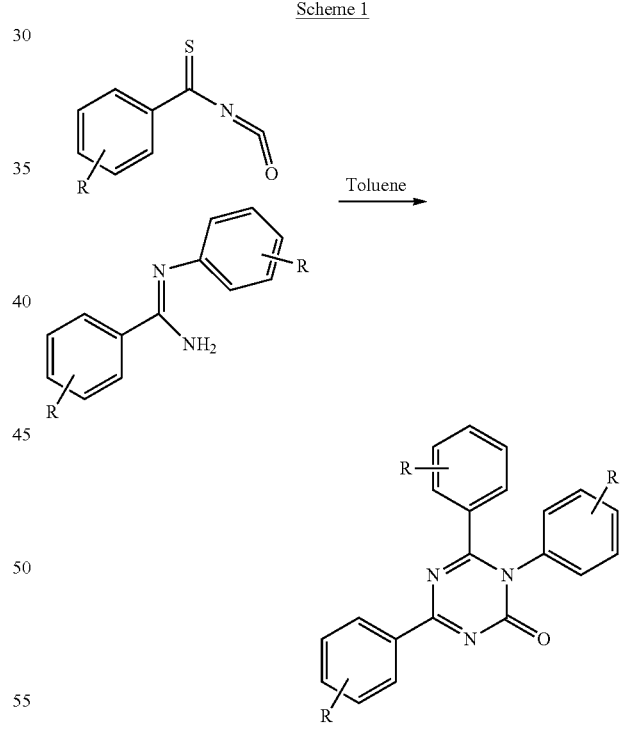
Chem. Ber. 105, 3136-3160 (1972)
Scheme 2
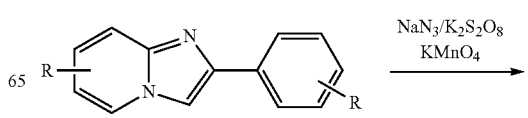

-continued
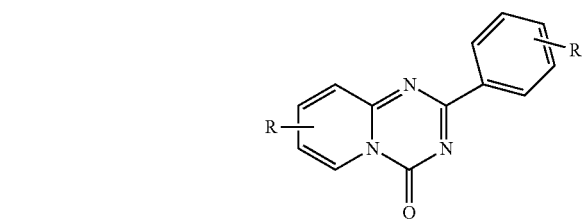
Advanced Synthesis & Catalysis (2018), 360(5), 881-886
Scheme 3
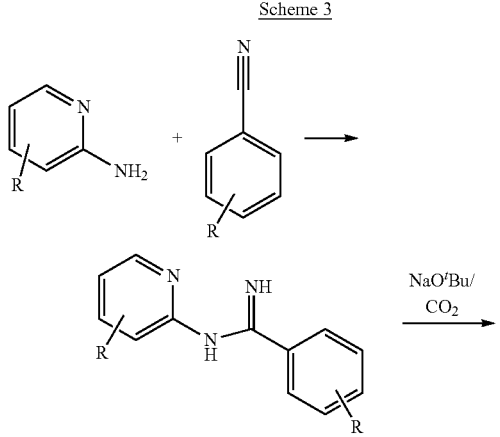
Organic & Biomolecular Chemistry (2017), 15(19), 4064-4067
Scheme 4
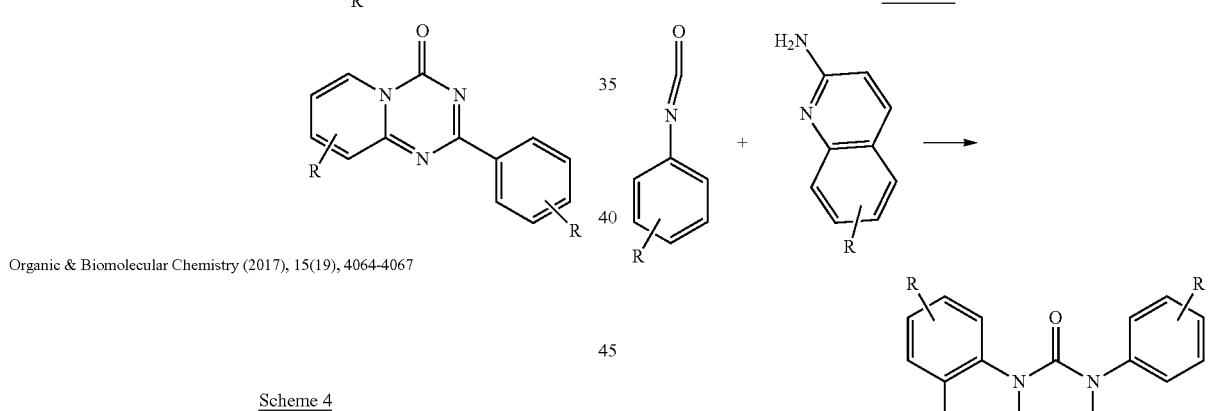
e-EROS Encyclopedia of Reagents for Organic Synthesis, 1-5; 2011
Scheme 5
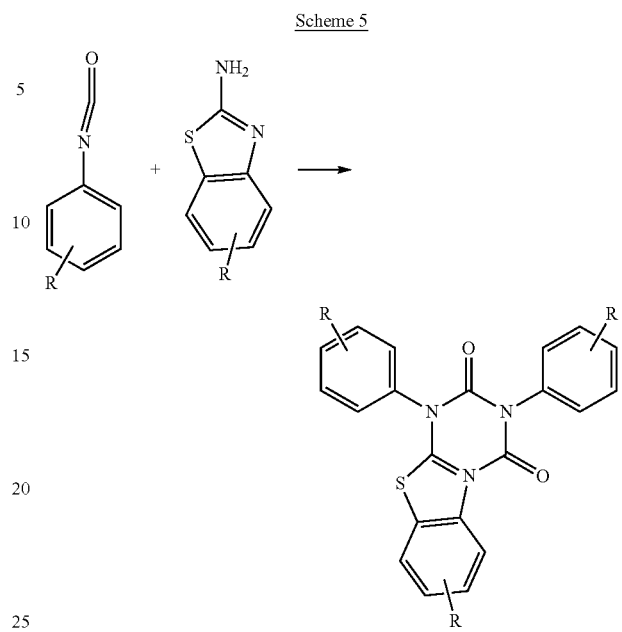
Chemische Berichte, 109(2), 723-39; 1976
Scheme 6
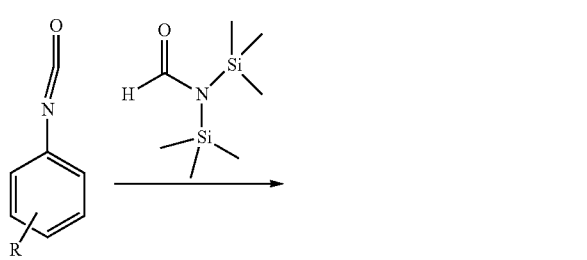
Chemische Berichte, 109(2), 723-39; 1976
Scheme 7
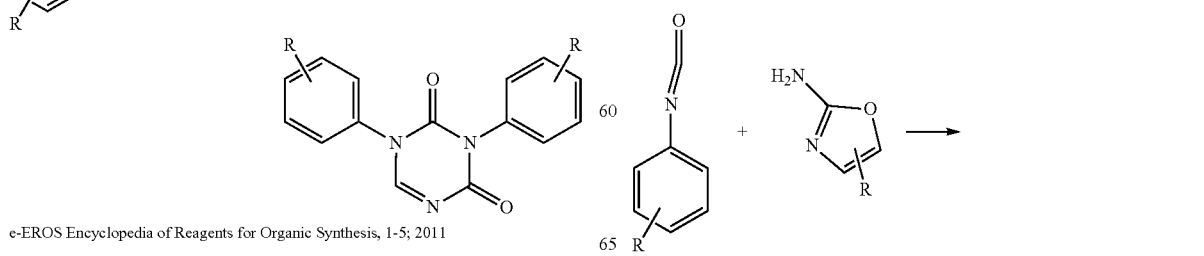

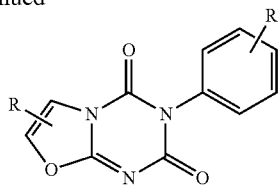

Chemical & Pharmaceutical Bulletin, 30(11), 4195-8; 1982

Scheme 8

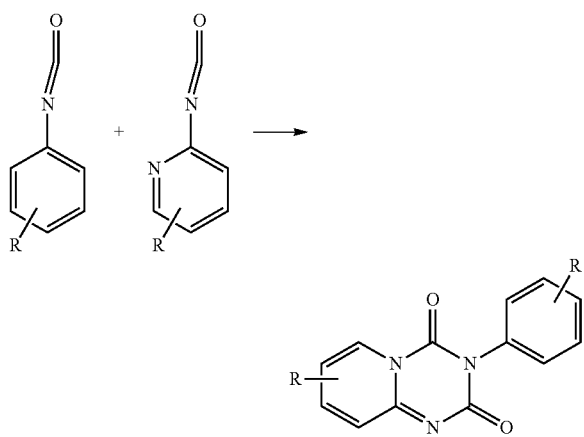

Journal of the Chemical Society, Chemical Communications, (7), 313-14; 1980

For the processing of the compounds of formula (1) or the preferred embodiments from the liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The compounds of the formula (1) or the above-detailed preferred embodiments are used in accordance with the invention in an electronic device, especially in an organic electroluminescent device.

An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem OLED, especially for white-emitting OLEDs.

The compound according to the above-detailed embodiments may be used in different layers, according to the exact structure. Preference is given to an organic electroluminescent device comprising a compound of formula (1) or the above-recited preferred embodiments in an emitting layer as matrix material for phosphorescent emitters or for emitters that exhibit TADF (thermally activated delayed fluorescence), especially for phosphorescent emitters. In this case, the organic electroluminescent device may contain an emitting layer, or it may contain a plurality of emitting layers, where at least one emitting layer contains at least one compound of the invention as matrix material. In addition, the compound of the invention can also be used in an electron transport layer and/or in a hole blocker layer and/or in a hole transport layer and/or in an exciton blocker layer.

When the compound is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

The mixture of the compound of the formula (1) or of the preferred embodiments and the emitting compound contains between 99% and 1% by volume, preferably between 98% and 10% by volume, more preferably between 97% and 60% by volume and especially between 95% and 80% by volume of the compound of the formula (1) or of the preferred embodiments, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the formula (1) or of the preferred embodiments as matrix material for a phosphorescent emitter in combination with a further matrix material. Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, or dibenzofuran derivatives, for example according to WO 2015/169412, WO 2016/015810, WO 2016/023608, WO 2017/148564 or WO 2017/148565. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

In a preferred embodiment of the invention, the materials are used in combination with a further matrix material. The compounds of the formula (1) or the preferred embodiments are electron-deficient compounds. Preferred co-matrix materials are therefore selected from the group of the biscarbazoles, the bridged carbazoles, the triarylamines, the dibenzofuran-carbazole derivatives or dibenzofuran-amine derivatives, and the carbazoleamines.

Preferred biscarbazoles are the structures of the following formulae (9) and (10):

Formula (9)

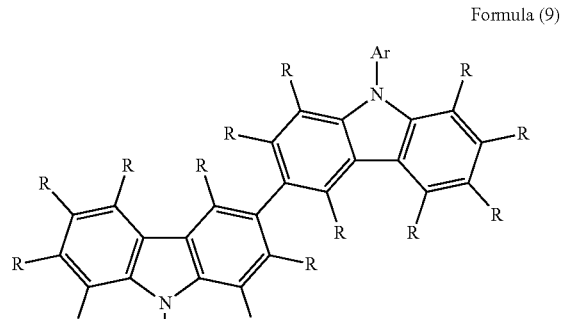

Formula (10)

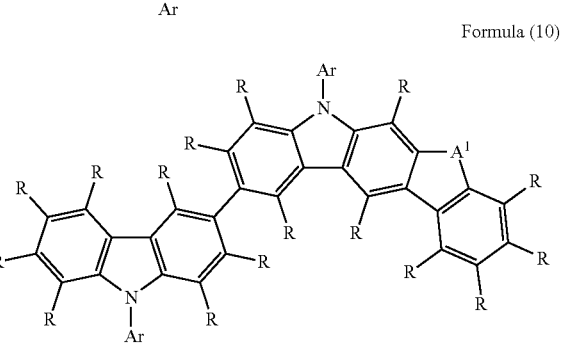

where R, $Ar^1$ and $A^1$ have the definitions given above. In a preferred embodiment of the invention, $A^1$ is $CR_2$.

Preferred embodiments of the compounds of the formulae (9) and (10) are the compounds of the following formulae (9a) and (10a):

Formula (9a)

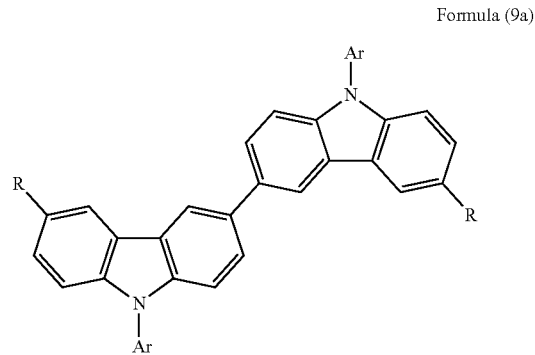

Formula (10a)

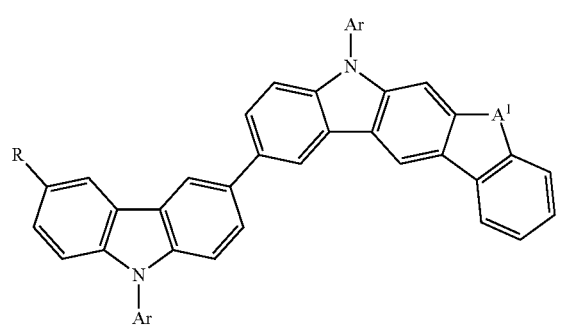

where the symbols used have the definitions given above.

Examples of suitable compounds of formulae (9) and (10) are the compounds depicted below:
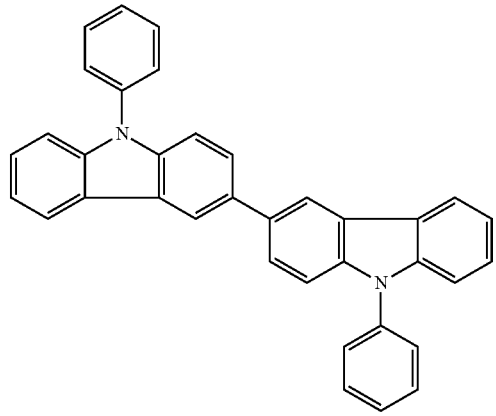
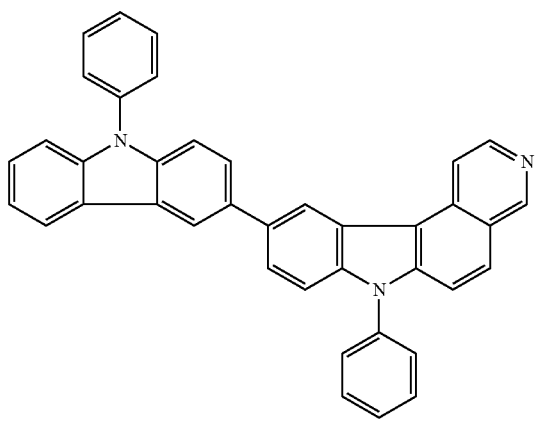
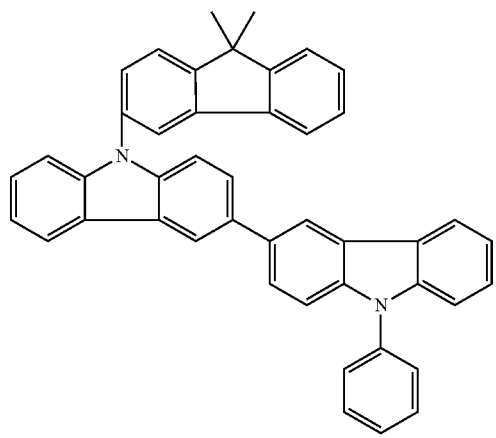
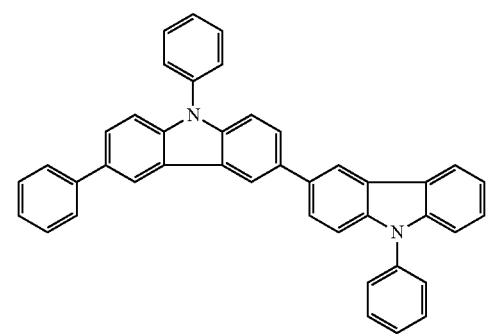
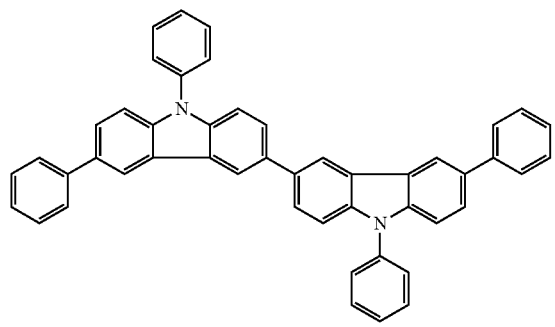
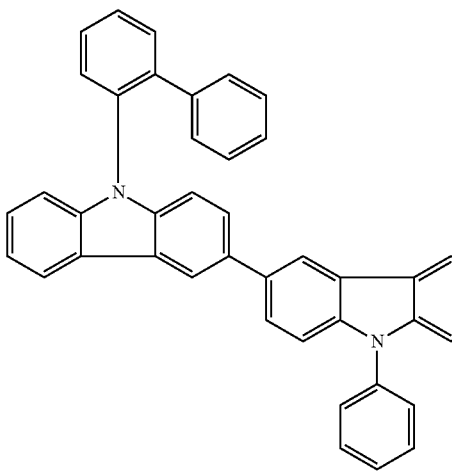
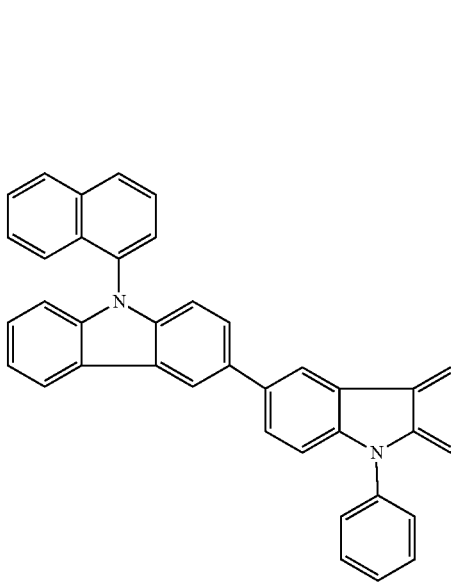

131
-continued
132
-continued
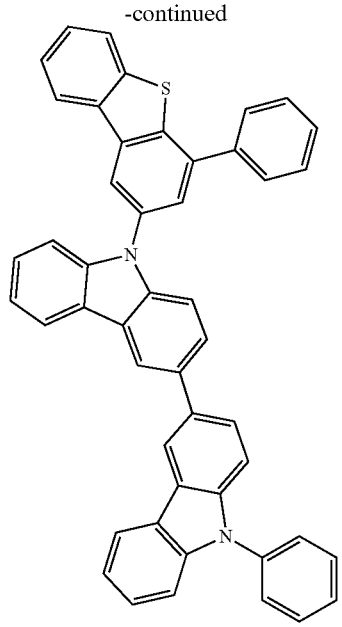
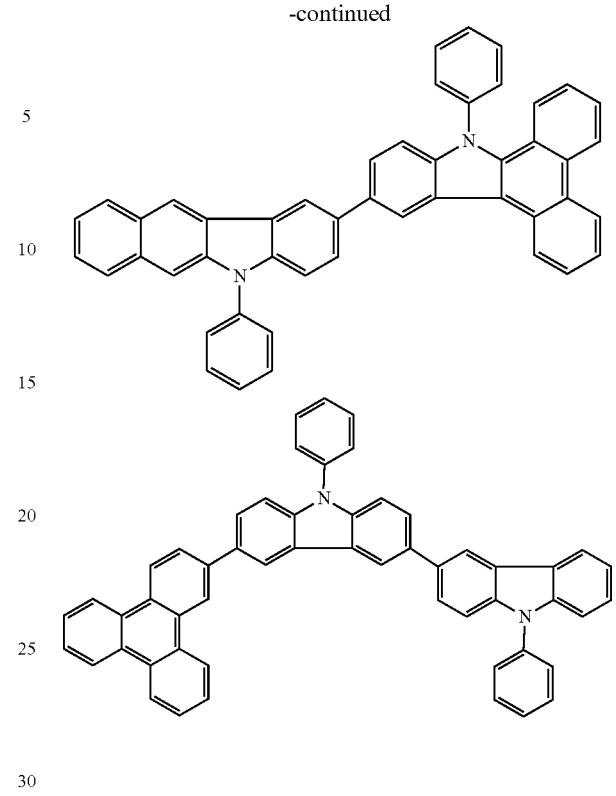
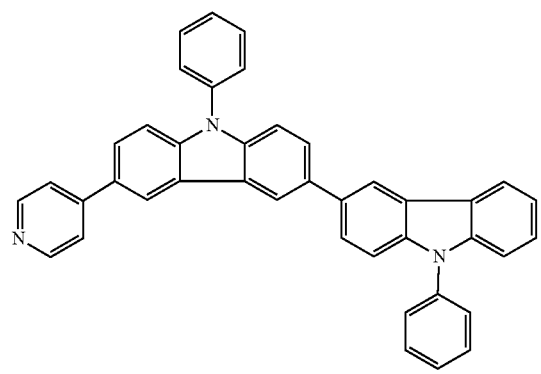
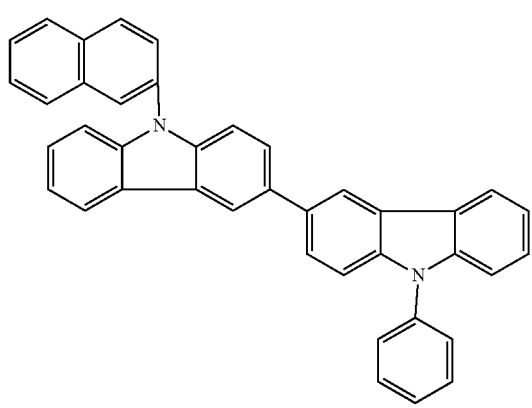

133
-continued
134
-continued
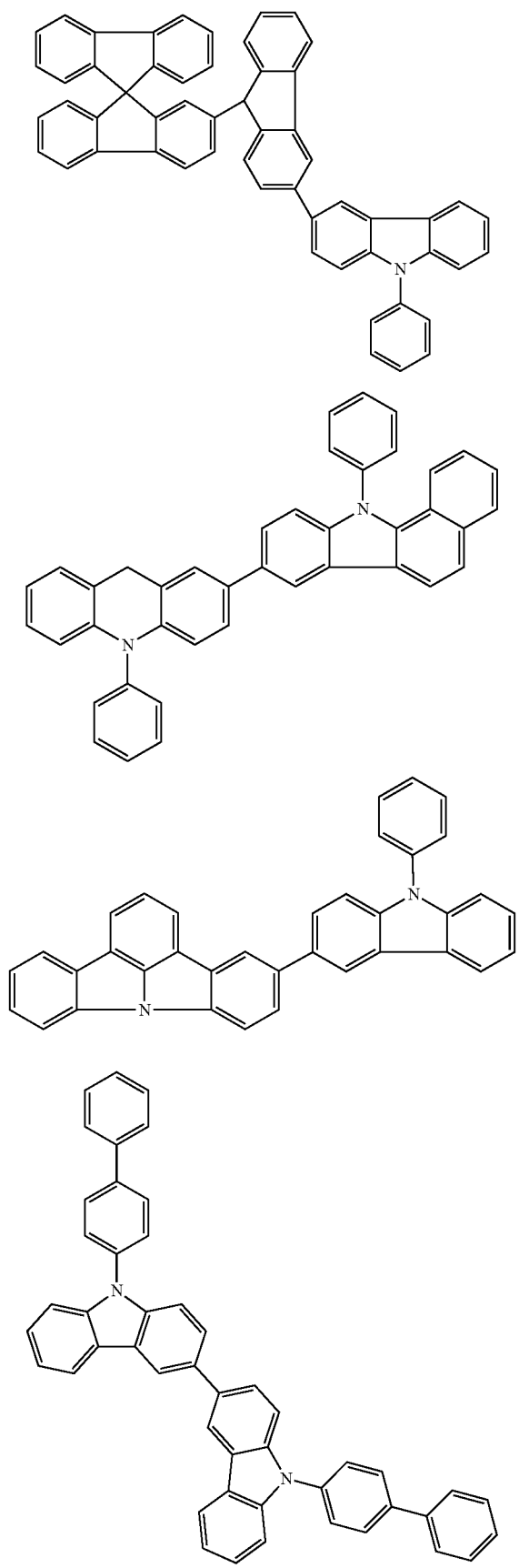
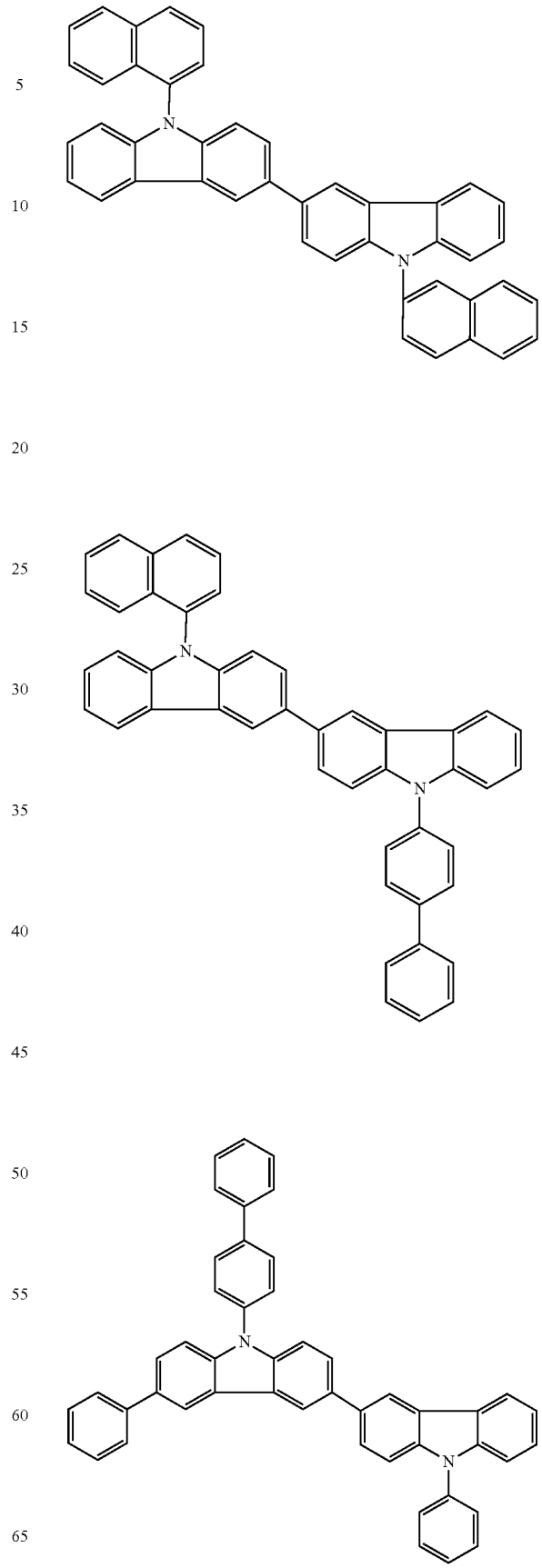

135
-continued
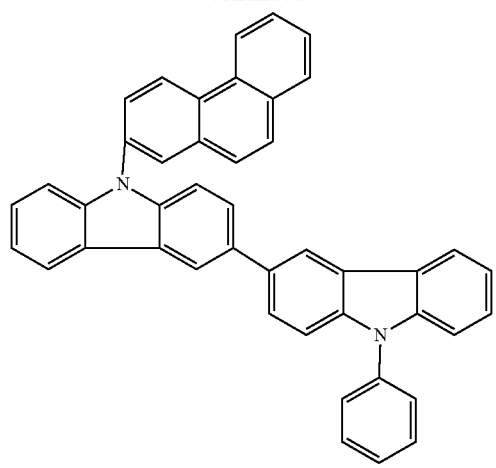
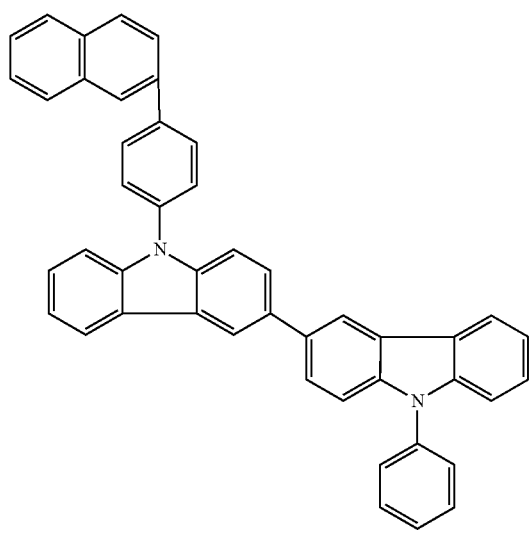
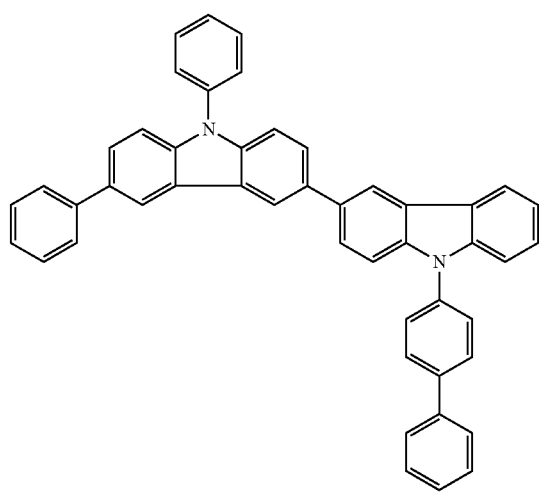
136
-continued
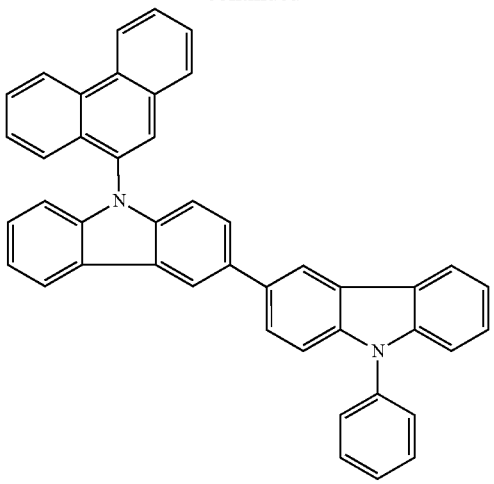
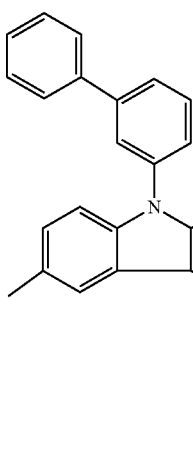
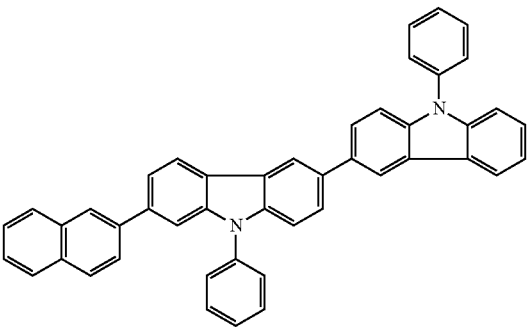

137
-continued
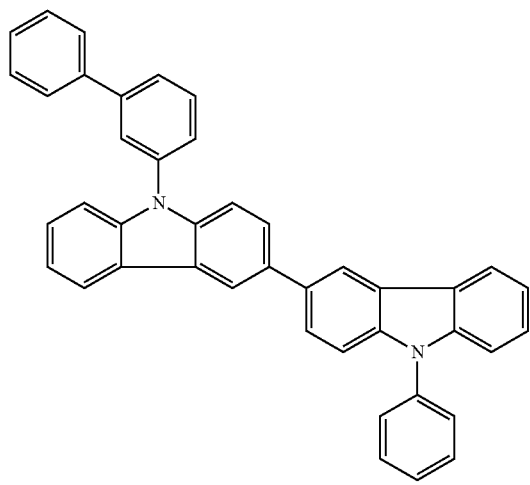
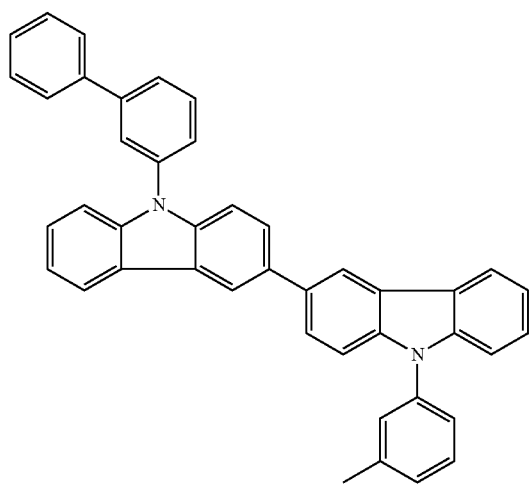
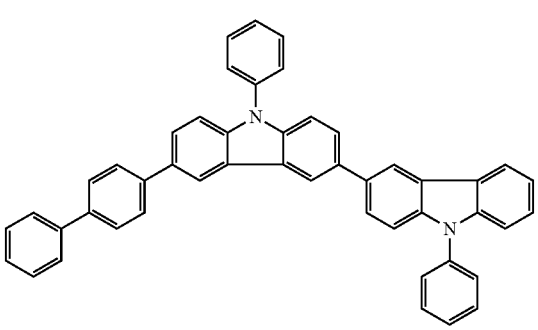
138
-continued
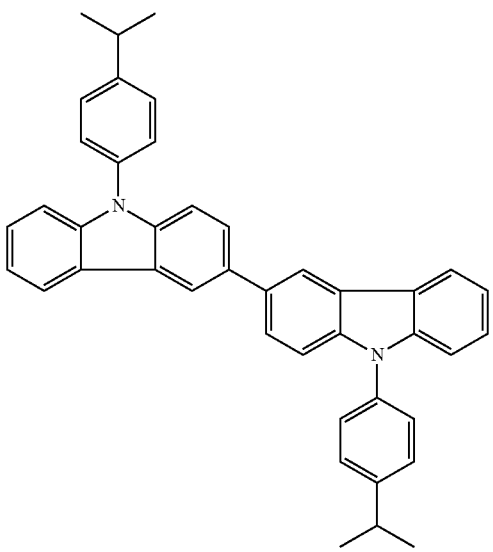
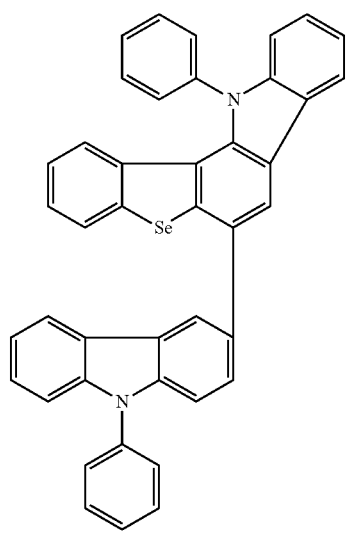
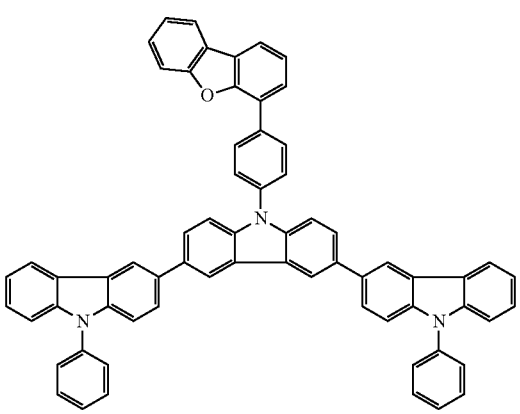

139
-continued
140
-continued
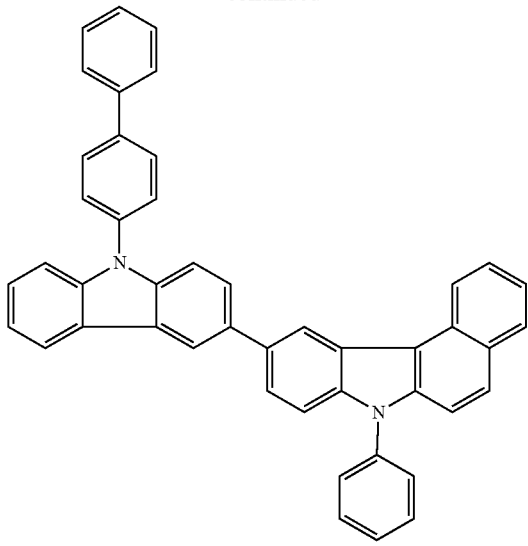
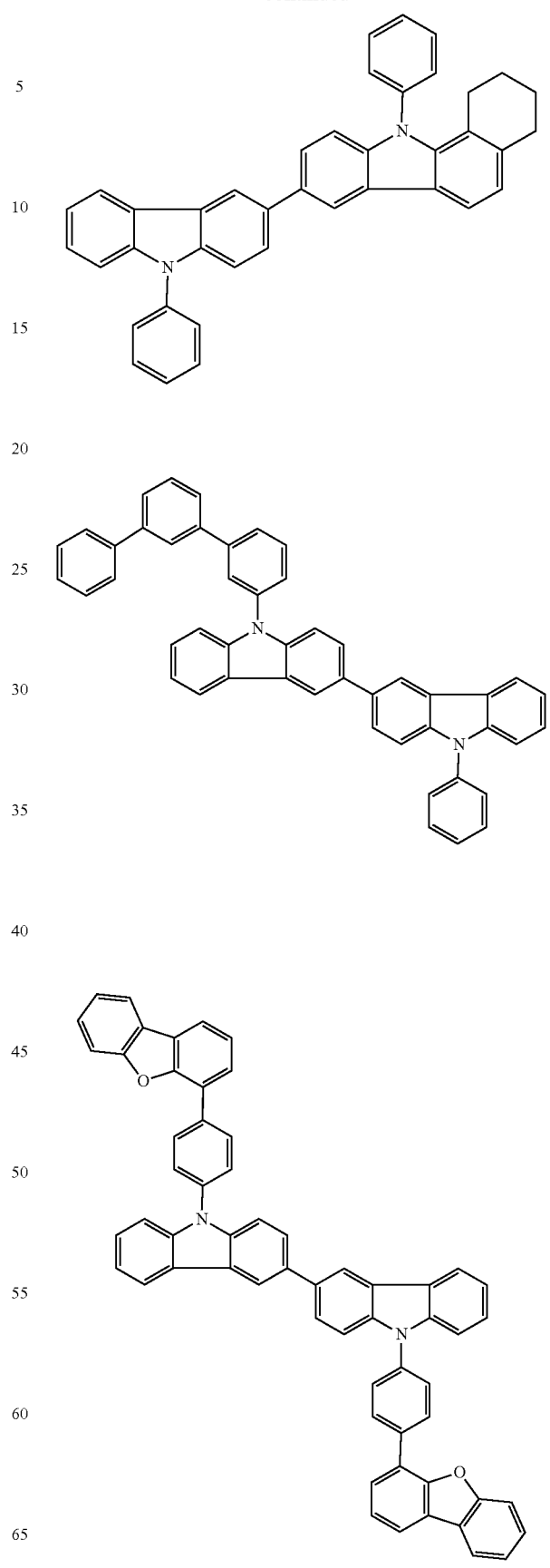

-continued
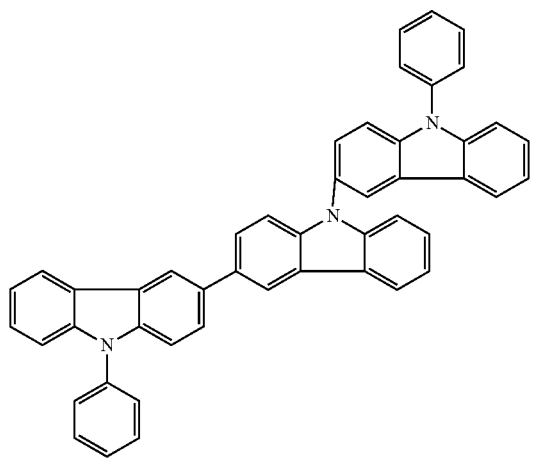
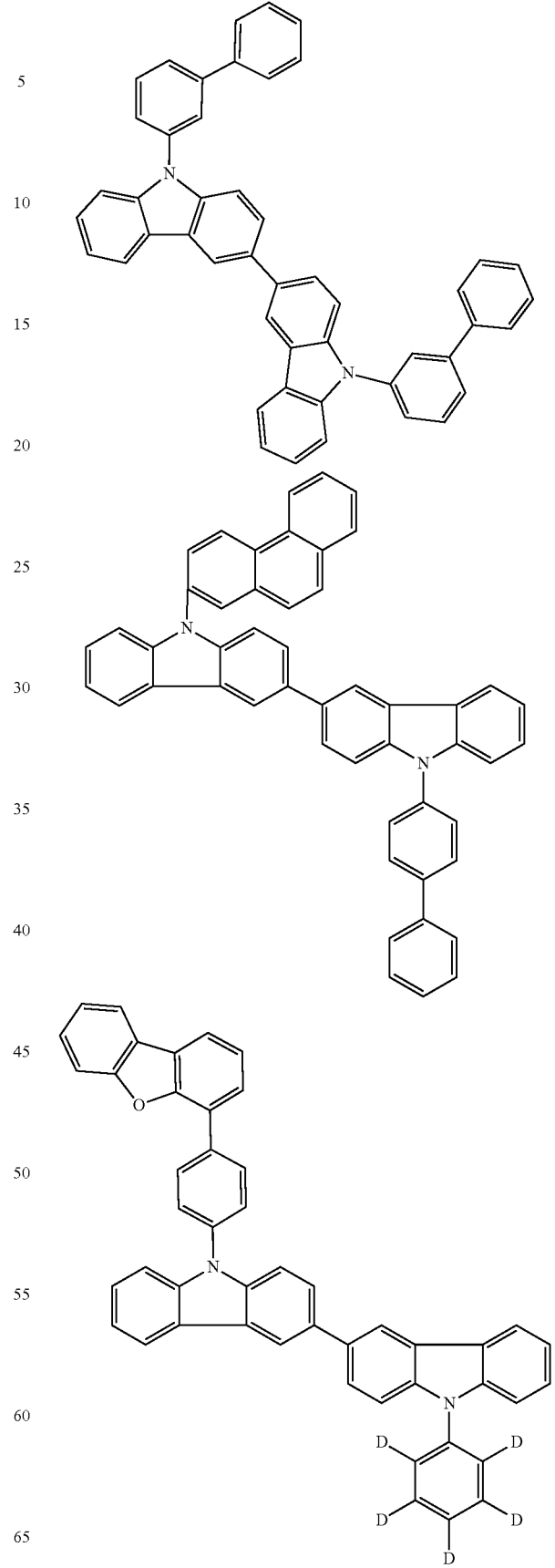

-continued
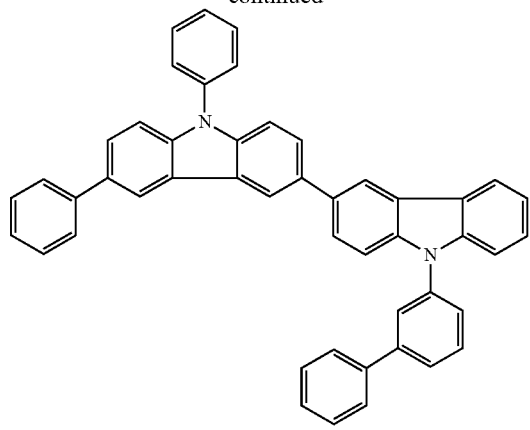
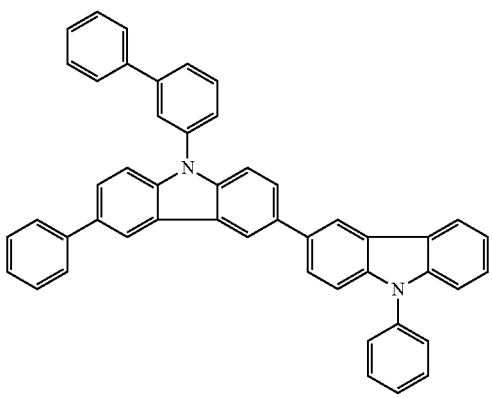
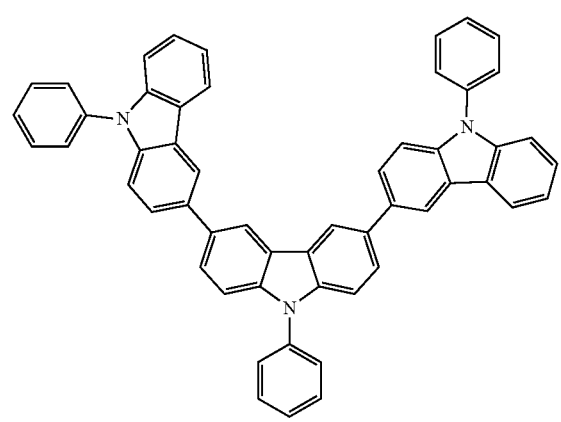
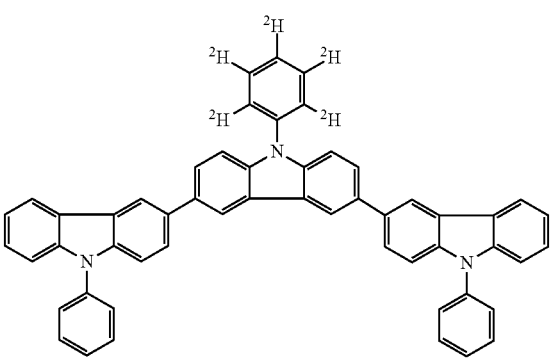
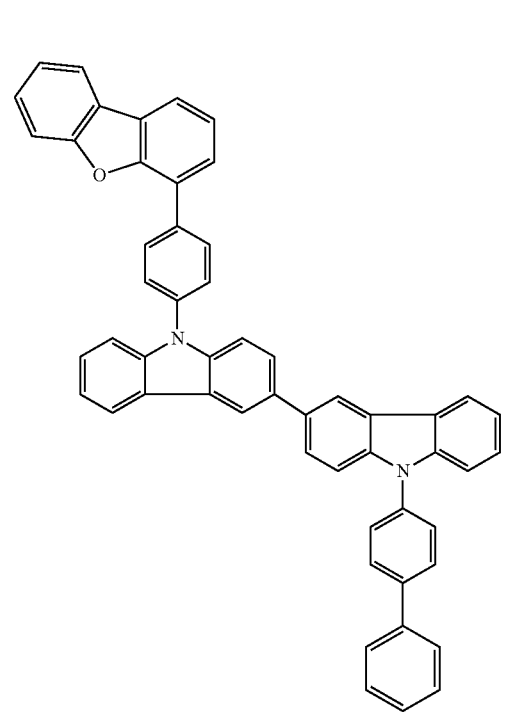
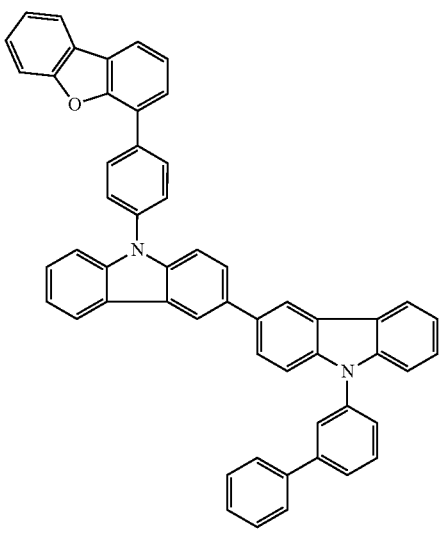

145
-continued
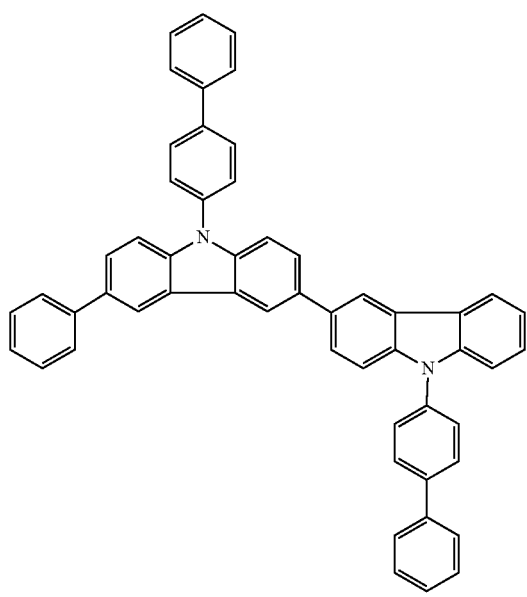
146
-continued
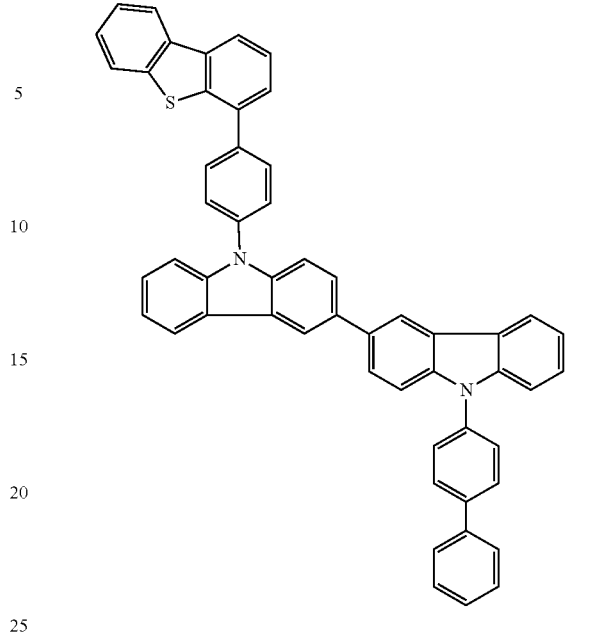
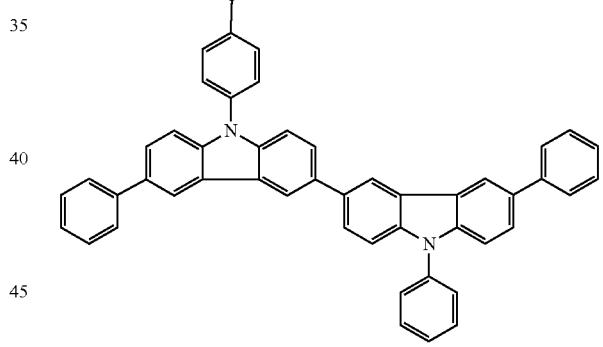
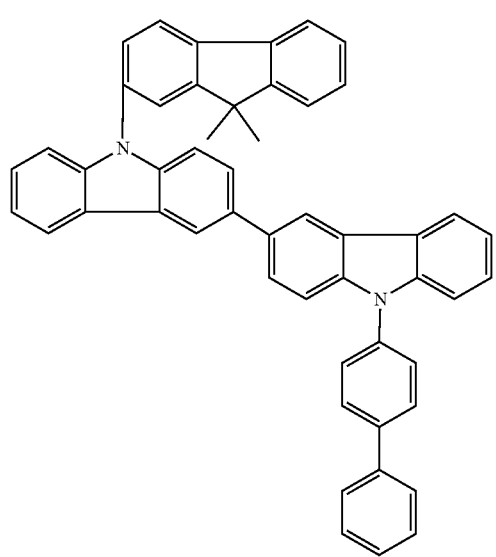
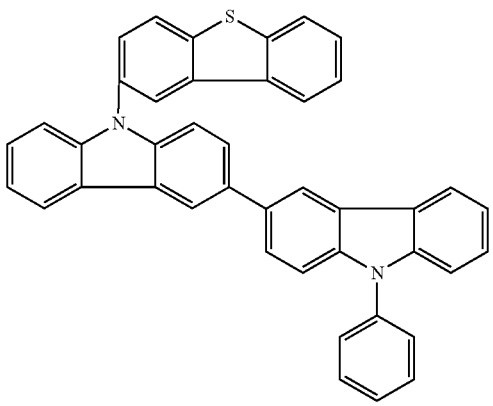

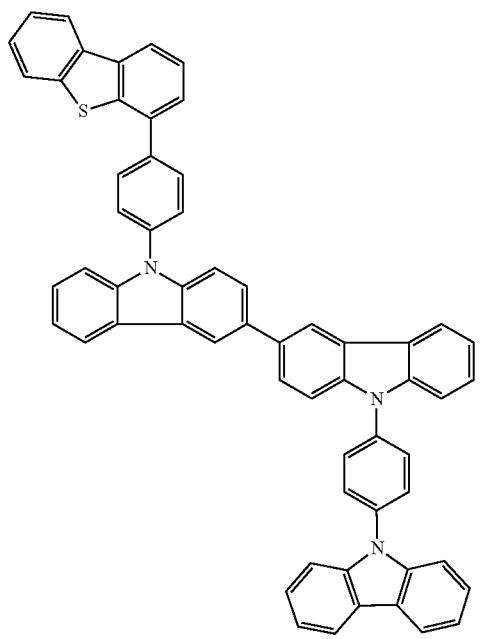
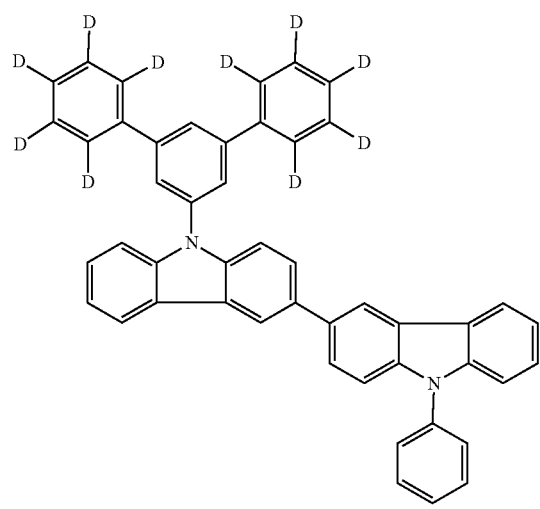
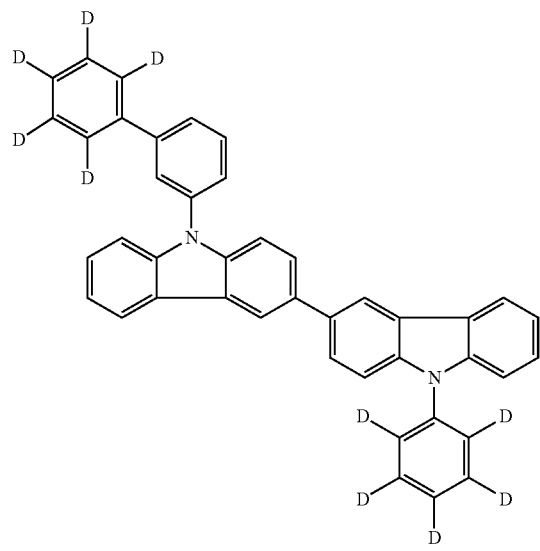
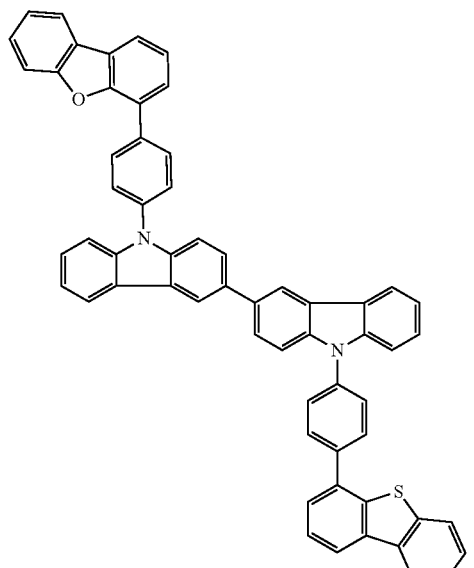
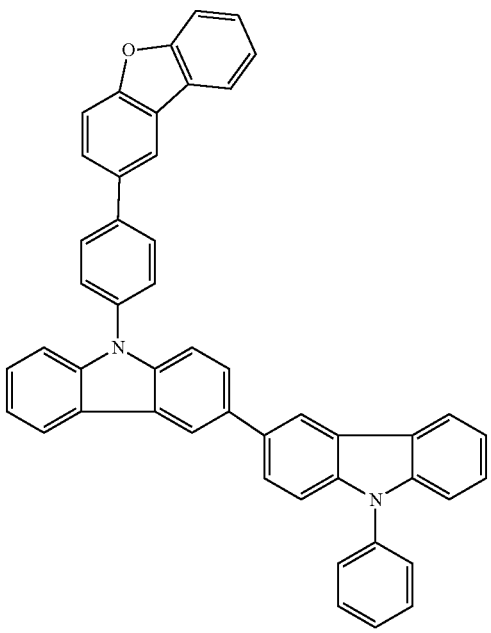

149
-continued
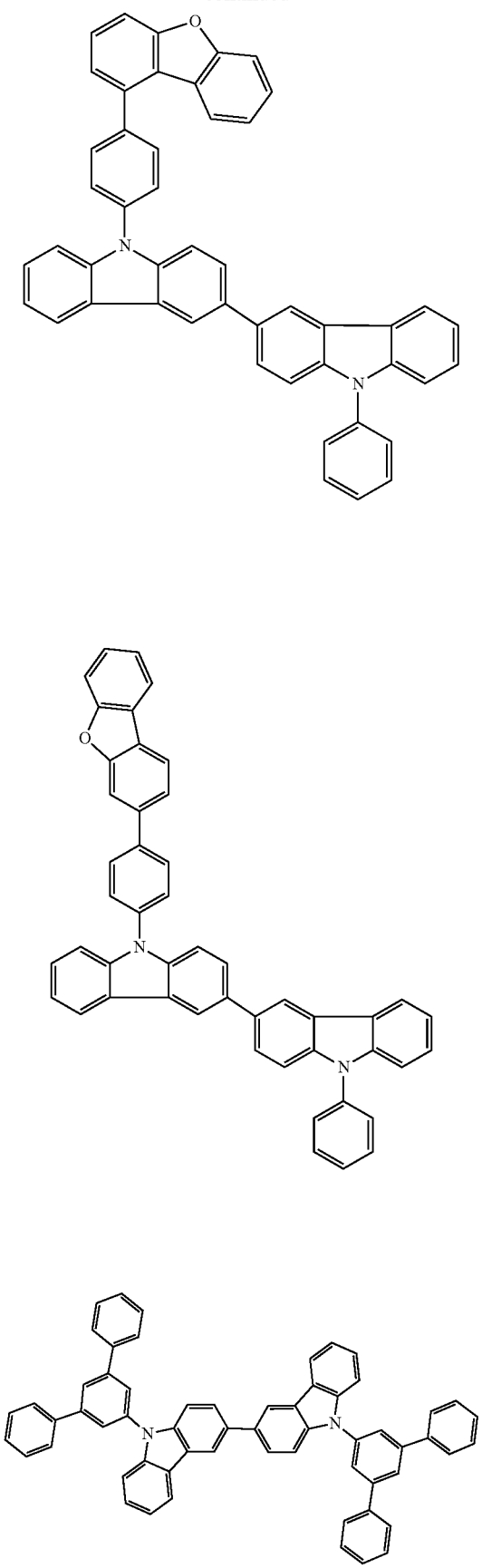
150
-continued
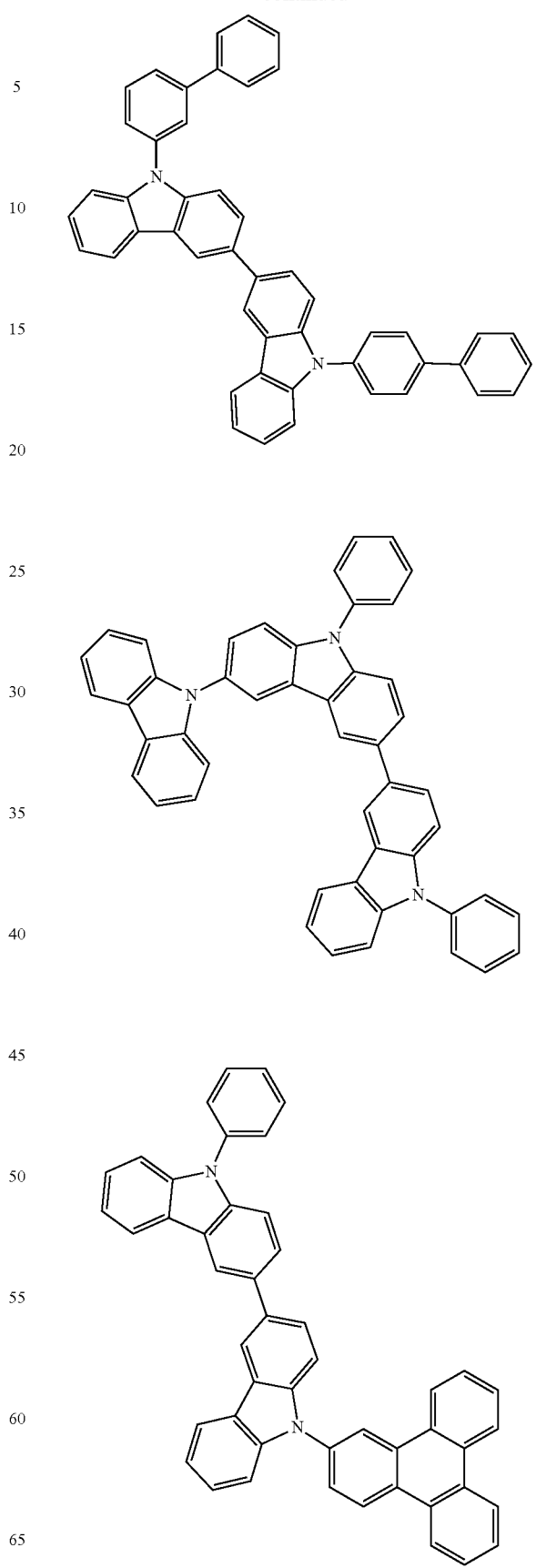

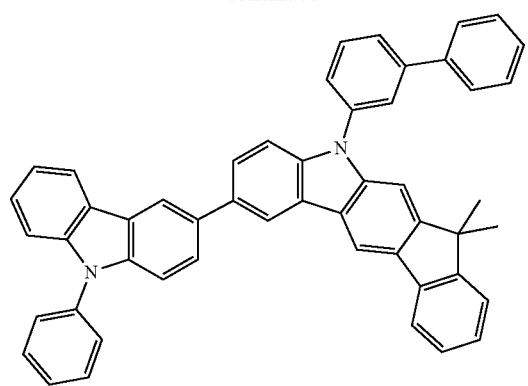
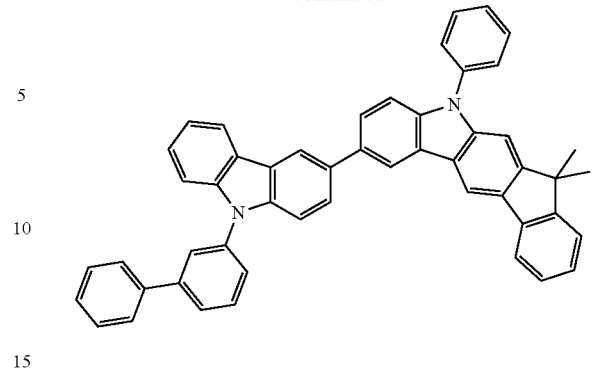
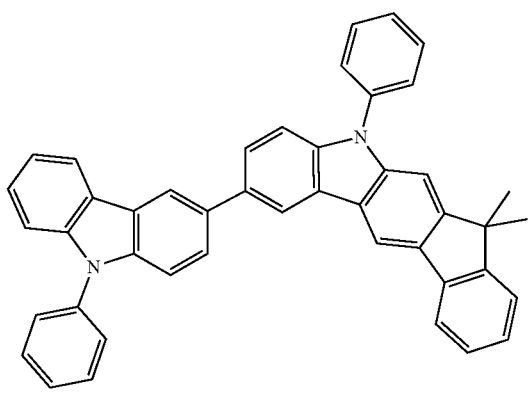
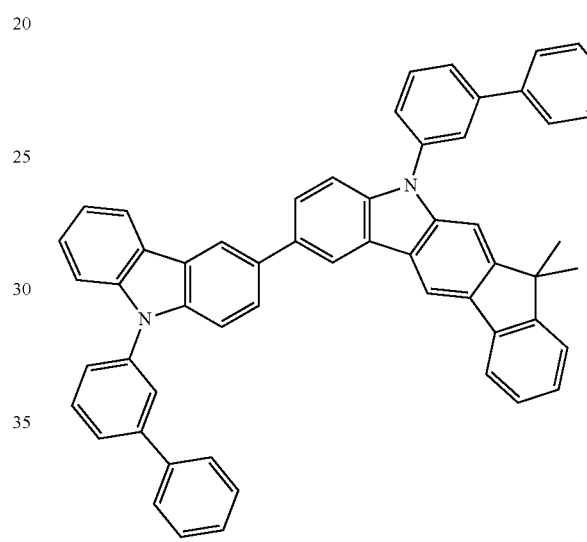
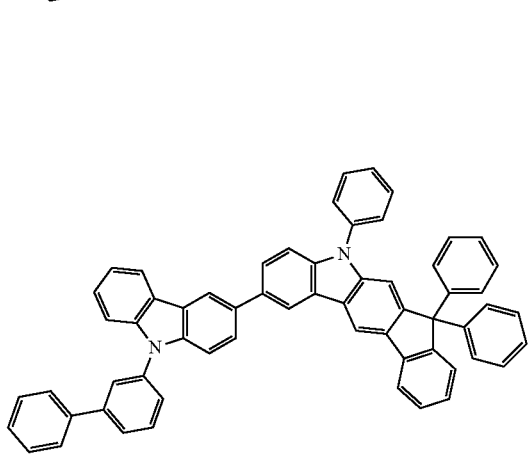
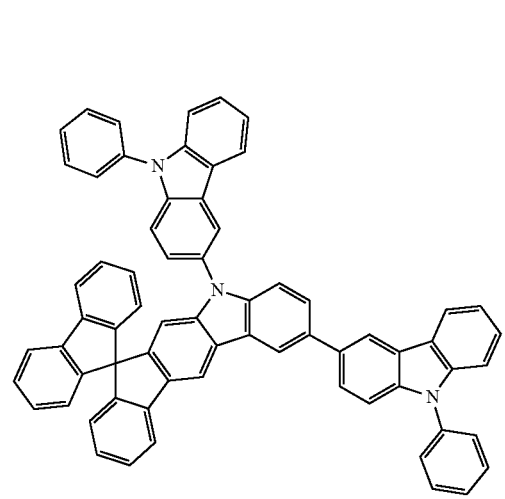
Preferred bridged carbazoles are the structures of the following formula (11):
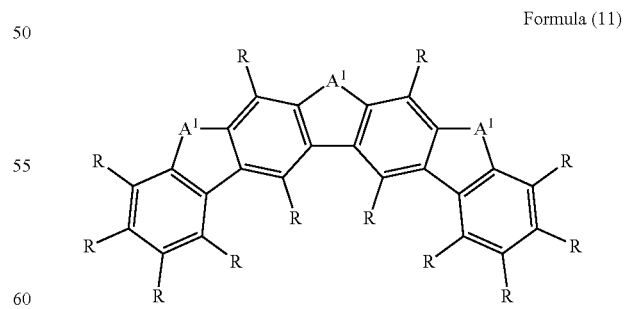
Formula (11)
where $A^1$ and R have the definitions given above and $A^1$ is preferably the same or different at each instance and is selected from the group consisting of $NAr^1$ and $CR_2$.

Preferred dibenzofuran derivatives are the compounds of the following formula (12):

Formula (12)

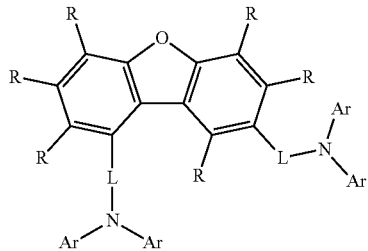

where the oxygen may also be replaced by sulfur so as to form a dibenzothiophene, L is a single bond or an aromatic or heteroaromatic ring system which has 5 to 30 aromatic ring atoms and may also be substituted by one or more R radicals, and R and $Ar^1$ have the definitions given above. It is also possible here for the two $Ar^1$ groups that bind to the same nitrogen atom, or for one $Ar^1$ group and one L group that bind to the same nitrogen atom, to be bonded to one another, for example to give a carbazole.

Examples of suitable dibenzofuran derivatives are the compounds depicted below.

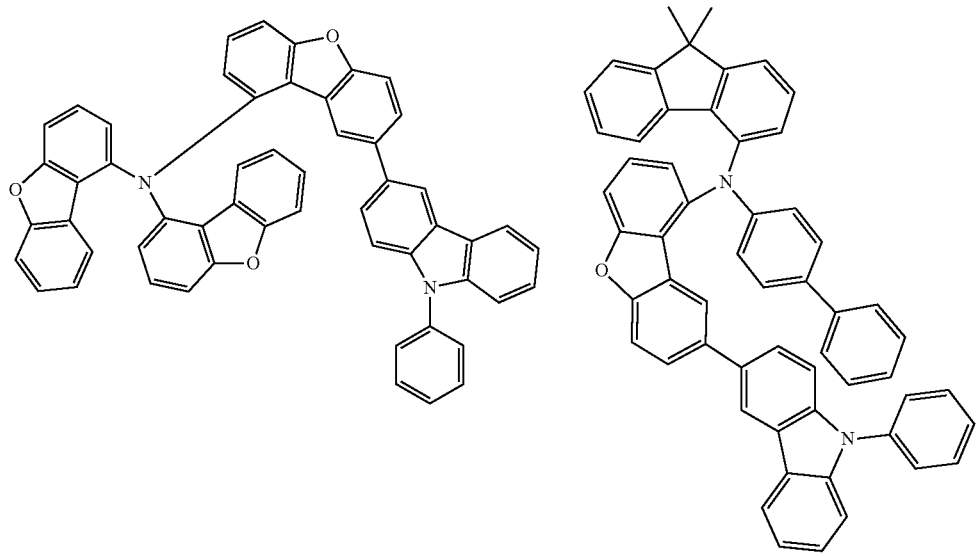

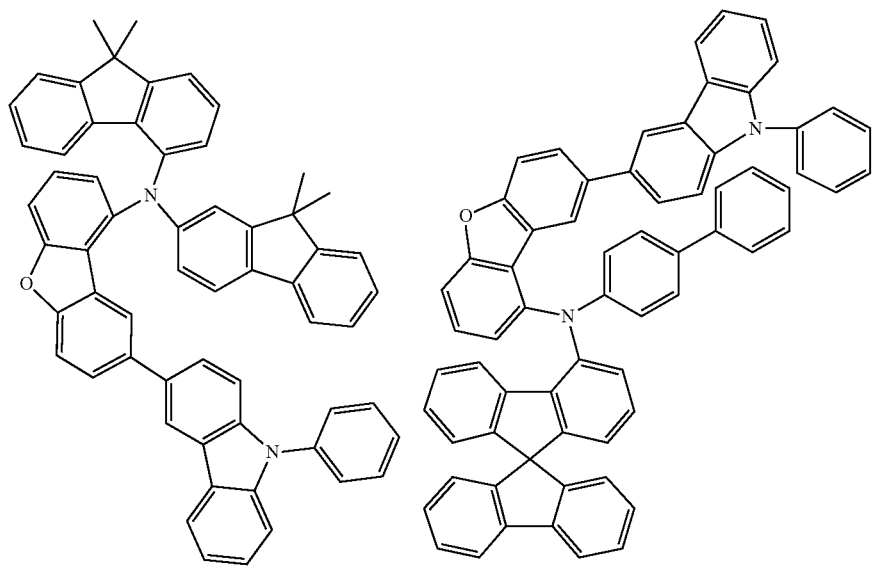

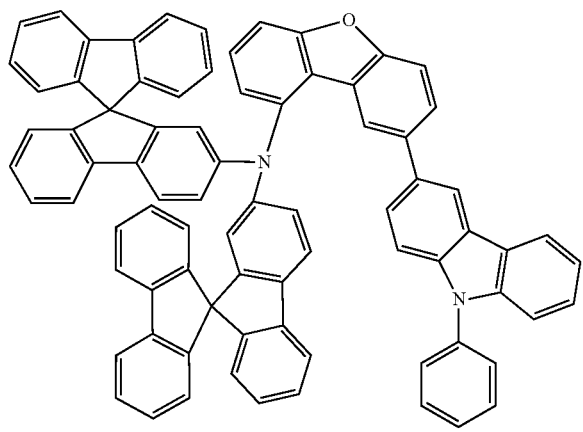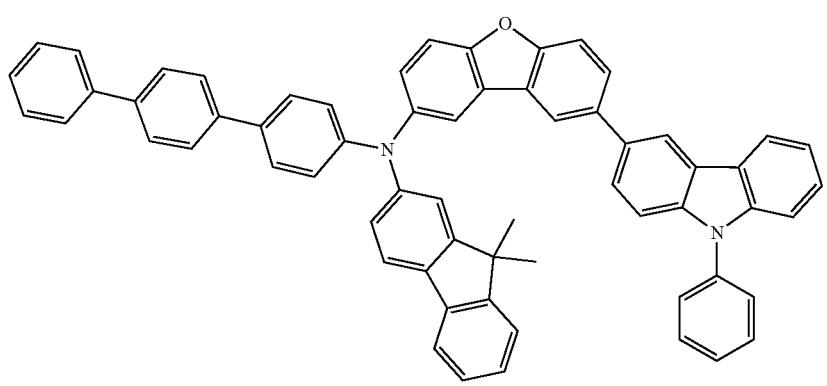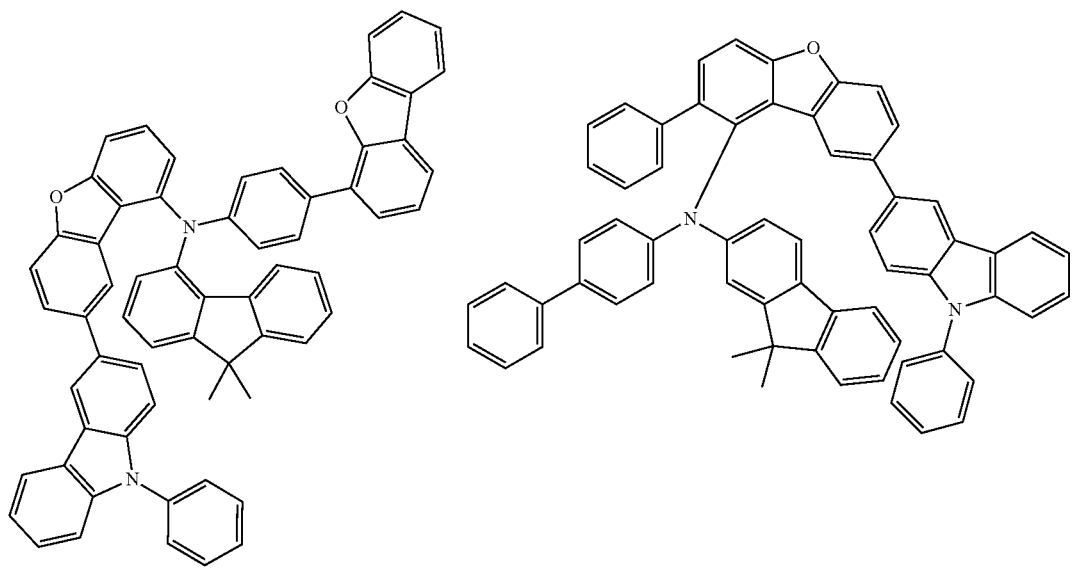

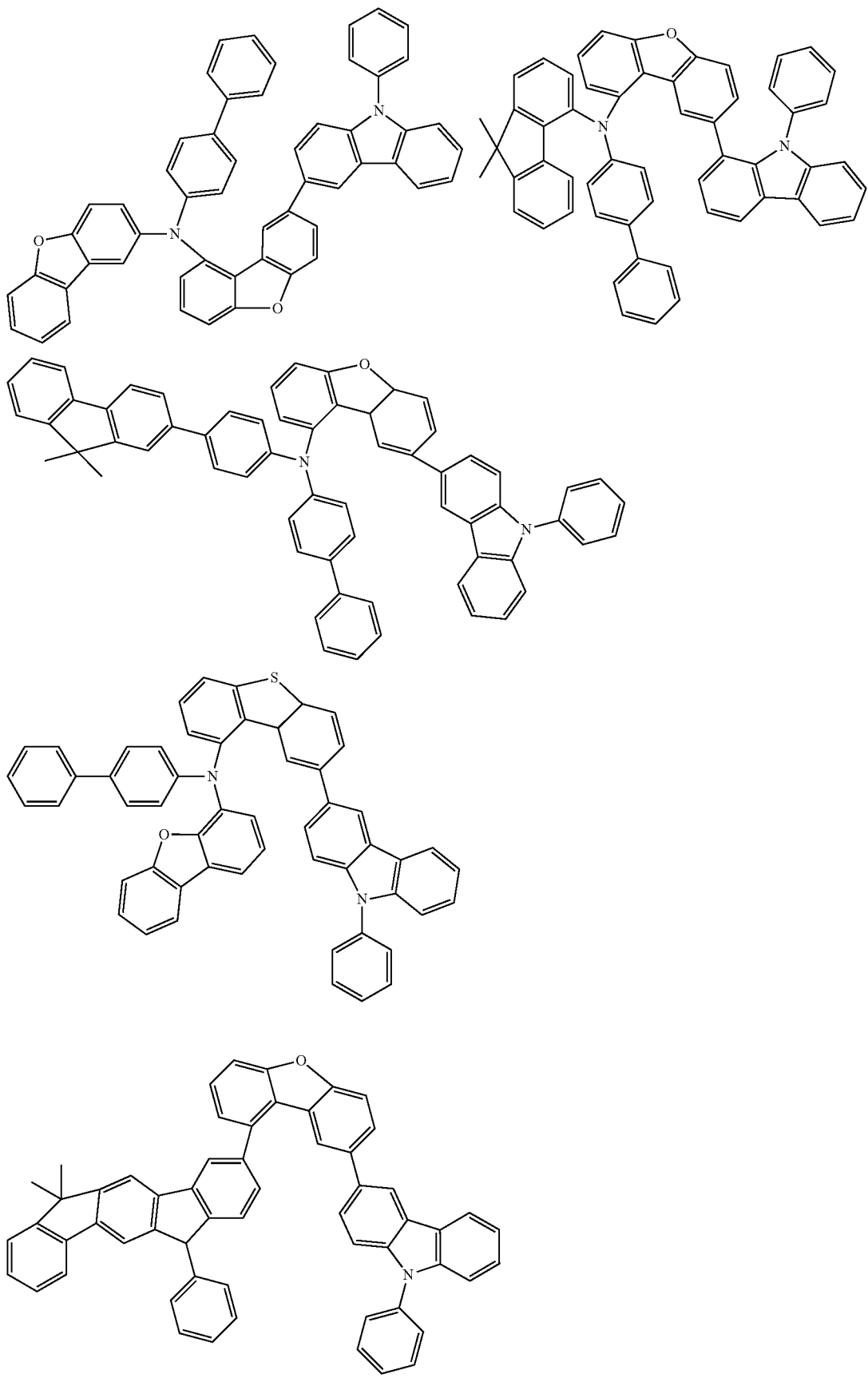

159 160
-continued
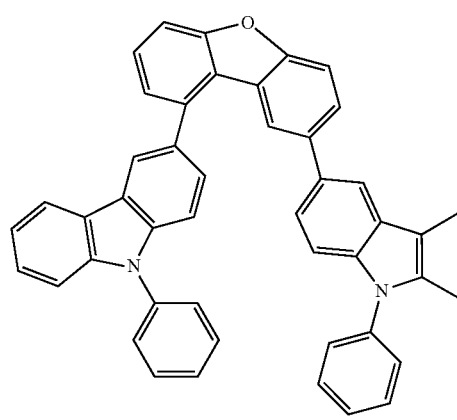
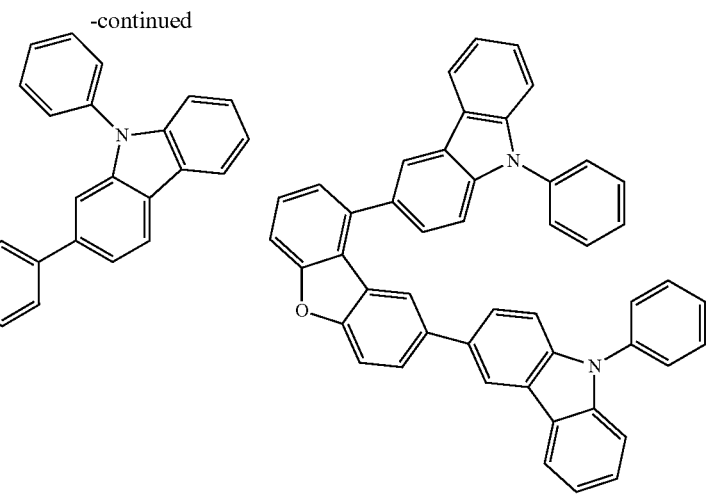
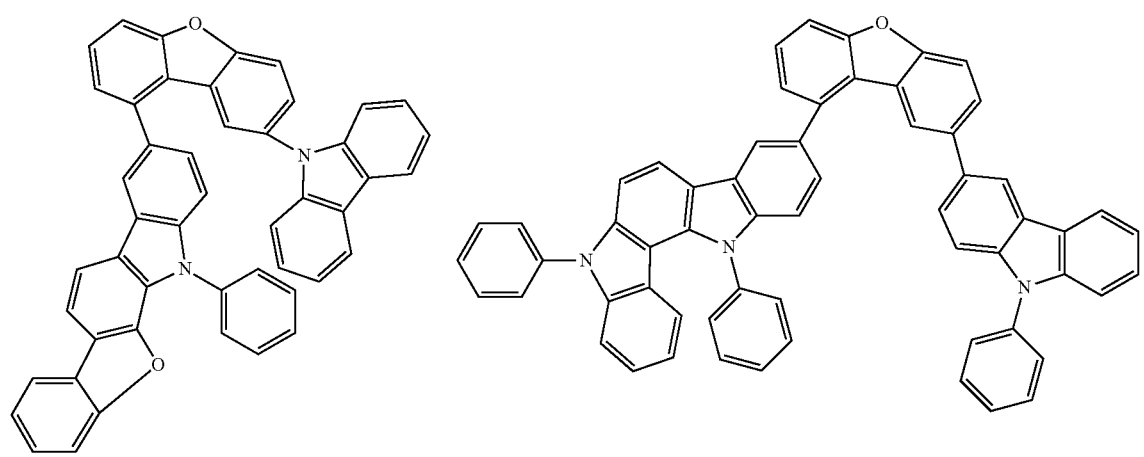
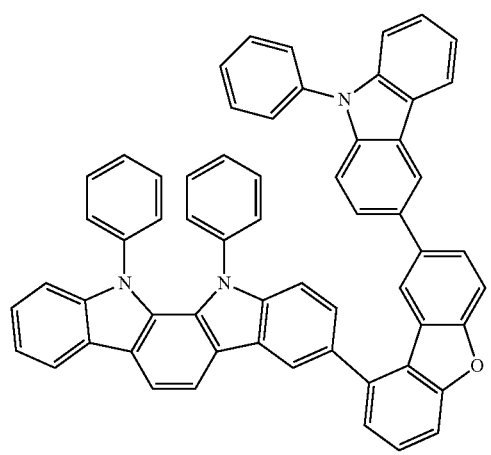

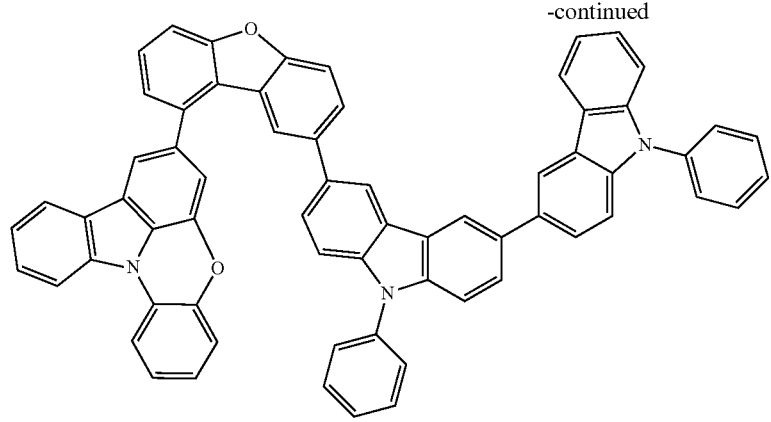
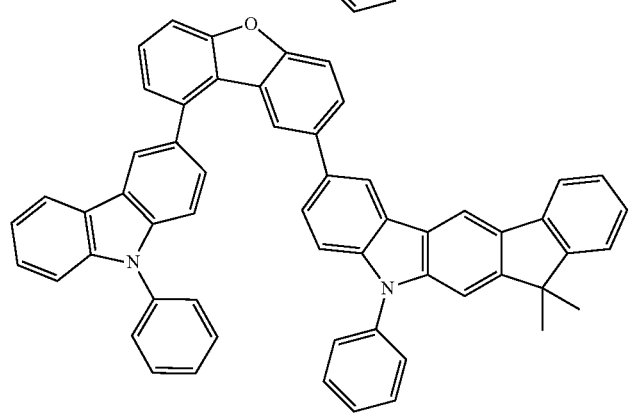
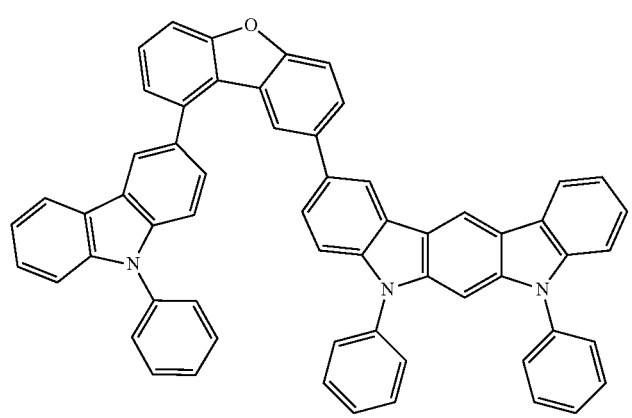 [SMILES: c1ccc(-n2c3ccccc3c3cc(-c4cccc5oc6ccc(-c7ccc8c(c7)c7cc9c%10ccccc%10n(-c%10ccccc%10)c9cc7n8-c7ccccc7)cc6c45)ccc32)cc1]
Preferred carbazoleamines are the structures of the following formulae (13), (14) and (15):
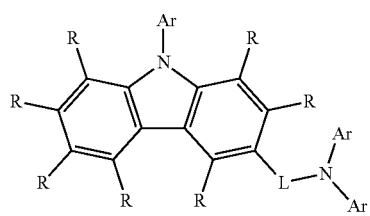
Formula (13)
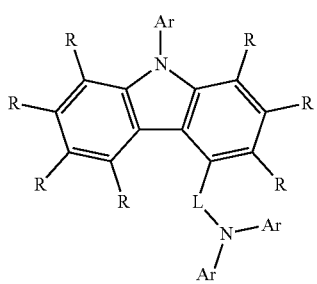
Formula (14)

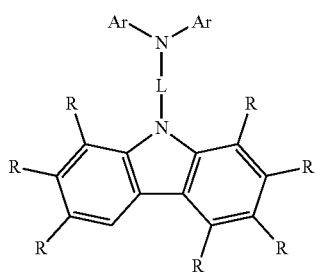
Formula (15)
where L is an aromatic or heteroaromatic ring system which has 5 to 30 aromatic ring atoms and may be substituted by one or more R radicals, and R and Ar<sup>b</sup> have the definitions given above.
Examples of suitable carbazoleamine derivatives are the compounds depicted below.
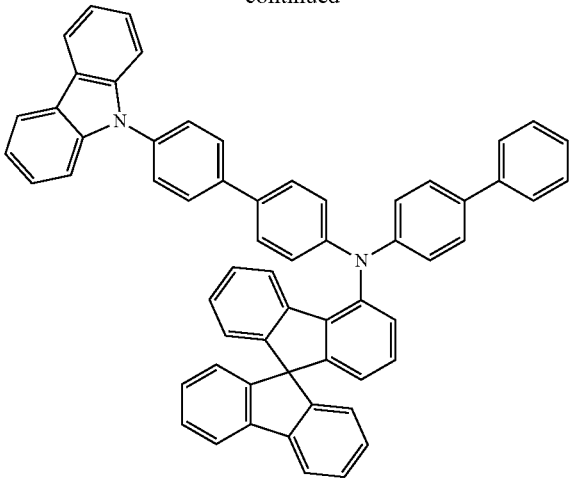
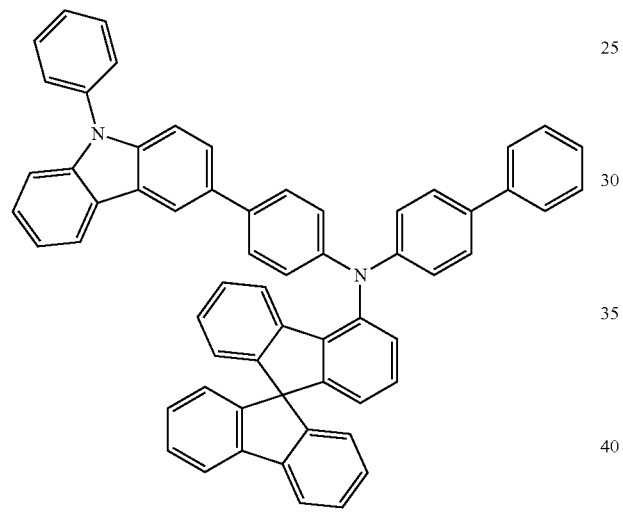
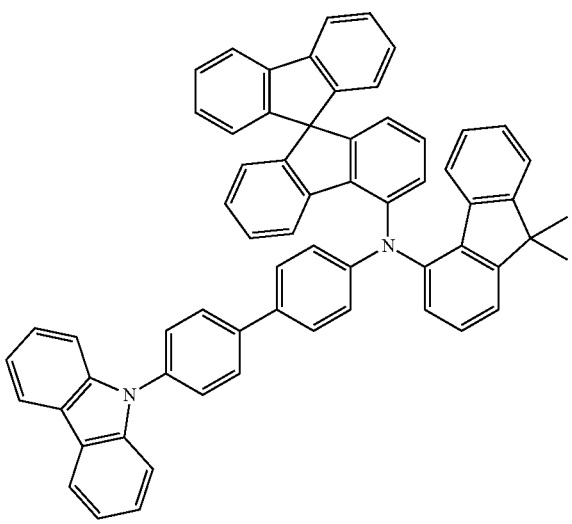
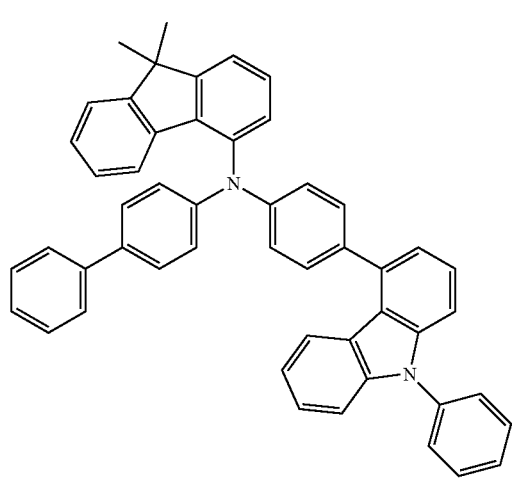
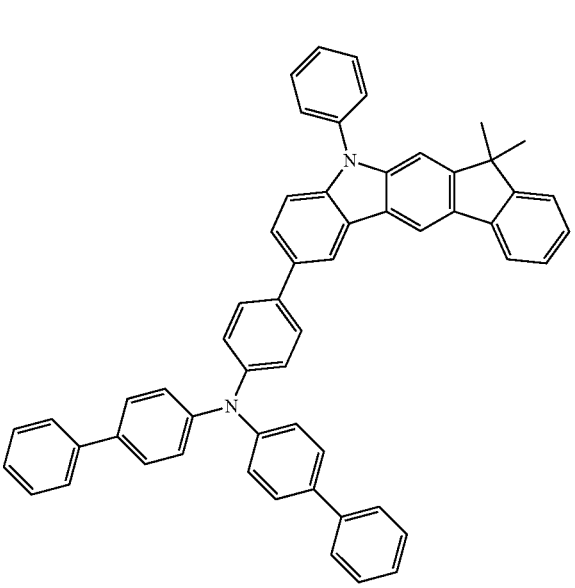

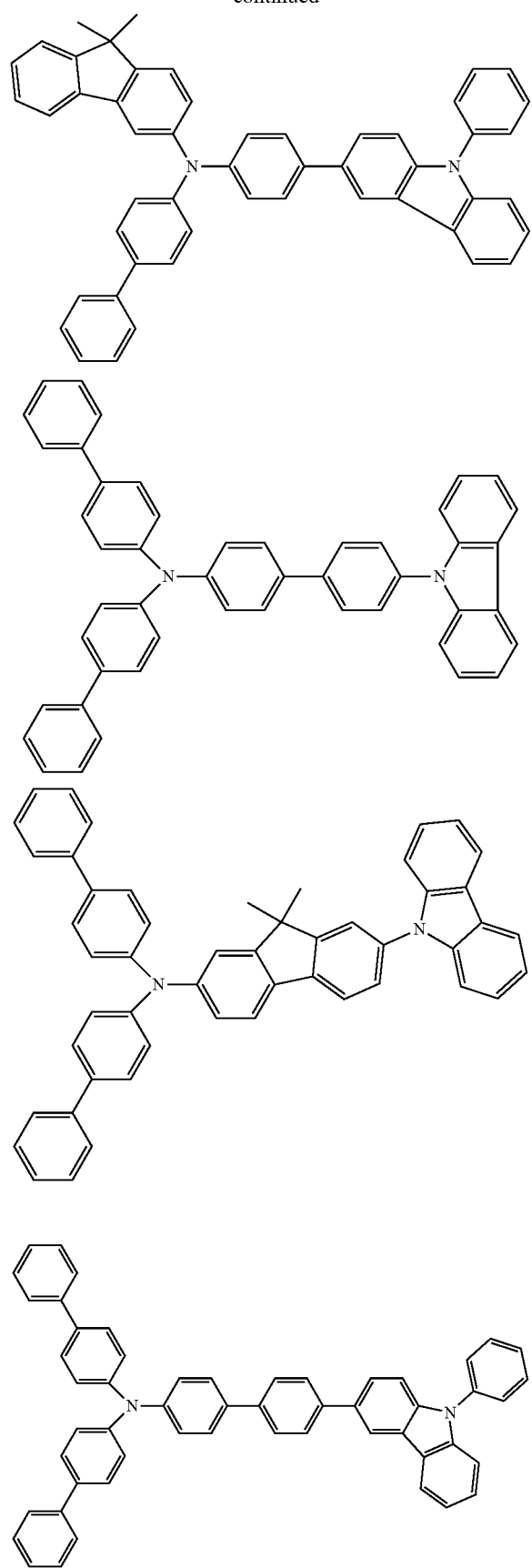
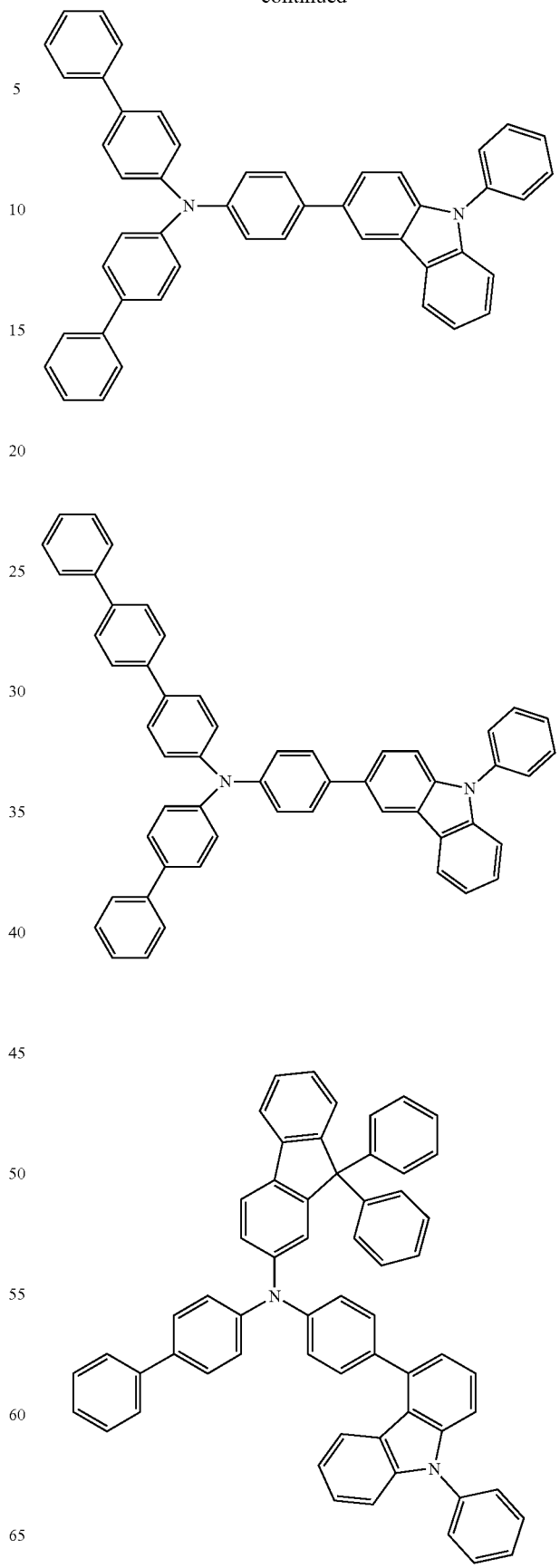

167
-continued
168
-continued
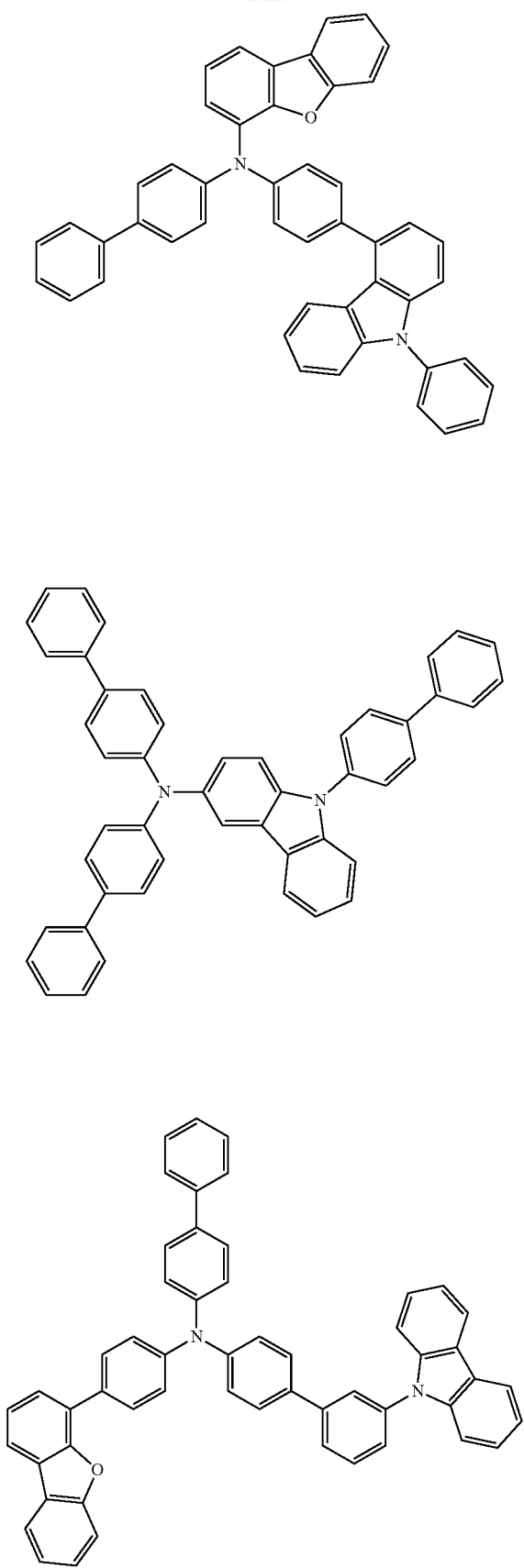
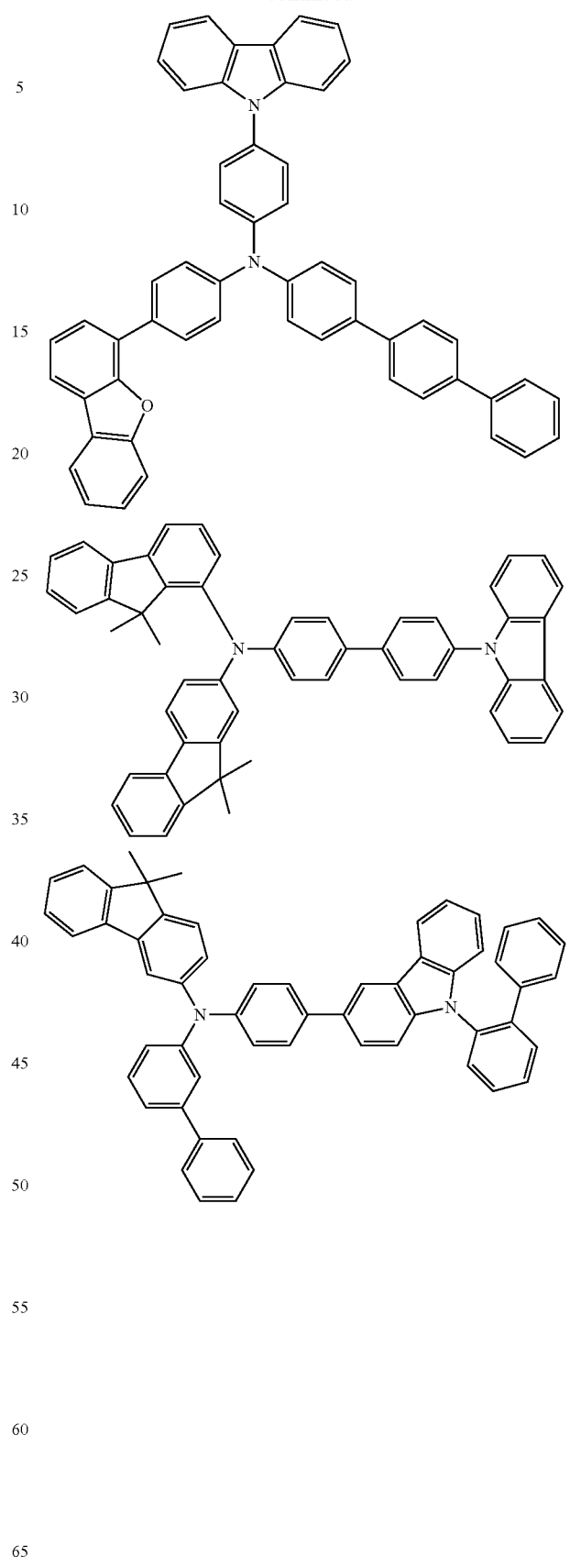

-continued

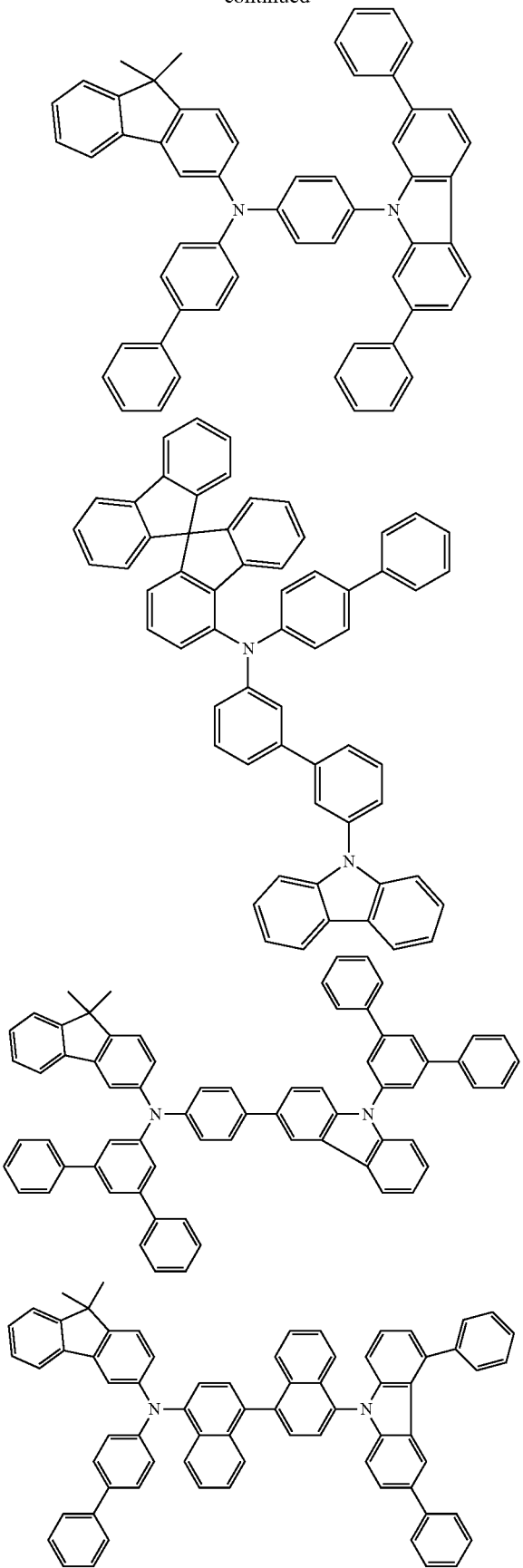

-continued

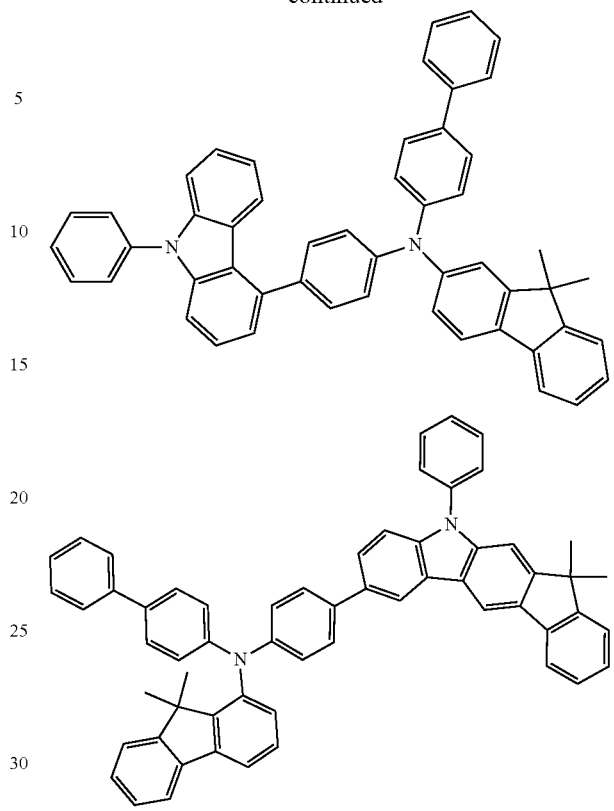

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the emitters described above can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186 and WO 2018/041769, WO 2019/020538, WO 2018/178001, WO 2019/115423, and the as yet unpublished patent application EP 18156388.3. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of phosphorescent dopants are adduced below.
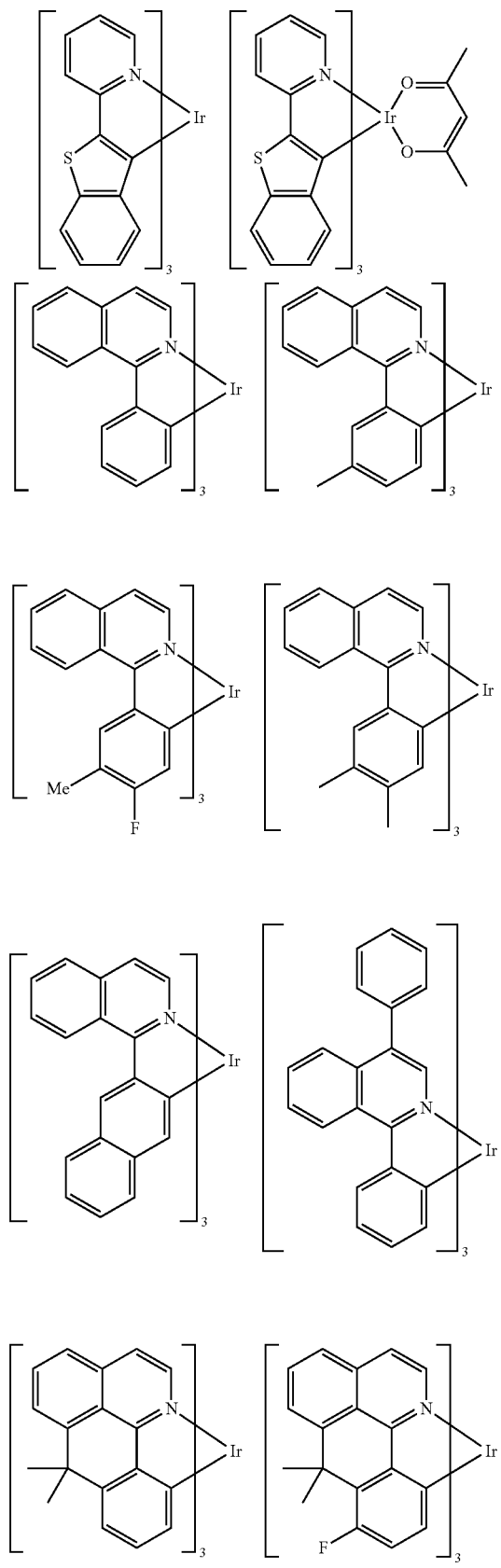
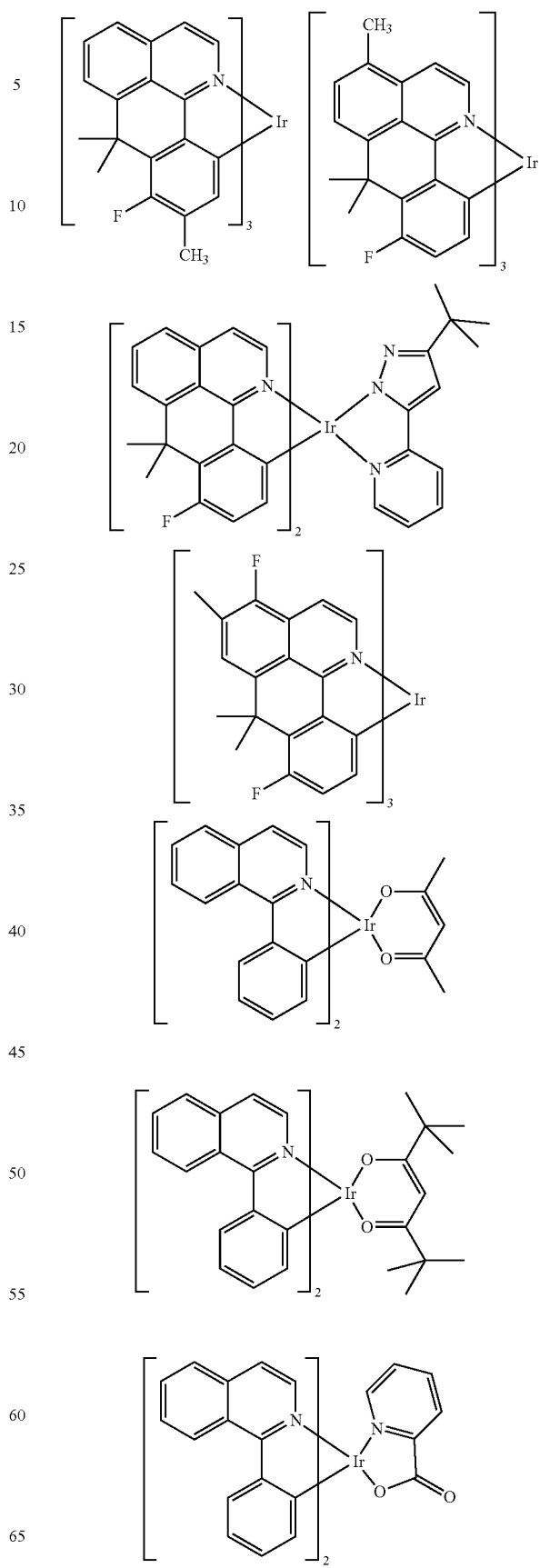
-continued

173
-continued
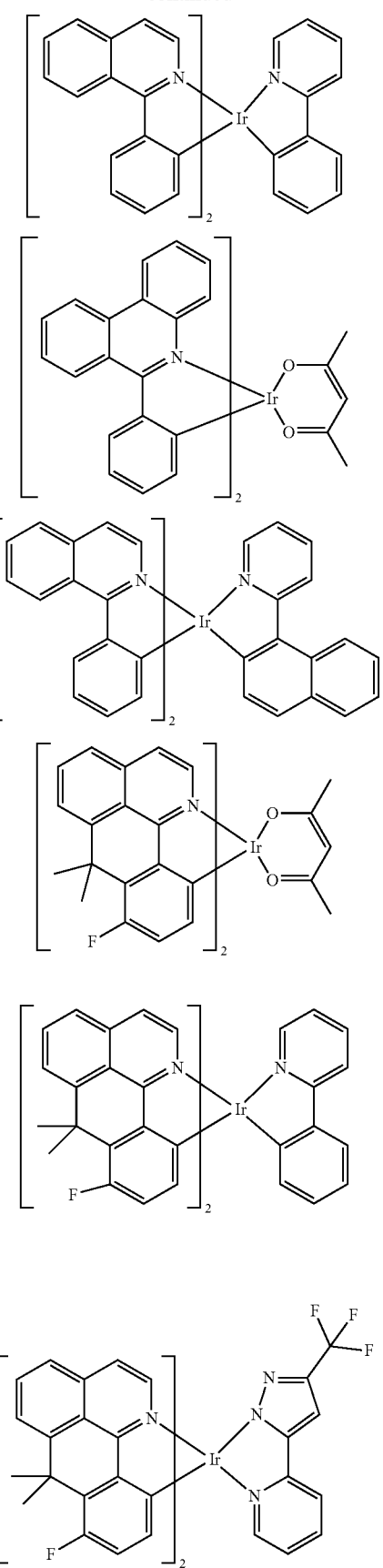
174
-continued
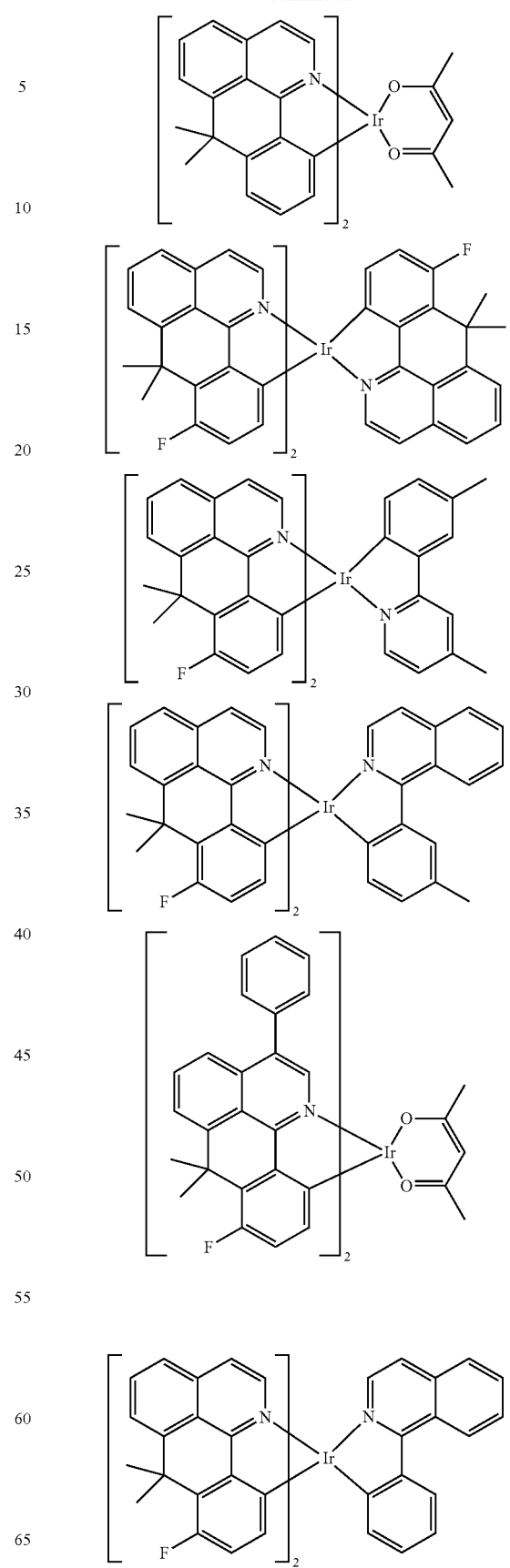

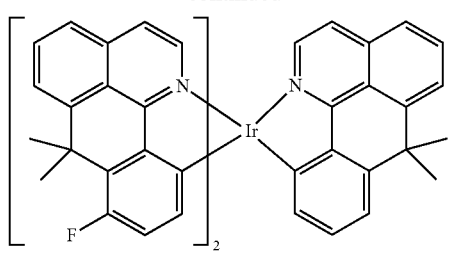
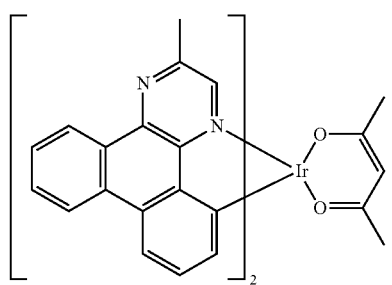
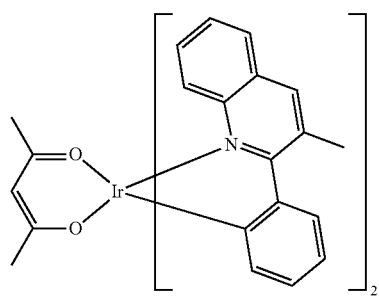
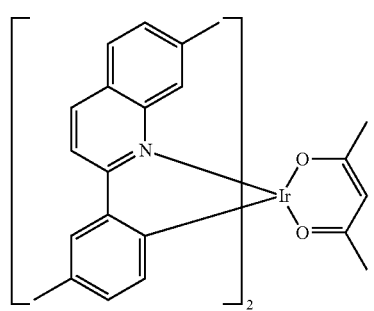
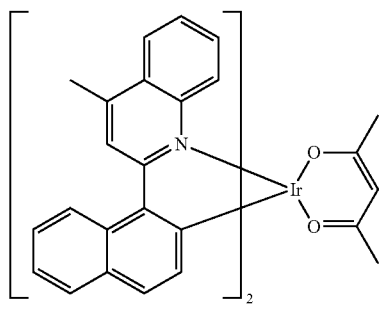
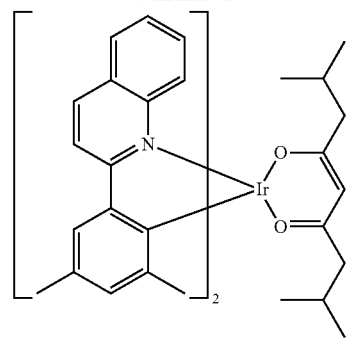
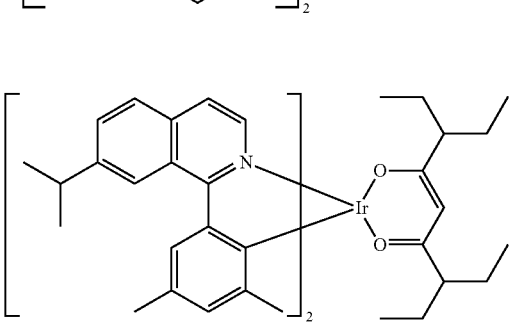
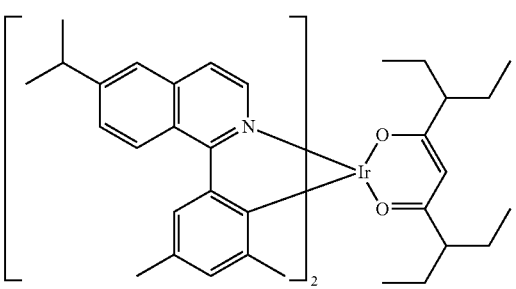
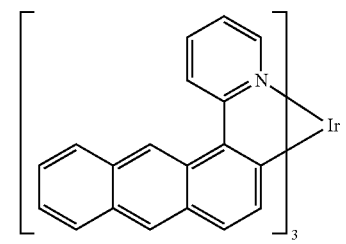

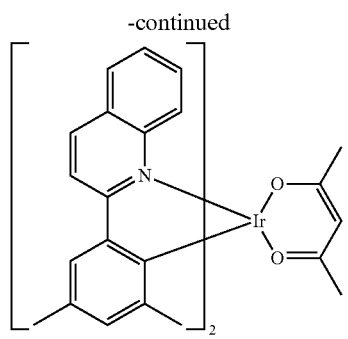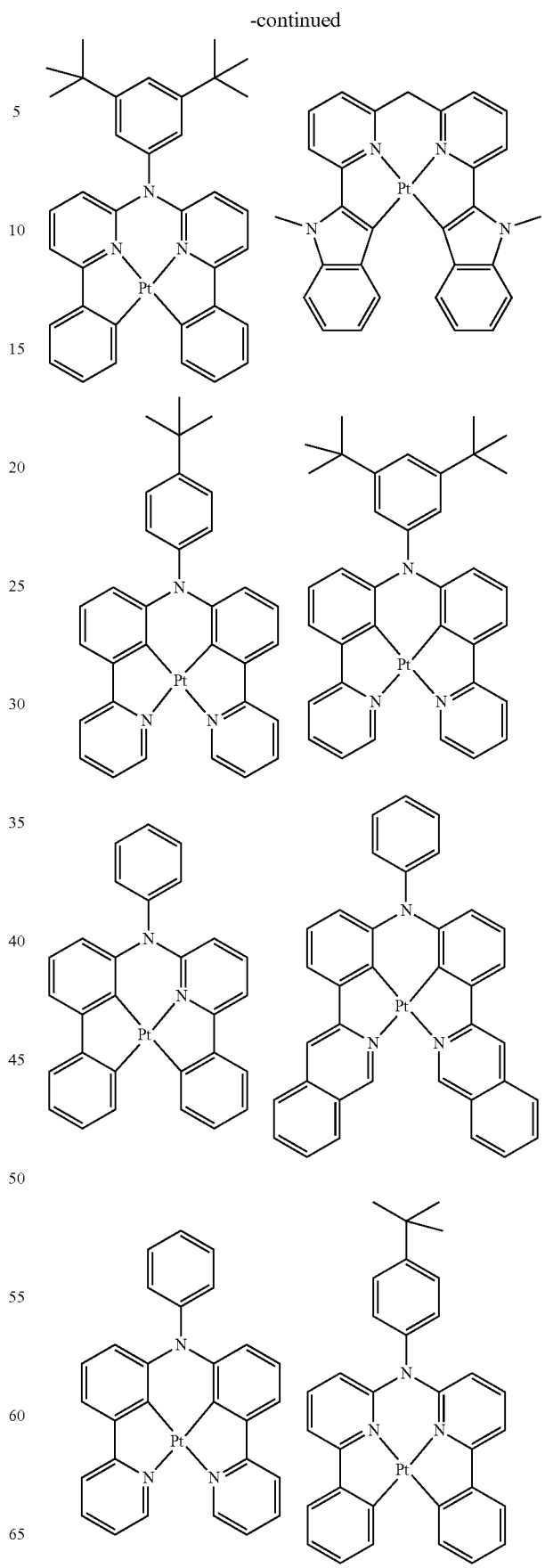

179
-continued
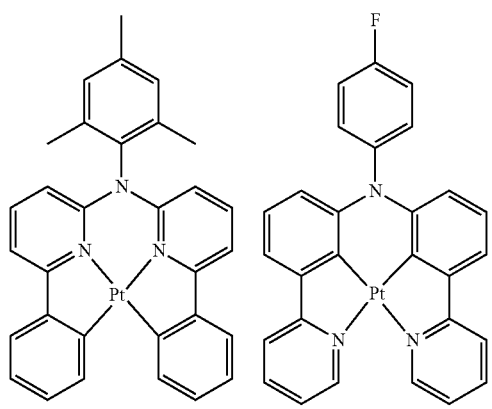
180
-continued
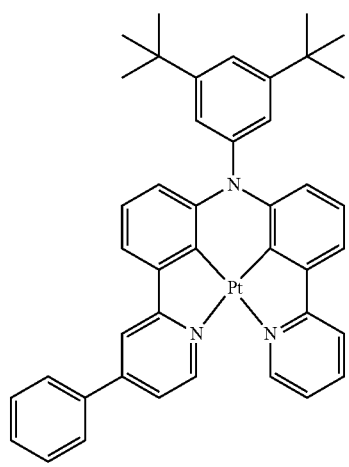
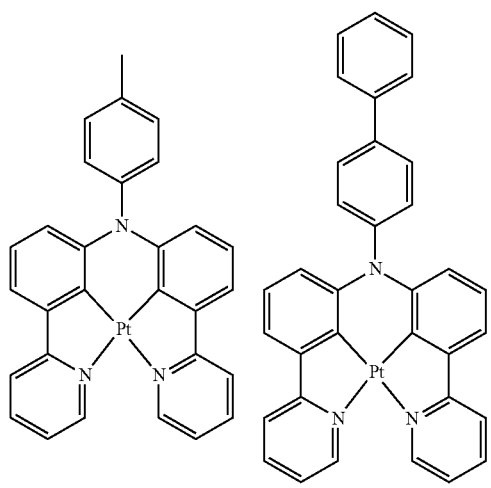
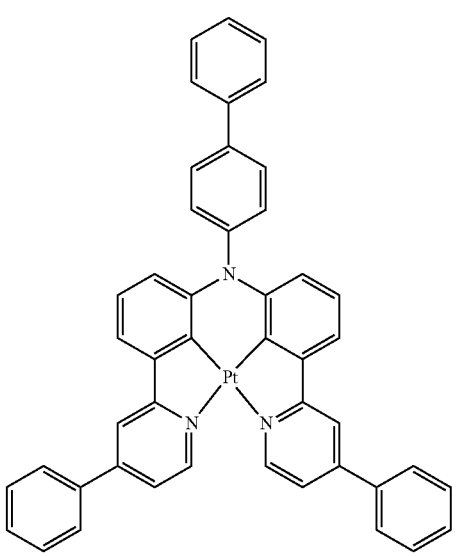
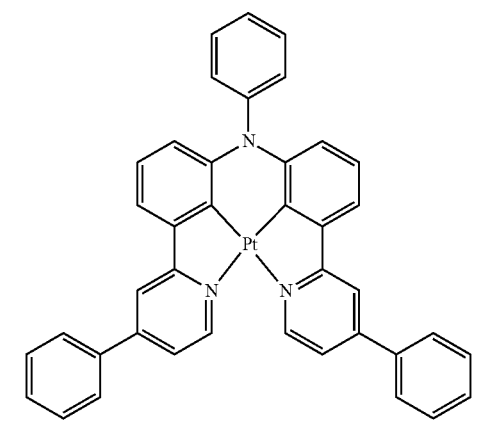
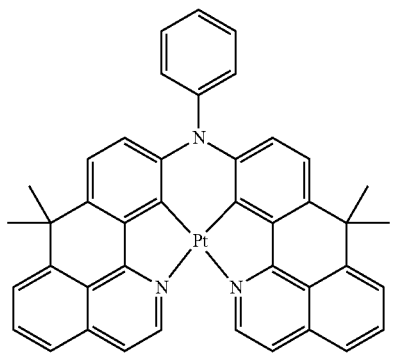

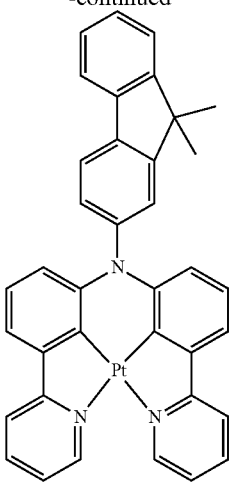
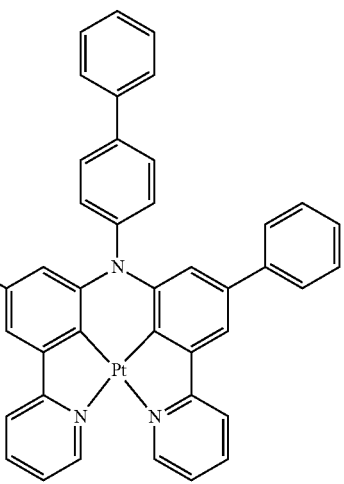
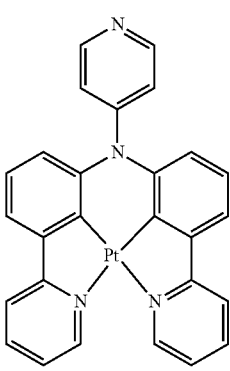
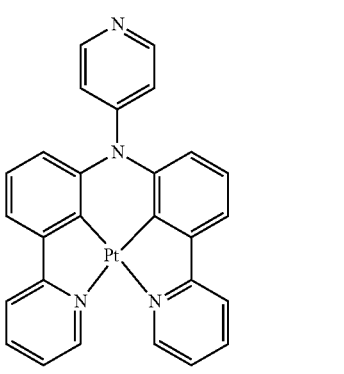
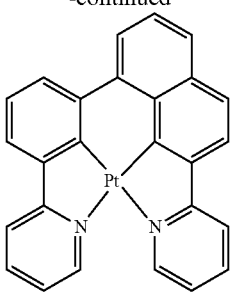
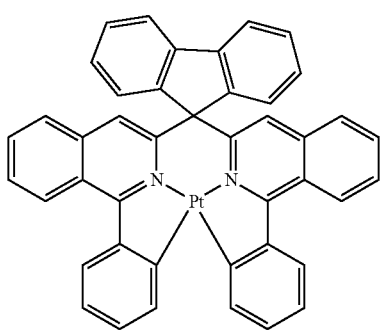
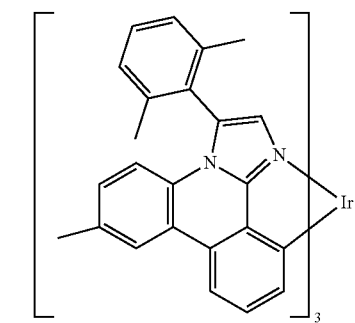
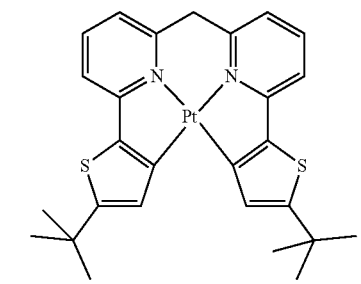
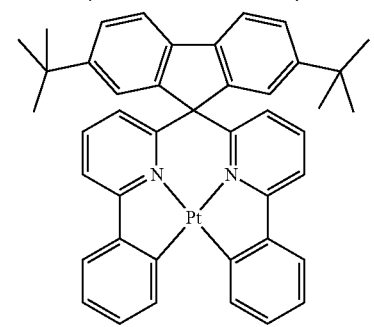

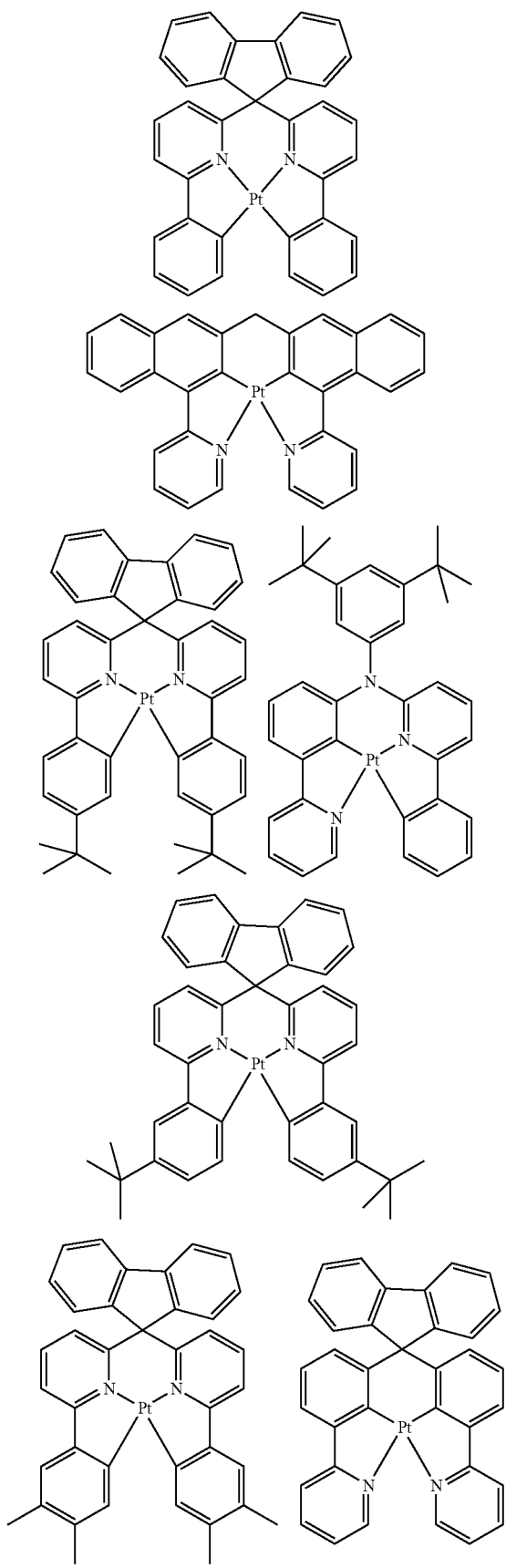

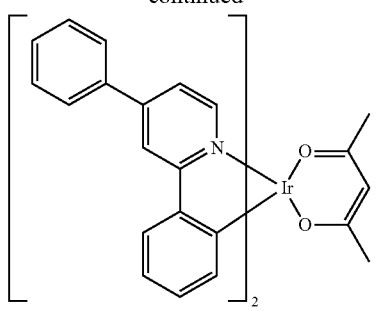
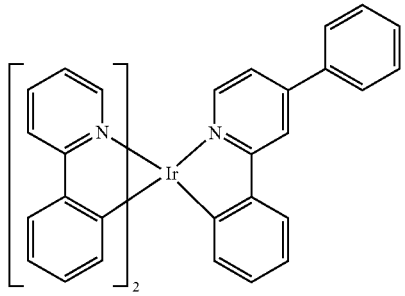
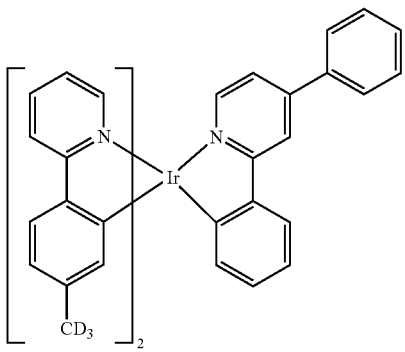
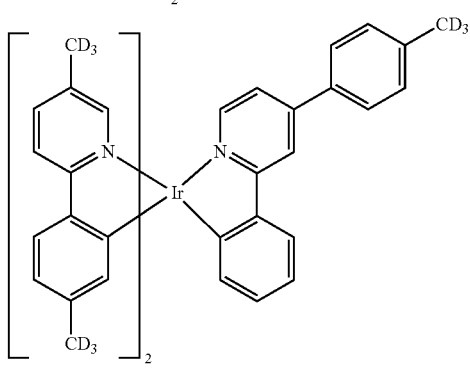
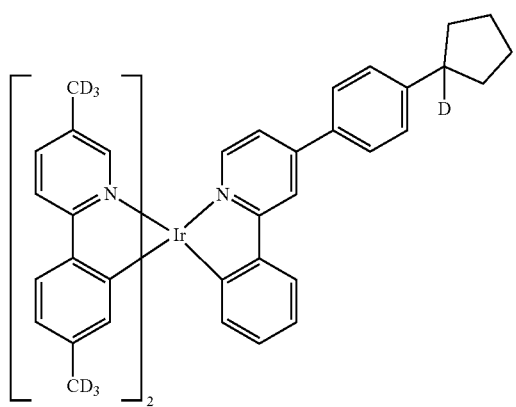
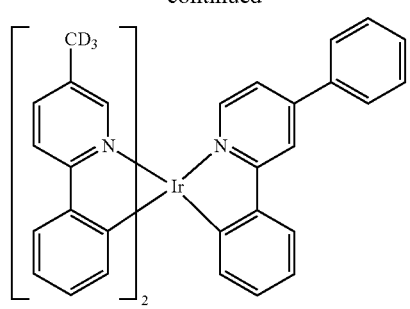
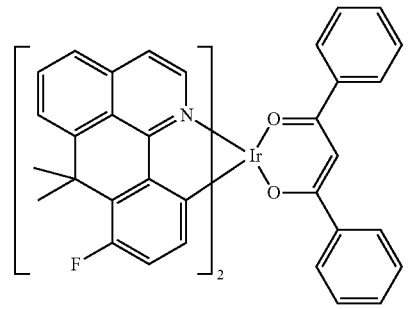
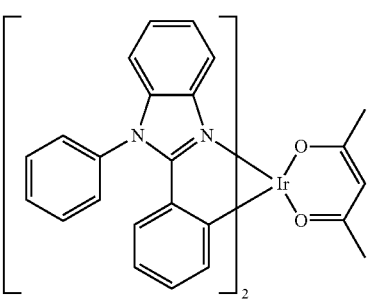
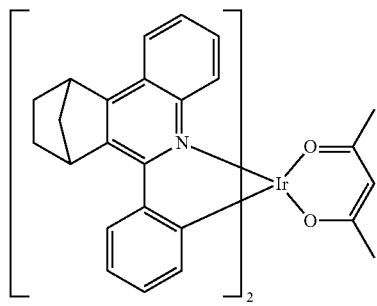
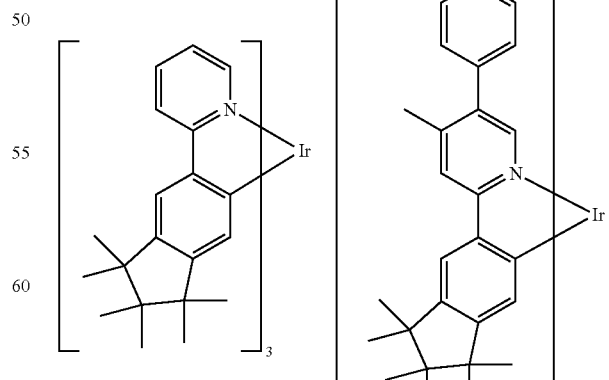

187
-continued
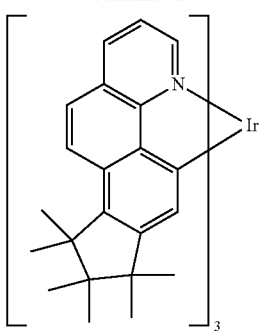
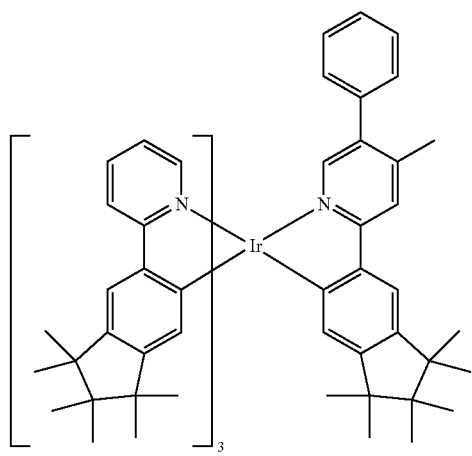
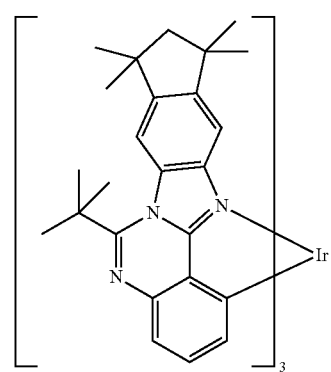
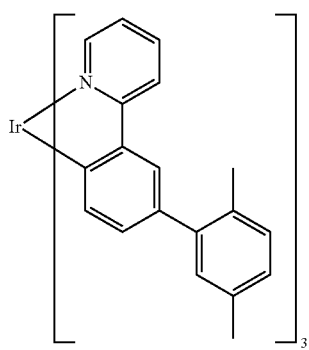
188
-continued
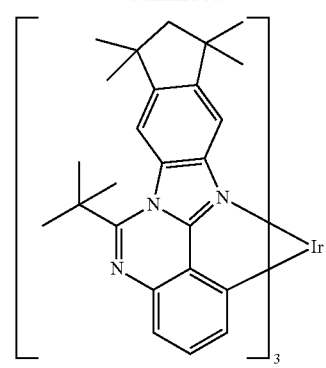
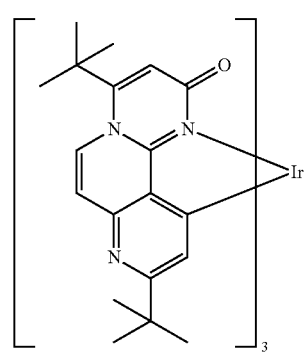
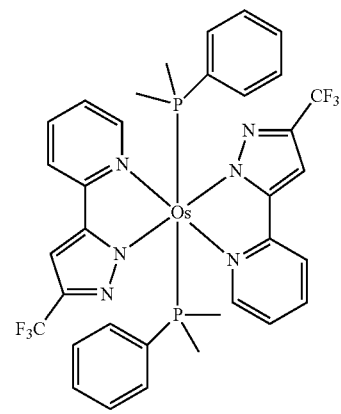
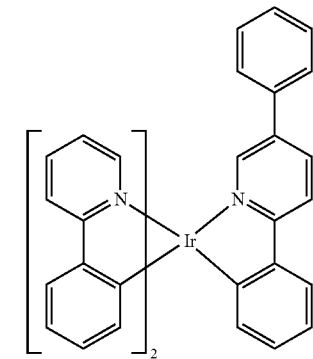

189
-continued
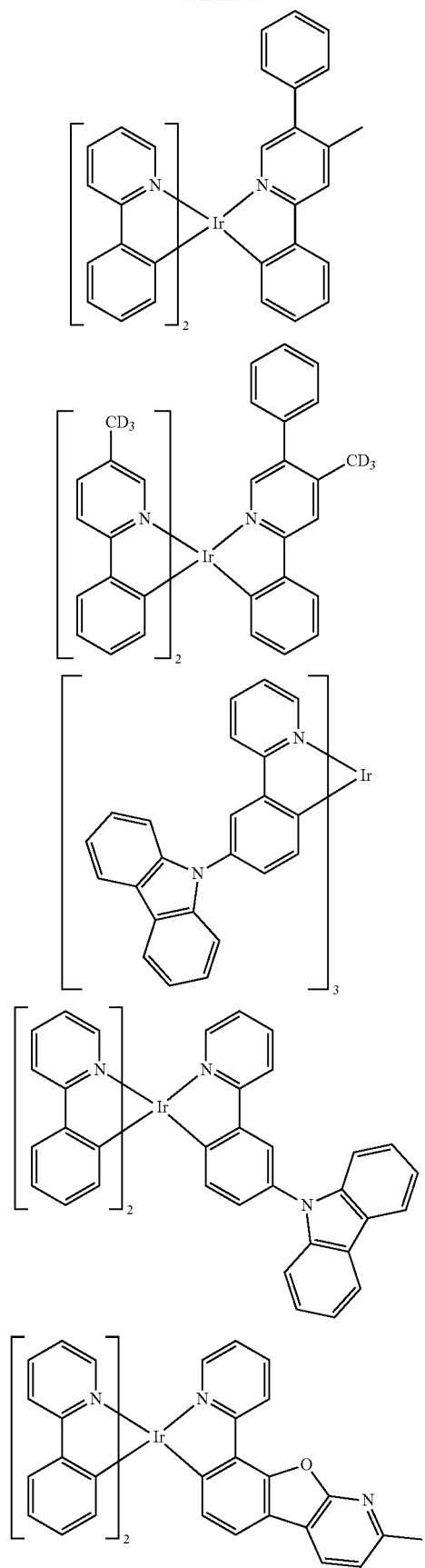
190
-continued
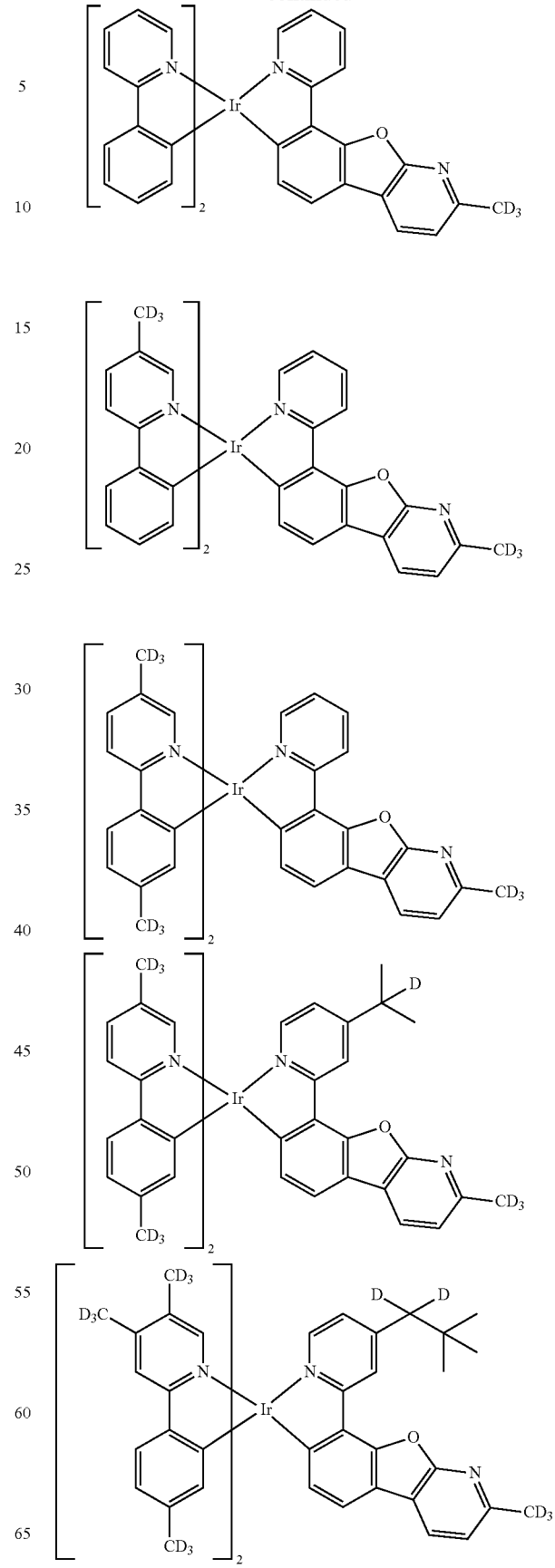

191
-continued
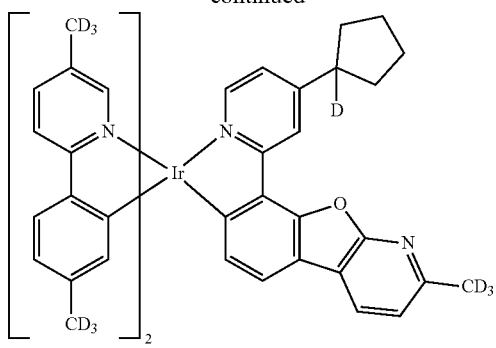
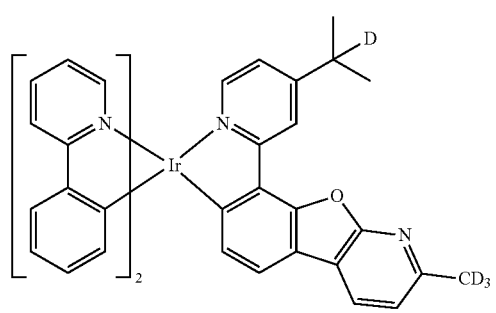
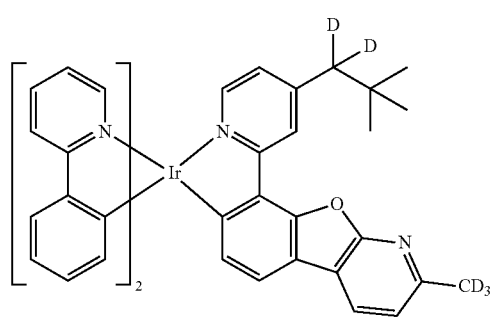
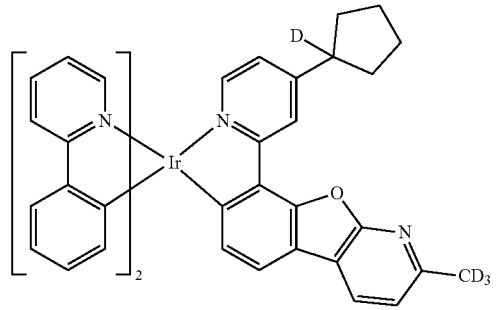
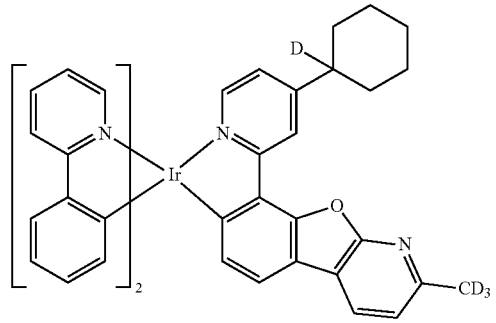
192
-continued
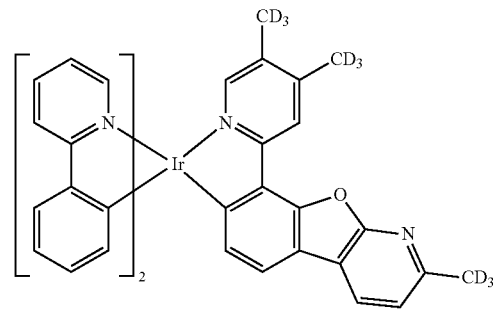
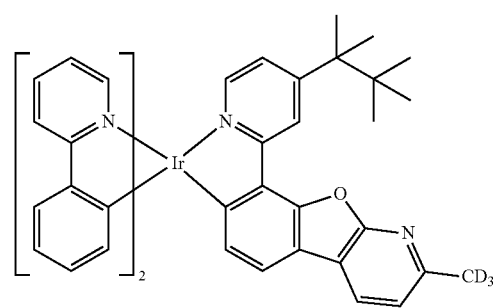
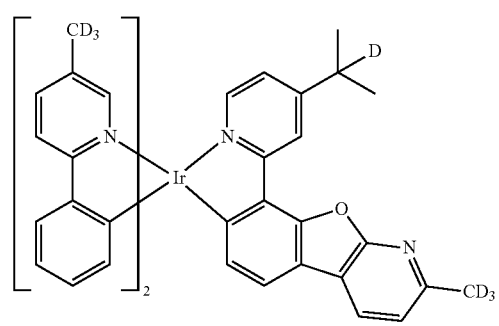
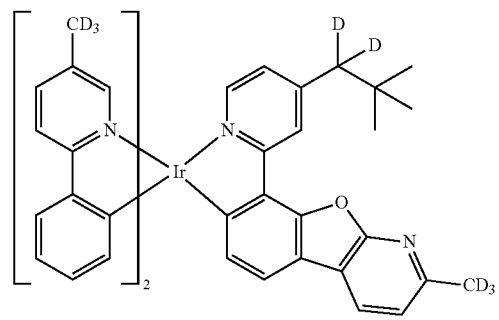
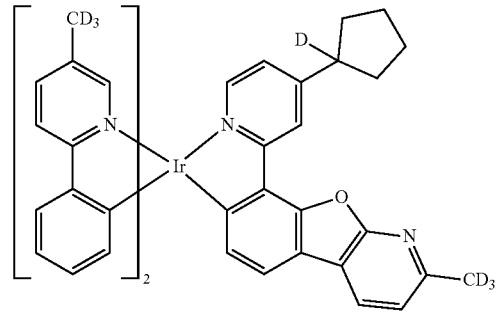

193
-continued
194
-continued
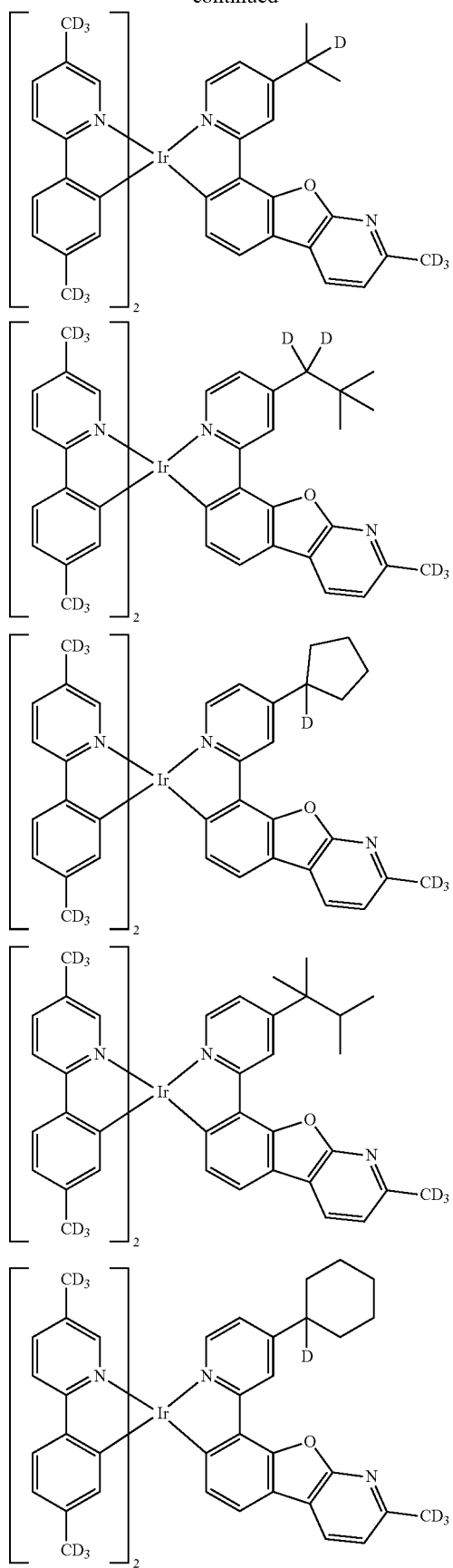
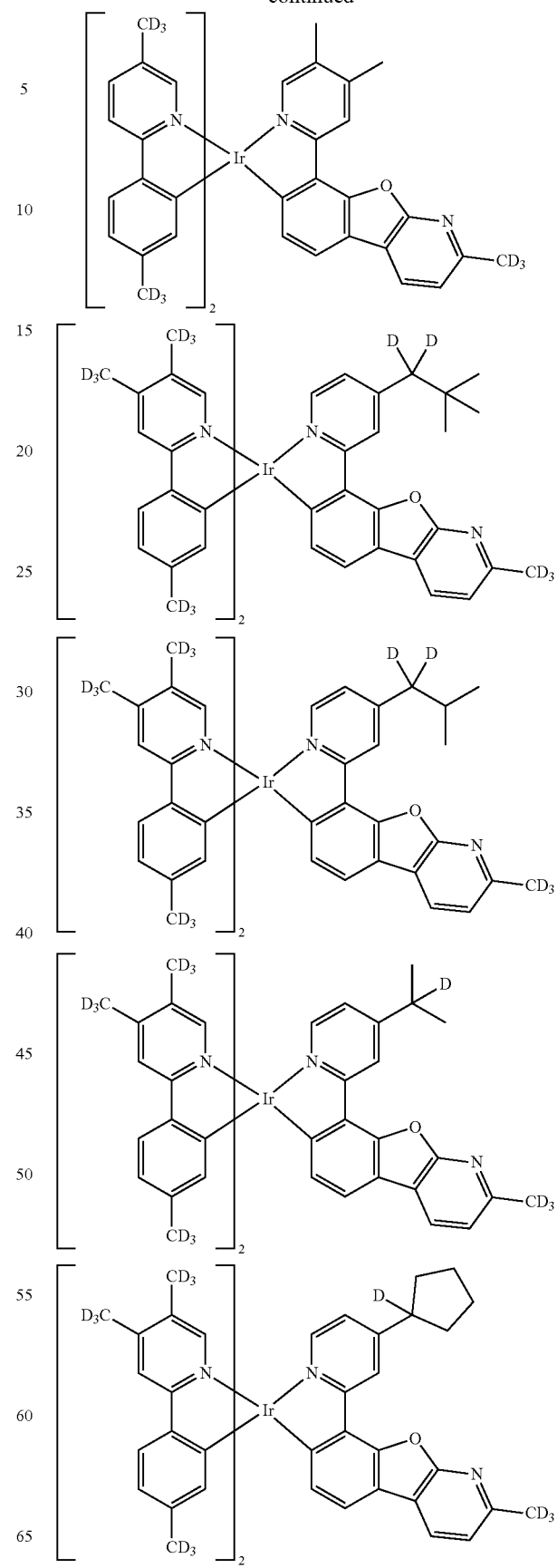

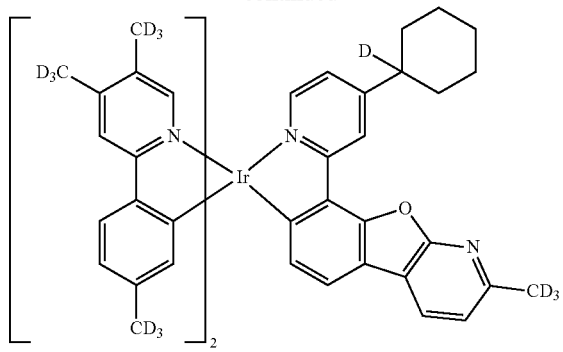

-continued
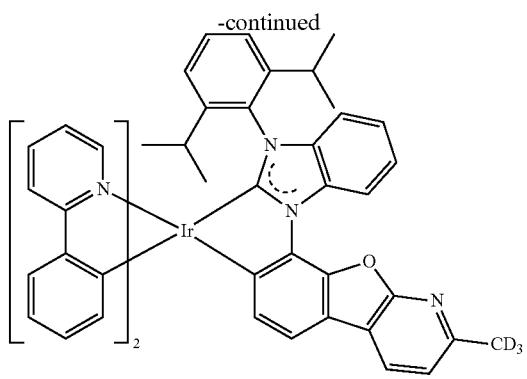
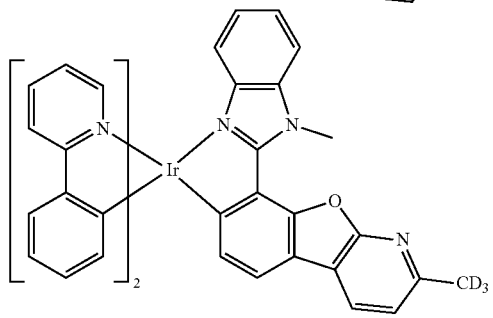
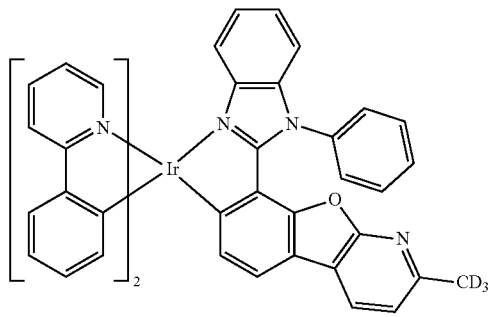
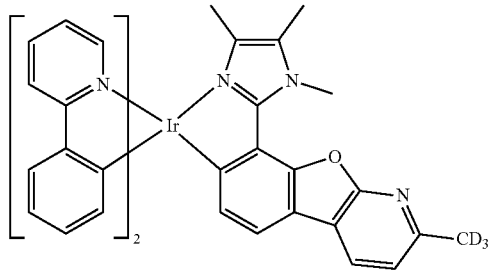
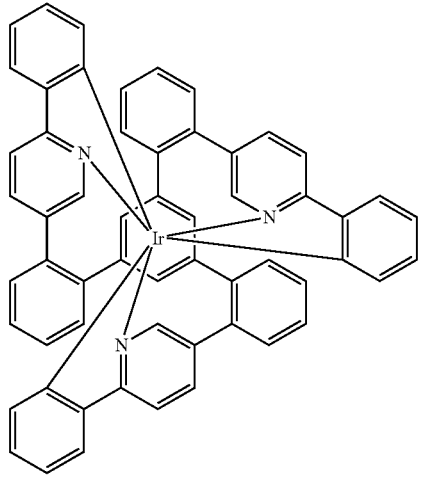
-continued
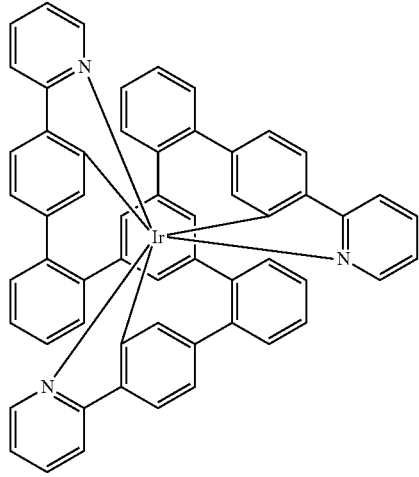
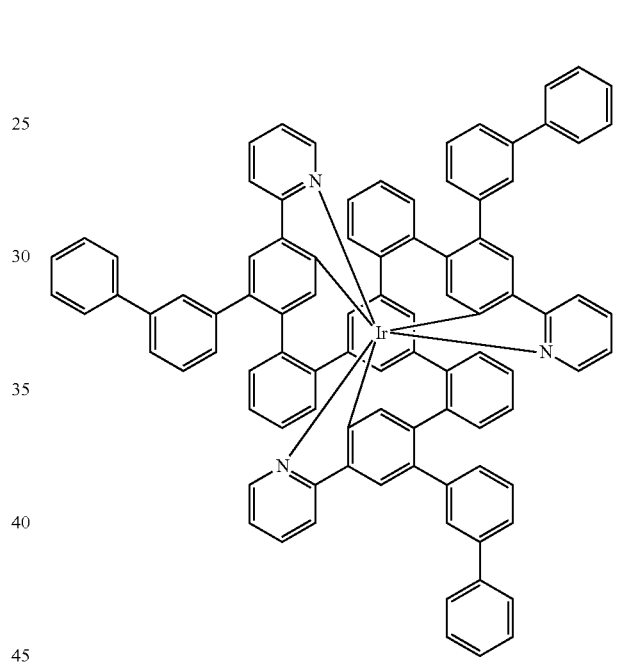
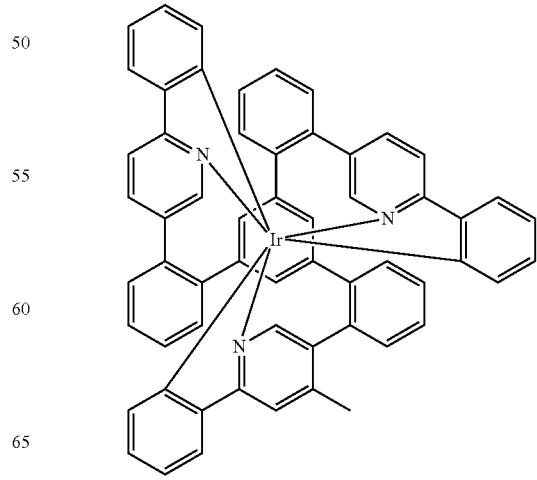

199
-continued
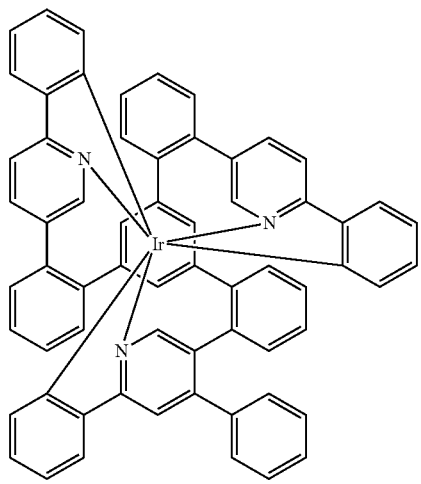
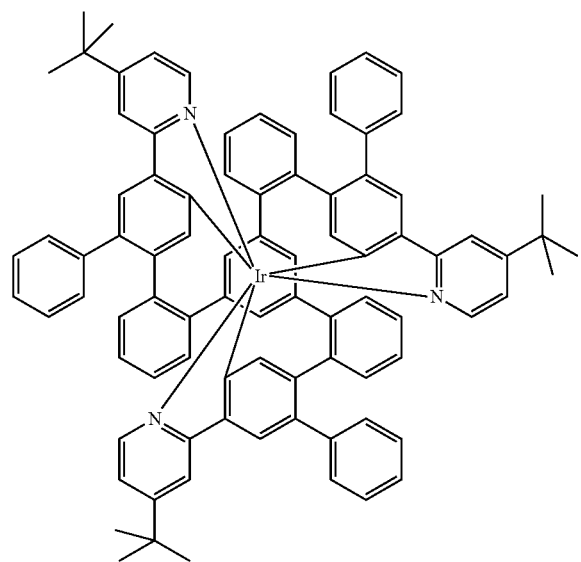
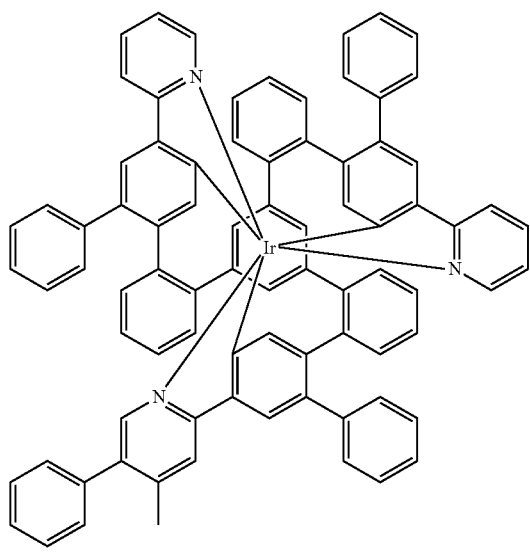
200
-continued
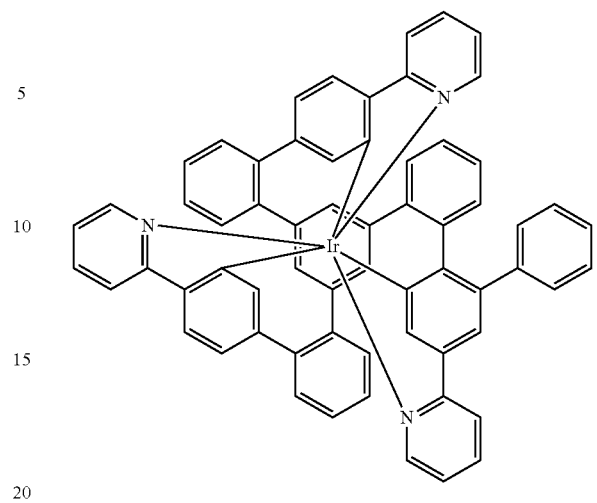
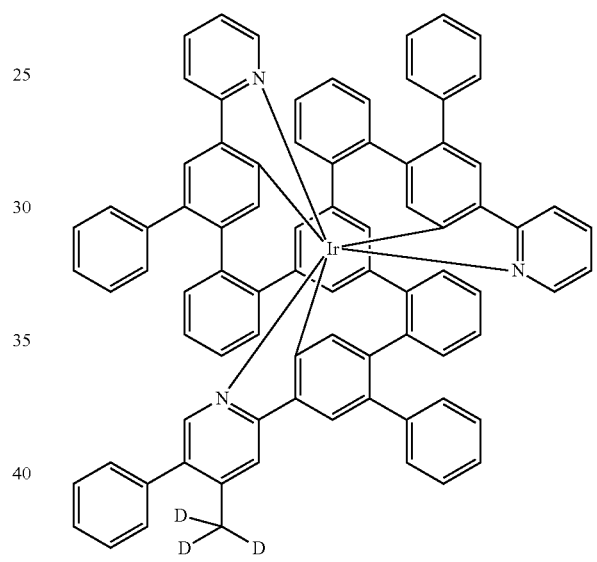
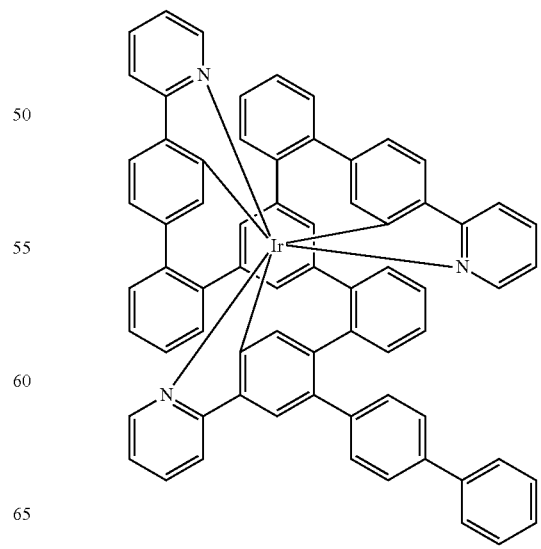

201
-continued
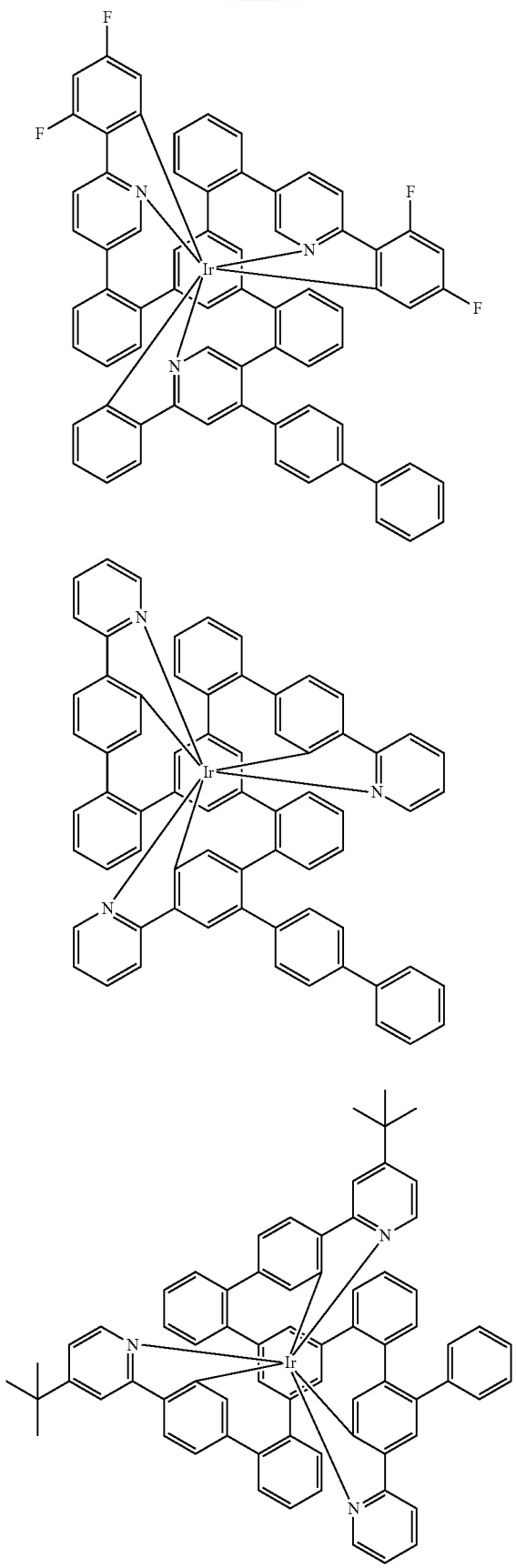
202
-continued
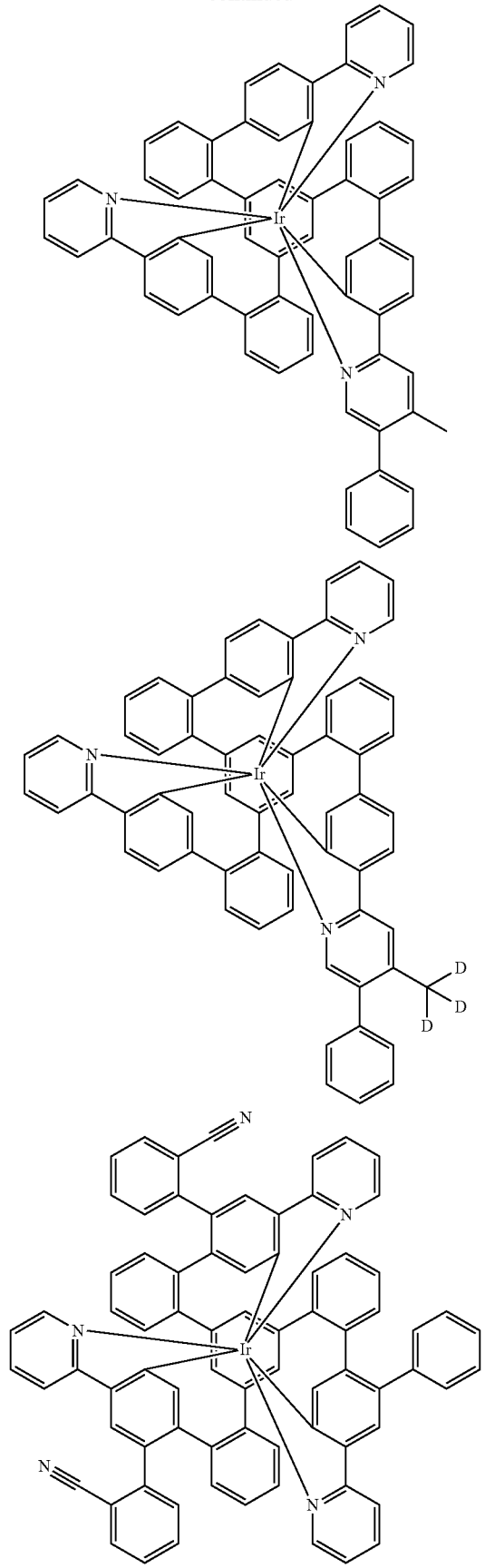

203
-continued
204
-continued
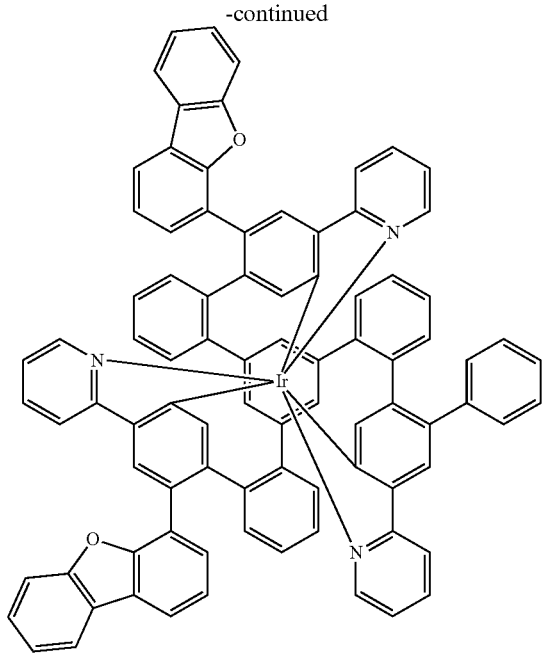
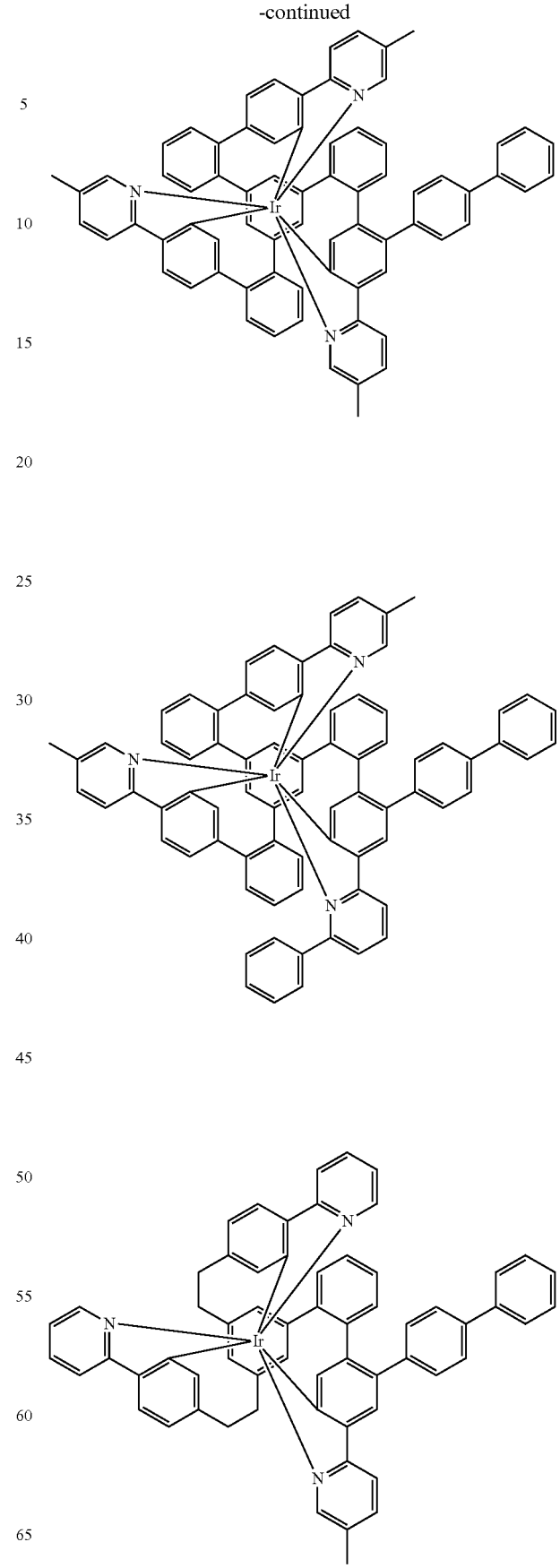

205
-continued
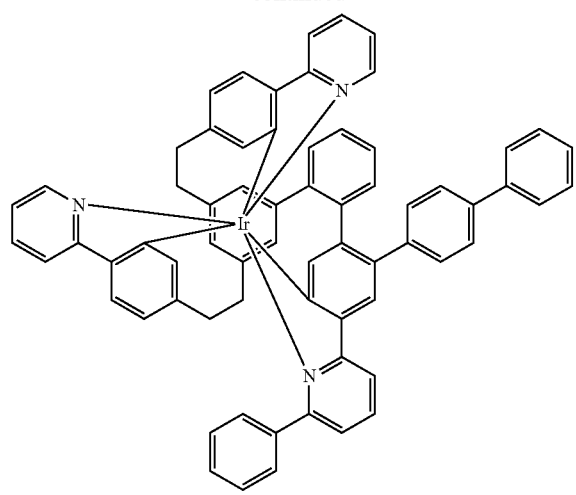
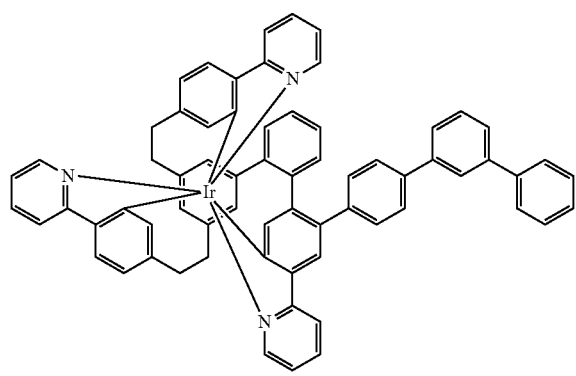
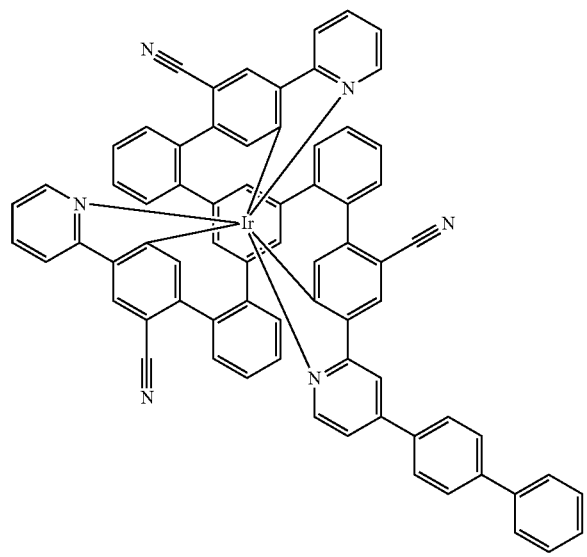
206
-continued
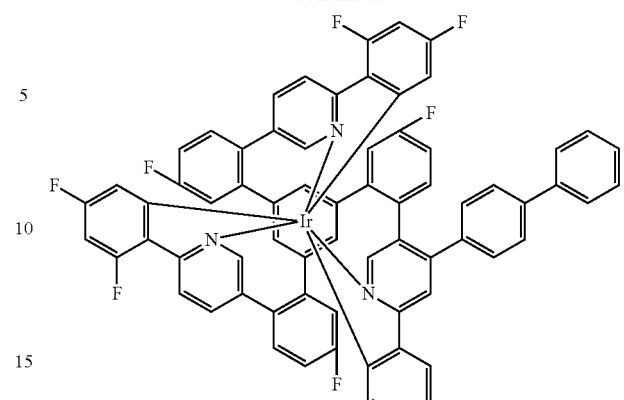
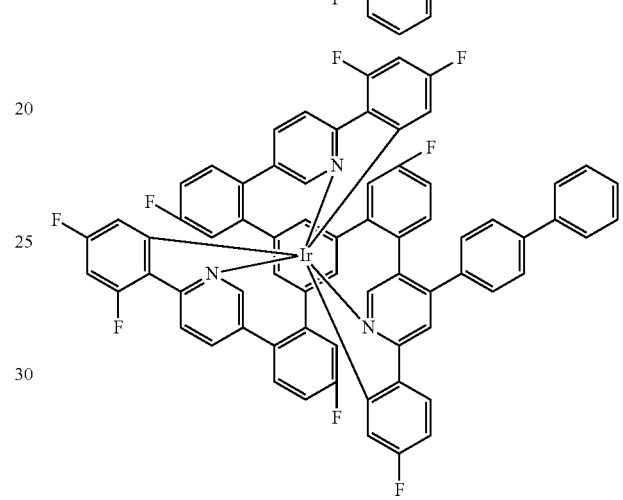
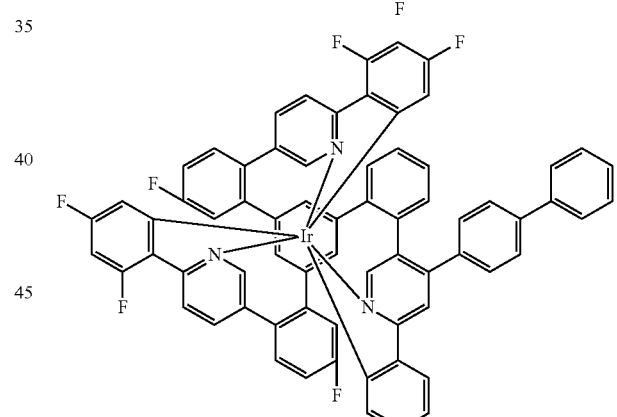
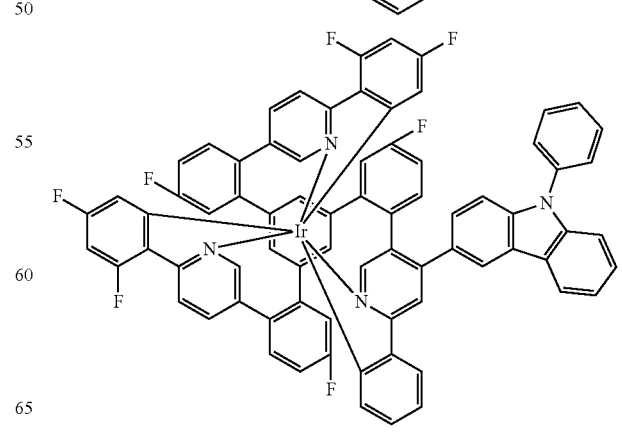

207
-continued
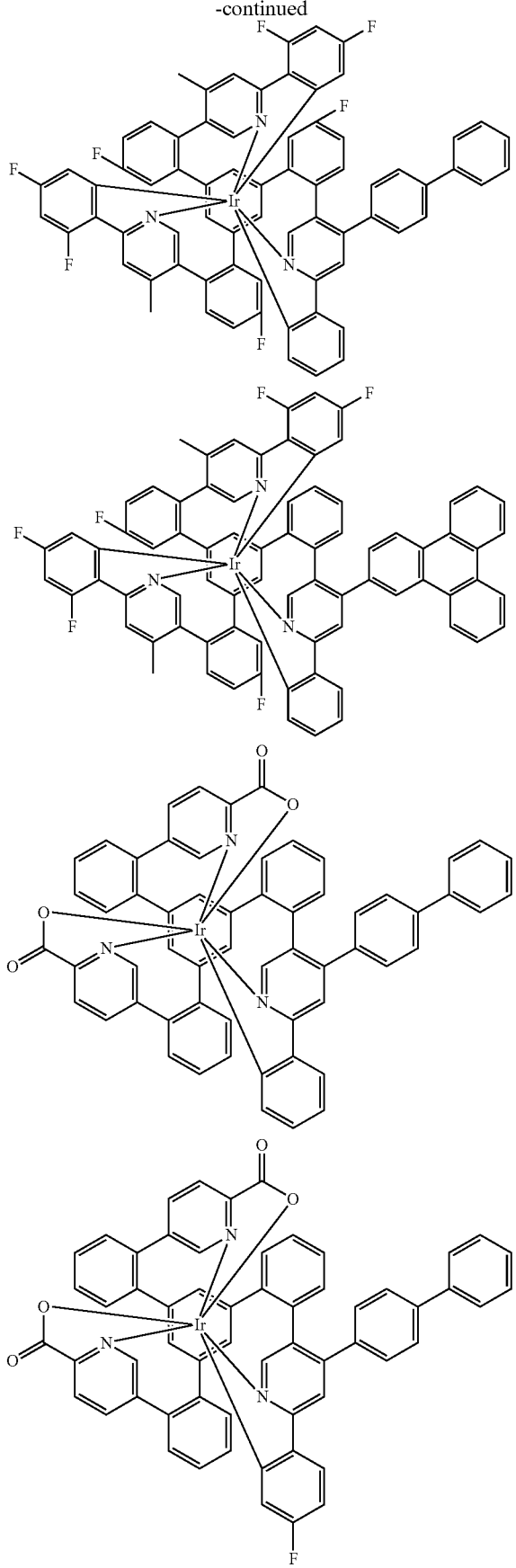
208
-continued
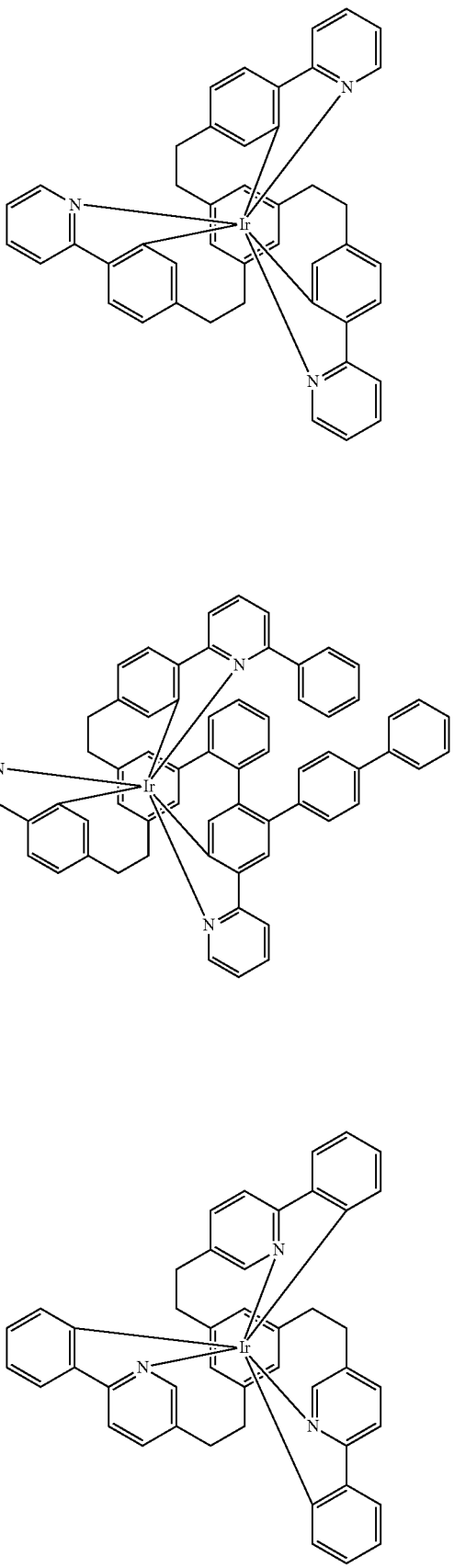

209
-continued
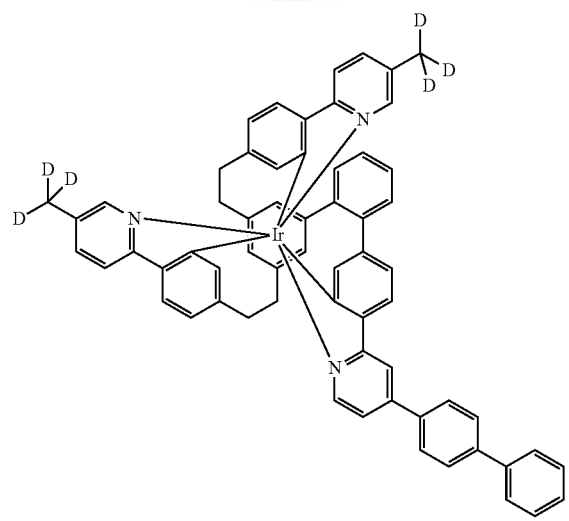
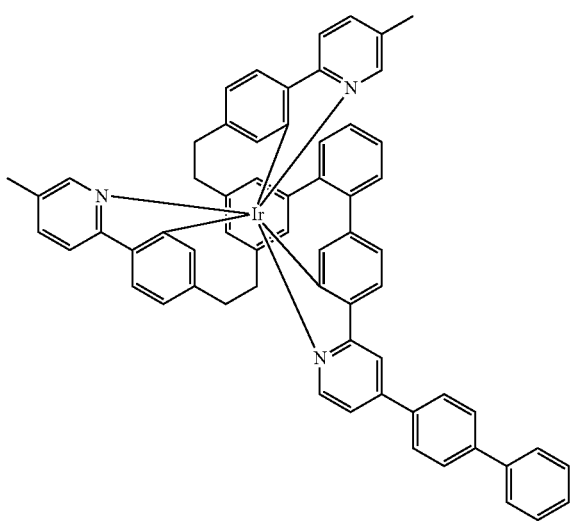
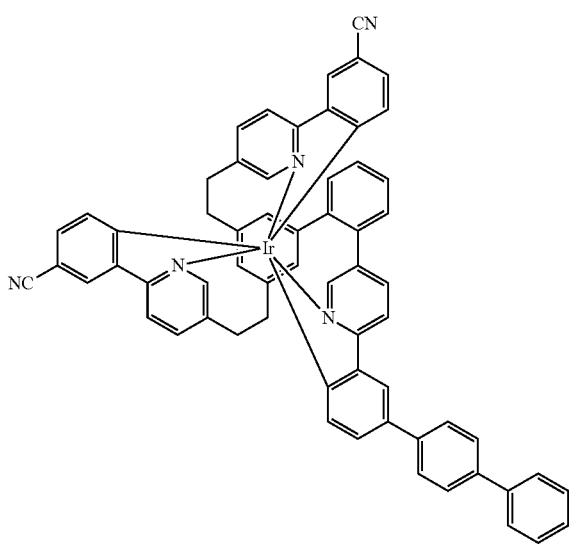
210
-continued
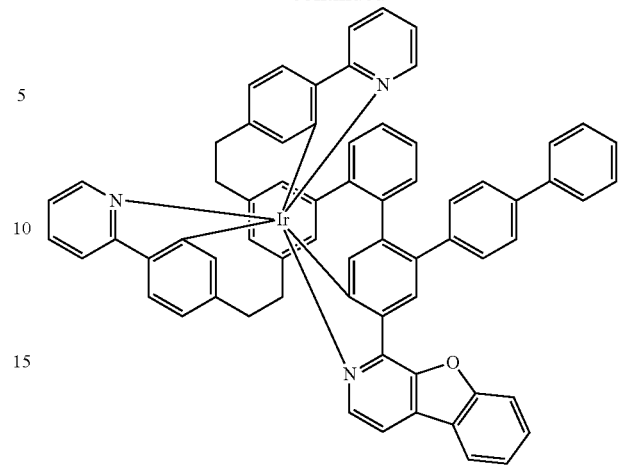
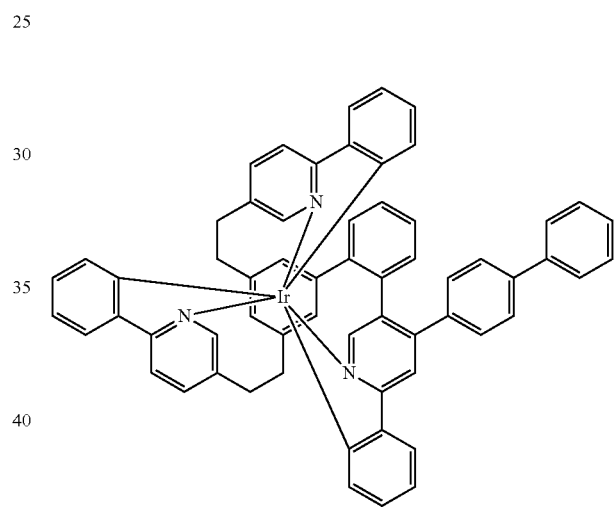
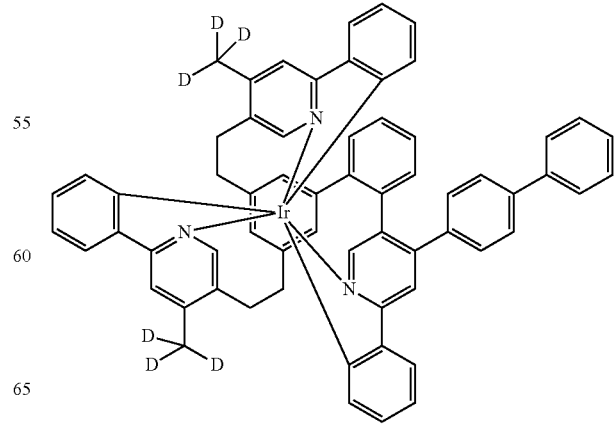

211
-continued
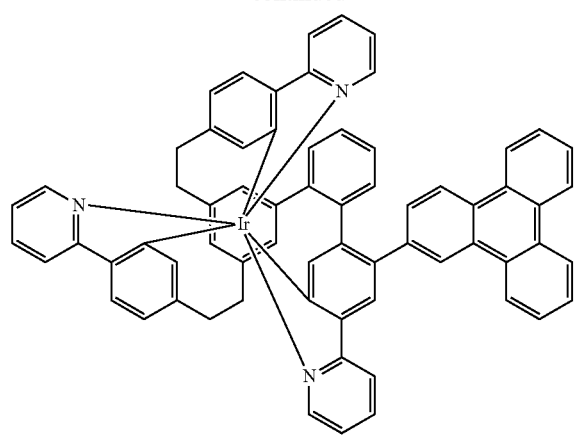
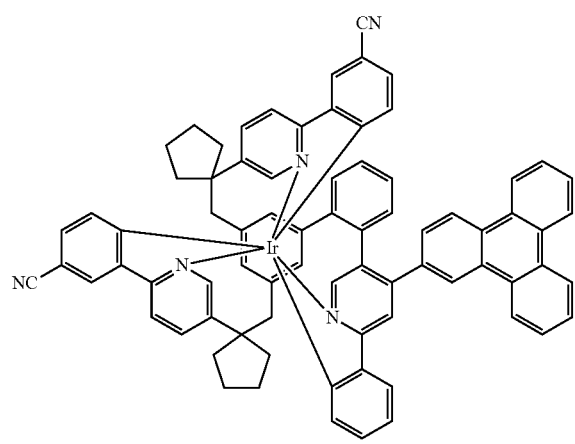
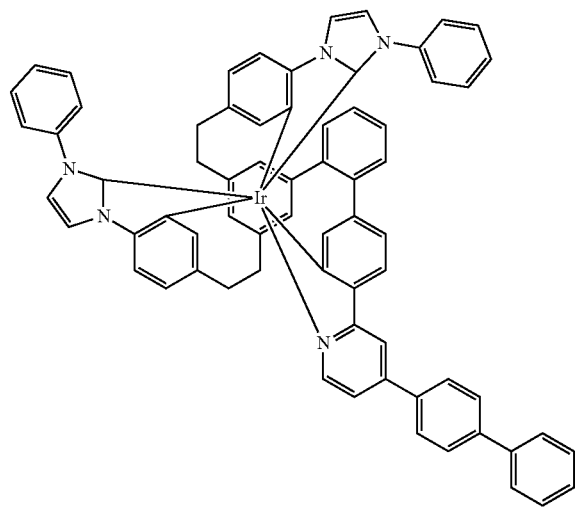
212
-continued
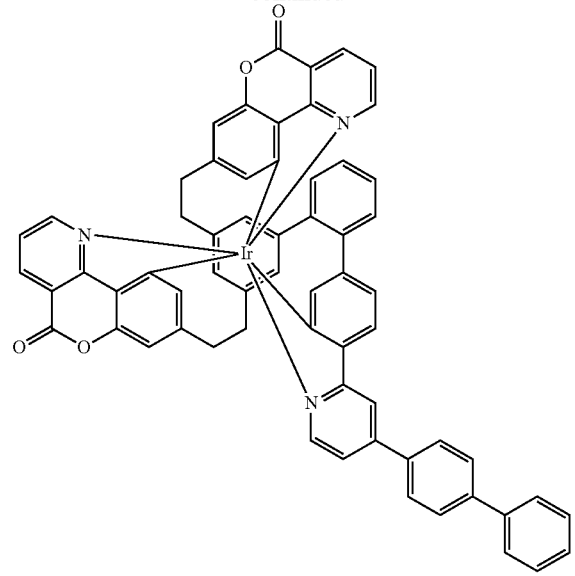
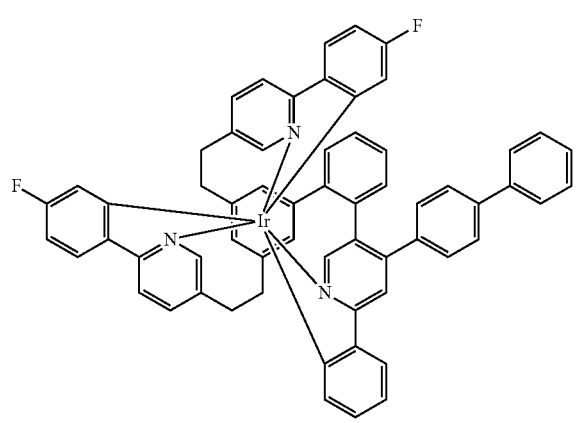

213
-continued
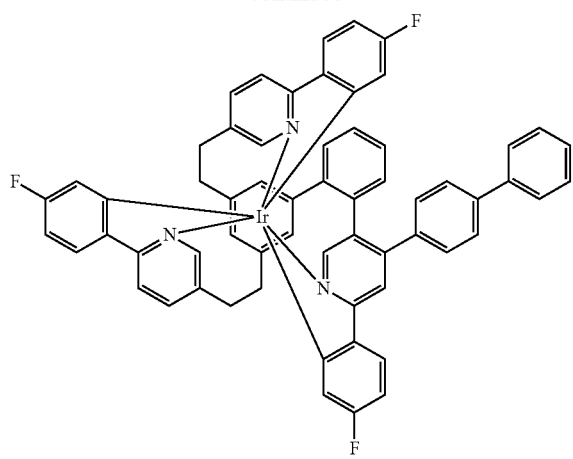
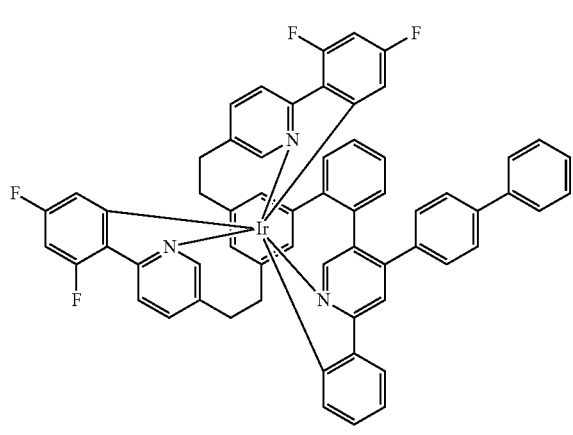
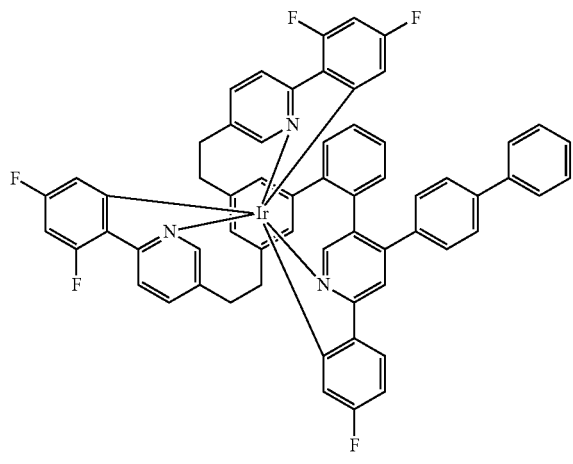
214
-continued
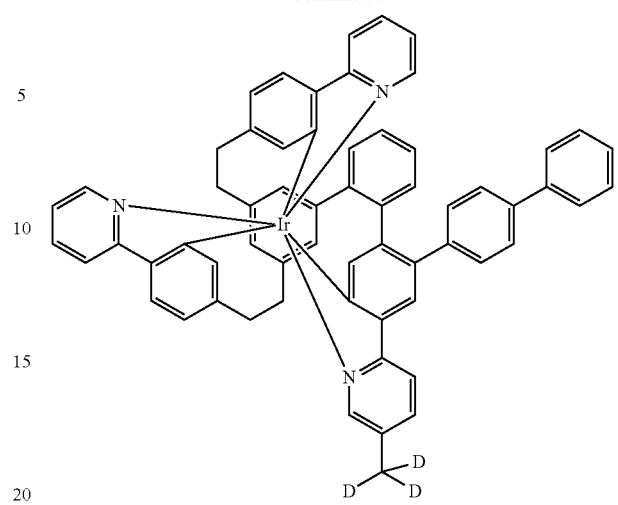
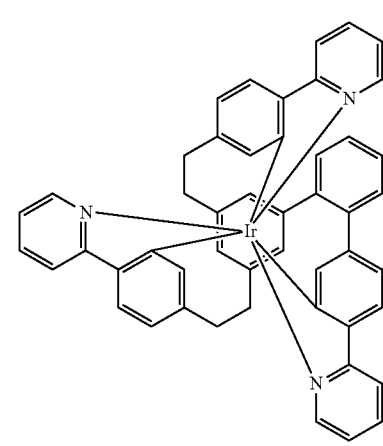
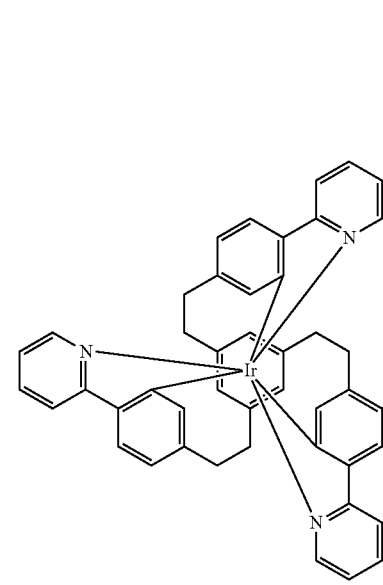

215
-continued
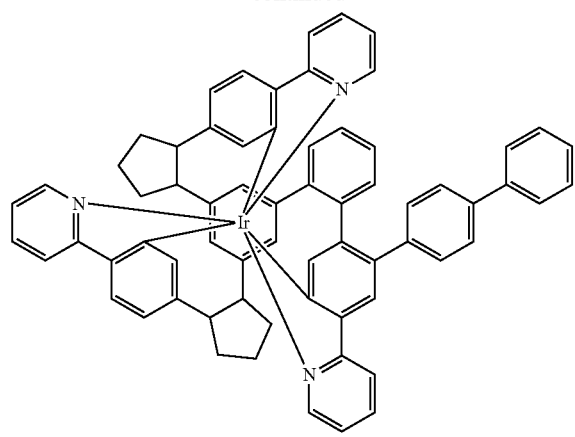
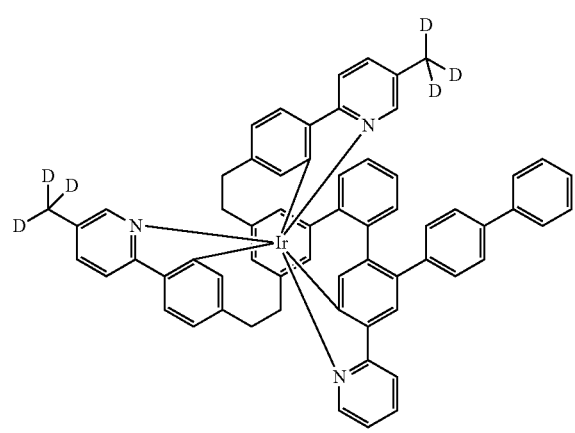
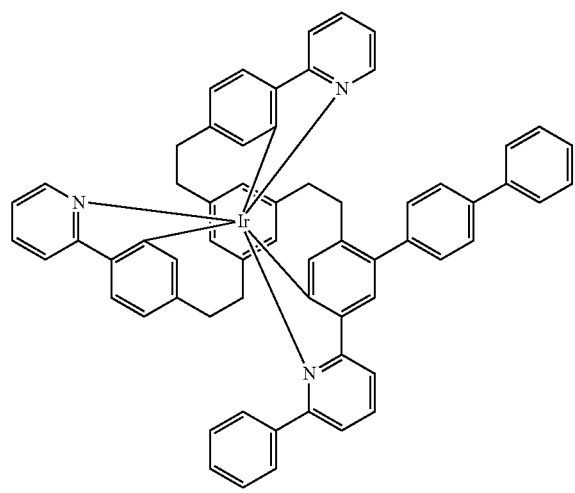
216
-continued
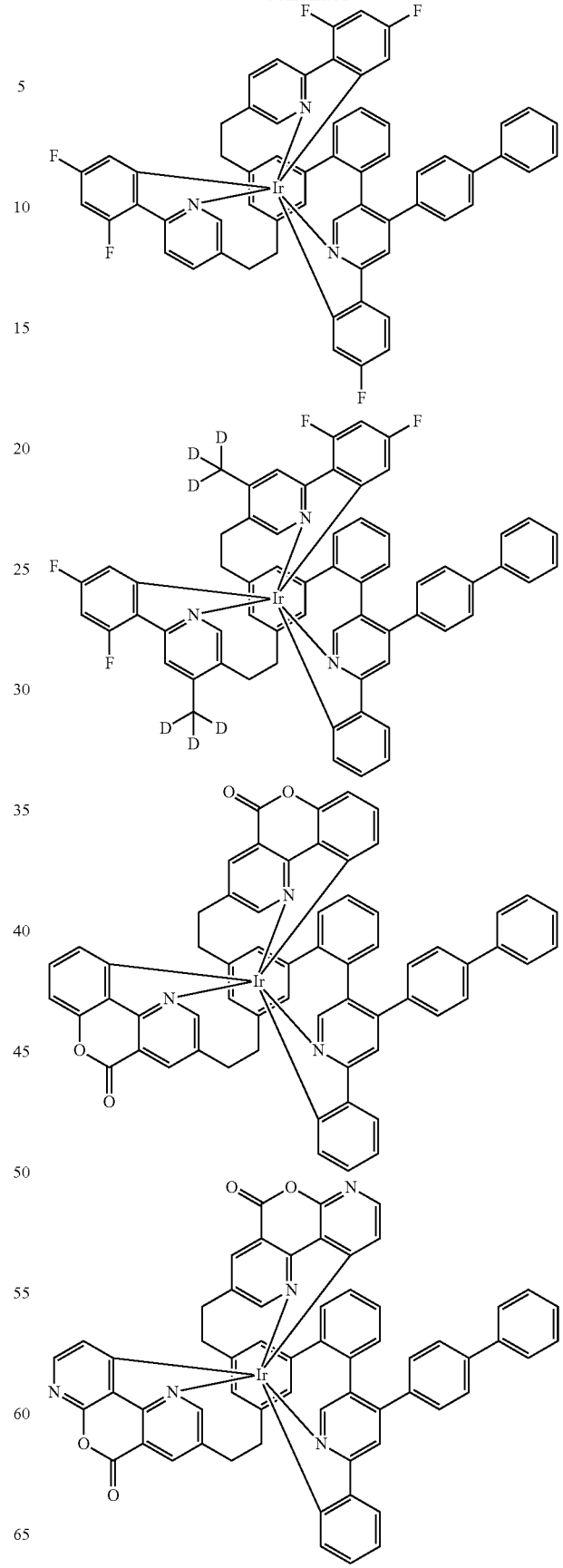

217
-continued
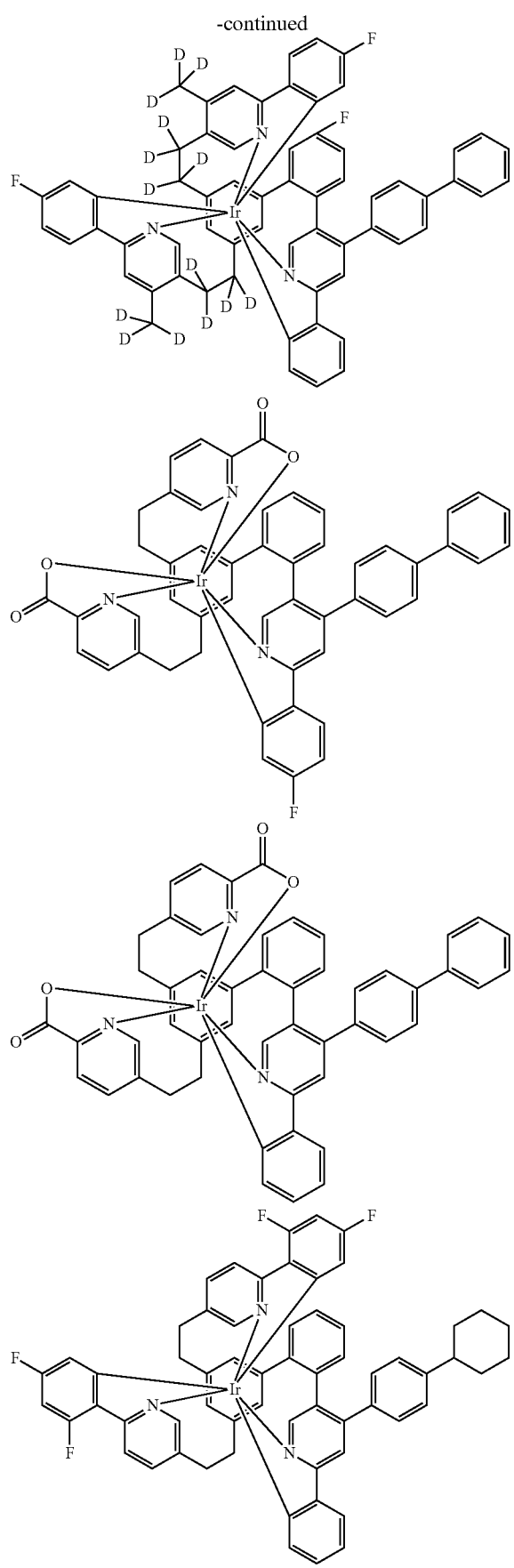
218
-continued
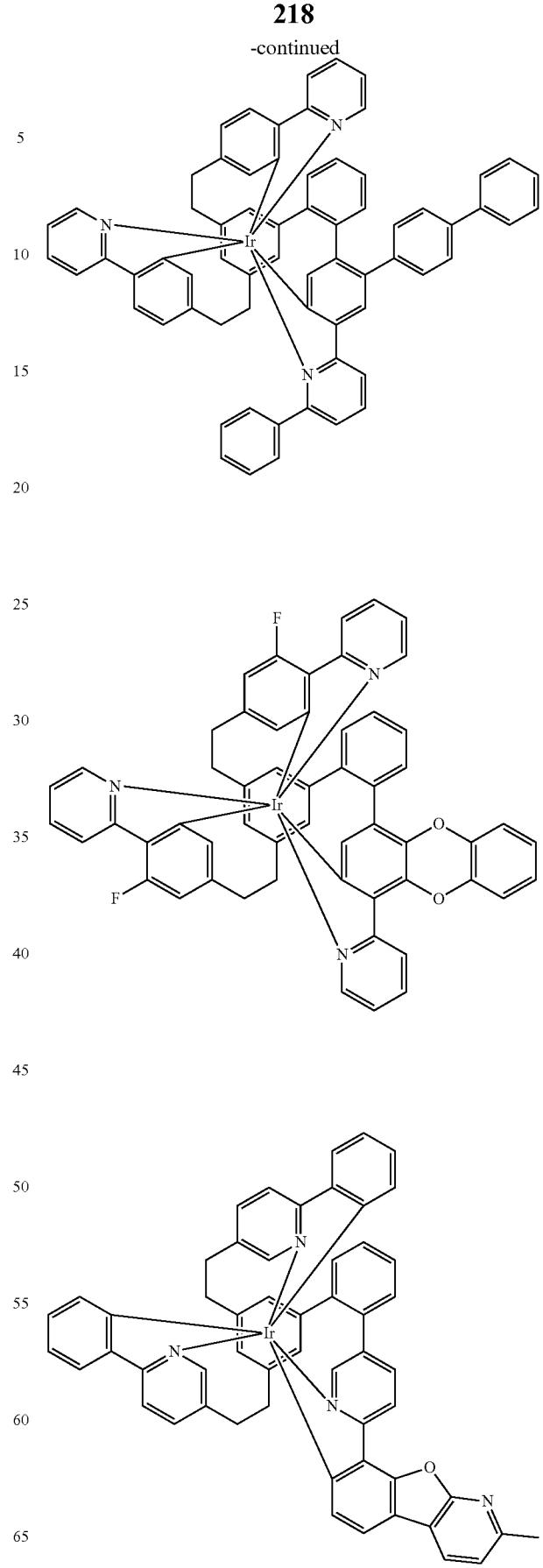

219
-continued
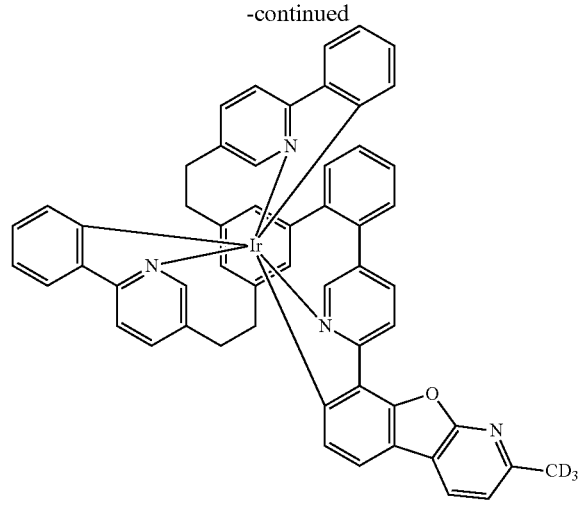
220
-continued
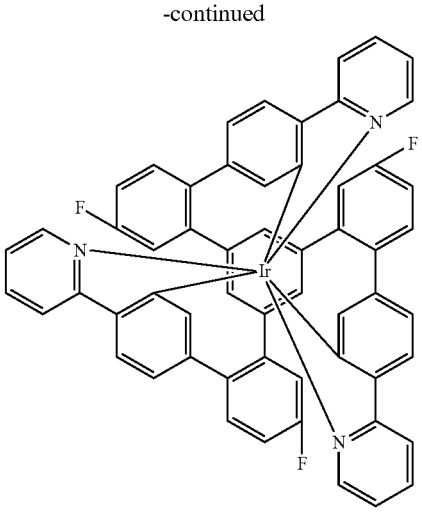
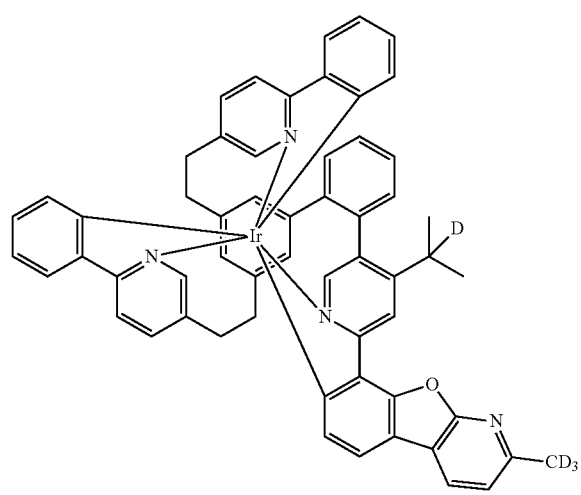
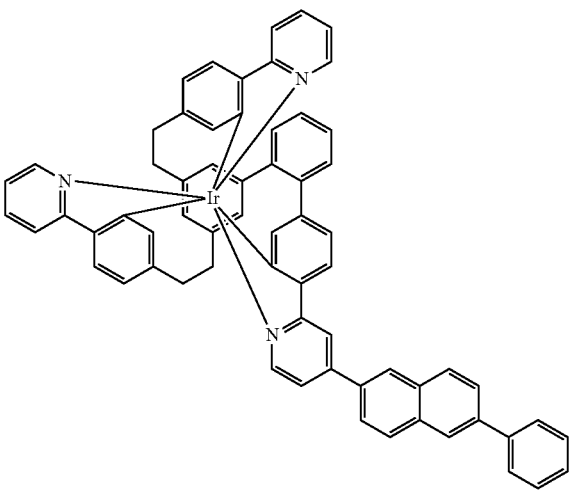
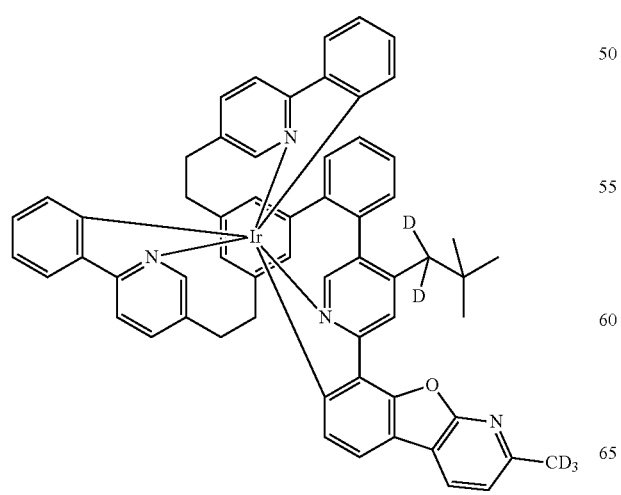

221
-continued
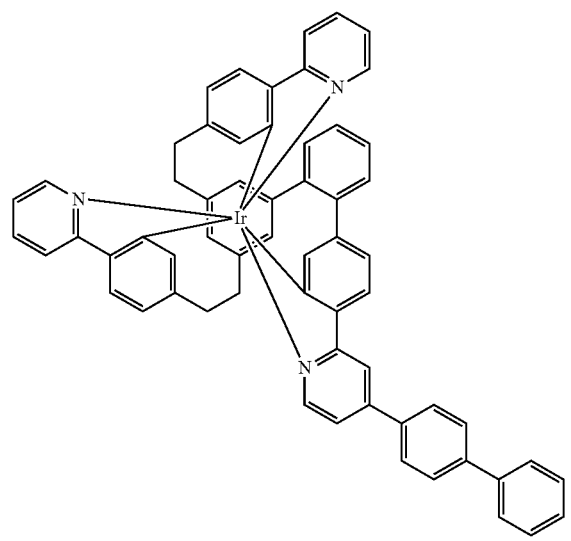
222
-continued
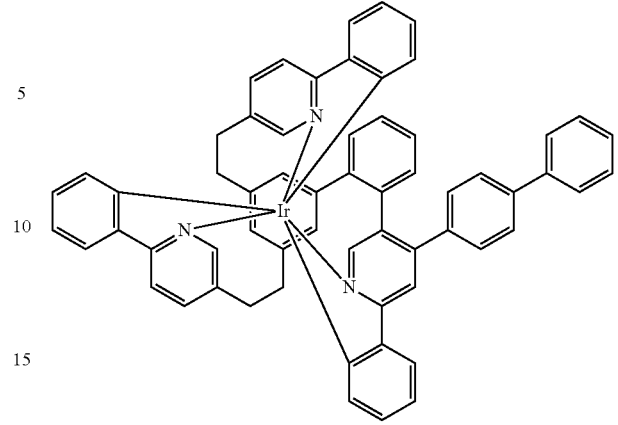
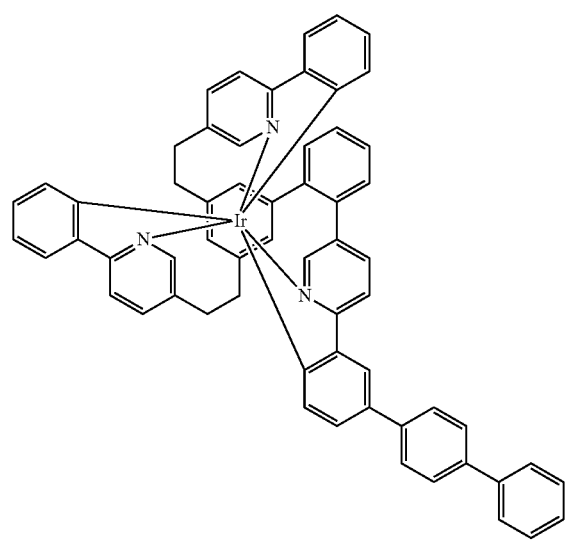
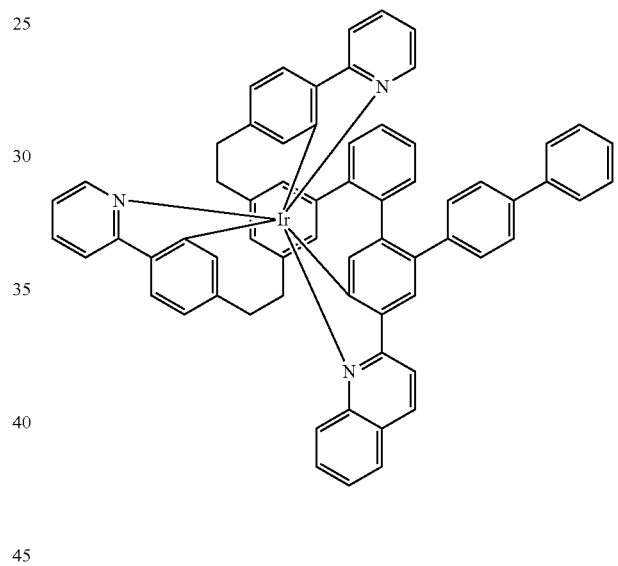
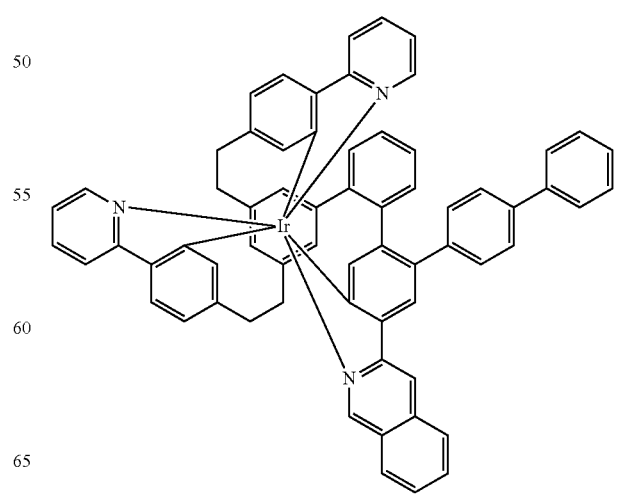

223
-continued

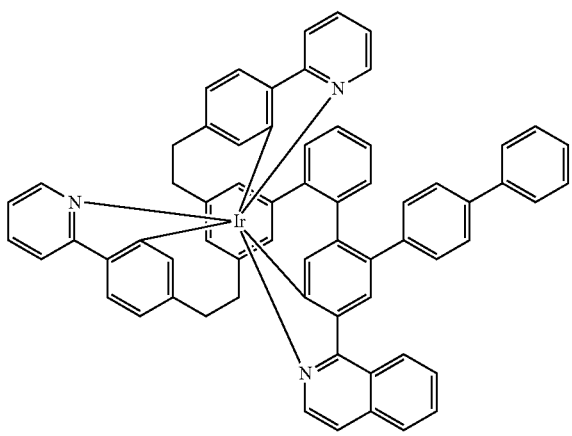

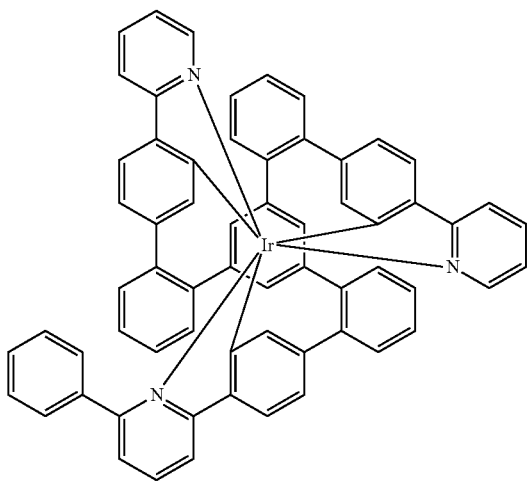

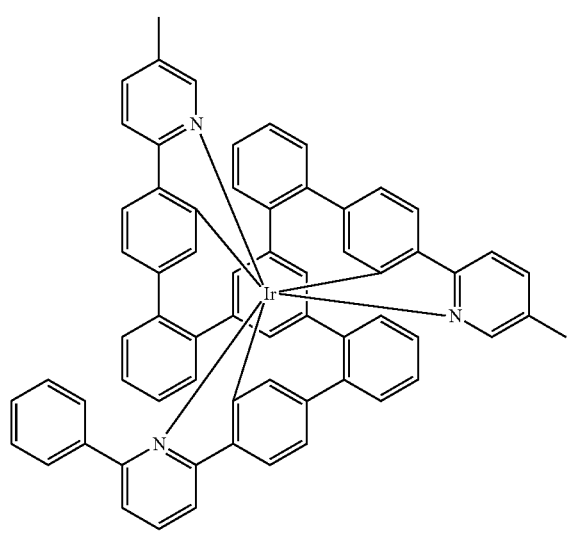

224
-continued

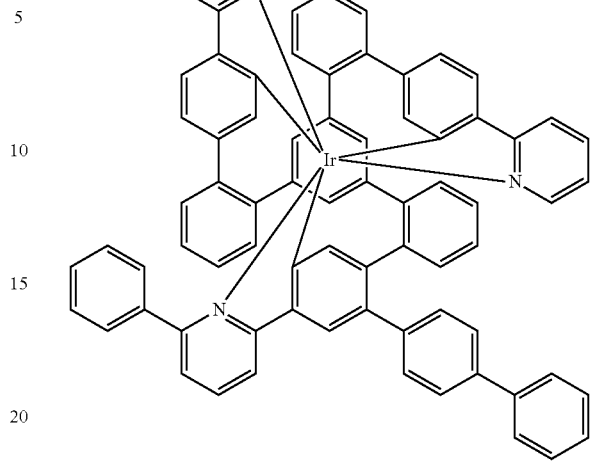

In the further layers of the organic electroluminescent device of the invention, it is possible to use any materials as typically used according to the prior art. The person skilled in the art will therefore be able, without exercising inventive skill, to use any materials known for organic electroluminescent devices in combination with the compounds of formula (1) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapor deposition.

These methods are known in general terms to those skilled in the art and can be applied by those skilled in the art without exercising inventive skill to organic electroluminescent devices comprising the compounds of formula (1).

Compounds of formula (1) containing at least one dibenzofuran, dibenzothiophene or carbazolyl group in one of the substituents are novel.

The present invention therefore further provides compounds of formula (1')

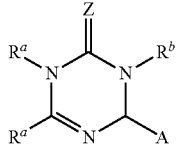

Formula (1')

where the symbols used have the definitions given above, characterized in that the compound contains a heteroaryl group or a heteroaromatic ring system in at least one of the substituents Ar or R. The heteroaryl group here is preferably selected from the group consisting of dibenzofuran, dibenzothiophene and carbazole.

The preferred embodiments detailed above for the compound of the formula (1) are likewise also applicable here to the formula (1').

Preferred heteroaryl groups here are the Ar-12 to Ar-42, Ar-47 to Ar-68, Ar-76 to Ar-83, R-12 to R-42, R-47 to R-68 and R-76 to R-83 groups shown above.

The materials of the invention and the organic electroluminescent devices of the invention are notable for one or more of the following surprising advantages over the prior art:

1. OLEDs containing the compounds of formula (1) or (1') as matrix material for phosphorescent emitters lead to long lifetimes.
2. OLEDs containing the compounds of formula (1) or (1') lead to high efficiencies. This is especially true when the compounds are used as matrix material for a phosphorescent emitter.
3. OLEDs containing the compounds of formula (1) or (1') lead to low operating voltages. This is especially true when the compounds are used as matrix material for a phosphorescent emitter.

The invention is illustrated in more detail by the examples which follow, without any intention of restricting it thereby. The person skilled in the art will be able to use the information given to execute the invention over the entire scope disclosed and produce further inventive electronic devices without exercising inventive skill.

EXAMPLES

The syntheses which follow, unless stated otherwise, are conducted under a protective gas atmosphere in dried solvents. The solvents and reagents can be purchased, for example, from Sigma-ALDRICH or ABCR. For the compounds known from the literature, the corresponding CAS numbers are also reported in each case.

Synthesis Examples a) 1-(4-Bromophenyl)-4,6-diphenyl-1,3,5-triazin-2-one

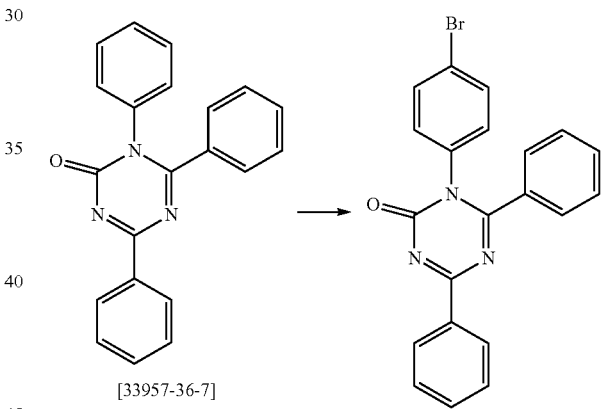

[33957-36-7]

To a solution of 48.8 g (150 mmol) of 1,4,6-triphenyl-1,3,5-triazin-2-one in chloroform (900 ml) is added N-bromosuccinimide (26.6 g, 150 mmol) in portions at 0° C. with exclusion of light, and the mixture is stirred at this temperature for 2 h. The reaction is ended by addition of sodium sulfite solution and the mixture is stirred at room temperature for a further 30 min. After phase separation, the organic phase is washed with water and the aqueous phase is extracted with dichloromethane. The combined organic phases are dried over sodium sulfate and concentrated under reduced pressure. The residue is dissolved in toluene and filtered through silica gel. Subsequently, the crude product is recrystallized from toluene/heptane. Yield: 45 g (112 mmol), 75% of theory, colorless solid.

The following compounds can be obtained analogously:

| Reactant 1 | Product 1 | Product 2 | Yield |
|---|---|---|---|
| 1a [63139-70-8] | | | 50% |
| 2a [2097-49-28-3] | | | 40%/ 50% |
| 3a [36068-36-7] | | | 40%/ 50% |
| 4a [53085-14-6] | | | 50%/ 30% |

-continued

| | Reactant 1 | Product 1 | Product 2 | Yield |
|---|---|---|---|---|
| 5a | 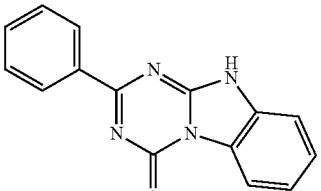 [4949-34-2] | 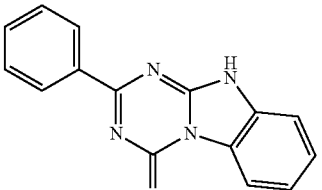 | 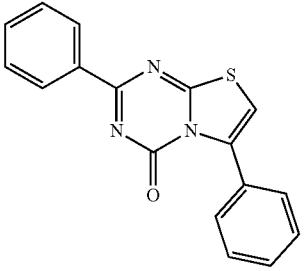 | 40% |
| 6a | 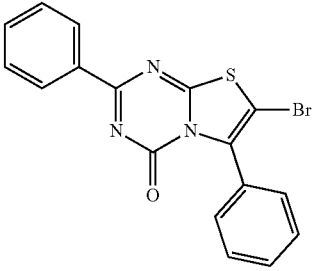 [SMILES: O=c1nc(-c2ccccc2)nc2sc(Br)c(-c3ccccc3)n12] [87614-08-2] | | | 55% | b) 1-[4-(9,9-Dimethylfluoren-2-yl)phenyl]-4,6-diphenyl-1,3,5-triazin-2-one

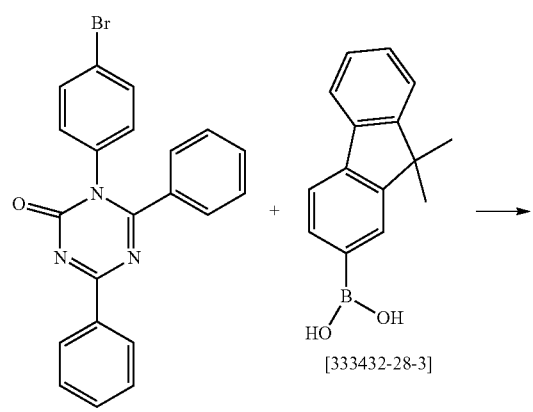

-continued

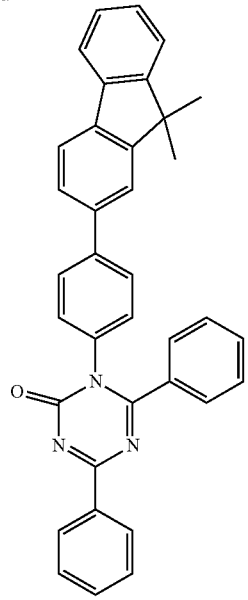

62.8 g (155 mmol) of 1-(4-bromophenyl)-4,6-diphenyl-1,3,5-triazin-2-one, 41 g (172 mmol) of 9,9-dimethyl-9H-fluorene-2-boronic acid and 36 g (340 mmol) of sodium carbonate are suspended in 1000 ml of ethylene glycol dimethyl ether and 280 ml of water. 1.8 g (1.5 mmol) of tetrakis(triphenylphosphine)palladium(0) are added to this suspension, and the reaction mixture is heated under reflux for 16 h. After cooling, the organic phase is removed, filtered through silica gel and then concentrated to dryness. The product is purified via column chromatography on silica gel with toluene/heptane (1:2) and finally sublimed under high vacuum (p=5×10$^{-7}$ mbar) (99.9% purity). The yield is 57 g (112 mmol), corresponding to 72% of theory.

The following compounds are prepared in an analogous manner:

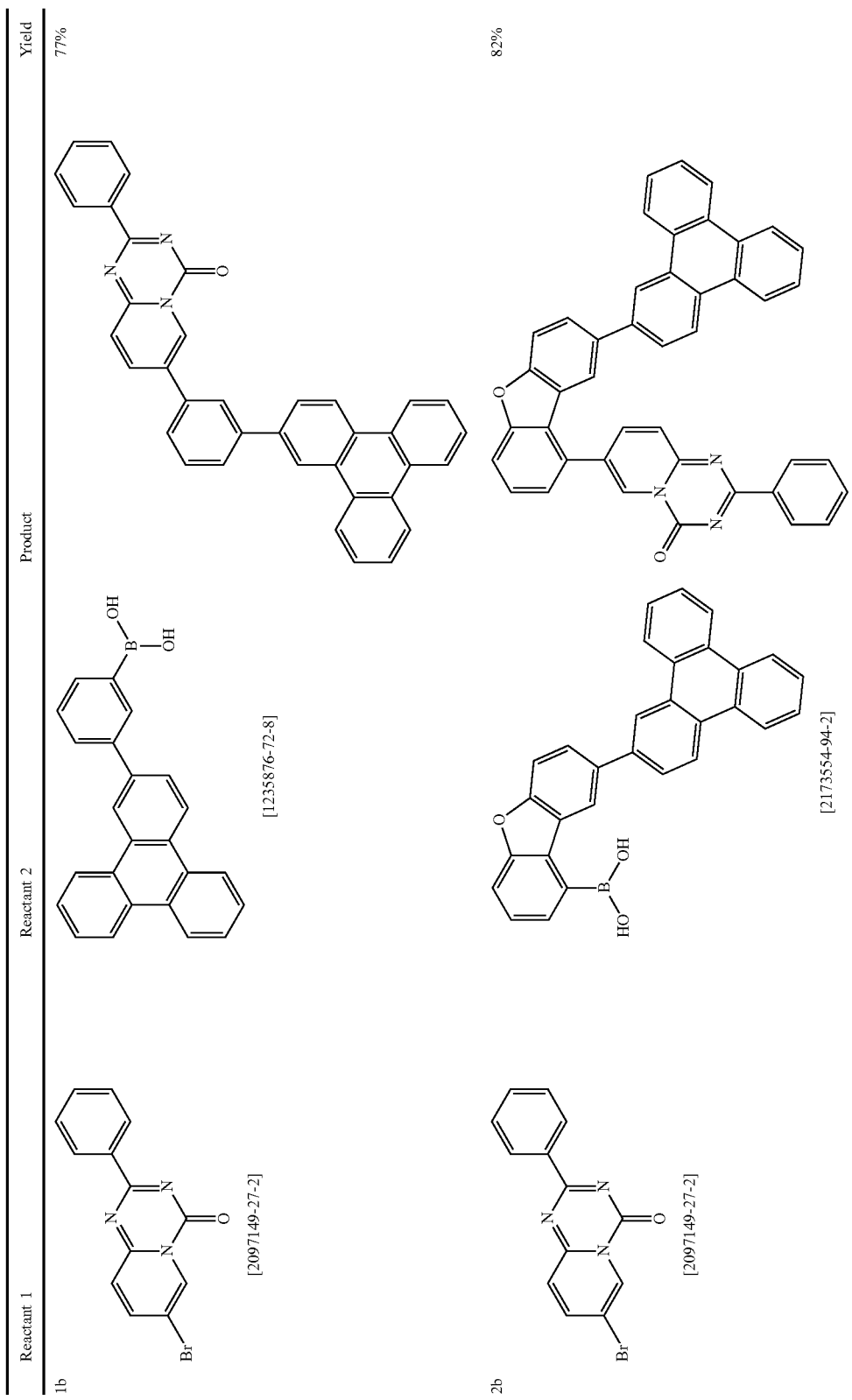

-continued

| Reactant 1 | Reactant 2 | Product | Yield |
|---|---|---|---|
| 3b [18510-67-3] | [2138490-96-5] | | 77% |
| 4b [2097149-27-2] | [2138490-96-5] | | 81% |

| Reactant 1 | Reactant 2 | Product | Yield |
|---|---|---|---|
| 5b | [1822310-23-5] | | 74% |
| 6b | [1883265-31-3] | | 76% |

| Reactant 1 | Reactant 2 | Product | Yield |
|---|---|---|---|
| 7b | B(OH)₂ dibenzofuran [100124-06-9] | | 81% |
| 8b | biphenyl-dibenzofuran-Bpin [2173555-09-2] | | 88% |

| Reactant 1 | Reactant 2 | Product | Yield |
|---|---|---|---|
| 9b | [1235876-72-8] | | 80% |

| | Reactant 1 | Reactant 2 | Product | Yield |
|---|---|---|---|---|
| 10b | (bromo-phenyl-thiazolo-pyrimidinone with phenyl) | 3-(triphenylenyl)phenylboronic acid [1235876-72-8] | (triphenylenyl-phenyl-thiazolo-pyrimidinone) | 89% |
| 11b | 2-(4-chlorophenyl)-4,6-diphenyl-1,3,5-triazine-2-thione [34747-89-2] | (4,6-diphenylpyrimidin-2-yl)boronic acid [1251825-65-6] | bis(triazine)-phenylene product | 63% |

| | Reactant 1 | Reactant 2 | Product | Yield |
|---|---|---|---|---|
| 12b | 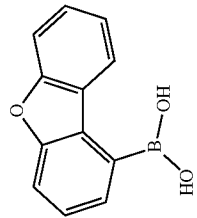 | 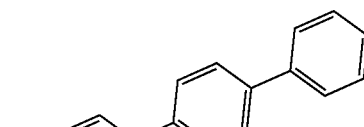 | 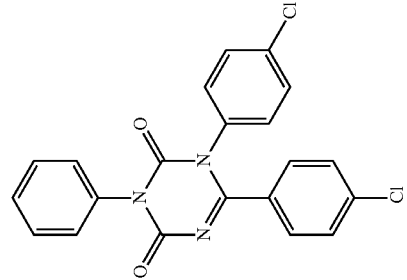 | 66% |
| 13b | 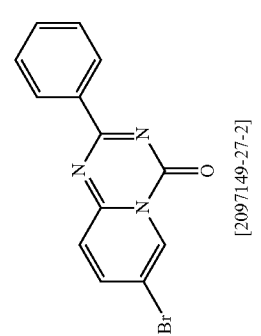 | | | 85% |

| Reactant 1 | Reactant 2 | Product | Yield |
|---|---|---|---|
| 14b 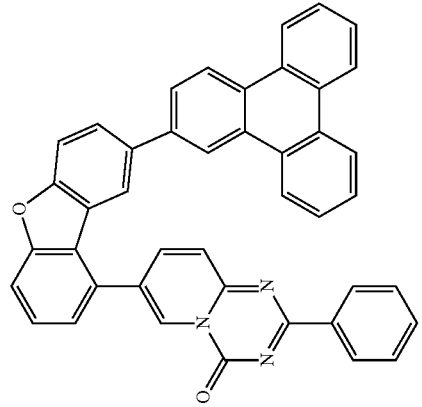 | 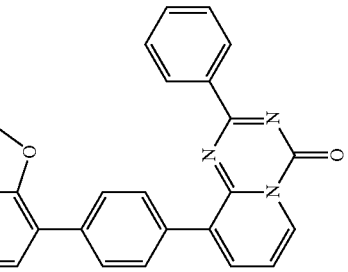 | 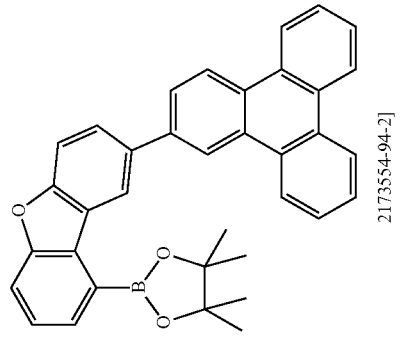 | 86% |
| 15b 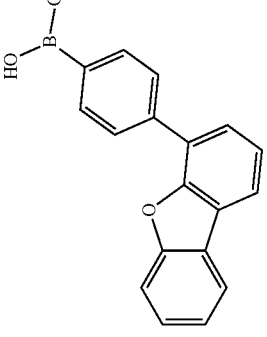 | | | 82% |

| Reactant 1 | Reactant 2 | Product | Yield |
|---|---|---|---|
| 16b [2097149-21-6] | [1235876-72-8] | | 90% |
| 17b [2270171-24-7] | [1251825-65-6] | | 78% |

| Reactant 1 | Reactant 2 | Product | Yield |
|---|---|---|---|
| 18b 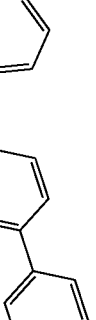 [1334624-98-4] | 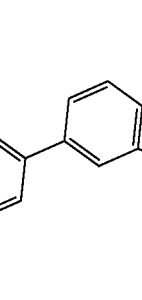 [1572537-61-1] | 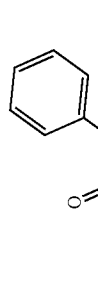 | 78% |

| Reactant 1 | Reactant 2 | Product | Yield |
|---|---|---|---|
| 19b [30006-96-3] | [236389-21-2] | | 67% |
| 20b [1334624-98-4] | [236389-21-2] | | 71% |

| Reactant 1 | Reactant 2 | Product | Yield |
|---|---|---|---|
| 21b [41195-84-0] | [2138490-96-5] | | 63% |

| Reactant 1 | Reactant 2 | Product | Yield |
|---|---|---|---|
| 22b | [2138490-96-5] | | 64% |
| 23b | [1251825-65-6] | | 61% |

| Reactant 1 | Reactant 2 | Product | Yield |
|---|---|---|---|
| 24b [35629-67-5] | [1556069-50-1] | | 73% |
| 25b [35629-68-6] | [33432-28-3] | | 62% |

| | Reactant 1 | Reactant 2 | Product | Yield |
|---|---|---|---|---|
| 26b | 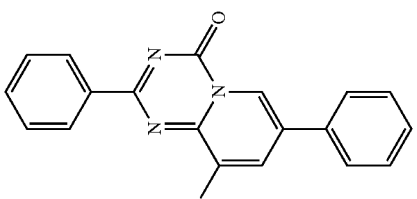 | 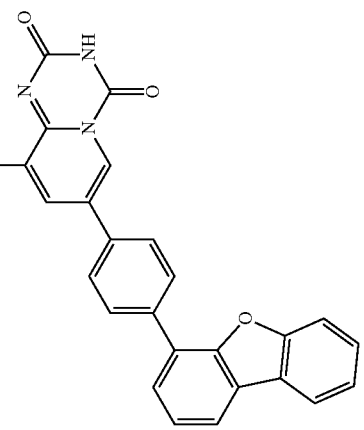 | 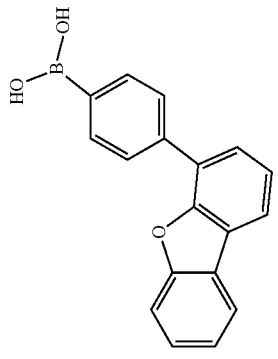 | 65% |
| 27b | 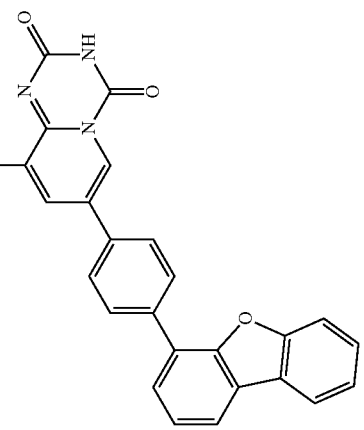 | 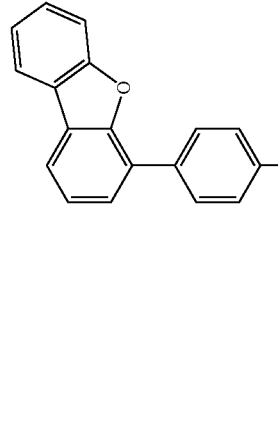 | 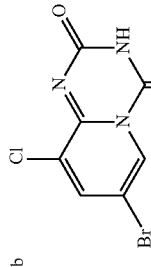 | 66% |

| Reactant 1 | Reactant 2 | Product | Yield |
|---|---|---|---|
| 28b | 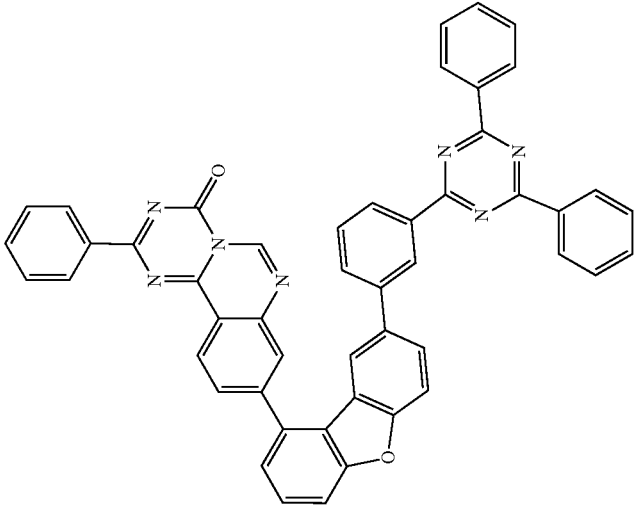 | 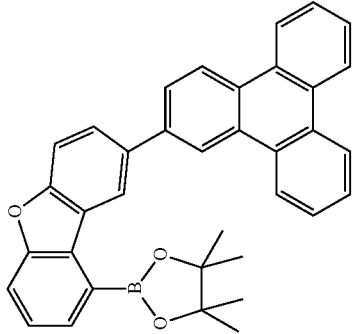 | 65% |
| 29b | 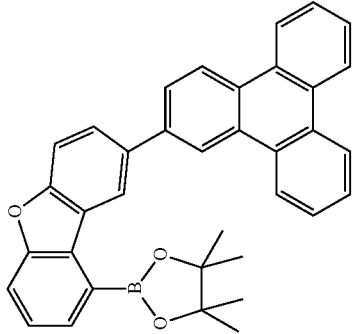 | 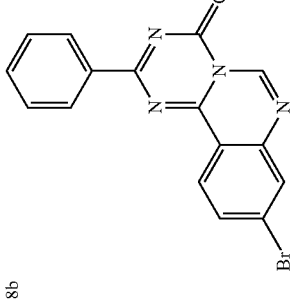 | 72% |

-continued
| Reactant 1 | Reactant 2 | Product | Yield |
|---|---|---|---|
| 30b 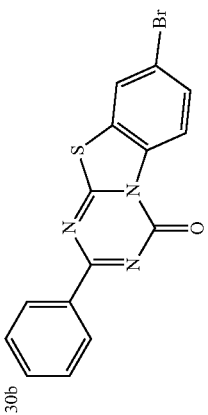 | [2138490-96-5] 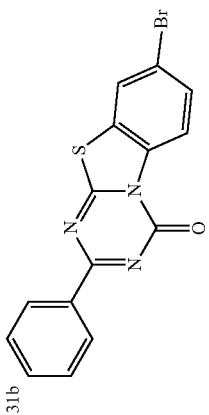 | 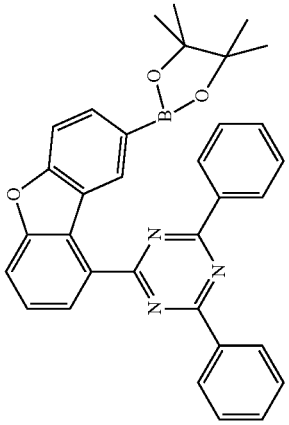 | 78% |
| 31b 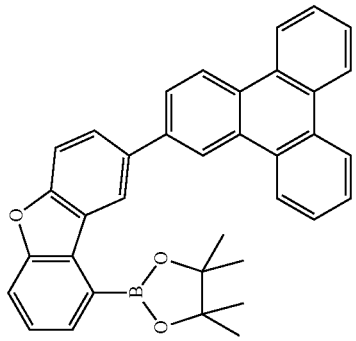 | 2173554-94-2 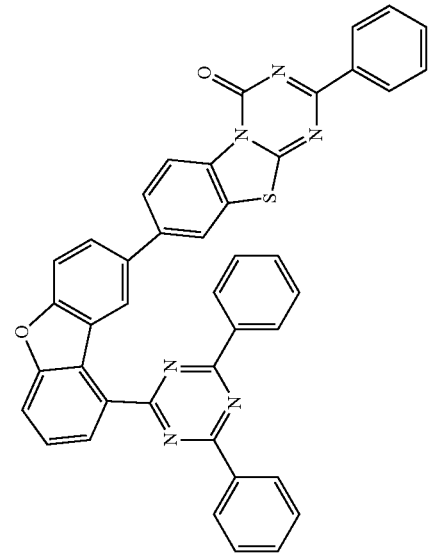 | 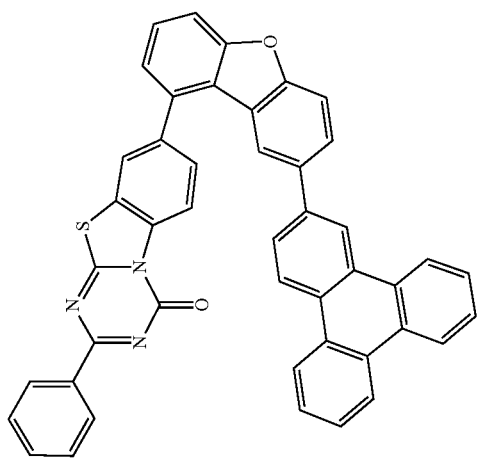 | 68% |

| Reactant 1 | Reactant 2 | Product | Yield |
|---|---|---|---|
| 32b [1334624-98-4] | [1235876-72-8] | | 59% |
| 33b [2097149-27-2] | [1369369-44-7] | | 67% |
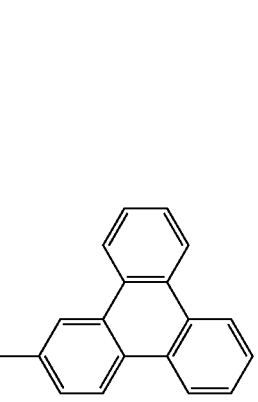

-continued
| Reactant 1 | Reactant 2 | Product | Yield |
|---|---|---|---|
| 34b | 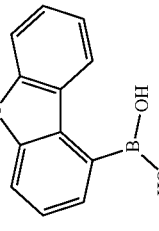 [162607-19-4] | 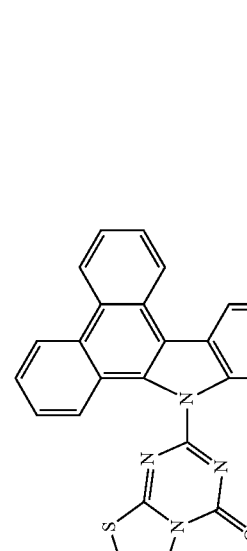 4f | 78% | c) 7,9-Bis(4-dibenzofuran-4-ylphenyl)-3-phenylpyrido[1,2-a][1,3,5]triazine-2,4-dione

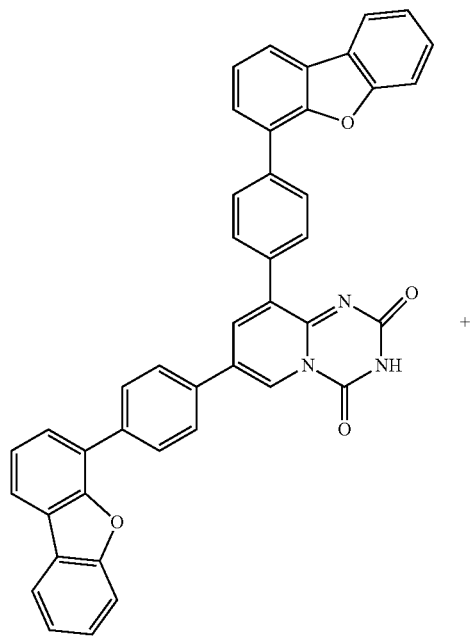

+

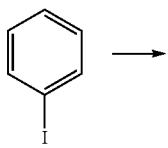

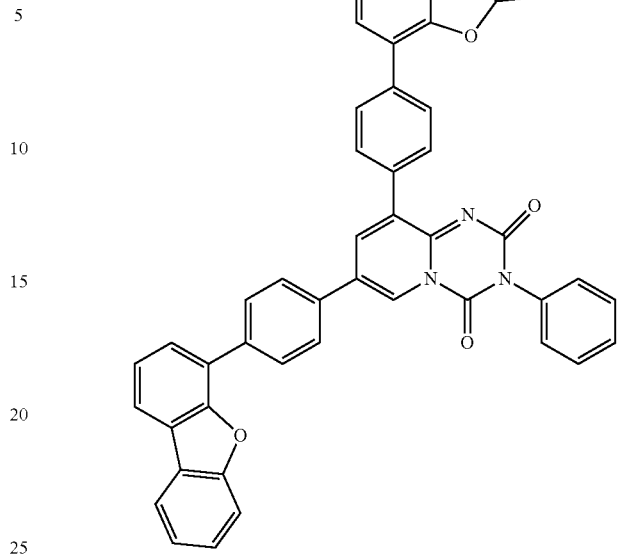

25.8 g (40 mmol) of 6-phenyl-1H-quinazoline-2,4-dione, 61.2 g (85 mmol) of 4-iodobenzene, 44.7 g (320 mmol) of potassium carbonate, 3 g (16 mmol) of copper(I) iodide and 3.6 g (16 mmol) of 1,3-di(pyridin-2-yl)propane-1,3-dione are stirred in 100 ml of DMF at 150° C. for 30 h. The solution is diluted with water and extracted twice with ethyl acetate. The combined organic phases are dried over $Na_2SO_4$ and concentrated by rotary evaporation. The residue is purified by chromatography (EtOAc/hexane: ⅔). The residue is recrystallized from toluene and finally sublimed under high vacuum (p=$5\times10^{-5}$ mbar). The purity is 99.9%. The yield is 20.8 g (28.8 mmol); 72% of theory.

The following compounds are prepared in an analogous manner:

| | Reactant 1 | Reactant 2 | Product | Yield |
|---|---|---|---|---|
| 1c | [32622-40-5] | [502161-03-7] | | 68% |

-continued
| Reactant 1 | Reactant 2 | Product | Yield |
|---|---|---|---|
| 2c 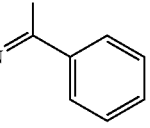 [30886-13-6] | 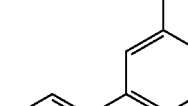 [87666-86-2] | 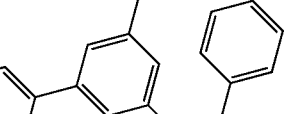 | 64% |
| 3c 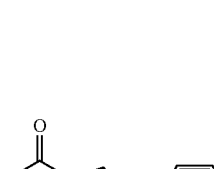 [54450-50-9] | 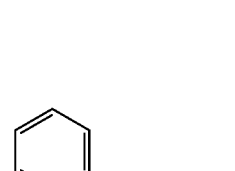 [1591-31-7] | 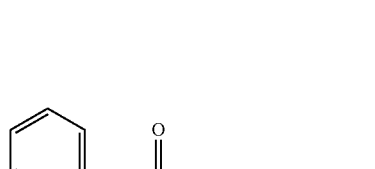 | 71% |
| 4c  [1647107-43-4] |  [65344-26-5] |  | 83% |

-continued
| Reactant 1 | Reactant 2 | Product | Yield |
|---|---|---|---|
| 5c 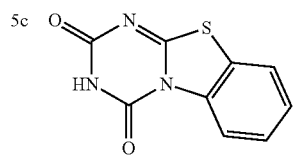 [378205-67-5] | 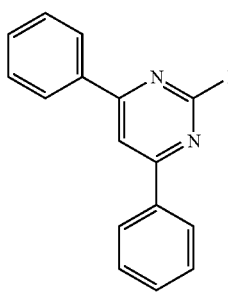 [374077-23-3] | 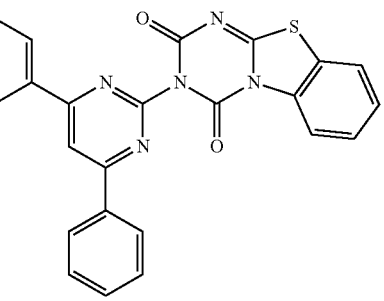 | 75% |
| 6c 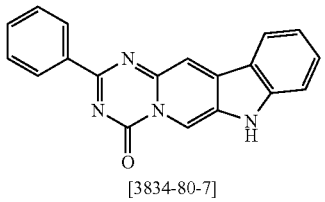 [SMILES: O=c1nc(-c2ccccc2)nc2cc3c(cn12)[nH]c1ccccc13] [3834-80-7] | 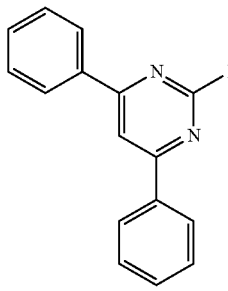 [374077-23-3] | 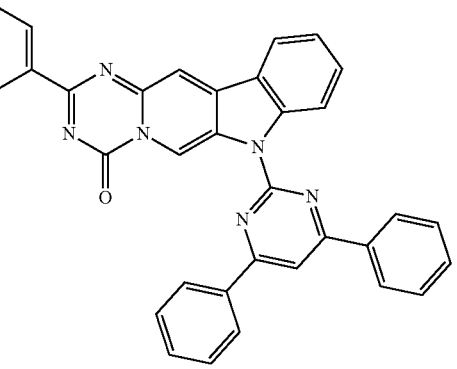 | 67% |
| 7c 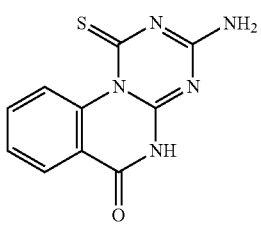 [1266497-72-6] | 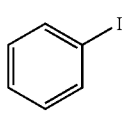 | 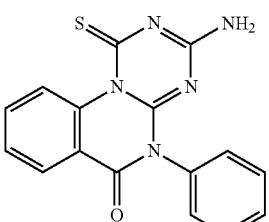 | 66% |
| 8c 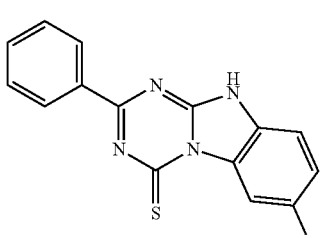 | 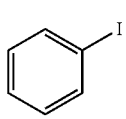 | 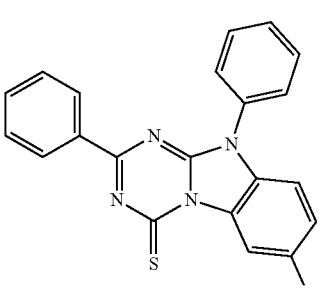 | 63% |
| 9c 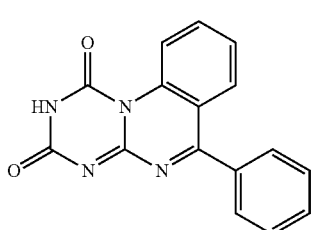 [104425-83-4] | 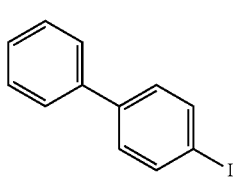 [1591-31-7] | 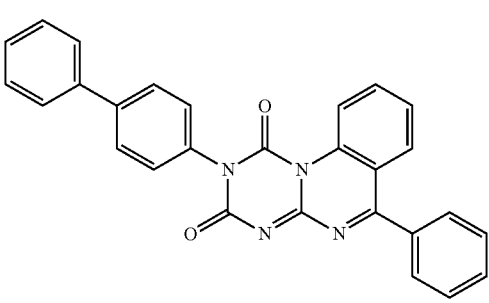 [SMILES: O=c1nc2nc(-c3ccccc3)c3ccccc3n2c(=O)n1-c1ccc(-c2ccccc2)cc1] | 71% |

-continued
| Reactant 1 | Reactant 2 | Product | Yield |
|---|---|---|---|
| 10c 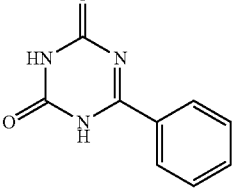 [7459-63-4] | 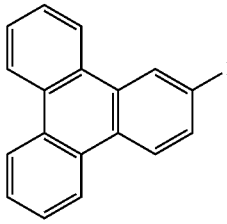 [1228778-59-3] | 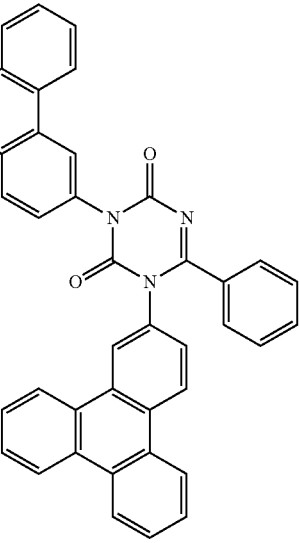 | 59% |
| 11c 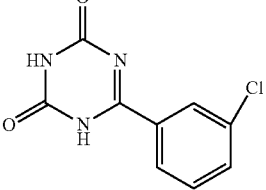 [2131012-07-0] | 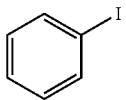 | 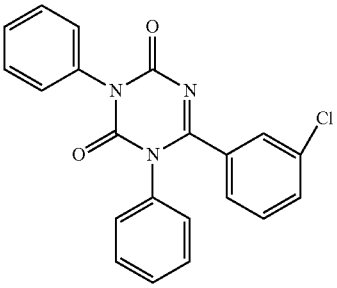 [SMILES: O=c1nc(-c2cccc(Cl)c2)n(-c2ccccc2)c(=O)n1-c1ccccc1] | 75% |
e) 2-Phenyl-7-[3-(9-phenylcarbazol-3-yl)carbazol-9-yl]pyrido[1,2-a][1,3,5]triazin-4-one
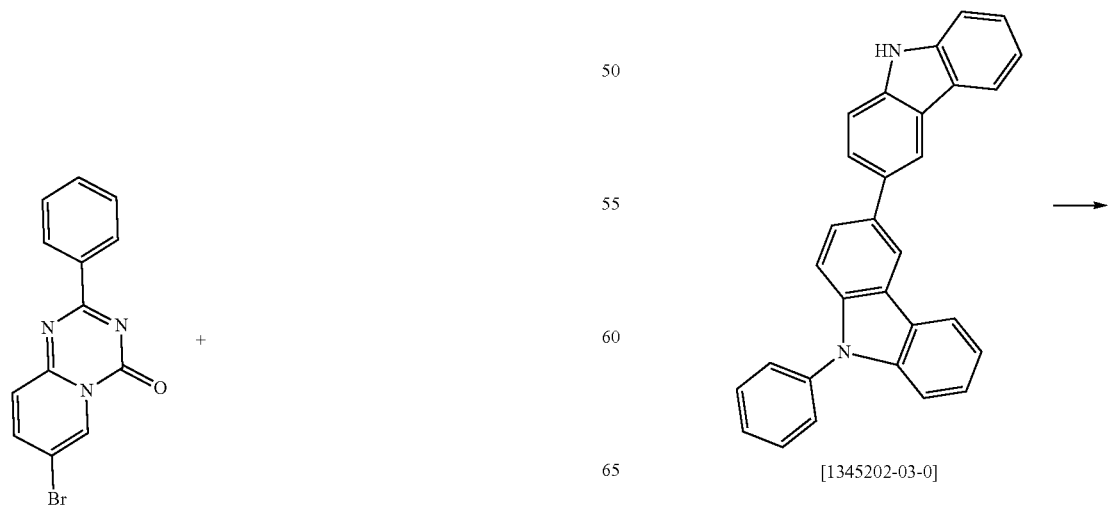
[1345202-03-0]

-continued

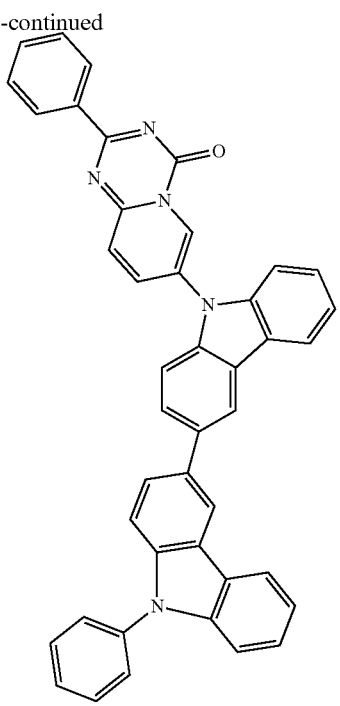

20.4 g (50 mmol) of 9-phenyl-3,3'-bi-9H-carbazole and 17.1 g (50 mmol) of 7-bromo-2-phenylpyrido[1,2-a][1,3,5]triazin-4-one are dissolved in 400 ml of toluene under an argon atmosphere. 1.0 g (5 mmol) of tri-tert-butylphosphine is added and the mixture is stirred under an argon atmosphere. 0.6 g (2 mmol) of Pd(OAc)$_2$ is added and the mixture is stirred under an argon atmosphere, and then 9.5 g (99 mmol) of sodium tert-butoxide are added. The reaction mixture is stirred under reflux for 24 h. After cooling, the organic phase is separated, washed three times with 200 ml of water, dried over MgSO$_4$ and filtered, and the solvent is removed under reduced pressure. The residue is purified by column chromatography using silica gel (eluent: DCM/heptane (1:3)). The residue is subjected to hot extraction with toluene and recrystallized from toluene/n-heptane and finally sublimed under high vacuum. The yield is 28.4 g (42 mmol), corresponding to 85% of theory.

The following compounds can be prepared analogously:

| | Reactant 1 | Reactant 2 | Product | Yield |
|---|---|---|---|---|
| 1e | [2097149-27-2] | [1024598-06-8] | | 73% |
| 2e | [2097149-27-2] | [1345202-03-0] | | 70% |

| | Reactant 1 | Reactant 2 | Product | Yield |
|---|---|---|---|---|
| 3e | 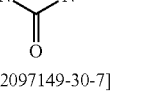 [2097149-30-7] | 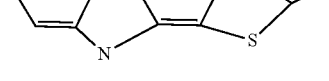 [1313395-18-4] | 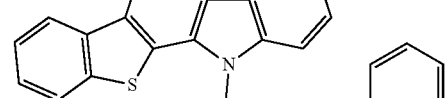 | 68% |
| 4e | 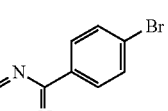 [2097149-21-6] |  [1345202-03-0] | 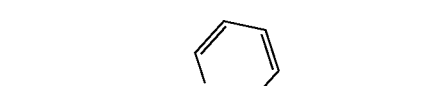 | 73% |
| 5e | 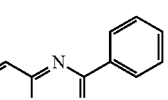 [2097149-27-2] | 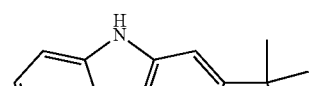 [1257220-47-5] | 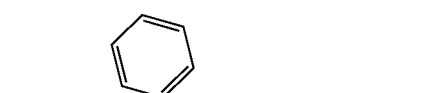 | 84% |

| Reactant 1 | Reactant 2 | Product | Yield |
|---|---|---|---|
| 6e [34747-89-2] | [1257220-47-5] | | 82% |
| 7e [18510-68-4] | [1024598-06-8] | | 67% |
| 8e | | | 62% |

| Reactant 1 | Reactant 2 | Product | Yield |
|---|---|---|---|
| 9e | [1313395-18-4] | | 60% |
| 10e | [1257220-47-5] | | 83% |
| 11e | [1257220-47-5] | | 88% |

| Reactant 1 | Reactant 2 | Product | Yield |
|---|---|---|---|
| 12e 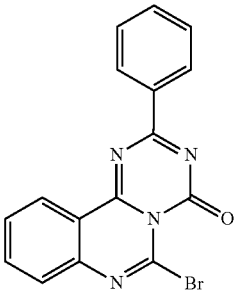 | 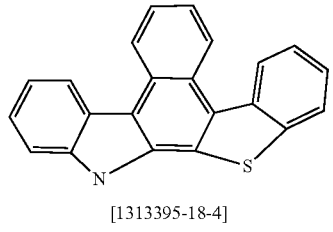 [1313395-18-4] | 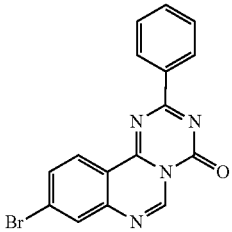 [SMILES: O=c1nc(-c2ccccc2)nc2c3ccc(Br)cc3ncn12] | 78% |
| 13e 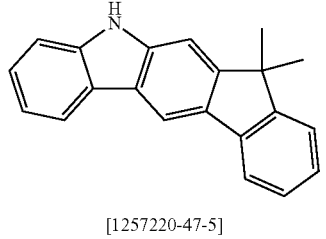 [SMILES: CC1(C)c2ccccc2-c2cc3c(cc21)[nH]c1ccccc13] | 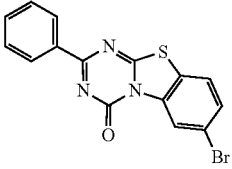 [SMILES: O=c1nc(-c2ccccc2)nc2sc3ccc(Br)cc3n12] [1257220-47-5] | 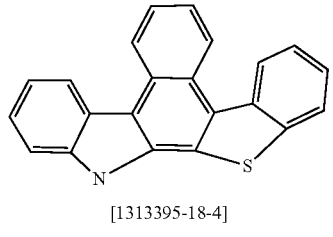 | 90% |
| 14e | | | 71% |

-continued
| Reactant 1 | Reactant 2 | Product | Yield |
|---|---|---|---|
| 15e 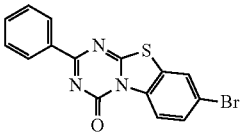 [SMILES: O=c1nc(-c2ccccc2)nc2sc3cc(Br)ccc3n12] | 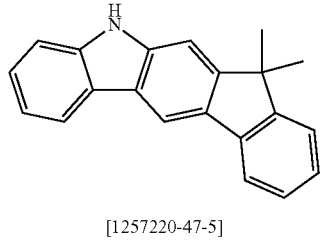 [SMILES: CC1(C)c2ccccc2-c2cc3c(cc21)[nH]c1ccccc13][1257220-47-5] | 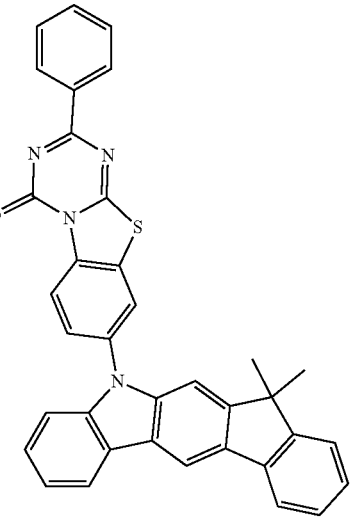 | 92% |
| 16e 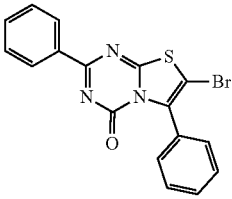 [SMILES: O=c1nc(-c2ccccc2)nc2sc(Br)c(-c3ccccc3)n12] | 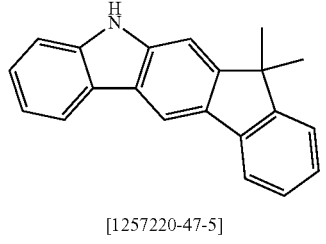 [SMILES: CC1(C)c2ccccc2-c2cc3c(cc21)[nH]c1ccccc13][1257220-47-5] | 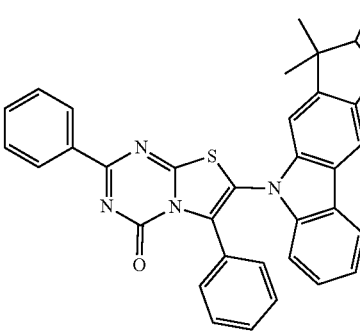 | 89% |
| 17e 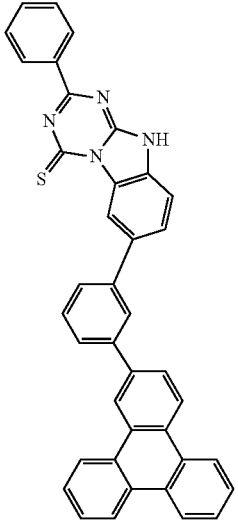 [SMILES: S=c1nc(-c2ccccc2)nc2[nH]c3ccc(-c4cccc(-c5ccc6c7ccccc7c7ccccc7c6c5)c4)cc3n12] | 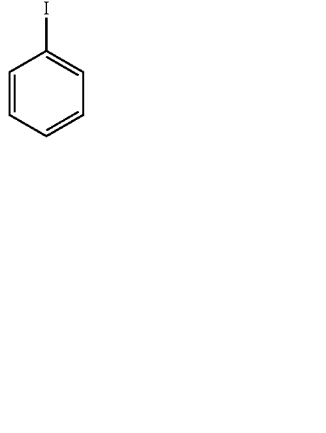 | 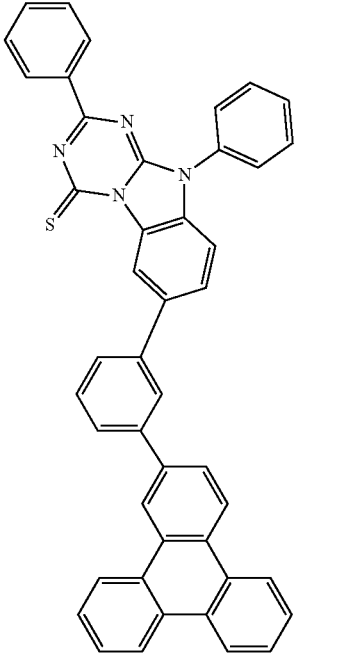 [SMILES: S=c1nc(-c2ccccc2)nc2n(-c3ccccc3)c3ccc(-c4cccc(-c5ccc6c7ccccc7c7ccccc7c6c5)c4)cc3n12] | 77% |

-continued
| Reactant 1 | Reactant 2 | Product | Yield |
|---|---|---|---|
| 18e 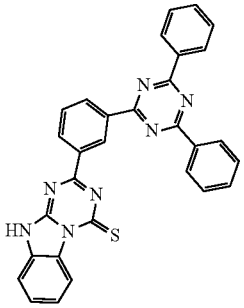 [SMILES: S=c1nc(-c2cccc(-c3nc(-c4ccccc4)nc(-c4ccccc4)n3)c2)nc2[nH]c3ccccc3n12] | 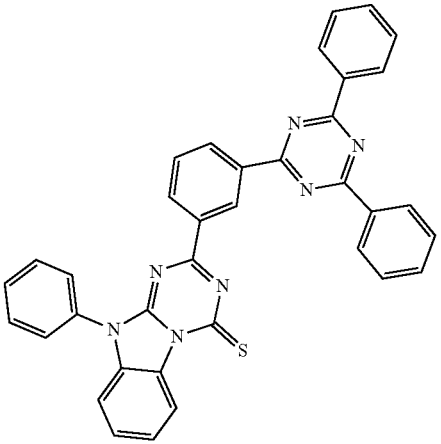 [SMILES: S=c1nc(-c2cccc(-c3nc(-c4ccccc4)nc(-c4ccccc4)n3)c2)nc2n(-c3ccccc3)c3ccccc3n12] [591-50-4] | 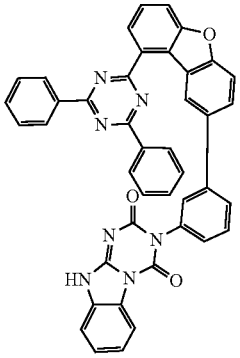 [SMILES: O=c1nc2[nH]c3ccccc3n2c(=O)n1-c1cccc(-c2ccc3oc4cccc(-c5nc(-c6ccccc6)nc(-c6ccccc6)n5)c4c3c2)c1] | 73% |
| 19e 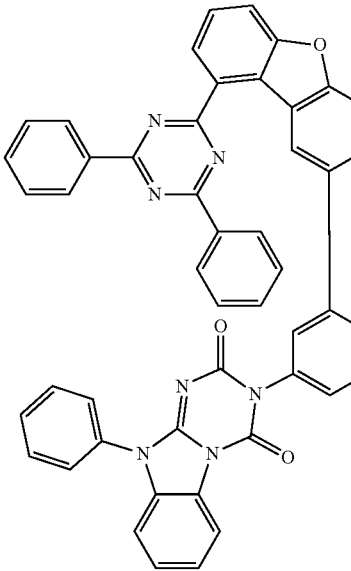 | I | | 65% |

| Reactant 1 | Reactant 2 | Product | Yield |
|---|---|---|---|
| 20e 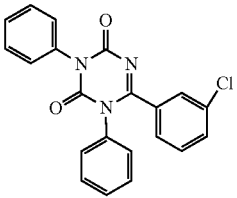 [SMILES: O=c1nc(-c2cccc(Cl)c2)n(-c2ccccc2)c(=O)n1-c1ccccc1] | 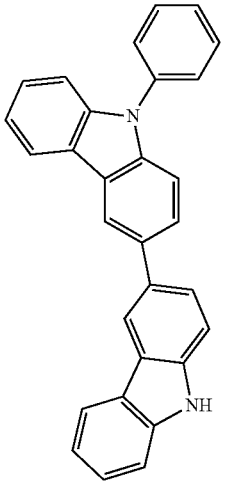  [1345202-03-0] | 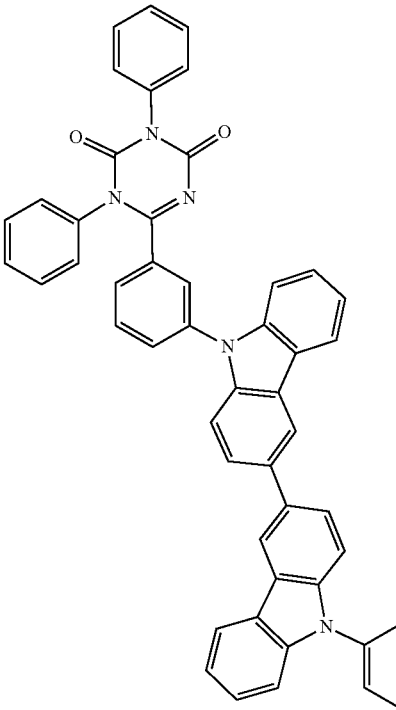 | 67% | f) Benzofuro[3,2-c]carbazol-5-yl-[1,3,5]triazino[2,1-b][1,3]benzoxazol-4-one

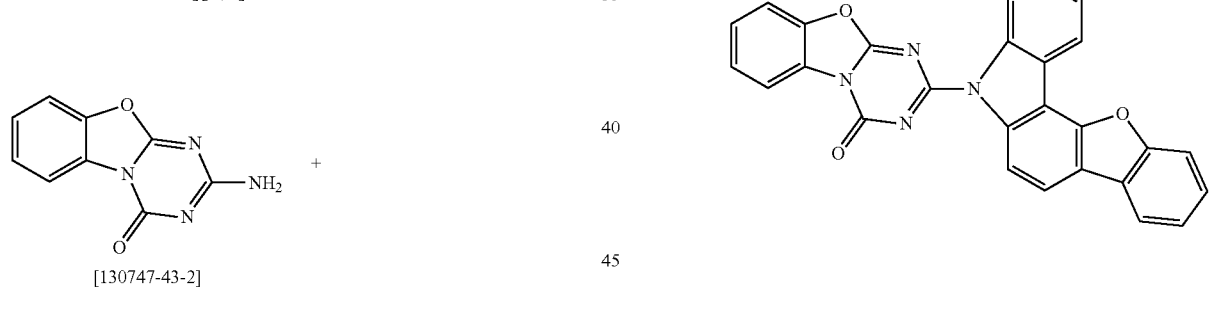

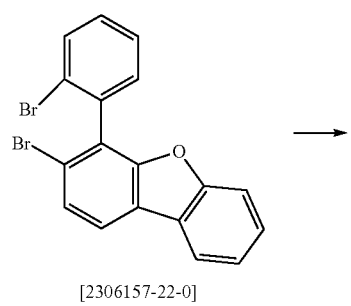

[2306157-22-0]

To 20 g (50 mmol) of 3-bromo-4-(2-bromophenyl)dibenzofuran are added 500 ml of toluene, 2.3 g (2.5 mmol) of tris(dibenzylideneacetone)dipalladium(0), 10 ml of 1 M t-Bu₃P in toluene and 11.5 g (120 mmol) of sodium tert-butoxide. Subsequently, 8.8 g (40 mmol) of 2-amino-[1,3,5]triazino[2,1-b][1,3]benzoxazol-4-one is added. The mixture is heated to 110° C. for 20 h, then cooled to room temperature, and 400 ml of water is added. The mixture is extracted with ethyl acetate, then the combined organic phases are dried over sodium sulfate and concentrated under reduced pressure. The residue is recrystallized from toluene and from dichloromethane/iso-propanol and finally sublimed under high vacuum. The purity is 99.9%. The yield is 10.6 g (24.5 mmol), corresponding to 49% of theory.

The following compounds can be prepared analogously:
| Reactant 1 | Reactant 2 | Product | Yield |
|---|---|---|---|
| 1f 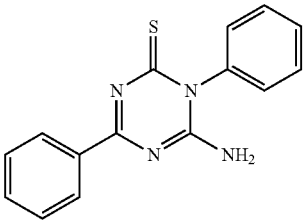 [841119-18-6] | 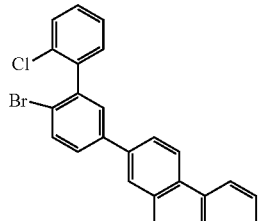 [2274771-95-6] | 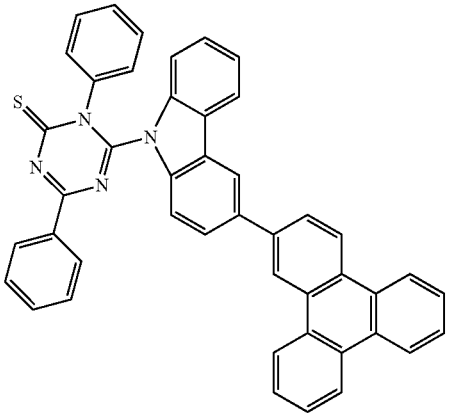 [SMILES: S=c1nc(-c2ccccc2)nc(-n2c3ccccc3c3cc(-c4ccc5c6ccccc6c6ccccc6c5c4)ccc32)n1-c1ccccc1] | 45% |
| 2f 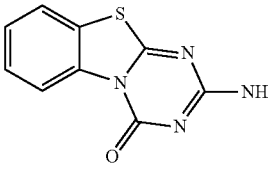 [130747-42-1] | 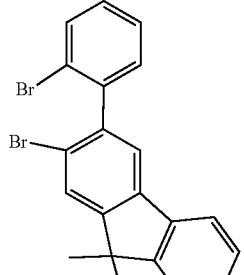 [2306157-06-0] | 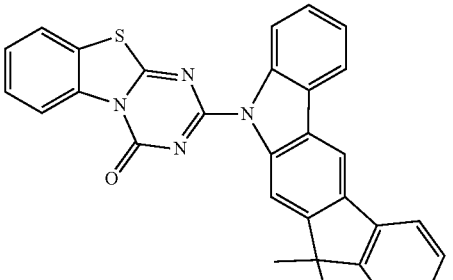 | 51% |
| 3f 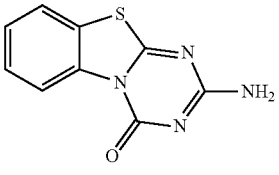 [130747-42-1] | 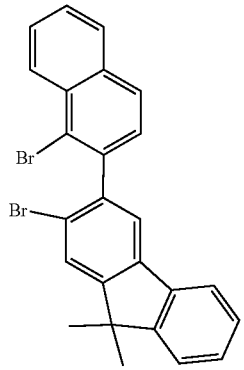 [2306157-10-6] | 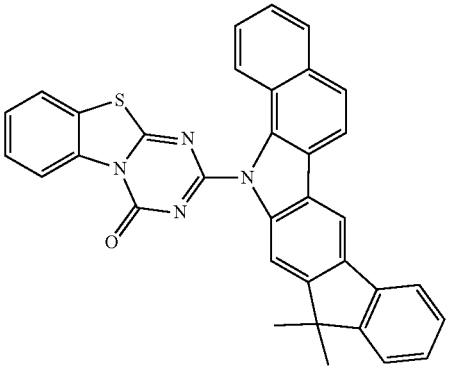 [SMILES: CC1(C)c2ccccc2-c2cc3c4ccc5ccccc5c4n(-c4nc(=O)n5c(n4)sc4ccccc45)c3cc21] | 43% |
| 4f 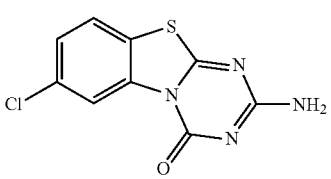 [885044-07-5] | 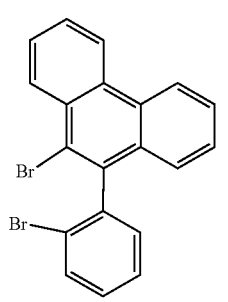 [3582-47-6] | 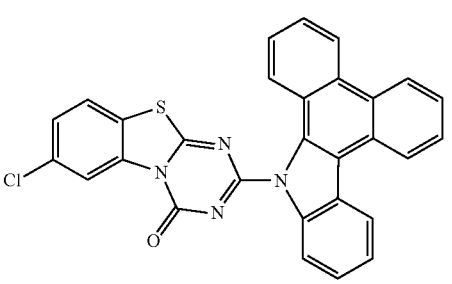 [SMILES: O=c1nc(-n2c3ccccc3c3c4ccccc4c4ccccc4c32)nc2sc3ccc(Cl)cc3n12] | 41% |

-continued

| Reactant 1 | Reactant 2 | Product | Yield |
|---|---|---|---|
| 5f 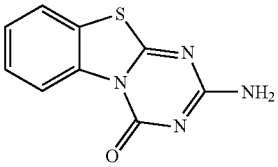 [130747-42-1] | 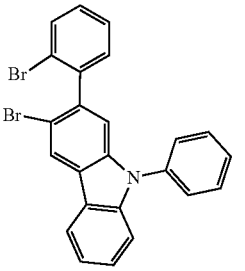 [1521093-11-7] | 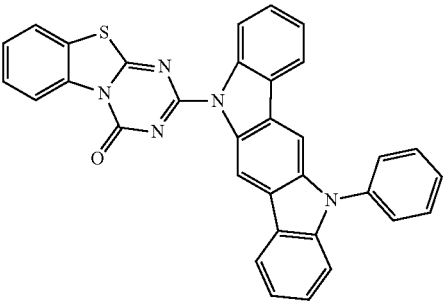 [SMILES: O=c1nc(-n2c3ccccc3c3cc4c(cc32)c2ccccc2n4-c2ccccc2)nc2sc3ccccc3n12] | 46% |
| 6f 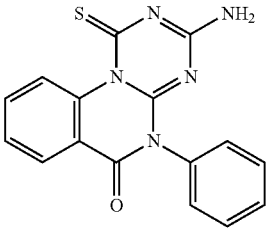 [SMILES: Nc1nc(=S)n2c3ccccc3c(=O)n(-c3ccccc3)c2n1] | 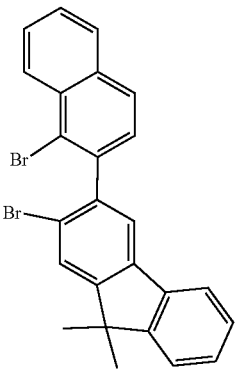 [2306157-10-6] | 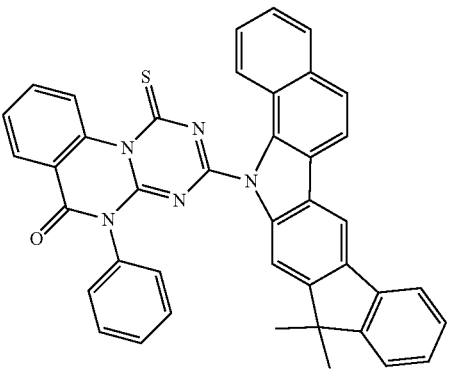 [SMILES: CC1(C)c2ccccc2-c2cc3c4ccc5ccccc5c4n(-c4nc(=S)n5c6ccccc6c(=O)n(-c6ccccc6)c5n4)c3cc21] | 39% |

Production of the OLEDs

Examples E1 to E27 which follow (see table 1) present the use of the materials of the invention in OLEDs.

Pretreatment for examples E1 to E27: Glass plates coated with structured ITO (indium tin oxide) of thickness 50 nm are treated prior to coating with an oxygen plasma, followed by an argon plasma. These plasma-treated glass plates form the substrates to which the OLEDs are applied.

The OLEDs basically have the following layer structure: substrate/hole injection layer (HIL)/hole transport layer (HTL)/electron blocker layer (EBL)/emission layer (EML)/ optional hole blocker layer (HBL)/electron transport layer (ETL)/optional electron injection layer (EIL) and finally a cathode. The cathode is formed by an aluminum layer of thickness 100 nm. The exact structure of the OLEDs can be found in table 1. The materials required for production of the OLEDs are shown in table 2.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. What is meant here by details given in such a form as EG1:IC2:TEG1 (49%:44%:7%) is that the material EG1 is present in the layer in a proportion by volume of 49%, IC2 in a proportion by volume of 44%, and TEG1 in a proportion by volume of 7%. Analogously, the electron transport layer may also consist of a mixture of two materials.

The OLEDs are characterized in a standard manner. For this purpose, electroluminescence spectra, current efficiency (CE, measured in cd/A) and external quantum efficiency (EQE, measured in %) are determined as a function of luminance, calculated from current-voltage-luminance characteristics assuming Lambertian emission characteristics. Electroluminescence spectra are determined at a luminance of 1000 cd/m², and these are used to calculate the CIE 1931 x and y color coordinates. The results thus obtained can be found in table 3.

Compounds EG1 to EG11 and EG17 to EG25 are used in examples E1 to E20 as matrix material in the emission layer of phosphorescent green OLEDs. Compounds EG12 to EG16 are used in examples E21 to E25 as matrix material in the emission layer of phosphorescent red OLEDs. Compounds EG5 to EG7 are used in examples E26 to E27 as electron transporter in the ETM layer of phosphorescent green OLEDs.

TABLE 1

Structure of the OLEDs

| Ex. | HIL thickness | HTL thickness | EBL thickness | EML thickness | HBL thickness | ETL thickness | EIL thickness |
|---|---|---|---|---|---|---|---|
| E1 | HATCN 5 nm | SpMA1 230 nm | SpMA2 20 nm | EG1:IC2:TEG1 (49%:44%:7%) 40 nm | ST2 5 nm | ST2:LiQ (50%:50%) 30 nm | LiQ 1 nm |

TABLE 1-continued

| | | | | Structure of the OLEDs | | | |
|---|---|---|---|---|---|---|---|
| Ex. | HIL thickness | HTL thickness | EBL thickness | EML thickness | HBL thickness | ETL thickness | EIL thickness |
| E2 | HATCN 5 nm | SpMA1 230 nm | SpMA2 20 nm | EG2:IC2:TEG1 (49%:44%:7%) 40 nm | ST2 5 nm | ST2:LiQ (50%:50%) 30 nm | LiQ 1 nm |
| E3 | HATCN 5 nm | SpMA1 230 nm | SpMA2 20 nm | EG3:IC2:TEG1 (49%:44%:7%) 40 nm | ST2 5 nm | ST2:LiQ (50%:50%) 30 nm | LiQ 1 nm |
| E4 | HATCN 5 nm | SpMA1 230 nm | SpMA2 20 nm | EG4:IC2:TEG1 (49%:44%:7%) 40 nm | ST2 5 nm | ST2:LiQ (50%:50%) 30 nm | LiQ 1 nm |
| E5 | HATCN 5 nm | SpMA1 230 nm | SpMA2 20 nm | EG5:IC3:TEG1 (45%:45%:10%) 30 nm | ST2 10 nm | ST2:LiQ (50%:50%) 30 nm | LiQ 1 nm |
| E6 | HATCN 5 nm | SpMA1 230 nm | SpMA2 20 nm | EG6: IC3:TEG1 (44%:44%:12%) 30 nm | ST2 10 nm | ST2:LiQ (50%:50%) 30 nm | LiQ 1 nm |
| E7 | HATCN 5 nm | SpMA1 230 nm | SpMA2 20 nm | EG7: IC3:TEG1 (44%:44%:12%) 30 nm | ST2 10 nm | ST2:LiQ (50%:50%) 30 nm | LiQ 1 nm |
| E8 | HATCN 5 nm | SpMA1 230 nm | SpMA2 20 nm | EG8: IC3:TEG1 (46%:47%:7%) 30 nm | ST2 10 nm | ST2:LiQ (50%:50%) 30 nm | LiQ 1 nm |
| E9 | HATCN 5 nm | SpMA1 230 nm | SpMA2 20 nm | EG9: IC3:TEG1 (46%:47%:7%) 30 nm | ST2 10 nm | ST2:LiQ (50%:50%) 30 nm | LiQ 1 nm |
| E10 | HATCN 5 nm | SpMA1 230 nm | SpMA2 20 nm | EG10: IC3:TEG1 (46%:47%:7%) 30 nm | ST2 10 nm | ST2:LiQ (50%:50%) 30 nm | LiQ 1 nm |
| E11 | HATCN 5 nm | SpMA1 230 nm | SpMA2 20 nm | EG11: IC3:TEG1 (46%:47%:7%) 30 nm | ST2 10 nm | ST2:LiQ (50%:50%) 30 nm | LiQ 1 nm |
| E12 | HATCN 5 nm | SpMA1 230 nm | SpMA2 20 nm | EG17: IC3:TEG1 (46%:47%:7%) 30 nm | ST2 10 nm | ST2:LiQ (50%:50%) 30 nm | LiQ 1 nm |
| E13 | HATCN 5 nm | SpMA1 230 nm | SpMA2 20 nm | EG18: IC3:TEG1 (46%:47%:7%) 30 nm | ST2 10 nm | ST2:LiQ (50%:50%) 30 nm | LiQ 1 nm |
| E14 | HATCN 5 nm | SpMA1 230 nm | SpMA2 20 nm | EG19: IC3:TEG1 (46%:47%:7%) 30 nm | ST2 10 nm | ST2:LiQ (50%:50%) 30 nm | LiQ 1 nm |
| E15 | HATCN 5 nm | SpMA1 230 nm | SpMA2 20 nm | EG20: IC3:TEG1 (46%:47%:7%) 30 nm | ST2 10 nm | ST2:LiQ (50%:50%) 30 nm | LiQ 1 nm |
| E16 | HATCN 5 nm | SpMA1 230 nm | SpMA2 20 nm | EG21: IC3:TEG1 (46%:47%:7%) 30 nm | ST2 10 nm | ST2:LiQ (50%:50%) 30 nm | LiQ 1 nm |
| E17 | HATCN 5 nm | SpMA1 230 nm | SpMA2 20 nm | EG22: IC3:TEG1 (46%:47%:7%) 30 nm | ST2 10 nm | ST2:LiQ (50%:50%) 30 nm | LiQ 1 nm |
| E18 | HATCN 5 nm | SpMA1 230 nm | SpMA2 20 nm | EG23: IC3:TEG1 (46%:47%:7%) 30 nm | ST2 10 nm | ST2:LiQ (50%:50%) 30 nm | LiQ 1 nm |
| E19 | HATCN 5 nm | SpMA1 230 nm | SpMA2 20 nm | EG24: IC3:TEG1 (46%:47%:7%) 30 nm | ST2 10 nm | ST2:LiQ (50%:50%) 30 nm | LiQ 1 nm |
| E20 | HATCN 5 nm | SpMA1 230 nm | SpMA2 20 nm | EG25: IC3:TEG1 (46%:47%:7%) 30 nm | ST2 10 nm | ST2:LiQ (50%:50%) 30 nm | LiQ 1 nm |
| E21 | HATCN 5 nm | SpMA1 125 nm | SpMA2 10 nm | EG12:TER5 (97%:3%) 35 nm | ST2 10 nm | ST2:LiQ (50%:50%) 30 nm | LiQ 1 nm |
| E22 | HATCN 5 nm | SpMA1 125 nm | SpMA2 10 nm | EG13:TER5 (97%:3%) 35 nm | ST2 10 nm | ST2:LiQ (50%:50%) 30 nm | LiQ 1 nm |
| E23 | HATCN 5 nm | SpMA1 125 nm | SpMA2 10 nm | EG14:TER5 (97%:3%) 35 nm | ST2 10 nm | ST2:LiQ (50%:50%) 30 nm | LiQ 1 nm |
| E24 | HATCN 5 nm | SpMA1 125 nm | SpMA2 10 nm | EG15:TER5 (97%:3%) 35 nm | ST2 10 nm | ST2:LiQ (50%:50%) 30 nm | LiQ 1 nm |
| E25 | HATCN 5 nm | SpMA1 125 nm | SpMA2 10 nm | EG16:TER5 (97%:3%) 35 nm | ST2 10 nm | ST2:LiQ (50%:50%) 30 nm | LiQ 1 nm |
| E26 | HATCN 5 nm | SpMA1 70 nm | SpMA2 15 nm | IC1:TEG1 (90%:10%) 25 nm | — | EG5 45 nm | LiQ 3 nm |
| E27 | HATCN 5 nm | SpMA1 70 nm | SpMA2 15 nm | IC1:TEG1 (90%:10%) 25 nm | — | EG7 45 nm | LiQ 3 nm |

TABLE 2
Structural formulae of the materials for the OLEDs
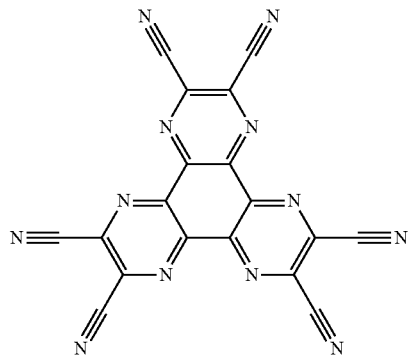
HATCN
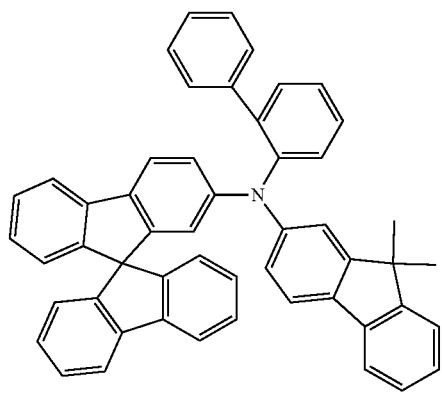
SpMA1
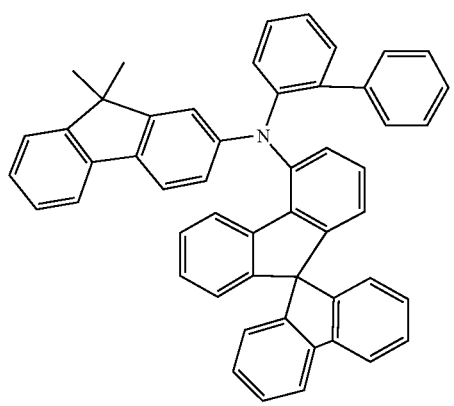
SpMA3

TABLE 2-continued
Structural formulae of the materials for the OLEDs
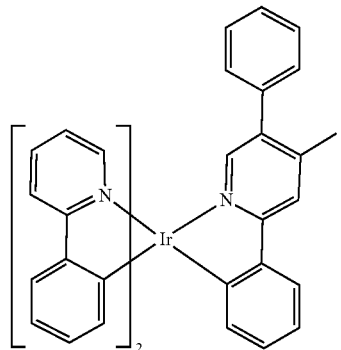
TEG1
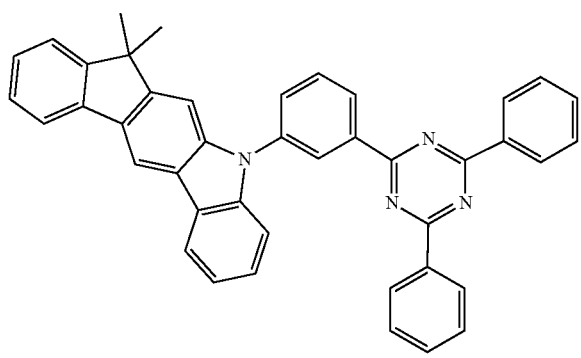
IC1
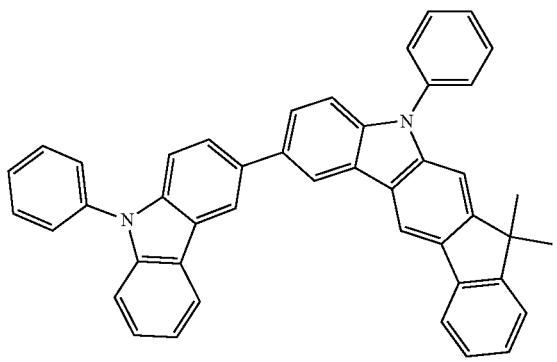
IC2
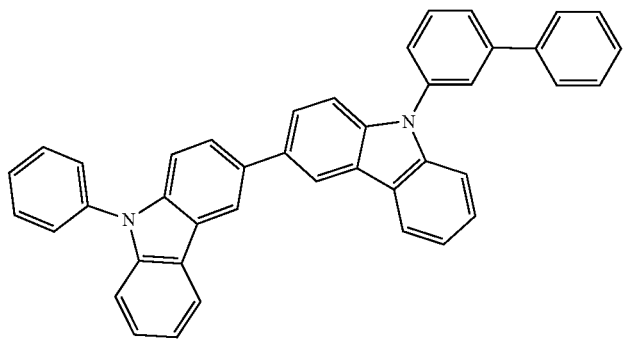
IC3

TABLE 2-continued
Structural formulae of the materials for the OLEDs
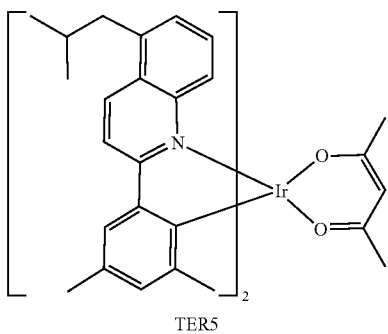
TER5
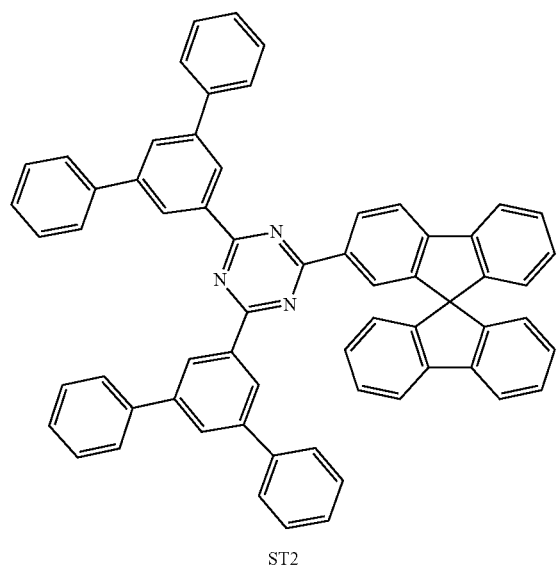
ST2
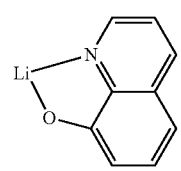
LiQ TABLE 2-continued
Structural formulae of the materials for the OLEDs
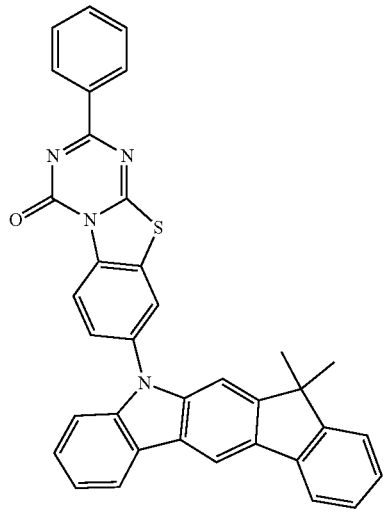
EG1 (15e)
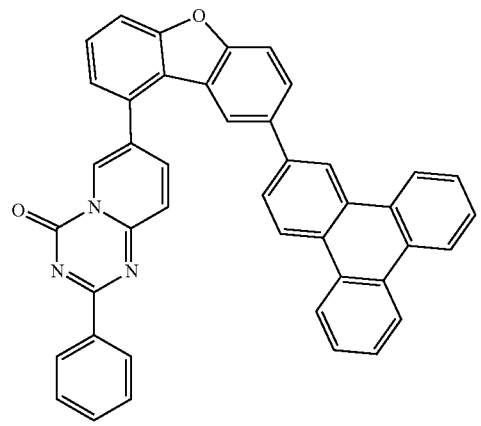
EG2 (2b)
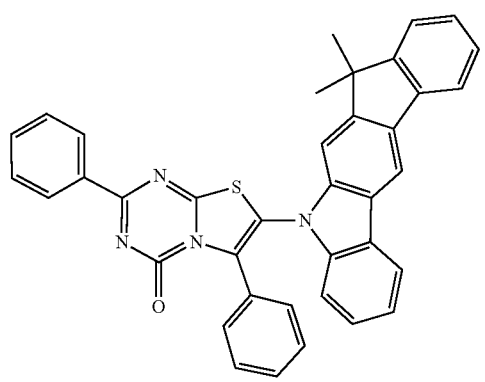
EG3 (16a)

TABLE 2-continued
Structural formulae of the materials for the OLEDs
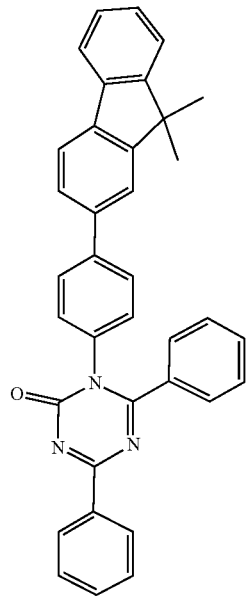
EG4 (b)
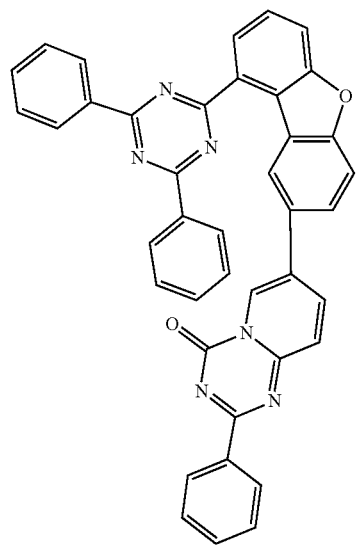
EG5 (4b)

TABLE 2-continued
Structural formulae of the materials for the OLEDs
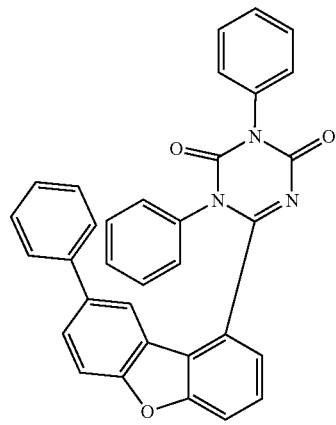
EG6 (5b)
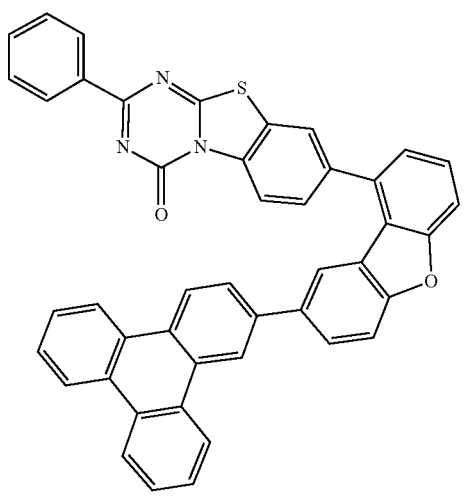
EG7 (31b)
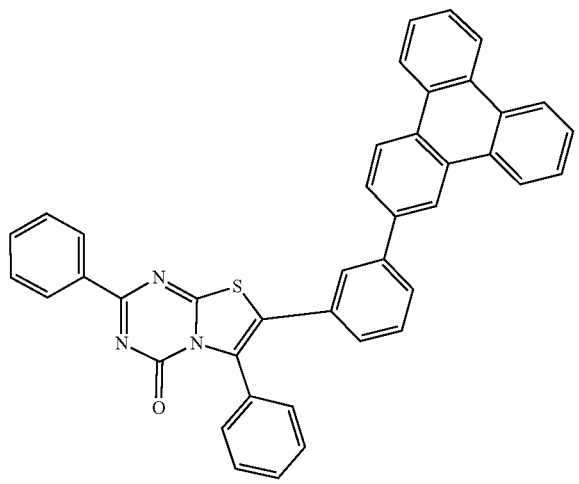
EG8 (10b)

TABLE 2-continued
Structural formulae of the materials for the OLEDs
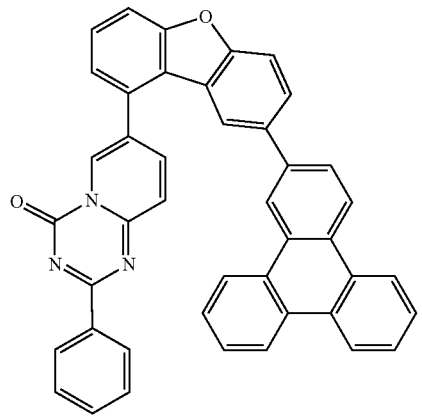
EG9 (14b)
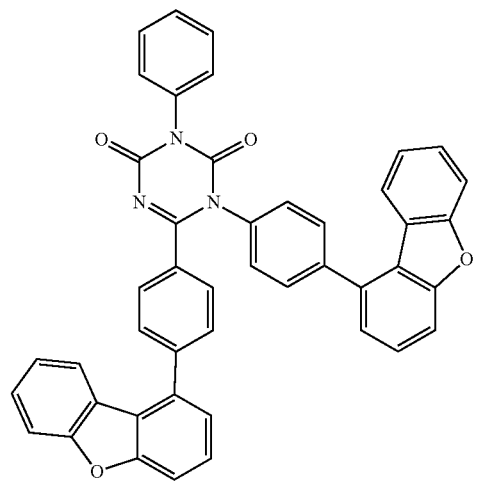
EG10 (12b)

TABLE 2-continued
Structural formulae of the materials for the OLEDs
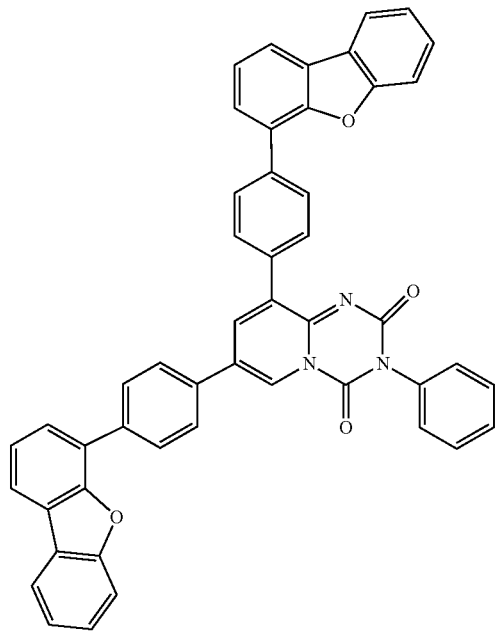
EG11 (c)
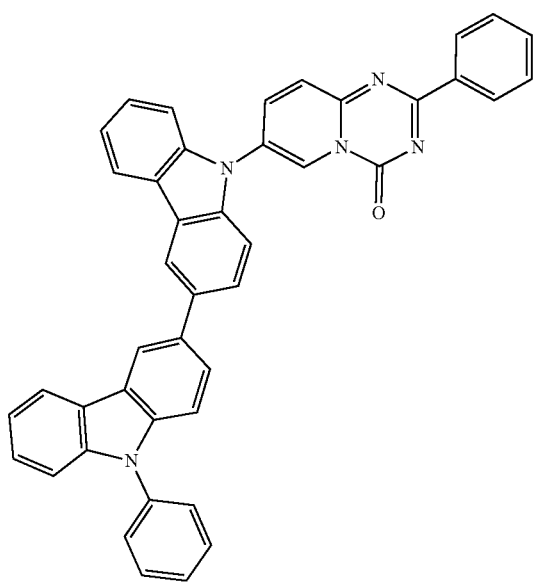
EG12 (2e)

TABLE 2-continued
Structural formulae of the materials for the OLEDs
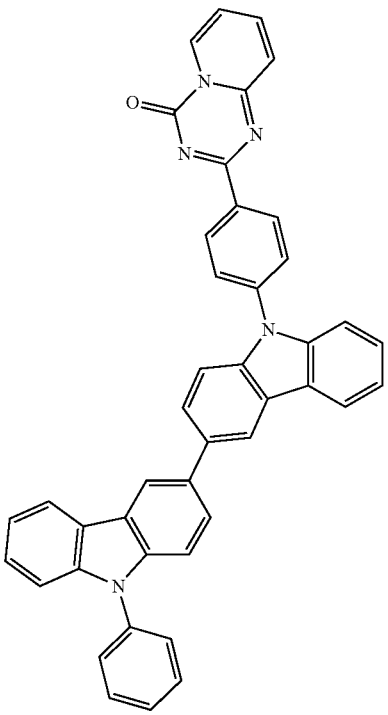
EG13 (4e)
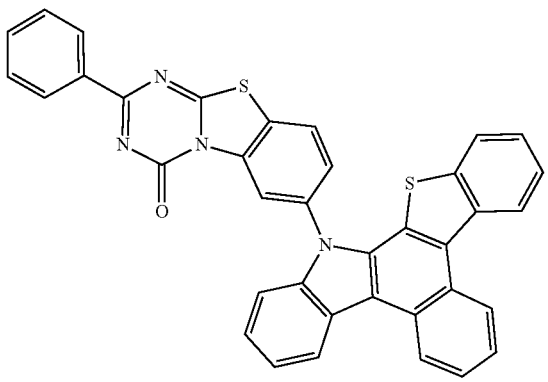
EG14 (14e)
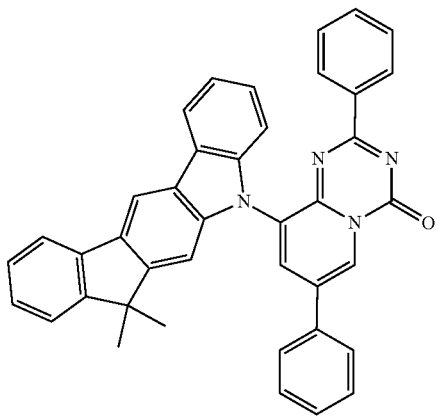
EG15 (11e)

TABLE 2-continued
Structural formulae of the materials for the OLEDs
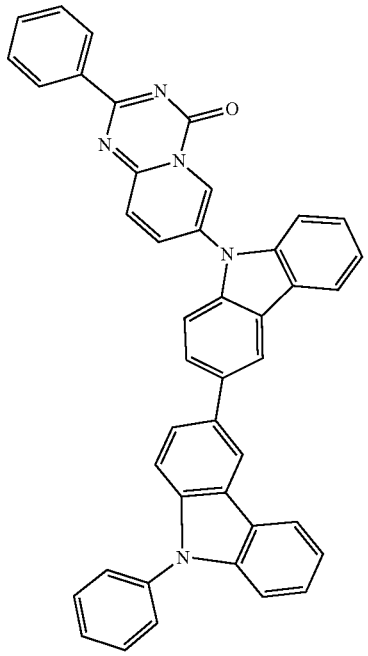
EG16 (e)
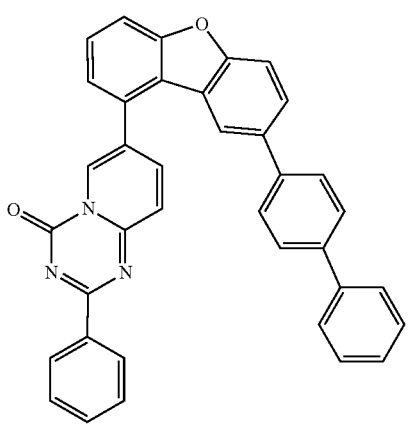
EG17 (13b)

TABLE 2-continued
Structural formulae of the materials for the OLEDs
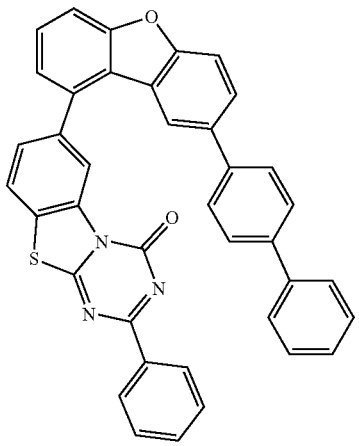
EG18 (8b)
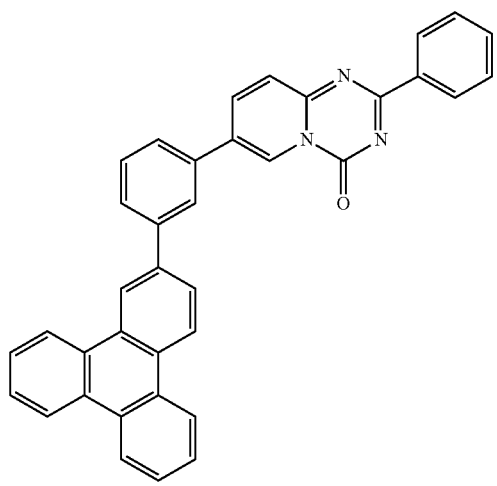
EG19 (1b)
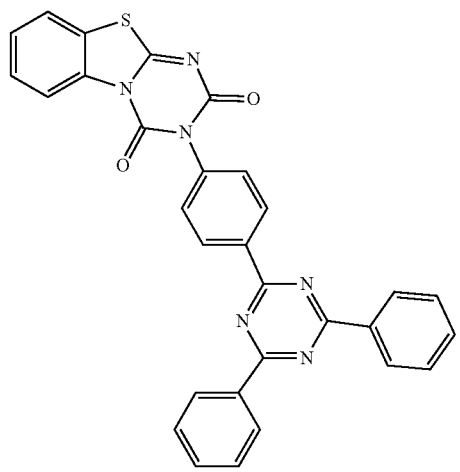
EG20 (23b)

TABLE 2-continued
Structural formulae of the materials for the OLEDs
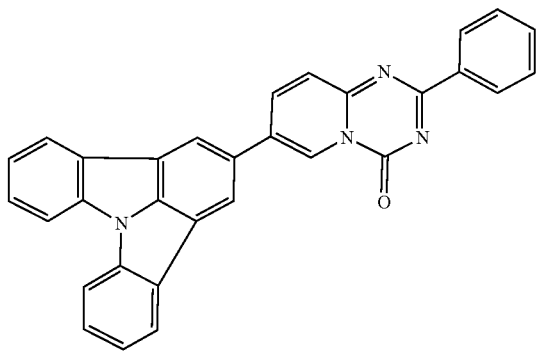
EG21 (33b)
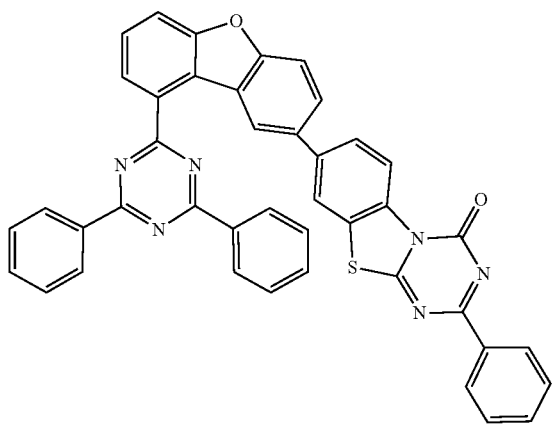
EG22 (30b)
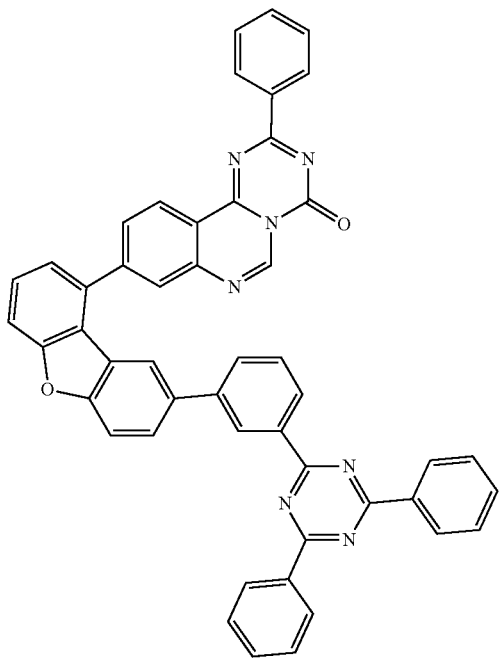
EG23 (28b)

TABLE 2-continued

Structural formulae of the materials for the OLEDs

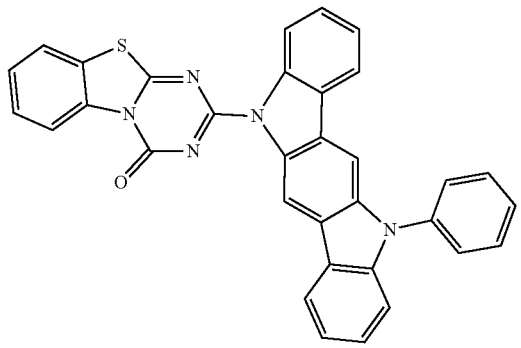

EG24 (5f)

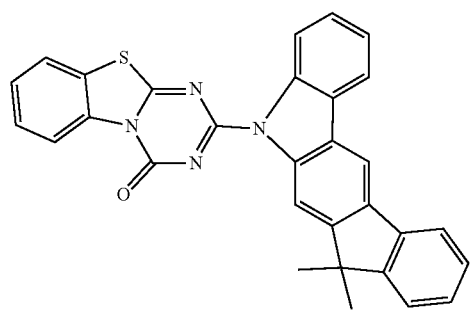

EG25 (2f)

TABLE 3

Data of the OLEDs

| Ex. | U1000 (V) | CE1000 (cd/A) | EQE 1000 (%) | CIE x/y at 1000 cd/m² |
|---|---|---|---|---|
| E1 | 3.5 | 68 | 19 | 0.35/0.61 |
| E2 | 3.4 | 67 | 17 | 0.33/0.62 |
| E3 | 3.4 | 69 | 18 | 0.35/0.61 |
| E4 | 3.3 | 71 | 16 | 0.35/0.62 |
| E5 | 3.2 | 70 | 18.4 | 0.33/0.63 |
| E6 | 3.1 | 67 | 18.0 | 0.33/0.62 |
| E7 | 3.2 | 69 | 18.8 | 0.32/0.64 |
| E8 | 3.1 | 74 | 20.1 | 0.32/0.63 |
| E9 | 3.1 | 73 | 20.8 | 0.33/0.62 |
| E10 | 3.1 | 73 | 19.8 | 0.33/0.63 |
| E11 | 3.1 | 72 | 20.7 | 0.33/0.63 |
| E12 | 3.2 | 73 | 20.8 | 0.33/0.63 |
| E13 | 3.1 | 68 | 19.8 | 0.33/0.63 |
| E14 | 3.1 | 73 | 20.8 | 0.33/0.62 |
| E15 | 3.3 | 67 | 19.3 | 0.33/0.63 |
| E16 | 3.1 | 72 | 20.2 | 0.33/0.63 |
| E17 | 3.2 | 70 | 21.1 | 0.33/0.62 |
| E18 | 3.1 | 73 | 19.8 | 0.33/0.62 |
| E19 | 3.2 | 71 | 20.2 | 0.33/0.63 |
| E20 | 3.1 | 73 | 21.7 | 0.33/0.62 |
| E21 | 3.8 | 22 | 20 | 0.66/0.34 |
| E22 | 3.9 | 21 | 22 | 0.65/0.33 |
| E23 | 3.8 | 22 | 21 | 0.66/0.34 |
| E24 | 3.7 | 24 | 22 | 0.67/0.34 |
| E25 | 3.5 | 23 | 21 | 0.66/0.34 |
| E26 | 3.4 | 64 | 18 | 0.33/0.63 |
| E27 | 3.3 | 64 | 18.5 | 0.33/0.62 |

The invention claimed is:

1. An electronic device comprising at least one compound of formula (1)

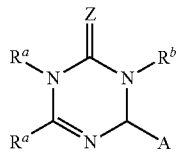

Formula (1)

wherein

Z is the same or different at each instance and is O or S;

A is R or Z;

$R^b$ is Ar or a free electron pair;

where, when A=Z, the oxygen or sulfur atom represented by Z is bonded to the carbon atom via a double bond, and $R^b$ is Ar;

in addition, $R^b$ is a free electron pair when A=R, and there is a double bond between the carbon atom to which A is bonded and the nitrogen atom to which $R^b$ is bonded;

$R^a$ is the same or different and is R, or the two $R^a$ groups together with the nitrogen atom and the carbon atom to which they bind form a group of one of the formulae (2), (3) and (4); R radical is an aromatic or heteroaromatic ring system which has 5 to 40 aromatic ring atoms and which may be substituted by one or more $R^1$ radicals;

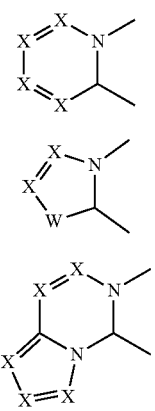

Formula (2)

Formula (3)

Formula (4)

where the dotted bond in each case indicates the linkage within formula (1);

X is the same or different at each instance and is CR or N; or two adjacent X groups are a group of the formula (5) or (6)

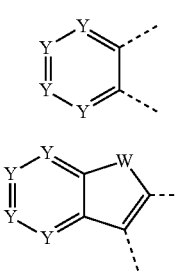

Formula (5)

Formula (6)

where the dotted bonds indicate the linkage of this group in the formula (2), formula (3) or formula (4);

Y is the same or different at each instance and is CR or N;

W is the same or different at each instance and is NAr, O, S or C(R)$_2$;

Ar is the same or different at each instance and is an aromatic or heteroaromatic ring system which has 5 to 40 aromatic ring atoms and may be substituted by one or more R radicals;

R is the same or different at each instance and is H, D, F, Cl, Br, I, N(Ar')$_2$, N(R$^1$)$_2$, OAr', SAr', CN, NO$_2$, OR$^1$, SR$^1$, COOR$^1$, C(=O)N(R$^1$)$_2$, Si(R$^1$)$_3$, B(OR$^1$)$_2$, C(=O)R$^1$, P(=O)(R$^1$)$_2$, S(=O)R$^1$, S(=O)$_2$R$^1$, OSO$_2$R$^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more R$^1$ radicals, where one or more nonadjacent CH$_2$ groups may be replaced by Si(R$^1$)$_2$, C=O, NR$^1$, O, S or CONR$^1$, or an aromatic or heteroaromatic ring system which has 5 to 60 aromatic ring atoms, preferably 5 to 40 aromatic ring atoms, and may be substituted in each case by one or more R$^1$ radicals; at the same time, two R radicals together may also form an aliphatic, heteroaliphatic, aromatic or heteroaromatic ring system;

Ar' is the same or different at each instance and is an aromatic or heteroaromatic ring system which has 5 to 40 aromatic ring atoms and may be substituted by one or more R$^1$ radicals;

R$^1$ is the same or different at each instance and is H, D, F, Cl, Br, I, N(R$^2$)$_2$, CN NO$_2$, OR$^2$, SR$^2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may each be substituted by one or more R$^2$ radicals, where one or more nonadjacent CH$_2$ groups may be replaced by Si(R$^2$)$_2$, C=O, NR$^2$, O, S or CONR$^2$ and where one or more hydrogen atoms in the alkyl, alkenyl or alkynyl group may be replaced by D, F, Cl, Br, I or CN, or an aromatic or heteroaromatic ring system which has 5 to 40 aromatic ring atoms and may be substituted in each case by one or more R$^2$ radicals; at the same time, two or more R$^1$ radicals together may form an aliphatic ring system;

R$^2$ is the same or different at each instance and is H, D, F, CN or an aliphatic, aromatic or heteroaromatic organic radical, especially a hydrocarbyl radical, having 1 to 20 carbon atoms, in which one or more hydrogen atoms may also be replaced by F.

2. The electronic device as claimed in claim 1, wherein the compound of the formula (1) contains at least one substituent Ar and at least one substituent R which is an aromatic or heteroaromatic ring system.

3. The electronic device as claimed in claim 1, wherein the compound of the formula (1) is selected from the compounds of the formulae (7a) and (8a)

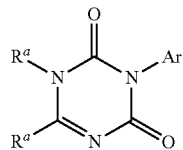

Formula (7a)

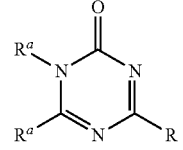

Formula (8a)

where the symbols used have the definitions given in claim 1.

4. The electronic device as claimed in claim 1, selected from the compounds of the formulae (7-1) to (7-9) and (8-1) to (8-11)

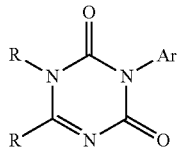

Formula (7-1)

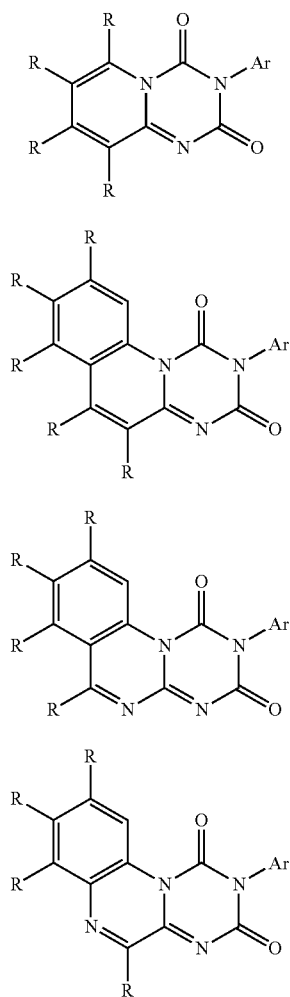
Formula (7-2)
Formula (7-3)
Formula (7-4)
Formula (7-5)
Formula (7-6)
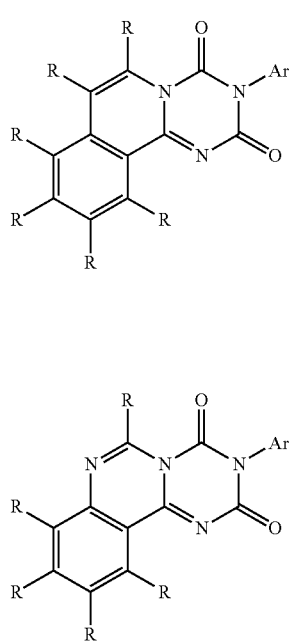
Formula (7-7)
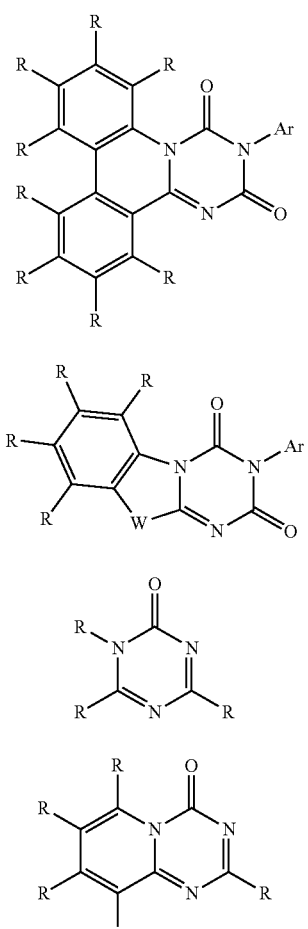
Formula (7-8)
Formula (7-9)
Formula (8-1)
Formula (8-2)
Formula (8-3)
Formula (8-4)

-continued

Formula (8-5)
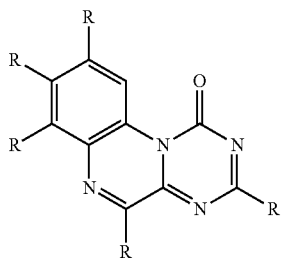

Formula (8-6)
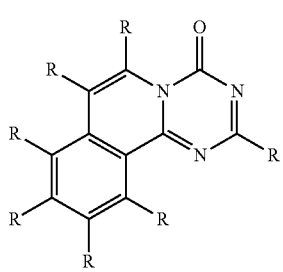

Formula (8-7)
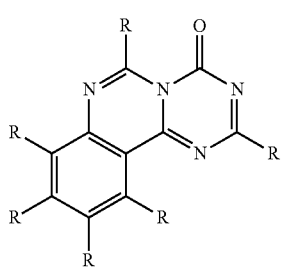

Formula (8-8)
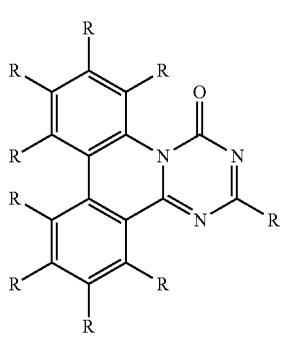

Formula (8-9)
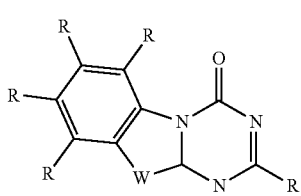

-continued

Formula (8-10)
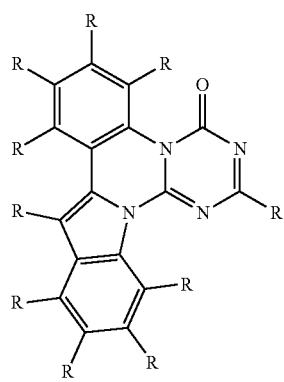

Formula (8-11)
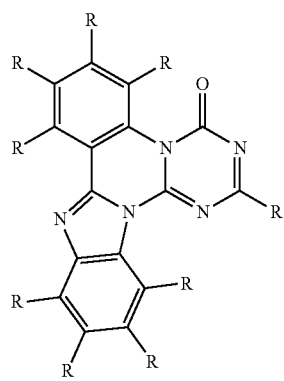

where the symbols have the definitions given in claim 1.

5. The electronic device as claimed in claim 4, wherein, when A=R, the R radical shown explicitly in formulae (8) and (8-1) to (8-11) which is bonded to the triazinone skeleton is an aromatic or heteroaromatic ring system which has 5 to 40 aromatic ring atoms and may be substituted by one or more $R^1$ radicals.

6. The electronic device as claimed in claim 1, wherein the compound of the formula (1) is selected from the compounds of the formulae (7-1a) to (7-9a) and (8-1a) to (8-11a)

Formula (7-1a)
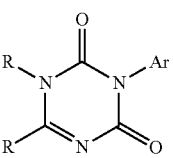

Formula (7-2a)
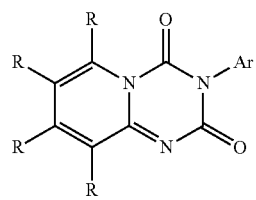

Formula (7-3a)
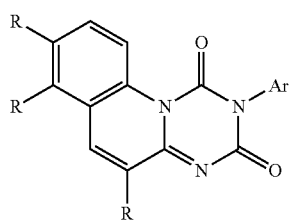
Formula (7-4a)
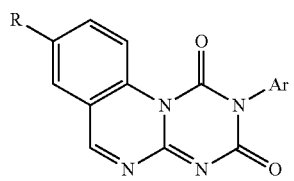
Formula (7-5a)
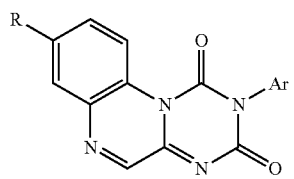
Formula (7-6a)
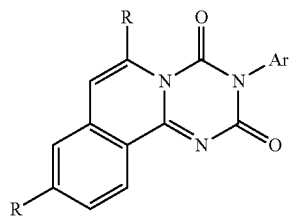
Formula (7-7a)
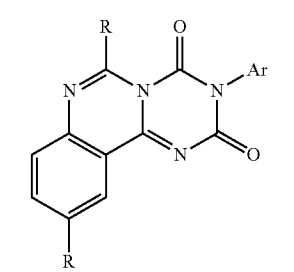
Formula (7-8a)
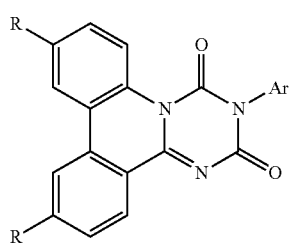
Formula (7-9a)
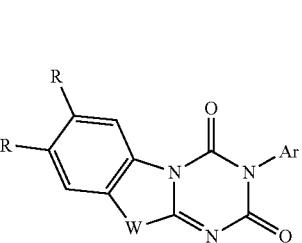
Formula (8-1a)
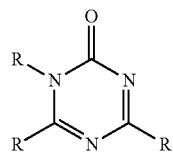
Formula (8-2a)
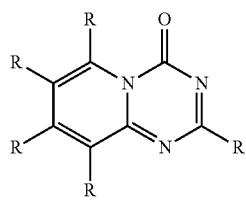
Formula (8-3a)
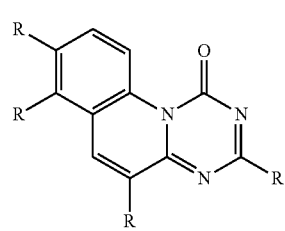
Formula (8-4a)
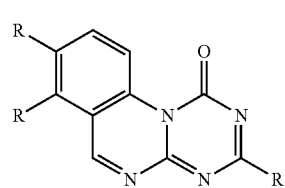
Formula (8-5a)
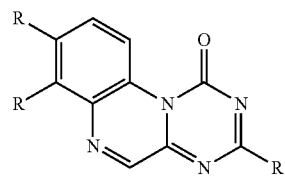
Formula (8-6a)
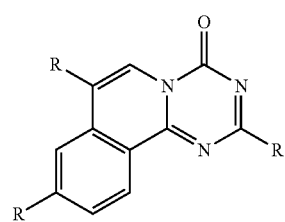
Formula (8-7a)
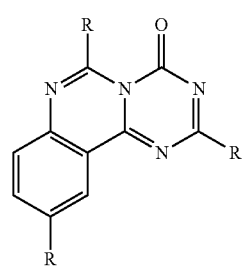

-continued

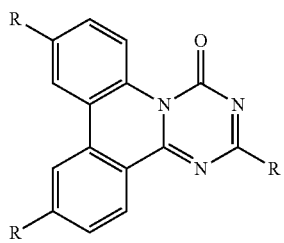

Formula (8-8a)

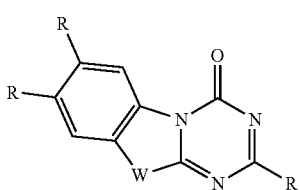

Formula (8-9a)

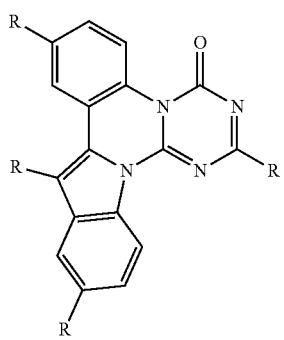

Formula (8-10a)

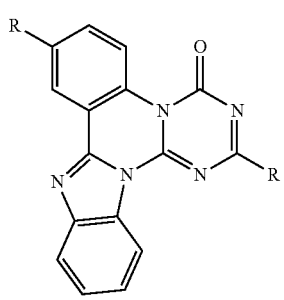

Formula (8-11a)

where the symbols have the definitions given in claim 1.

7. The electronic device as claimed in claim 1, wherein Ar is the same or different at each instance and represents an aromatic or heteroaromatic ring system which has 6 to 30 aromatic ring atoms and may be substituted by one or more R radicals.

8. The electronic device as claimed in claim 1, wherein R is the same or different at each instance and is selected from the group consisting of H, D, F, N(Ar')$_2$, CN, OR$^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more R$^1$ radicals, but is preferably unsubstituted, and where one or more nonadjacent CH$_2$ groups may be replaced by O, or an aromatic or heteroaromatic ring system which has 6 to 30 aromatic ring atoms and may be substituted in each case by one or more R$^1$ radicals; at the same time, two R radicals together may also form an aliphatic, aromatic or heteroaromatic ring system.

9. The electronic device as claimed in claim 1, wherein Ar and R, if R is an aromatic or heteroaromatic ring system, are the same or different at each instance and are selected from the group consisting of phenyl, biphenyl, terphenyl, quaterphenyl, fluorene, spirobifluorene, naphthalene, indole, benzofuran, benzothiophene, carbazole, dibenzofuran, dibenzothiophene, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more R radicals.

10. The electronic device as claimed in claim 1, selected from the group consisting of organic electroluminescent devices, organic integrated circuits, organic field-effect transistors, organic thin-film transistors, organic light-emitting transistors, organic solar cells, dye-sensitized organic solar cells, organic optical detectors, organic photoreceptors, organic field-quench devices, light-emitting electrochemical cells, organic laser diodes and organic plasmon-emitting devices.

11. The electronic device as claimed in claim 1 which is an organic electroluminescent device, wherein the compound of formula (1) is used in an emitting layer as matrix material for phosphorescent emitters or for emitters that exhibit TADF and/or in an electron transport layer and/or in a hole blocker layer.

12. The electronic device as claimed in claim 1 which is an organic electroluminescent device, wherein the compound of the formula (1) is used as matrix material for a phosphorescent emitter in combination with a further matrix material, and in that the further matrix material is selected from the group consisting of aromatic ketones, aromatic phosphine oxides, aromatic sulfoxides, aromatic sulfones, triarylamines, carbazole derivatives, biscarbazoles, indolocarbazole derivatives, indenocarbazole derivatives, azacarbazole derivatives, bipolar matrix materials, azaboroles, boronic esters, triazine derivatives, zinc complexes, diazasilole or tetraazasilole derivatives, diazaphosphole derivatives, bridged carbazole derivatives, triphenylene derivatives, dibenzofuran derivatives, dibenzothiophene derivatives, dibenzofuran-carbazole derivatives, dibenzofuran-amine derivatives or carbazoleamines.

13. A compound of formula (1')

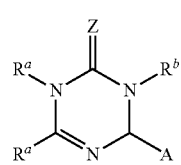

Formula (1')

where the symbols used have the definitions given in claim 1, wherein the compound contains a heteroaryl group in at least one of the substituents Ar or R.

14. A compound as claimed in claim 13, wherein the heteroaryl group is selected from the group consisting of dibenzofuran, dibenzothiophene and carbazole.

* * * * *